United States Patent
Barrish et al.

(10) Patent No.: US 6,235,740 B1
(45) Date of Patent: *May 22, 2001

(54) IMIDAZOQUINOXALINE PROTEIN TYROSINE KINASE INHIBITORS

(75) Inventors: Joel C. Barrish, Holland, PA (US); Ping Chen, Lawrenceville, NJ (US); Jagabandhu Das, Mercerville, NJ (US); Edwin J. Iwanowicz, Cranbury, NJ (US); Derek J. Norris, Trenton, NJ (US); Ramesh Padmanabha, Hamden, CT (US); Jacques Y. Roberge, Princeton; Gary L. Schieven, Lawrenceville, both of NJ (US)

(73) Assignee: Bristol-Myers Squibb Co., Princeton, NJ (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/097,338

(22) Filed: Jun. 15, 1998

Related U.S. Application Data

(60) Provisional application No. 60/056,770, filed on Aug. 25, 1997, and provisional application No. 60/069,159, filed on Dec. 9, 1997.

(51) Int. Cl.[7] .................... C07D 487/04; A61K 31/4745
(52) U.S. Cl. ............................ 514/250; 544/346
(58) Field of Search ............... 544/346; 514/250

(56) References Cited

U.S. PATENT DOCUMENTS

| | | |
|---|---|---|
| 4,160,097 | 7/1979 | Warner et al. . |
| 4,172,947 | 10/1979 | Warner et al. . |
| 4,191,766 | 3/1980 | Warner et al. . |
| 4,191,767 | 3/1980 | Warner et al. . |
| 4,197,403 | 4/1980 | Warner et al. . |
| 4,198,508 | 4/1980 | Warner et al. . |
| 4,200,750 | 4/1980 | Warner et al. . |
| 4,225,724 | 9/1980 | Warner et al. . |
| 4,229,452 | 10/1980 | Warner et al. . |
| 4,236,015 | 11/1980 | Warner et al. . |
| 4,317,682 | 3/1982 | Katsura et al. . |
| 4,440,929 | 4/1984 | Lee et al. . |
| 5,034,530 | 7/1991 | Hansen et al. . |
| 5,276,028 | 1/1994 | Hansen . |

FOREIGN PATENT DOCUMENTS

| | | | |
|---|---|---|---|
| 728481 | 8/1996 | (EP) . | |
| 92/00298 | * 1/1992 | (WO) | .................................. 544/346 |
| WO 97/19079 | 5/1997 | (WO) . | |

OTHER PUBLICATIONS

Colotta Eur J Med chem 30(2) 133–9, 1995.*
Bolen, J. B., et al., *FASEB Journal*, "The Src family of tyrosine protein kinases in hemopoietic signal transduction", vol. 6, pp. 3403–3409 (1992).
Chan, A.C., et al., *EMBO Journal*, "Activation of ZAP–70 kinase activity by phosphorylation of tyrosine 493 is required for lymphocyte antigen receptor function", vol. 14, pp. 2499–2508, (1995).
Ihle, J. N., *Seminars in Immunology*, "The Janus protein tyrosine kinases in hematopoietic cytokine", vol. 7, pp. 247–254 (1995).
Iwashima, M., et al., *Science*, "Sequential Interactions of the TCR with Two Distinct Cytoplasmic Tyrosine Kinases", vol. 263, pp. 1136–1139 (1994).
Schieven, G. L., et al., *Journal of Biological Chemistry*, "ZAP–70 Tyrosine Kinase, CD45, and T Cell Receptor Involvement in UV–and $H_2O_2$–induced T Cell Signal Transduction", vol. 269, No. 32, pp. 20718–20726 (1994).
Ulrich, A., et al., *Cell*, "Signal Transduction by Receptors with Tyrosine Kinase Activity", vol. 61, pp. 203–212 (1990).
Weiss, A., et al., *Cell*, "Signal Transduction by Lymphocyte Antigen Receptors", vol. 76, pp. 263–274 (1994).
Cooper, J. A., et al., *Journal of Biological Chemistry*, "Phosphorylation Sites in Enolase and Lactate Dehydrogenase Utilized by Tyrosine Protein Kinases in Vivo and in Vitro", vol. 259, No. 12, pp. 7835–7841 (1984).

* cited by examiner

*Primary Examiner*—Robert Gerstl
(74) *Attorney, Agent, or Firm*—Ronald S. Hermenau; Audrey F. Sher; Suzanne E. Babajko

(57) ABSTRACT

Novel imidazoquinoxalines and salts thereof, pharmaceutical compositions containing such compounds, and methods of using such compounds in the treatment of protein tyrosine kinase-associated disorders such as immunologic disorders.

41 Claims, No Drawings

IMIDAZOQUINOXALINE PROTEIN TYROSINE KINASE INHIBITORS

This application claims priority from provisional U.S. application Ser. Nos. 60/056,770, filed Aug. 25, 1997 and 60/069,159, filed Dec. 19, 1997, each incorporated herein by reference in its entirety.

FIELD OF THE INVENTION

The present invention relates to imidazoquinoxalines and salts thereof, to methods of using such compounds in treating protein tyrosine kinase-associated disorders such as immunologic disorders, and to pharmaceutical compositions containing such compounds.

BACKGROUND OF THE INVENTION

Protein tyrosine kinases (PTKs) are enzymes which, in conjuction with ATP as a substrate, phosphorylate tyrosine residues in peptides and proteins. These enzymes are key elements in the regulation of cell signaling including cell proliferation and cell differentiation. PTKs comprise, inter alia, receptor tyrosine kinases (RPTKs), including members of the epidermal growth factor kinase family (e.g., HER1 and HER2), platelet derived growth factor (PDGF), and kinases that play a role in angiogenesis (Tie-2 and KDR); and, in addition, non-receptor tyrosine kinases, including members of the Syk, JAK and Src (e.g. src, fyn, lyn, Lck and blk) families (see Bolen, J. B., Rowley, R. B., Spana, C., and Tsygankov, A. Y., "The src family of tyrosine protein kinases in hemopoietic signal transduction", *FASEB J.*, 6, 3403–3409 (1992); Ullrich, A. and Schlessinger, J., "Signal transduction by receptors with tyrosine kinase activity", *Cell*, 61, 203–212 (1990); and Ihle, J. N., "The Janus protein tyrosine kinases in hematopoetic cytokine signaling", *Sem. Immunol.*, 7, 247–254 (1995)).

Enhanced activity of PTKs has been implicated in a variety of malignant and nonmalignant proliferative diseases. In addition, PTKs play a central role in the regulation of cells of the immune system. PTK inhibitors can thus impact a wide variety of oncologic and immunologic disorders. Such disorders may be ameliorated by selective inhibition of a certain receptor or non-receptor PTK, such as Lck, or due to the homology among PTK classes, by inhibition of more than one PTK by an inhibitor.

A PTK of particular interest is Lck which is found in T cells where it is involved in phosphorylating key protein substrates. It is required for productive antigen receptor signaling and cell activation. In the absence of Lck activity, the T cell receptor (TCR) zeta chain is not phosphorylated, the kinase ZAP-70 is not activated, and $Ca^{2+}$ mobilization essential for T cell activation does not occur (see Weiss, A. and Littman, D. R. "Signal transduction by lymphocyte antigen receptors", *Cell*, 76, 263–274 (1994); Iwashima, M., Irving, B. A., van Oers, N. S. C., Chan, A. C., and Weiss, A., "Sequential interactions of the TCR with two distinct cytoplasmic tyrosine kinases", *Science*, 263, 1136–1139 (1994); and Chan, A. C., Dalton, M., Johnson, R., Kong, G., Wang, T., Thoma, R., and Kurosaki, T., "Activation of ZAP-70 kinase activity by phosphorylation of tyrosine 493 is required for lymphocyte antigen receptor function", *EMBO J.*, 14, 2499–2508 (1995)). Inhibitors of Lck are thus useful in the treatment of T-cell mediated disorders such as chronic diseases with an important T cell component, for example rheumatoid arthritis, multiple sclerosis and lupus, as well as acute diseases where T cells are known to play an essential role, for example acute transplant rejection and delayed-type hypersensitivity (DTH) reactions.

SUMMARY OF THE INVENTION

The present invention provides imidazoquinoxaline compounds of the following formula I and salts thereof, for use as protein tyrosine kinase inhibitors:

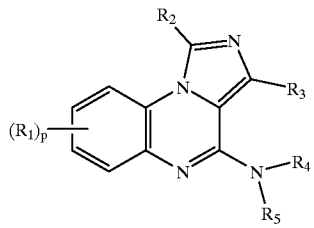

(I)

where
p is 0, 1, 2, 3 or 4;
each $R_1$, and $R_2$ and $R_3$, are independently selected from:
(1) hydrogen or $R_6$,
where $R_6$ is alkyl, alkenyl, alkynyl, cycloalkyl, cycloalkylalkyl, cycloalkenyl, cycloalkenylalkyl, aryl, aralkyl, heterocyclo, or heterocycloalkyl, each of which is unsubstituted or substituted with $Z_1$, $Z_2$ and one or more (preferably, one or two) groups $Z_3$;
(2) —OH or —$OR_6$;
(3) —SH or —$SR_6$;
(4) —$C(O)_qH$, —$C(O)_qR_6$, or —O—$C(O)_qR_6$, where q is 1 or 2;
(5) —$SO_3H$ or —$S(O)_qR_6$;
(6) halo;
(7) cyano;
(8) nitro;
(9) —$Z_4$—$NR_7R_8$;
(10) —$Z_4$—$N(R_9)$—$Z_5$—$NR_{10}R_{11}$;
(11) —$Z_4$—$N(R_{12})$—$Z_5$—$R_6$;
(12) —$SiR_{13}R_{14}R_{15}$;
(13) —$P(O)(OR_6)_2$;
(14) —CH=N—$OR_6$;
(15) any two groups $R_1$ may together be alkylene or alkenylene completing a 3- to 8-membered saturated or unsaturated ring together with the carbon atoms to which they are attached, which ring is unsubstituted or substituted with $Z_1$, $Z_2$ and $Z_3$; or
(16) any two groups $R_1$ may, together with the carbons to which they are attached, form a heterocyclo group, which group is unsubstituted or substituted with $Z_1$, $Z_2$ and $Z_3$;

$R_4$ and $R_5$:
(1) are each independently hydrogen, $R_6$, or —$C(O)R_6$; or
(2) together with the nitrogen atom to which they are attached complete a 3- to 8-membered saturated or unsaturated heterocyclic ring which is unsubstituted or substituted with $Z_1$, $Z_2$ and $Z_3$, which heterocyclic ring may optionally have fused to it a benzene ring itself unsubstituted or substituted with $Z_1$, $Z_2$ and $Z_3$;

$R_7$, $R_8$, $R_9$, $R_{10}$, $R_{11}$ and $R_{12}$:
(1) are each independently hydrogen or $R_6$;
(2) $R_7$ and $R_8$ may together be alkylene or alkenylene, completing a 3- to 8-membered saturated or unsaturated ring with the nitrogen atom to which they are attached, which ring is unsubstituted or substituted with $Z_1$, $Z_2$ and $Z_3$; or
(3) any two of $R_9$, $R_{10}$ and $R_{11}$ may together be alkylene or alkenylene completing a 3- to 8-membered saturated or unsaturated ring together with the nitrogen atoms to which they are attached, which ring is unsubstituted or substituted with $Z_1$, $Z_2$ and $Z_3$;

$R_{13}$, $R_{14}$ and $R_{15}$ are each independently:
   (1) alkyl; or
   (2) phenyl;

$Z_1$, $Z_2$ and $Z_3$ are each independently:
   (1) hydrogen or $Z_6$, where $Z_6$ is (i) alkyl, alkenyl, alkynyl, cycloalkyl, cycloalkylalkyl, cycloalkenyl, cycloalkenylalkyl, aryl, aralkyl, alkylaryl, cycloalkylaryl, heterocyclo, or heterocycloalkyl; (ii) a group (i) which is itself substituted by one or more of the same or different groups (i); or (iii) a group (i) or (ii) which is substituted by one or more of the following groups (2) to (16) of the definition of $Z_1$, $Z_2$ and $Z_3$;
   (2) —OH or —$OZ_6$;
   (3) —SH or —$SZ_6$;
   (4) —C(O)$_q$H, —C(O)$_q Z_6$, or —O—C(O)$_q Z_6$;
   (5) —SO$_3$H or —S(O)$_q Z_6$;
   (6) halo;
   (7) cyano;
   (8) nitro;
   (9) —$Z_4$—$NZ_7 Z_8$;
   (10) —$Z_4$—N($Z_9$)—$Z_5$—$NZ_7 Z_8$;
   (11) —$Z_4$—N($Z_{10}$)—$Z_5$—$Z_6$;
   (12) —$Z_4$—N($Z_{10}$)—$Z_5$—H;
   (13) oxo;
   (14) —O—C(O)—$Z_6$;
   (15) any two of $Z_1$, $Z_2$, and $Z_3$ may together be alkylene or alkenylene completing a 3- to 8-membered saturated or unsaturated ring together with the atoms to which they are attached; or
   (16) any two of $Z_1$, $Z_2$, and $Z_3$ may together be —O—(CH$_2$)$_q$—O—; $Z_4$ and $Z_5$ are each independently:
   (1) a single bond;
   (2) —$Z_{11}$—S(O)$_q$—$Z_{12}$—;
   (3) —$Z_{11}$—C(O)—$Z_{12}$—;
   (4) —$Z_{11}$—C(S)—$Z_{12}$—;
   (5) —$Z_{11}$—O—$Z_{12}$—;
   (6) —$Z_{11}$—S—$Z_{12}$—;
   (7) —$Z_{11}$—O—C(O)—$Z_{12}$—; or
   (8) —$Z_{11}$—C(O)—O—$Z_{12}$—;

$Z_7$, $Z_8$, $Z_9$ and $Z_{10}$:
   (1) are each independently hydrogen or $Z_6$;
   (2) $Z_7$ and $Z_8$, or $Z_6$ and $Z_{10}$, may together be alkylene or alkenylene, completing a 3- to 8-membered saturated or unsaturated ring together with the atoms to which they are attached, which ring is unsubstituted or substituted with $Z_1$, $Z_2$ and $Z_3$; or
   (3) $Z_7$ or $Z_8$, together with $Z_9$, may be alkylene or alkenylene completing a 3- to 8-membered saturated or unsaturated ring together with the nitrogen atoms to which they are attached, which ring is unsubstituted or substituted with $Z_1$, $Z_2$ and $Z_3$; and $Z_{11}$ and $Z_{12}$ are each independently:
   (1) a single bond;
   (2) alkylene;
   (3) alkenylene; or
   (4) alkynylene.

Compounds of the formula I and salts thereof, excluding the compound 4-amino-7-trifluoromethylimidazo[1,5-a]quinoxaline-3-carboxylic acid ethyl ester, are novel.

DETAILED DESCRIPTION OF THE INVENTION

The following are definitions of terms used in this specification. The initial definition provided for a group or term herein applies to that group or term throughout the present specification, individually or as part of another group, unless otherwise indicated.

The terms "alk" or "alkyl" refer to straight or branched chain hydrocarbon groups having 1 to 12 carbon atoms, preferably 1 to 8 carbon atoms. The expression "lower alkyl" refers to alkyl groups of 1 to 4 carbon atoms.

The term "alkenyl" refers to straight or branched chain hydrocarbon groups of 2 to 10, preferably 2 to 4, carbon atoms having at least one double bond. Where an alkenyl group is bonded to a nitrogen atom, it is preferred that such group not be bonded directly through a carbon bearing a double bond.

The term "alkynyl" refers to straight or branched chain hydrocarbon groups of 2 to 10, preferably 2 to 4, carbon atoms having at least one triple bond. Where an alkynyl group is bonded to a nitrogen atom, it is preferred that such group not be bonded directly through a carbon bearing a triple bond.

The term "alkylene" refers to a straight chain bridge of 1 to 5 carbon atoms connected by single bonds (e.g., —(CH$_2$)$_x$— wherein x is 1 to 5), which may be substituted with 1 to 3 lower alkyl groups.

The term "alkenylene" refers to a straight chain bridge of 2 to 5 carbon atoms having one or two double bonds that is connected by single bonds and may be substituted with 1 to 3 lower alkyl groups. Exemplary alkenylene groups are —CH=CH—CH=CH—, —CH$_2$—CH=CH—, —CH$_2$—CH=CH—CH$_2$—, —C(CH$_3$)$_2$CH=CH— and —CH(C$_2$H$_5$)—CH=CH—.

The term "alkynylene" refers to a straight chain bridge of 2 to 5 carbon atoms that has a triple bond therein, is connected by single bonds, and may be substituted with 1 to 3 lower alkyl groups. Exemplary alkynylene groups are —C≡C—, —CH$_2$—C≡C—, —CH(CH$_3$)—C≡C— and —C≡C—CH(C$_2$H$_5$)CH$_2$—.

The terms "ar" or "aryl" refer to phenyl, naphthyl and biphenyl.

The terms "cycloalkyl" and "cycloalkenyl" refer to cyclic hydrocarbon groups of 3 to 8 carbon atoms.

The terms "halogen" and "halo" refer to fluorine, chlorine, bromine and iodine.

The term "unsaturated ring" includes partially unsaturated and aromatic rings.

The terms "heterocycle", "heterocyclic" or "heterocyclo" refer to fully saturated or unsaturated, including aromatic ("heteroaryl") or nonaromatic cyclic groups, for example, 4 to 7 membered monocyclic, 7 to 11 membered bicyclic, or 10 to 15 membered tricyclic ring systems, which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system.

Exemplary monocyclic heterocyclic groups include pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, hexahydroazepinyl, 4-piperidonyl, pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, and the like.

Exemplary bicyclic heterocyclic groups include indolyl, benzothiazolyl, benzoxazolyl, benzothienyl, quinuclidinyl, quinolinyl, tetra-hydroisoquinolinyl, isoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b] pyridinyl), dihydroisoindolyl, dihydroquinazolinyl (such as 3,4-dihydro-4-oxo-quinazolinyl), dihydrobenzodioxinyl (such as 2,3-dihydro-1,4-benzodioxinyl), benzodioxolyl (such as 1,3-benzodioxolyl), tetrahydroquinolinyl and the like.

Exemplary tricyclic heterocyclic groups include carbazolyl, benzidolyl, phenanthrolinyl, acridinyl, phenanthridinyl, xanthenyl and the like.

Where q is 1 or 2, "—C(O)$_q$H" denotes —C(O)—H or —C(O)—OH; "—C(O)$_q$R$_6$" or "—C(O)$_q$Z$_6$" denote, respectively, —C(O)—R$_6$ or —C(O)—OR$_6$, or —C(O)—Z$_6$ or —C(O)—OZ$_6$; "—O—C(O)$_q$R$_6$" or "—O—C(O)$_q$Z$_6$2) denote, respectively, —O—C(O)—R$_6$ or —O—C(O)—OR$_6$, or —O—C(O)—Z$_6$ or —O—C(O)—OZ$_6$; and "—S(O)$_q$R$_6$" or "—S(O)$_q$Z$_6$" denote, respectively, —SO—R$_6$ or —SO$_2$—R$_6$, or —SO—Z$_6$ or —SO$_2$—Z$_6$.

The compounds of formula I form salts which are also within the scope of this invention. Reference to a compound of the formula I herein is understood to include reference to salts thereof, unless otherwise indicated. The term "salt(s)", as employed herein, denotes acidic and/or basic salts formed with inorganic and/or organic acids and bases. Zwitterions (internal or inner salts) are included within the term "salt(s)" as used herein (and may be formed, for example, where the R substituents comprise an acid moiety such as a carboxyl group). Also included herein are quaternary ammonium salts such as alkylammonium salts. Pharmaceutically acceptable (i.e., non-toxic, physiologically acceptable) salts are preferred, although other salts are useful, for example, in isolation or purification steps which may be employed during preparation. Salts of the compounds of the formula I may be formed, for example, by reacting a compound I with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts (formed, for example, where the R substituents comprise an acidic moiety such as a carboxyl group) include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines, N-methyl-D-glucamines, N-methyl-D-glucamides, t-butyl amines, and salts with amino acids such as arginine, lysine and the like. The basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

Prodrugs and solvates of the compounds of the invention are also contemplated herein. The term "prodrug", as employed herein, denotes a compound which, upon administration to a subject, undergoes chemical conversion by metabolic or chemical processes to yield a compound of the formula I, or a salt and/or solvate thereof. Solvates of the compounds of formula I are preferably hydrates.

In certain instances, compounds of the formula I, and salts thereof, may exist in their tautomeric form, for example, the form having the following structure, and salts thereof, where $R_5$ is hydrogen and p, $R_1$, $R_2$, $R_3$ and $R_4$ are as defined above:

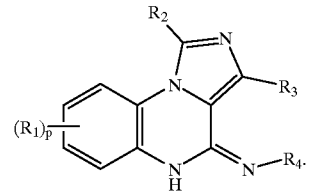

Such tautomers, and any other tautomers, are contemplated herein as part of the present invention.

All stereoisomers of the present compounds, such as those which may exist due to asymmetric carbons on the R substituents of the compound of the formula I, including enantiomeric and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations.

Throughout the specification, groups and substituents thereof are chosen to provide stable moieties and compounds.

PREFERRED COMPOUNDS

Compounds of the formula I, and salts thereof, wherein one or more, and especially all, of p, $R_1$, $R_2$, $R_3$, $R_4$, and $R_5$ are selected from the following definitions, are preferred compounds of the present invention:

p is 0, 1 or 2;

each $R_1$ is independently selected from hydrogen, alkyl, alkoxy, nitro, aryl, halo, heterocyclo, —$Z_4$—NR$_7$R$_8$ or —$Z_4$—N(R$_{12}$)—$Z_5$—R$_6$;

$R_2$ is selected from hydrogen or alkyl;

$R_3$ is selected from hydrogen or alkyl;

$R_4$ is selected from aryl such as phenyl, or heteroaryl, either of which is substituted with $Z_1$, $Z_2$ and one or two groups $Z_3$, where said $Z_1$, $Z_2$ and $Z_3$ substituents are selected from hydrogen, halo, lower alkyl, lower alkoxy or heterocyclo; and $R_5$ is selected from hydrogen or alkyl.

METHODS OF PREPARATION

The compounds of the formula I may be prepared by methods such as those illustrated in the following Schemes I to VI. Solvents, temperatures, pressures, and other reaction conditions may readily be selected by one of ordinary skill in the art. All documents cited are incorporated herein by reference in their entirety. Starting materials are commercially available or readily prepared by one of ordinary skill in the art.

The methods described herein may be carried out with starting materials and/or reagents in solution or alternatively, where appropriate, with one or more starting materials or reagents bound to a solid support (see (1) Thompson, L. A., Ellman, J. A., *Chemical Reviews*, 96, 555–600 (1996); (2) Terrett, N. K., Gardner, M., Gordon, D. W., Kobylecki, R. J., Steele, J., *Tetrahedron*, 51, 8135–8173 (1995); (3) Gallop, M. A., Barrett, R. W., Dower, W. J., Fodor, S. P. A., Gordon, E. M., *Journal of Medicinal Chemistry*, 37, 1233–1251 (1994); (4) Gordon, E. M., Barrett, R. W., Dower, W. J., Fodor, S. P. A., Gallop, M. A., *Journal of Medicinal Chemistry*, 37, 1385–1401 (1994); (5) Balkenhohl, F., von dem Bussche-Hütnnefeld, Lansky, A., Zechel, C., *Angewandte Chemie International Edition in English*, 35, 2288–2337 (1996); (6) Balkenhohl, F., von dem Bussche-Hünnefeld, Lansky, A., Zechel, C., *Angewandte Chemie*, 108, 2436–2487 (1996); and (7) Sofia, M. J., *Drugs Discovery Today*, 1, 27–34 (1996)).

As shown in Scheme I, an appropriately substituted 2-nitro halobenzene 1 can be reacted with a substituted imidazole 2 in the presence of a base such as sodium, potassium, or cessium carbonate, or an amine base such as triethyl amine, diisopropylethyl amine, 1,8-diazabicyclo[5.4.0]undec-7-ene ("DBU"), or the like, in an appropriate solvent to give the imidazole derivative 3 (Davey, et al., *J. Med. Chem.*, 34, 2671 (1991)). The reaction may also be carried out in the presence of a copper I salt such as cuprous chloride, cuprous bromide, or cuprous iodide (Sitkina, et al., *Khim Geterotskil Soed* in 143 (1966); Grimmett, et al., *Aust. J. Chem.*, 32, 2203 (1979); Sugaya, et al., *Synthesis*, 73 (1994)). Preferred X groups in 1 are F and Cl in the absence of a copper I salt and Br and I in the presence of a copper I salt.

The nitro group of 3 may then be reduced to provide the corresponding amine 4 by methods such as those known in the art (e.g., Hudlicky, "Reductions in Organic Chemistry", Wiley (1984)), for example, by catalytic hydrogenation, or by use of $SnCl_2$, $FeCl_3$, sodium dithionite, or the like.

When $R_5$ is hydrogen, the amine 4 may be converted to the urea 6 by treatment with an isocyanate 5. Alternatively, Scheme I

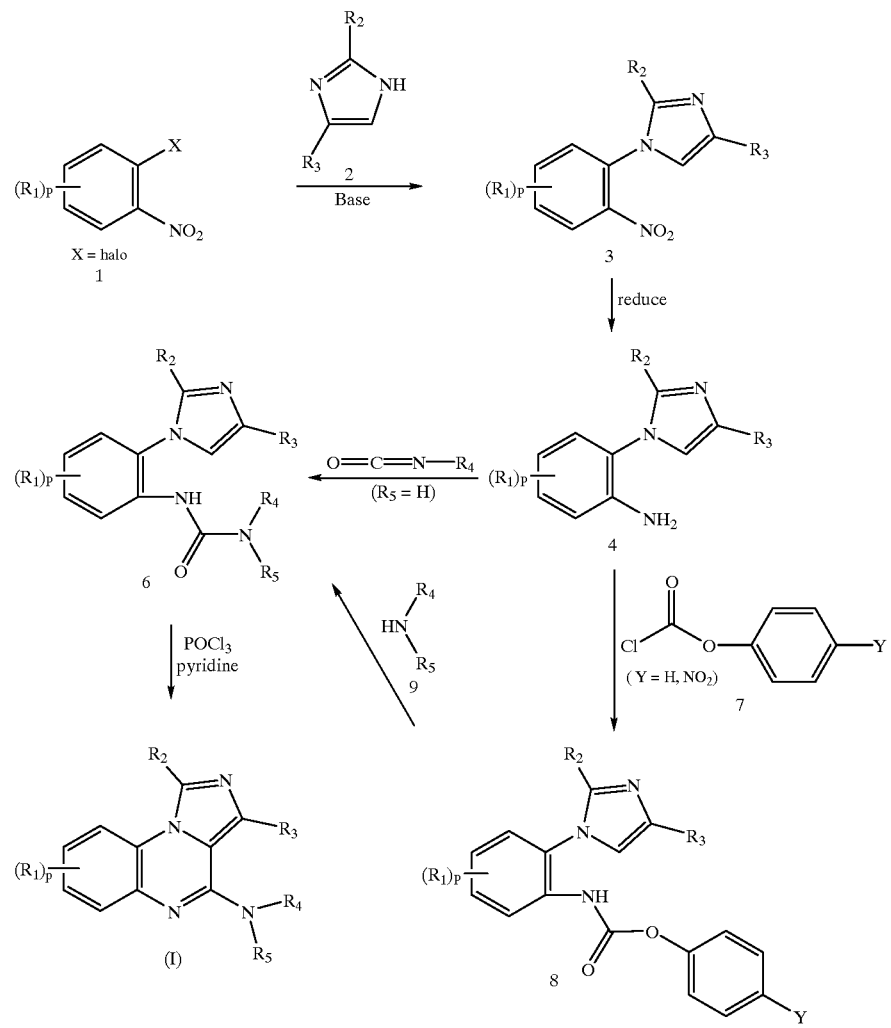

amine 4 may first be reacted with an aryl chloroformate such as 7 in the presence of an organic base such as diisopropylethyl amine to give an intermediate aryl carbamate 8. Treatment of the carbamate with the desired amine 9 provides the urea 6.

Cyclization of the urea 6 to the desired 1,5-imidazoquinoxaline I may be carried out using phosphorylchloride in the presence of pyridine via a chloroimidate intermediate (U.S. Pat. No. 4,191,766). Reagents other than $POCl_3$ which can also provide a reaction proceeding via the same chloroimidate intermediate (e.g., p-toluenesulfonyl chloride, $PCl_5$, and the like) may be used. In the cyclization step, when $R_2$ is hydrogen, 1,2- and 1,5-regioisomers may be formed, wherein the 2- or 5-position carbons of the imidazole ring of 6, respectively, become the bridgehead carbon of the fused imidazole ring of the final products. The 1,5-regioisomer is the compound of the formula I, and the corresponding 1,2-regioisomer is the compound having the following formula:

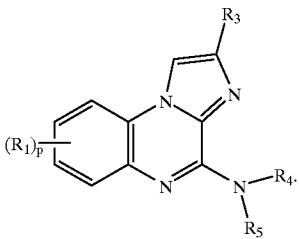

It is preferred to obtain a compound of the formula I substantially free of its corresponding 1,2-regioisomer, especially where $R^3$, and one of $R^4$ and $R^5$, as well as $R^2$, are hydrogen, and p is zero. The desired 1,5-regioisomer may be separated from the 1,2-isomer by methods such as fractional crystallization, or chromatography on silica gel or C-18.

When $R_2$ and $R_3$ are hydrogen in imidazole 2, preferred R groups may be introduced at later points in the sequence by methods such as those known in the art.

Scheme II

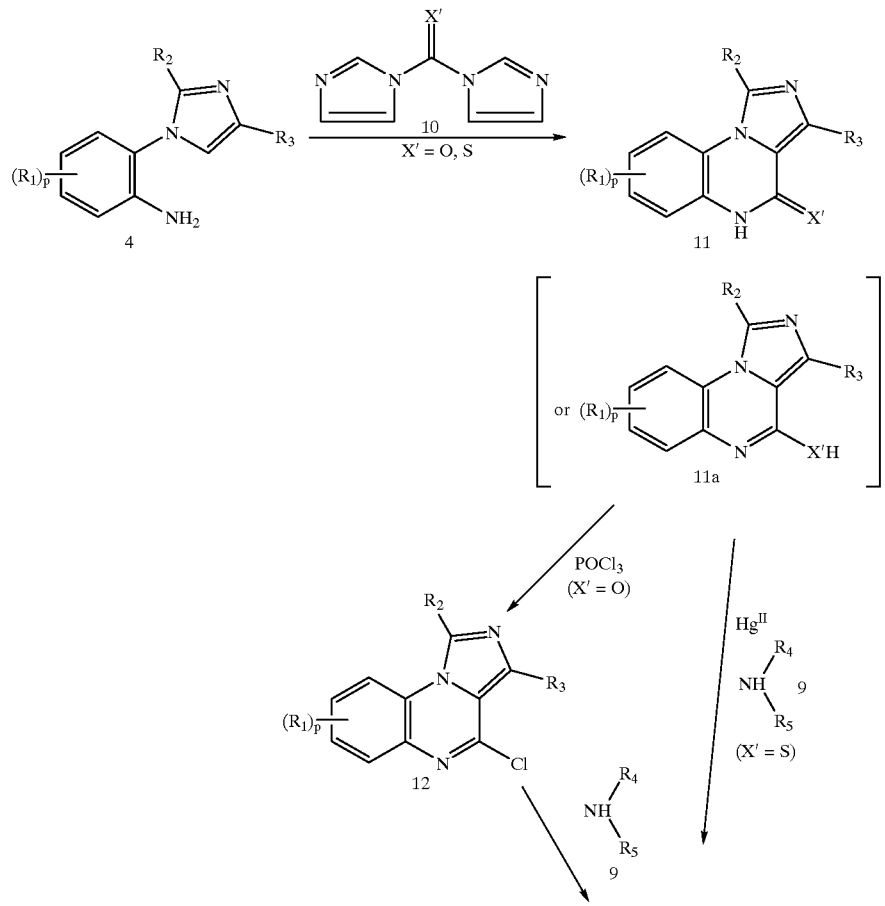

-continued

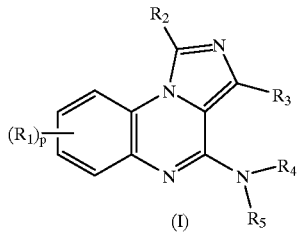

(I)

As shown in Scheme II, the aminoimidazole derivative 4 may be reacted with carbonyldiimidazole or thiacarbonyldiimidazole 10, or alternatively phosgene or phosgene equivalents, to give the quinoxolinone 11(Davey, et al., *J. Med. Chem.*, 34, 2671 (1991)). Quinoxolinone 11 may also exist as its tautomer 11a When $R_2$ is hydrogen, as in Scheme I, a mixture of regioisomers is possible and the desired 1,5-isomer is preferably separated from the 1,2-isomer by methods such as those described above.

When X'=S, conversion to I may be carried out with the appropriate amine 9 in the presence of a mercury II salt such as mercuric chloride or mercuric acetate (Gall and Kamdar, *J. Org. Chem.*, 46, 1575 (1981); Foloppe, et al., *Tetrahedron Lett.*, 33, 2803 (1992)). Alternatively, when X'=O, 11 may be converted into its chloroimidate 12 in the presence of phosphorylchloride, or analogous reagents such as $SOCl_2$, $PCl_5$, $PPh_3/CCl_4$, or the like, and 12 reacted with the appropriate amine 9, in the presence of a base such as sodium, potassium, or cessium carbonate, or an amine base such as triethylamine, diisopropylethyl amine, DBU, or the like as required, to give compound I (Davey, et al., *J. Med. Chem.*, 34, 2671 (1991)).

As shown following, compounds 12 or 11a may be converted to thioether 11b by addition of a thiol to 12 or alkylation of 11a (where X'=S) in the presence of a base such as sodium or potassium hydride, or the like. Addition of amine 9 in the presence of a mercury II salt may be carried out as described above (Foloppe, et al., *Heterocycles*, 36, 63 (1993)).

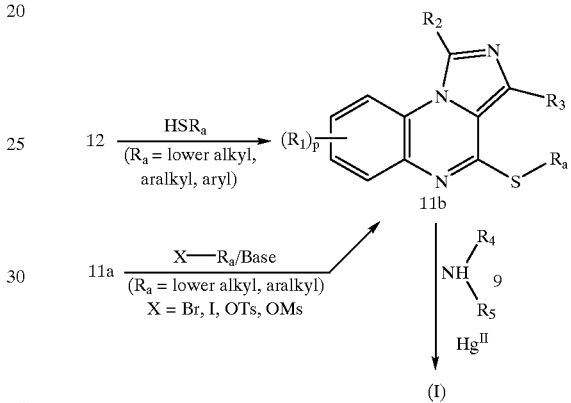

Scheme III

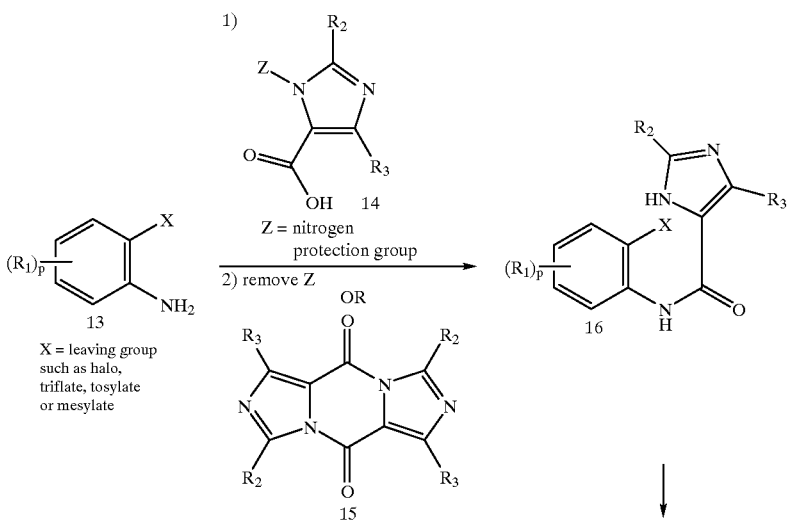

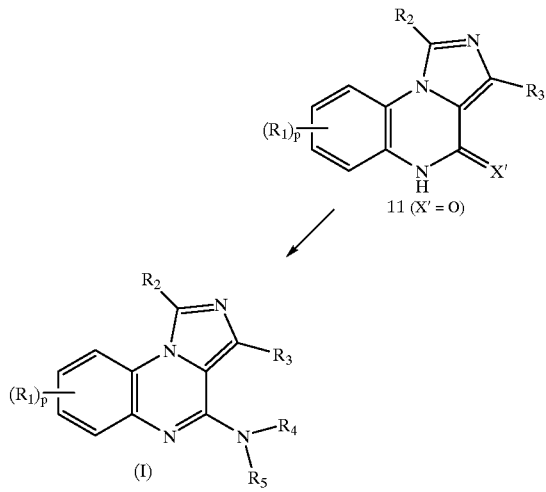

As shown in Scheme III, an appropriately substituted amino halobenzene 13, or related intermediate where the halogen is replaced by another suitable leaving group (e.g., triflate, tosylate or mesylate), may be converted to the corresponding amide 16 by either of two methods: 1) direct coupling with the N-protected imidazole carboxylic acid 14 using peptide coupling procedures such as standard methods known in the art (see, for example, Bodanszky, "Principles of peptide synthesis", Springer-Verlag (1984); Bodanszky and Bodansky, "The Practice of Peptide Chemistry", Springer-Verlag (1984)), followed by removal of the Z protecting group (see, for example, Greene, "Protective Groups in Organic Synthesis", Wiley (1991)); or 2) reaction of 13 with the dimer 15, the latter prepared by methods such as those known in the art (Kasina and Nematollahi, *Synthesis*, 162 (1975); Godefrol, et al., *J. Org. Chem.*, 29, 3707 (1964)). Exemplary nitrogen protecting groups include carbobenzyloxy or t-butoxycarbonyl. The dimer 15 may also be prepared by the novel method of coupling the imidazole carboxylic acid:

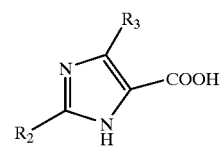

by contacting said acid with thionyl chloride or oxalyl chloride, preferably in the presence of dimethylformamide and heat.

Amide 16 may then be converted to the quinoxolinone 11 (X'=O) by methods analogous to those described for the conversion of 1 to 3 in Scheme I. Conversion of 11 (X'=O) to compound I may then be carried out as described in Scheme II.

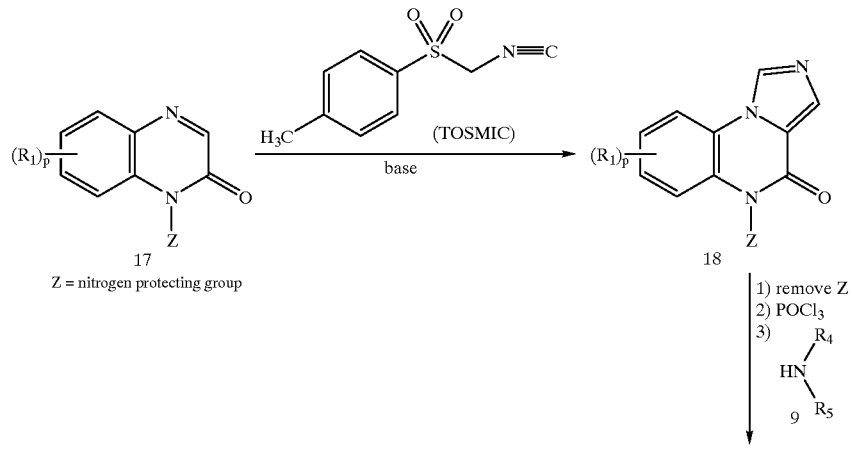

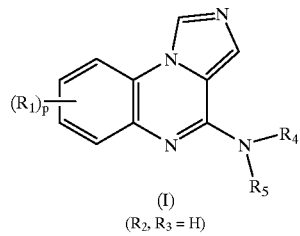

As shown in Scheme IV, the protected quinoxolone 17 may be reacted with tosylmethylisocyanide ("TOSMIC") in the presence of a base such as sodium hydride, n-butyl lithium, lithium, sodium, potassium, or cessium carbonate, or the like, to give the imidazoquinoxolone 18 (Silvestri, et al., *J. Heterocyclic Chem.*, 31, 1033 (1994); Massa, et al., *J. Heterocyclic Chem.*, 30, 749 (1993)). After removal of the nitrogen protecting group Z, conversion of 18 to compound I ($R_2$, $R_3$=H) can be carried out by methodology described in Scheme II.

Starting materials described herein for this Scheme are commercially available or may be readily prepared as described, for example, in 1) Japanese Patent JPO 5140120; 2) Epperson, et al., *Bioorg. Med. Chem. Lett.*, 3, 2801 (1993); 3) Bekerman, et al., *J. Heterocycl. Chem.*, 29, 129 (1992); 4) Kazimierczuk and Pfleiderer, *Liebigs Ann. Chem.*, 754 (1982); 5) a) Kalyanam and Manjunatha, *Indian J. Chem.*, Sect. B, 31, 415 (1992) and b) Wear and Hamilton, *J. Am. Chem. Soc.*, 72, 2893 (1950); and 6) Sakaata, et al., *Heterocycles*, 23, 143 (1983).

As shown in Scheme V, a chloro- or dichloroquinoxoline 19 may be reacted with 1 equivalent of the amine 9 by methods described in Scheme II. Where Y=Cl in 20 treatment with an isocyanide 21 and base as described in Scheme IV gives Compound I ($R_2$=H) (Jacobsen, et al., *J. Med. Chem.*, 39, 3820 (1996)). $R_3$ is selected such that the anion of 21 can readily form. When $R_3$ is a trimethylsilyl (TMS) group, it can subsequently be removed by protodesilylation with an acid such as trifluoracetic acid (Funk & Vollhardt, *J. Am. Chem. Soc.*, 99, 5483 (1977)) to give compound I ($R_2$, $R_3$=H). Alternatively, the above order of addition may be reversed whereby isocyanide 21 is first added to 19 (Y=Cl) followed by amine 9.

Where Y=H in 20, TOSMIC and base may be added as described in Scheme IV to give compound I ($R_2$, $R_3$=H).

Starting materials for this Scheme are commercially available or may be prepared, for example, as described in Curd et al., *J. Chem. Soc.*, 1271 (1949).

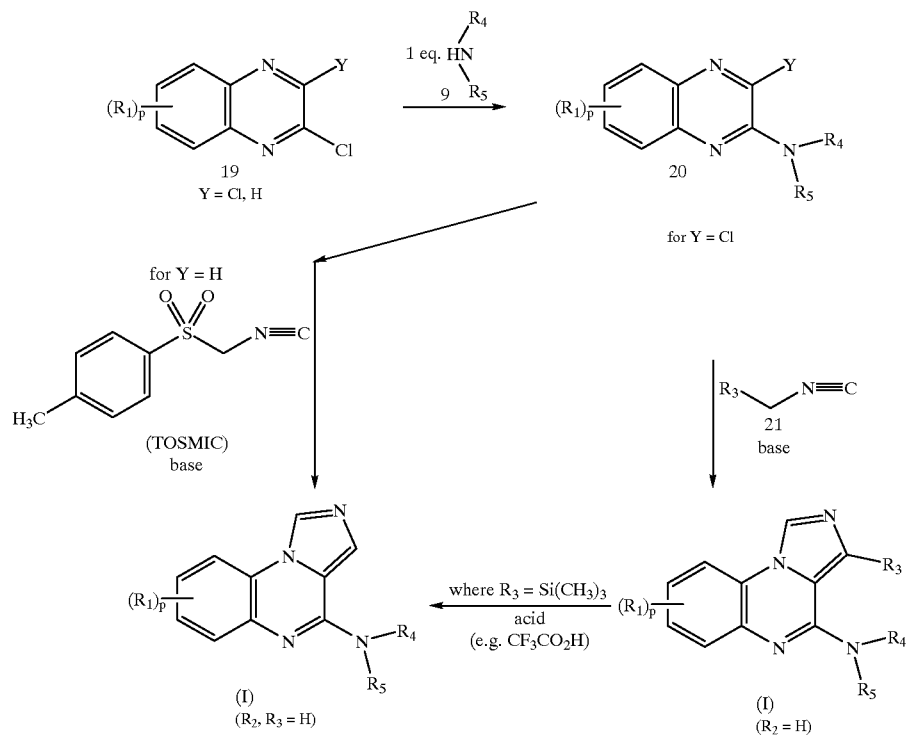

Scheme V

Scheme VI

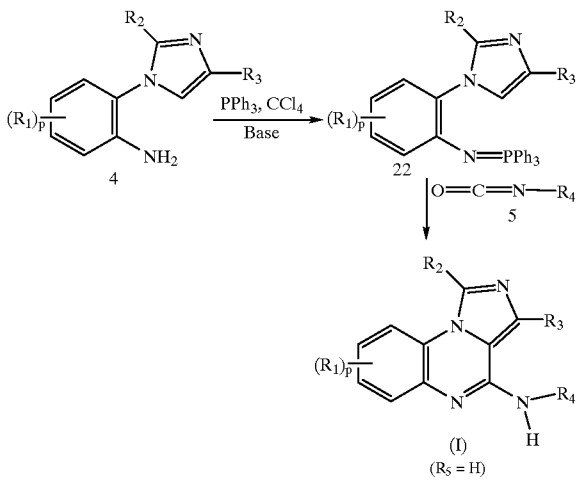

As shown in Scheme VI, amine 4 may alternatively be reacted with triphenylphosphine ("PPh$_3$") in the presence of carbon tetrachloride (or carbon tetrabromide) and a base such as triethylamine to give a nitrogen ylide 22 which may then be treated with an isocyanate 5 to give compound I (R$_5$=H) via an intermediate carbodiimide (Molina, et al., *J. Org. Chem.*, 57, 929 (1992); Takkahashi and Ohba, *Heterocycles*, 41 (1995)).

UTILITY

The compounds of the present invention inhibit protein tyrosine kinases, especially Src-family kinases such as Lck, Fyn, Lyn, Src, Yes, Hck, Fgr and Blk, and are thus useful in the treatment, including prevention and therapy, of protein tyrosine kinase-associated disorders such as immunologic disorders. "Protein tyrosine kinase-associated disorders" are those disorders which result from aberrant tyrosine kinase activity, and/or which are alleviated by the inhibition of one or more of these enzymes. For example, Lck inhibitors are of value in the treatment of a number of such disorders (for example, the treatment of autoimmune diseases), as Lck inhibition blocks T cell activation. The treatment of T cell mediated diseases, including inhibition of T cell activation and proliferation, is a particularly preferred embodiment of the present invention. Compounds which selectively block T cell activation and proliferation are preferred. Compounds of the present invention which block the activation of endothelial cell PTK by oxidative stress, thereby limiting surface expression of adhesion molecules that induce neutrophil binding, and which inhibit PTK necessary for neutrophil activation are useful, for example, in the treatment of ischemia and reperfusion injury.

The present invention thus provides methods for the treatment of protein tyrosine kinase-associated disorders, comprising the step of administering to a subject in need thereof at least one compound of the formula I in an amount effective therefor. Other therapeutic agents such as those described below may be employed with the inventive compounds in the present methods. In the methods of the present invention, such other therapeutic agent(s) may be administered prior to, simultaneously with or following the administration of the compound(s) of the present invention.

Use of the compounds of the present invention in treating protein tyrosine kinase-associated disorders is exemplified by, but is not limited to, treating a range of disorders such as: transplant (such as organ transplant, acute transplant or heterograft or homograft (such as is employed in burn treatment)) rejection; protection from ischemic or reperfusion injury such as ischemic or reperfusion injury incurred during organ transplantation, myocardial infarction, stroke or other causes; transplantation tolerance induction; arthritis (such as rheumatoid arthritis, psoriatic arthritis or osteoarthritis); multiple sclerosis; inflammatory bowel disease, including ulcerative colitis and Crohn's disease; lupus (systemic lupus erythematosis); graft vs. host disease; T-cell mediated hypersensitivity diseases, including contact hypersensitivity, delayed-type hypersensitivity, and gluten-sensitive enteropathy (Celiac disease); psoriasis; contact dermatitis (including that due to poison ivy); Hashimoto's thyroiditis; Sjogren's syndrome; Autoimmune Hyperthyroidism, such as Graves' Disease; Addison's disease (autoimmune disease of the adrenal glands); Autoimmune polyglandular disease (also known as autoimmune polyglandular syndrome); autoimmune alopecia; pernicious anemia; vitiligo; autoimmune hypopituatarism; Guillain-Barre syndrome; other autoimmune diseases; cancers where Lck or other Src-family kinases such as Src are activated or overexpressed, such as colon carcinoma and thymoma, or cancers where Src-family kinase activity facilitates tumor growth or survival; glomerulonephritis, serum sickness; uticaria; allergic diseases such as respiratory allergies (asthma, hayfever, allergic rhinitis) or skin allergies; scleracierma; mycosis fungoides; acute inflammatory responses (such as acute respiratory distress syndrome and ishchemia/reperfusion injury); dermatomyositis; alopecia areata; chronic actinic dermatitis; eczema; Behcet's disease; Pustulosis palmoplanteris; Pyoderma gangrenum; Sezary's syndrome; atopic dermatitis; systemic schlerosis; and morphea. The present invention also provides a method for treating the aforementioned disorders such as atopic dermatitis by administration of any compound capable of inhibiting protein tyrosine kinase.

Src-family kinases other than Lck, such as Hck and Fgr, are important in the Fc gamma receptor induced respiratory burst of neutrophils as well as the Fc gamma receptor responses of monocytes and macrophages. The compounds of the present invention inhibit the Fc gamma induced respiratory burst response in neutrophils, and also inhibit the Fc gamma dependent production of TNF alpha in the monocyte cell line THP-1 that does not express Lck. The ability to inhibit Fc gamma receptor dependent neutrophil, monocyte and macrophage responses results in additional anti-inflammatory activity for the present compounds beyond their effects on T cells. This activity is especially of value, for example, in the treatment of inflammatory diseases such as arthritis or inflammatory bowel disease. In particular, the present compounds are of value for the treatment of autoimmune glomerulonephritis and other instances of glomerulonephritis induced by deposition of immune complexes in the kidney that trigger Fc gamma receptor responses leading to kidney damage.

In addition, Src family kinases other than Lck, such as Lyn and Src, are important in the Fc epsilon receptor induced degranulation of mast cells and basophils that plays an important role in asthma, allergic rhinitis, and other allergic disease. Fc epsilon receptors are stimulated by IgE-antigen complexes. The compounds of the present invention inhibit the Fc epsilon induced degranulation responses, including in the basophil cell line RBL that does not express Lck. The ability to inhibit Fc epsilon receptor dependent mast cell and basophil responses results in additional anti-inflammatory activity for the present compounds beyond their effect on T cells. In particular, the present compounds are of value for the treatment of asthma, allergic rhinitis, and other instances of allergic disease.

The combined activity of the present compounds towards monocytes, macrophages, T cells, etc. may be of value in the treatment of any of the aforementioned disorders.

In a particular embodiment, the compounds of the present invention are useful for the treatment of the aforementioned exemplary disorders irrespective of their etiology, for example, for the treatment of transplant rejection, rheumatoid arthritis, multiple sclerosis, inflammatory bowel disease, lupus, graft v. host disease, T-cell mediated hypersensitivity disease, psoriasis, Hashimoto's thyroiditis, Guillain-Barre syndrome, cancer, contact dermatitis, allergic disease such as allergic rhinitis, asthma, ischemic or reperfusion injury, or atopic dermatitis whether or not associated with PTK.

The present invention also provides pharmaceutical compositions comprising at least one of the compounds of the formula I capable of treating a protein tyrosine kinase-associated disorder in an amount effective therefor, and a pharmaceutically acceptable vehicle or diluent. The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the formula I may be administered by any suitable means, for example, orally, such as in the form of tablets, capsules, granules or powders; sublingually; buccally; parenterally, such as by subcutaneous, intravenous, intramuscular, or intrasternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The present compounds may also be administered liposomally.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The present compounds may also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

The effective amount of a compound of the present invention may be determined by one of ordinary skill in the art, and includes exemplary dosage amounts for an adult human of from about 0.1 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to protein tyrosine kinase-associated disorders.

The compounds of the present invention may be employed alone or in combination with each other and/or other suitable therapeutic agents useful in the treatment of protein tyrosine kinase-associated disorders such as PTK inhibitors other than those of the present invention, antiinflammatories, antiproliferatives, chemotherapeutic agents, and immunosuppressants.

Exemplary such other therapeutic agents include the following: cyclosporins (e.g., cyclosporin A), CTLA4-Ig, antibodies such as anti-ICAM-3, anti-IL-2 receptor (Anti-Tac), anti-CD45RB, anti-CD2, anti-CD3 (OKT-3), anti-CD4, anti-CD80, anti-CD86, monoclonal antibody OKT3, agents blocking the interaction between CD40 and gp39, such as antibodies specific for CD40 and/or gp39 (i.e., CD154), fusion proteins constructed from CD40 and gp39 (CD40Ig and CD8gp39), inhibitors, such as nuclear translocation inhibitors, of NF-kappa B function, such as deoxyspergualin (DSG), non-steroidal antiinflammatory drugs (NSAIDs) such as ibuprofen, steroids such as prednisone or dexamethasone, gold compounds, antiproliferative agents such as methotrexate, FK506 (tacrolimus, Prograf), mycophenolate mofetil, cytotoxic drugs such as azathiprine and cyclophosphamide, TNF-α inhibitors such as tenidap, anti-TNF antibodies or soluble TNF receptor, and rapamycin (sirolimus or Rapamune) or derivatives thereof, and the PTK inhibitors disclosed in the following U.S. Patent Applications, incorporated herein by reference in their entirety: Ser. No. 60/056,797, filed Aug. 25, 1997 (Attorney Docket No. QA205*), Ser. No. 09/094,797 filed concurrently herewith by Joel C. Barrish et al., "Imidazoquinoxaline Protein Tyrosine Kinase Inhibitors" (Attorney Docket No. QA205a), Ser. No. 60/065,042, filed Nov. 10, 1997 (Attorney Docket No. QA207*), and Ser. No. 60/076,789, filed Mar. 4, 1998 (Attorney Docket No. QA208*). See the following documents and references cited therein: Hollenbaugh, D., Douthwright, J., McDonald, V., and Aruffo, A., "Cleavable CD40Ig fusion proteins and the binding to sgp39", *J. Immunol. Methods* (Netherlands), 188(1), p. 1–7 (Dec. 15, 1995); Hollenbaugh, D., Grosmaire, L. S., Kullas, C. D., Chalupny, N. J., Braesch-Andersen, S., Noelle, R. J., Stamenkovic, I., Ledbetter, J. A., and Aruffo, A., "The human T cell antigen gp39, a member of the TNF gene family, is a ligand for the CD40 receptor: expression of a soluble form of gp39 with B cell co-stimulatory activity", *EMBO J* (England), 11(12), p 4313–4321 (December 1992); and Moreland, L. W. et al., "Treatment of rheumatoid arthritis with a recombinant human tumor necrosis factor receptor (p75)-Fc fusion protein, *New England J. of Medicine*, 337(3), p. 141–147 (1997).

The above other therapeutic agents, when employed in combination with the compounds of the present invention, may be used, for example, in those amounts indicated in the Physicians' Desk Reference (PDR) or as otherwise determined by one of ordinary skill in the art.

The following assays can be employed in ascertaining the degree of activity of a compound ("test compound") as a PTK inhibitor. Compounds described in the following Examples have been tested in one or more of these assays, and have shown activity.

Lck Enzyme Assay

Recombinant Lck expressed as a His-tagged fusion protein in insect cells using a baculovirus expression system and purified by nickel affinity chromatography is incubated in kinase buffer (20 mM MOPS, pH7, 10 mM MgCl$_2$) in the presence of the test compound. The reaction is initiated by the addition of substrates to the final concentration of 1 $\mu$M ATP, 3.3 $\mu$Ci/ml [33P] g-ATP, and 0.1 mg/ml acid denatured enolase (prepared as described in Cooper, J. A., Esch, F. S., Taylor, S. S., and Hunter, T., "Phosphorylation sites in enolase and lactate dehydrogenase utilized by tyrosine protein kinases in vivo and in vitro", *J. Biol. Chem.*, 259, 7835–7841 (1984)). The reaction is stopped after 10 minutes by the addition of 10% trichloroacetic acid, 100 mM sodium pyrophosphate followed by 2 mg/ml bovine serum albumin. The labeled enolase protein substrate is precipitated at 4 degrees, harvested onto Packard Unifilter plates and counted in a Topcount scintillation counter to ascertain the Lck inhibitory activity of the test compound (activity inversely proportional to the amount of labeled enolase protein obtained). The exact concentration of reagents and the amount of label can be varied as needed.

This assay is advantageous as it employs an exogenous substrate (enolase) for more accurate enzyme kinetics, and can be conducted in a 96-well format that is readily automated. In addition, the His-tagged Lck offers much higher production yields and purity relative to GST-Lck fusion protein.

For the preparation of recombinant Lck: Human Lck was prepared as a His-tagged fusion protein using the Life Technologies (Gibco) baculovirus vector pFastBac Hta (commercially available) in insect cells. A cDNA encoding human Lck isolated by PCR (polymerase chain reaction) was inserted into the vector and the protein was expressed using the methods described by the manufacturer. For the production of Lck in insect cells using baculovirus, see Spana, C., O'Rourke, E. C., Bolen, J. B., and Fargnoli, J., "Analysis of the tyrosine kinase p56lck expressed as a glutathione S-transferase protein in *Spodoptera frugiperda* cells," *Protein expression and purification*, Vol. 4, p. 390–397 (1993).

Cell Assays (1) Cellular Tyrosine Phosphorylation

Jurkat T cells are incubated with the test compound and then stimulated by the addition of antibody to CD3 (monoclonal antibody G19-4). Cells are lysed after 4 minutes or at another desired time by the addition of a lysis buffer containing NP-40 detergent. Phosphorylation of proteins is detected by anti-phosphotyrosine immunoblotting. Detection of phosphorylation of specific proteins of interest such as ZAP-70 is detected by immunoprecipitation with anti-ZAP-70 antibody followed by anti-phosphotyrosine immunoblotting. Such procedures are described in Schieven, G. L., Mittler, R. S., Nadler, S. G., Kirihara, J. M., Bolen, J. B., Kanner, S. B., and Ledbetter, J. A., "ZAP-70 tyrosine kinase, CD45 and T cell receptor involvement in UV and H$_2$O$_2$ induced T cell signal transduction", *J. Biol. Chem.*, 269, 20718–20726 (1994), and the references incorporated therein. The Lck inhibitors inhibit the tyrosine phosphorylation of cellular proteins induced by anti-CD3 antibodies.

For the preparation of G19-4, see Hansen, J. A., Martin, P. J., Beatty, P. G., Clark, E. A., and Ledbetter, J. A., "Human T lymphocyte cell surface molecules defined by the workshop monoclonal antibodies," in *Leukocyte Typing I*, A. Bernard, J. Boumsell, J. Dausett, C. Milstein, and S. Schlossman, eds. (New York: Springer Verlag), p. 195–212 (1984); and Ledbetter, J. A., June, C. H., Rabinovitch, P. S., Grossman, A., Tsu, T. T., and Imboden, J. B., "Signal transduction through CD4 receptors: stimulatory vs. inhibitory activity is regulated by CD4 proximity to the CD3/T cell receptor", *Eur. J. Immunol.*, 18, 525 (1988).

(2) Calcium Assay

Lck inhibitors block calcium mobilization in T cells stimulated with anti-CD3 antibodies. Cells are loaded with the calcium indicator dye indo-1, treated with anti-CD3 antibody such as the monoclonal antibody G19-4, and calcium mobilization is measured using flow cytometry by recording changes in the blue/violet indo-1 ratio as described in Schieven, G. L., Mittler, R. S., Nadler, S. G., Kirihara, J. M., Bolen, J. B., Kanner, S. B., and Ledbetter, J. A., "ZAP-70 tyrosine kinase, CD45 and T cell receptor involvement in UV and H$_2$O$_2$ induced T cell signal transduction", *J. Biol. Chem.*, 269, 20718–20726 (1994), and the references incorporated therein.

(3) Proliferation Assays

Lck inhibitors inhibit the proliferation of normal human peripheral blood T cells stimulated to grow with anti-CD3 plus anti-CD28 antibodies. A 96 well plate is coated with a monoclonal antibody to CD3 (such as G19-4), the antibody is allowed to bind, and then the plate is washed. The antibody bound to the plate serves to stimulate the cells. Normal human peripheral blood T cells are added to the wells along with test compound plus anti-CD28 antibody to provide co-stimulation. After a desired period of time (e.g., 3 days), the [3H]-thymidine is added to the cells, and after further incubation to allow incorporation of the label into newly synthesized DNA, the cells are harvested and counted in a scintillation counter to measure cell proliferation.

The following Examples illustrate embodiments of the present invention, and are not intended to limit the scope of the claims. Abbreviations employed in the Examples are defined below. Compounds of the Examples are identified by the example and step in which they are prepared (for example, "1A" denotes the title compound of step A of Example 1), or by the example only where the compound is the title compound of the example (for example, "2" denotes the title compound of Example 2).

Abbreviations
  Ac=acetyl
  AcOH=acetic acid
  aq.=aqueous
  Bn=benzyl
  t-Bu=tert-butyl
  Boc=t-butoxycarbonyl
  Claisen Alkalie=88 g KOH in 63 mL $H_2O$ diluted to 250 mL with MeOH (Fanta, P. E., Tarbell, D. S., Org. Synth., 1945, 25, p. 78)
  DEAD=diethyl azodicarboxylate
  DMAP=4-dimethylaminopyridine
  DMF=dimethylformamide
  DMSO=dimethylsulfoxide
  Et=ethyl
  $Et_2O$=diethyl ether
  EtOAc=ethyl acetate
  EtOH=ethanol
  h=hours
  hex=hexanes
  prep HPLC=preparative high pressure liquid chromatography
  LAH=lithium aluminum hydride
  LDA=lithium diisopropylamide
  Me=methyl
  MeOH=methanol
  min.=minutes
  MOPS=4-morpholine-propanesulfonic acid
  MS=mass spectrometry
  Ms=mesyl
  n-Bu=n-butyl
  i-Pr=isopropyl
  Pd/C=palladium on carbon
  Ph=phenyl
  $Ph_3P$=triphenylphosphine
  Ret Time=retention time
  sat.=saturated
  TFA=trifluoroacetic acid
  THF=tetrahydrofuran
  Ts=tosyl

EXAMPLE 1

Preparation of N-(2-Chloro-6-methylphenyl)-8-nitroimidazo[1.5-a]quinoxalin-4-amine

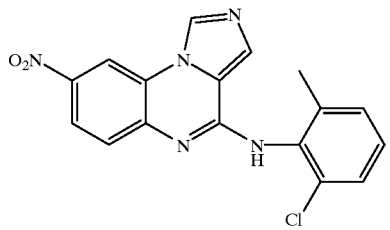

A. 6(or 7)-Nitro-2-quinoxalinol

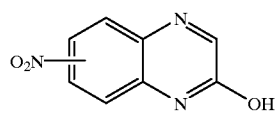

A solution of 4-nitro-1,2-diaminobenzene (15.42 g, 0.10 mol) and ethyl glyoxylate (5.04 M in toluene, 24 mL, 0.121 mol) in ethanol (132 mL) was refluxed for 2.5 h and allowed to cool to room temperature. Water was added, and the precipitate was washed with water followed by diethyl ether to give solid 1A as a mixture of regioisomers (16.47 g, 85%).

B. 1-[(4-Methoxyphenyl)methyl]-6-nitro-2(1H)-quinoxalinone (1Ba) and 1-[(4-Methoxyphenyl)methyl]-7-nitro-2(1H)-quinoxalinone (1Bb)

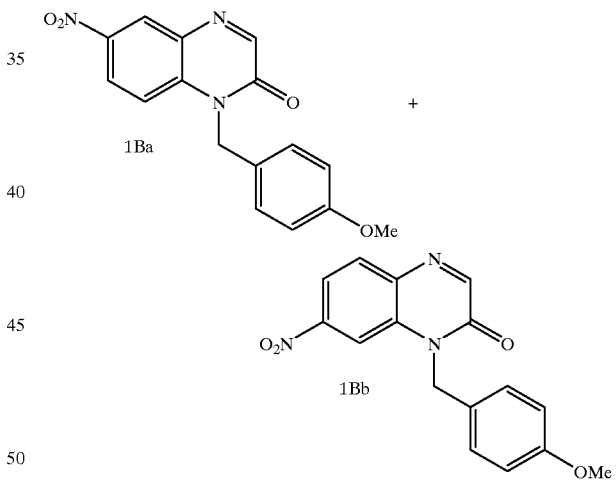

To a suspension of sodium hydride (60% in mineral oil, 0.264 g, 6.6 mmol, washed with hexane twice) in dimethyl formamide (2.9 mL) under nitrogen at 0° C. was added a suspension of 1A (1.1 g, 5.73 mmol) in dimethyl formamide (2.9 mL) and tetrahydrofuran (2.9 mL), then rinsed with dimethyl formamide (2.9 mL). After 0.5 h, a solution of p-methoxybenzyl chloride (0.86 mL, 6.34 mmol) in tetrahydrofuran (2.9 mL) followed by tetrabutylammonium iodide (0.21 g, 0.57 mmol) was added. The 0° C. bath was removed, and the reaction mixture was stirred for 2 h. Tetrabutylammonium iodide (0.248 g, 0.67 mmol) was added, and the reaction mixture was heated at 70° C. for 2 h. At 0° C., saturated aqueous ammonium chloride was added to the reaction mixture, which was then extracted with ethyl acetate twice. The organic layers were combined, washed with water, dried over sodium sulfate, filtered and concentrated in vacuo to give a solid. Diethyl ether was added, and after stirring for 1 h, the insoluble material was washed with diethyl ether to give 1Ba as a brown solid (0.856 g, 48%). The ether soluble material was chromatographed (55×220 mm silica gel; hexane:EtOAc 3:1) to give 1Bb as a brown solid (0.29 g, 16%).

C. 5-[(4-Methoxyphenyl)methyl]-8-nitroimidazo[1,5-a]quinoxalin-4(5H)-one

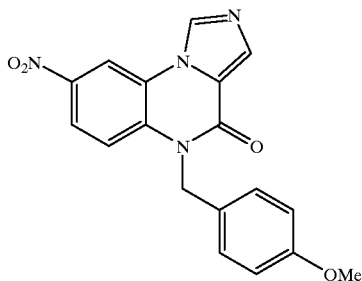

To a suspension of sodium hydride (60% in mineral oil, 2.86 g, 0.119 mol, washed with hexane twice) in tetrahydrofuran (200 mL) under nitrogen at 0° C. was added a suspension of 1Ba (16.39 g, 0.053 mol) and toluenesulfonylmethylisocyanide (11.31 g, 0.058 mol) in tetrahydrofuran (100 mL). After 0.5 h, the 0° C. bath was removed, and the reaction mixture was stirred at room temperature for 1.5 h. The solution was poured into ice water, and the precipitate was filtered and washed with water to give 1C as a tan solid (7.02 g, 38%). The filtrate was concentrated in vacuo to give a solid; water was added, and the insoluble material was filtered and washed with water to give additional 1C as a brown solid (6.86 g, 37%).

D. 8-Nitroimidazo[1,5-a]quinoxalin-4(5H)-one

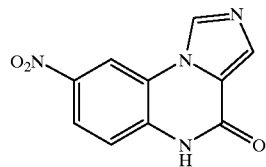

A solution of 1C (6.91 g, 19.7 mmol), anisole (39 mL), trifluoroacetic acid (93 mL) and triflic acid (trifluoromethanesulfonic acid) (20 mL) was stirred under nitrogen at 0° C. for 18 h. After concentrating in vacuo, the oil was poured into a mixture of ice and saturated aqueous sodium bicarbonate. The precipitate was filtered and washed to give crude 1D. Diethyl ether was added, and the precipitate was filtered and washed. Ethyl acetate was added to the precipitate which was then refluxed for several hours. After cooling to room temperature, the precipitate was filtered and washed with ethyl acetate to give 1D as a brown solid (3.53 g, 78%).

E. 4-Chloro-8-nitroimidazo[1,5-a]quinoxaline

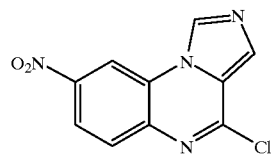

A solution of 1D (0.154 g, 0.67 mmol) in phosphorus oxychloride (2.5 mL) was refluxed under nitrogen for 16 h and concentrated in vacuo. At 5° C., dichloromethane and ice water were added, and the two layers separated. The aqueous layer was extracted with dichloromethane and the organic layers were combined, dried over sodium sulfate, filtered and concentrated in vacuo to give 1E as a yellow solid (0.13 g, 78%).

F. N-(2-Chloro-6-methylphenyl)-8-nitroimidazo[1,5-a]quinoxalin-4-amine

A solution of sodium bis(trimethylsilyl)amide (1 M in THF, 1.2 mL, 1.2 mmol) and 2-chloro-6-methylaniline (0.06 mL, 0.49 mmol) in tetrahydrofuran (0.55 mL) was heated at 75° C. under nitrogen for 0.5 h and cooled to room temperature. A solution of 1E (0.049 g, 0.2 mmol) in tetrahydrofuran (1.1 mL) was added, and the reaction mixture was heated at 75° C. for 0.75 h. After cooling to room temperature, dichloromethane and water were added; the layers were separated, and the aqueous layer was extracted with dichloromethane (2×). The organic layers were combined, dried over sodium sulfate, filtered and concentrated in vacuo to give a residue which was chromatographed (15×260 mm silica gel; dichloromethane:isopropyl alcohol 49:1) to give the title compound 1F as an orange solid (0.06 g, 86%): MS (M+H)$^+$=354. HPLC Retention time=28.96 minutes (HPLC conditions: same as used for Example 259).

EXAMPLE 2

Preparation of N$^4$-(2-Chloro-6-methylphenyl)imidazo[1,5-a]quinoxaline-4,8-diamine

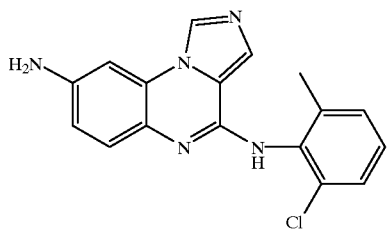

A solution of 1F (0.048 g, 0.136 mmol) and tin (II) chloride•dihydrate (0.136 g, 0.60 mmol) in ethanol (1.5 mL) was refluxed for 1.75 h, cooled to room temperature and concentrated in vacuo. Saturated aqueous potassium carbonate was added, and the precipitate was filtered and washed with water to give a residue which was chromatographed (15×200 mm silica gel; dichloromethane:methanol 9:1) to give the title compound 2 as a brown solid (0.033 g, 76%): MS (M+H)$^+$=324. HPLC Retention time=16.93 minutes (HPLC conditions: same as used for Example 259).

EXAMPLE 3

Preparation of N-[4-[(2-Chloro-6-methylphenyl) amino]imidazo[1,5-a]quinoxalin-8-yl]acetamide

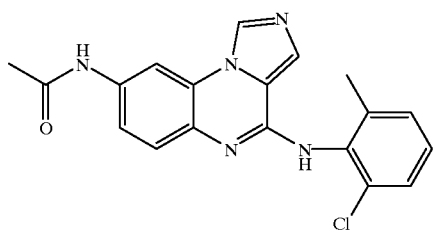

To a solution of acetic acid (0.006 mL, 0.105 mmol), N-hydroxybenzotriazole (0.0175 g, 0.114 mmol), duisopropylethyl amine (0.040 mL, 0.230 mmol) and 2 (0.03 g, 0.092 mmol) in dimethyl formamide (0.46 mL) at 0° C. was added 1-(3-dimethylaminopropyl)-3-ethylcarbodiimide hydrochloride (0.020 g, 0.10 mmol). After 3 h, the 0° C. bath was removed, and the reaction was stirred for 9.5 h. An acid-base workup led to presence of product in both organic and aqueous layers; all layers were combined and concentrated in vacuo to give a residue which was chromatographed (15×280 mm silica gel; dichloromethane:methanol 19:1) to give a solid. Trituration with diethyl ether afforded the title compound 3 as a tan solid (0.022 g, 64%): MS (M+H)$^+$=366. HPLC Retention time=20.54 minutes (HPLC conditions: same as used for Example 259).

EXAMPLE 4

Preparation of N-[4-[(2-Chloro-6-methylphenyl) amino]imidazo[1,5-a]quinoxalin-8-yl]hexanamide

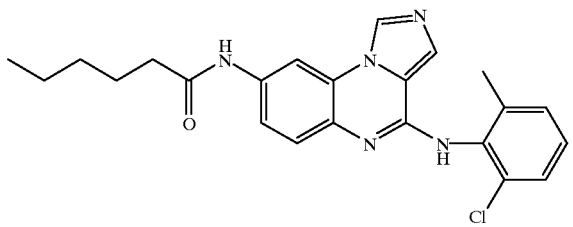

Analogous to the preparation of 3 using hexanoic acid to give the title compound 4 as a tan solid: MS (M+H)$^+$=422. HPLC Retention time=27.02 minutes (HPLC conditions: same as used for Example 259).

EXAMPLE 5

Preparation of N-[4-[(2-Chloro-6-methylphenyl) amino]imidazo[1,5-a]quinoxalin-8-yl]-3-methoxypropanamide

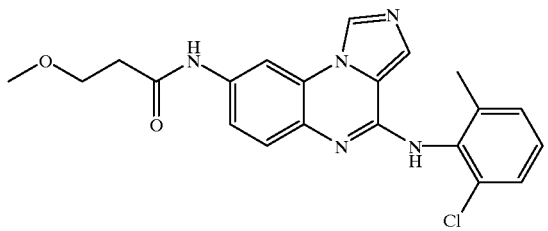

Analogous to preparation of 3 using 3-methoxypropanoic acid to give the title compound 5 as a tan solid: MS (M+H)$^+$=410. HPLC Retention time=20.17 minutes (HPLC conditions: same as used for Example 259).

EXAMPLE 6

Preparation of N-[4-[(2-Chloro-6-methylphenyl) amino]imidazo[1,5-a]quinoxalin-8-yl]-N'-ethylurea

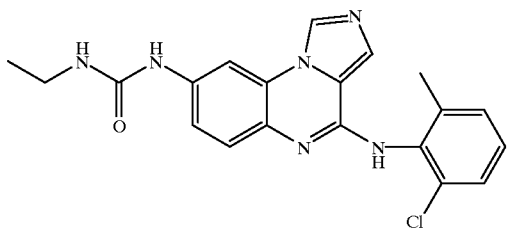

To a solution of 2 (0.027 g, 0.085 mmol) in dimethyl formamide (0.17 mL) at 0° C. was added ethyl isocyanate (0.0074 mL, 0.094 mmol). After 0.5 h, the 0° C. bath was removed, and the reaction was stirred for 3.5 h. The reaction mixture was chromatographed (15×230 mm silica gel; dichloromethane:methanol 30:1) twice to give the title compound 6 as a tan solid (0.0215 g, 64%): MS (M+H)$^+$=395. HPLC Retention time=23.14 minutes (HPLC conditions: same as used for Example 259).

EXAMPLE 7

Preparation of N-(2-Bromophenyl)-8-methylimidazo [1,5-a]quinoxalin-4-amine

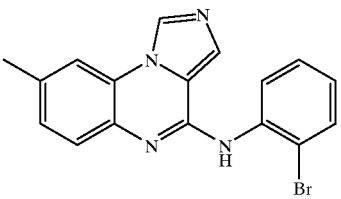

A. 1-(5-Methyl-2-nitrophenyl)-1H-imidazole

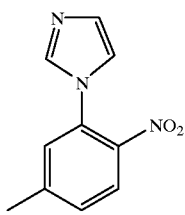

A solution of 4-methyl-2-fluoro-nitrobenzene (6.05 g, 39.0 mmol), imidazole (6.68 g, 98.1 mmol) and potassium carbonate (9.28 g, 67.2 mmol) in acetonitrile (56 mL) was refluxed for 19 h and cooled to room temperature. The reaction mixture was diluted with chloroform and washed with water (2×), dried over sodium sulfate, filtered and concentrated in vacuo to give a residue which was chromatographed (55×240 mm silica gel; dichloromethane:methanol 15:1) to give 7A as a yellow solid (7.71 g, 97%).

B. 2-(1H-Imidazol-1-yl)-4-methylbenzenamine

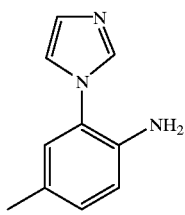

A solution of 7A (3.87 g, 19.0 mmol) and palladium hydroxide on carbon (0.78 g) in ethanol (40 mL) was stirred under a hydrogen atmosphere for 20 h and then flushed with nitrogen. Filtration through Celite and concentration of the filtrate in vacuo gave 7B as an olive-green solid (3.19 g, 97%).

C. N-(2-Bromophenyl)-N'-[2-(1H-imidazol-1-yl)-4-methylphenyl]urea

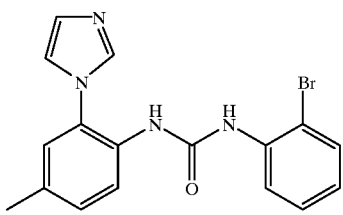

To a solution of 7B (1.07 g, 6.18 mmol) in dimethyl formamide (5.0 mL) at 0° C. was added 2-bromophenylisocyanate (0.84 mL, 6.82 mmol). After 0.5 h, the 0° C. bath was removed, and the reaction mixture was stirred for 2.75 h. Diethyl ether was added, and the reaction mixture was stirred for 1 h. The precipitate was filtered and washed with diethyl ether to give 7C as a white solid (1.43 g, 62%).

D. N-(2-Bromophenyl)-8-methylimidazo[1,5-a]quinoxalin-4-amine

A solution of 7C (0.1095 g, 0.295 mmol) and phosphorus oxychloride (0.031 mL, 0.333 mmol) in pyridine (0.5 mL) was refluxed for 17 h and then cooled to room temperature. The reaction mixture was diluted with ethyl acetate and washed with water (3×). The organic layer was dried over sodium sulfate, filtered and concentrated in vacuo to give a residue which was chromatographed (15×270 mm silica gel; dichloromethane:methanol 40:1) to give the title compound 7D as a tan solid (0.017 g, 16%): MS (M+H)$^+$=353. HPLC Retention time=22.78 minutes (HPLC conditions: same as used for Example 259).

EXAMPLE 8

Preparation of N-(2-Bromophenyl)-7-methylimidazo [1,5-a]quinoxalin-4-amine

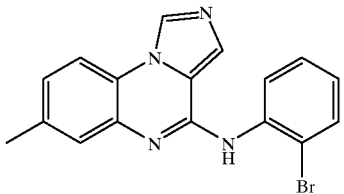

Analogous to the preparation of 7D using 5-methyl-2-fluoro nitrobenzene to give the title compound 8 as a brown solid: MS (M+H)$^+$=353. HPLC Retention time=23.03 minutes (HPLC conditions: same as used for Example 259).

EXAMPLE 9

Preparation of N-(2-Bromophenyl)-1-methylimidazo [1,5-a]quinoxalin-4-amine

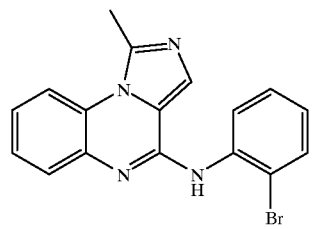

Analogous to the preparation of 7D using 2-methylimidazole and 2-fluoro nitrobenzene to give the title compound 9 as a brown solid: MS (M+H)$^+$=353. HPLC Retention time=20.00 minutes (HPLC conditions: same as used for Example 259).

EXAMPLE 10

Preparation of N-(2-Bromophenyl)-1-(phenylthio) imidazo[1,5-a]quinoxalin-4-amine

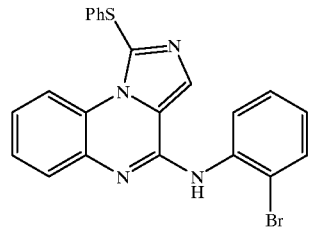

A. 2-(Phenylthio)-1H-imidazole

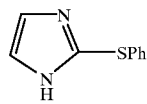

To a solution of 1-diethoxymethyl imidazole (0.35 g, 2.06 mmol) in tetrahydrofuran (3.0 mL) under nitrogen at −45° C. was added n-butyl lithium (2.5 M in hexane, 0.82 mL, 2.06 mmol). After 10 min, a solution of phenyl disulfide (0.453 g, 2.07 mmol) in tetrahydrofuran (1.0 mL) was added, and the reaction was stirred overnight to room temperature. Silica gel and water were added, and the reaction was stirred for several hours and concentrated in vacuo. It was diluted with ethyl acetate and filtered. The filtrate was concentrated in vacuo to give a residue which was chromatographed (25×180 mm silica gel; hexane:ethyl acetate 1:1) to give 10A as a colorless oil (0.071 g, 20%).

B. 1-(2-Nitrophenyl)-2-(phenylthio)-1H-imidazole

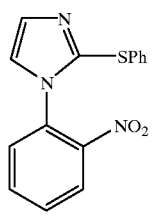

Analogous to the preparation of 7A using 2-fluoro nitrobenzene to give 10B as a yellow oil.

C. 2-[2-(Phenylthio)-1H-imidazol-1-yl]benzenamine

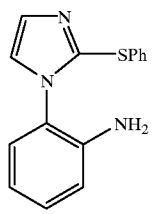

A solution of 10B (0.025 g, 0.084 mmol), iron (III) chloride (0.0001 g, 0.0006 mmol) and methylhydrazine (0.064 mL, 0.842 mmol) in methanol (0.14 mL) was refluxed for 0.5 h, cooled to room temperature and filtered through Celite. The filtrate was concentrated in vacuo to give crude 10C as a yellow oil which was used immediately in the next step.

D. N-(2-Bromophenyl)-1-(phenylthio)imidazo[1,5-a]quinoxalin-4-amine

Preparation from 10C analogous to the preparation of 7D to give the title compound 10D as a tan solid: MS (M+H)$^+$=447. HPLC Retention time=32.4 minutes (HPLC conditions: same as used for Example 259).

EXAMPLE 11

Preparation of N-(2,6-Dimethylphenyl)-8-nitroimidazo[1,5-a]quinoxalin-4-amine

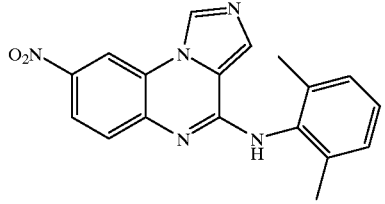

Analogous to the preparation of 1F using 2,6-dimethylaniline to give the title compound 11 as a brown solid: MS (M+H)$^+$=334. HPLC Retention time=26.67 minutes (HPLC conditions: same as used for Example 259).

EXAMPLE 12

Preparation of N$^4$-(2,6-Dimethylphenyl)imidazo[1,5-a]quinoxalin-4,8-diamine

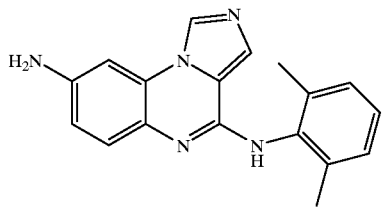

Analogous to preparation of 2 to give the title compound 12 as a yellow oil: MS (M+H)$^+$=304. HPLC Retention time=2.48 minutes (HPLC conditions: same as used for Example 260).

EXAMPLE 13

Preparation of N-[4-[(2,6-Dimethylphenyl)amino]imidazo[1,5-a]quinoxalin-8-yl]acetamide

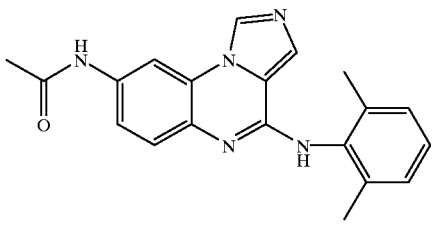

Analogous to the preparation of 3 to give the title compound 13 as a yellow oil: MS (M+H)$^+$=346. HPLC Retention time=17.88 minutes (HPLC conditions: same as used for Example 259).

EXAMPLE 14

Preparation of N-[4-[(2,6-Dimethylphenyl)amino]imidazo[1,5-a]quinoxalin-8-yl]hexanamide

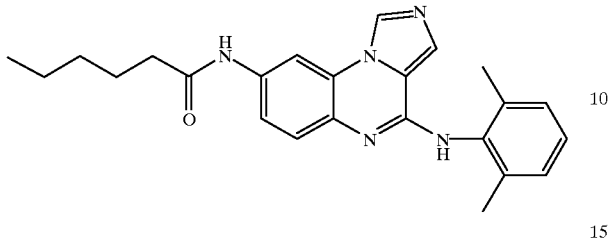

Analogous to the preparation of 3 to give the title compound 14 as a yellow oil: MS (M+H)$^+$=402. HPLC Retention time=25.72 minutes (HPLC conditions: same as used for Example 259).

EXAMPLE 15

Preparation of N-[4-[(2,6-Dimethylphenyl)amino]imidazo[1,5-a]quinoxalin-8-yl]benzeneacetamide

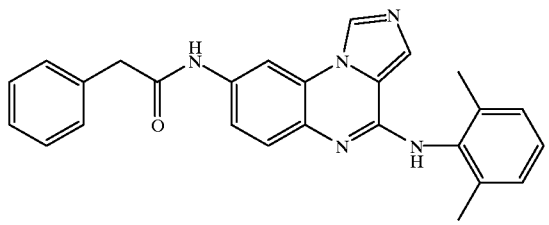

Analogous to preparation of 3 using phenylacetic acid to give the title compound 15 as a yellow oil: MS (M+H)$^+$=422. HPLC Retention time=3.60 minutes (HPLC conditions: same as used for Example 260).

EXAMPLE 16

Preparation of [2-[[4-[(2,6-Dimethylphenyl)amino]imidazo[1,5-a]quinoxalin-8-yl]amino]-2-oxoethyl]carbamic acid, 1,1-dimethylethyl ester

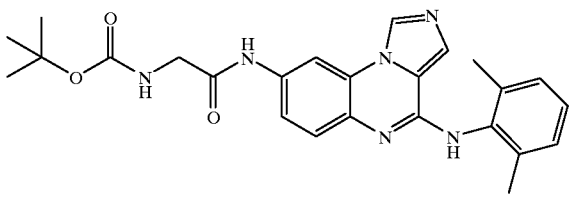

Analogous to preparation of 3 using N-Boc glycine to give the title compound 16 as a yellow solid: MS (M+H)$^+$=461. HPLC Retention time=3.51 minutes (HPLC conditions: same as used for Example 260).

EXAMPLE 17

Preparation of N-(2-Chloro-6-methylphenyl)imidazo[1,5-a]quinoxalin-4-amine

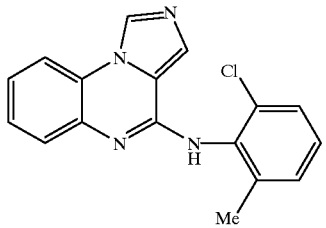

A. 2-Quinoxalinol

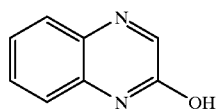

To a solution of 1,2-phenylene diamine (1.98 g, 18.34 mmol) in 25 mL of absolute EtOH was added a solution of ethyl glyoxylate in toluene (1.1 eq., 20.17 mmol, 19% w/w). The mixture was heated to reflux for 3 h. After cooling to room temperature, water (100 ml) was added. The precipitate was collected by filtration and washed with water, then dried under high vacuum to give 2.36 g (88%) of 17A as a beige-colored solid.

B. 1-[(4-Methoxyphenyl)methyl]-2(1H)-quinoxalinone

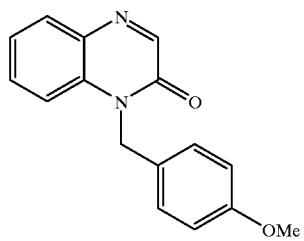

4.4 g of NaH (1.1 eq., 0.11 mol, 60% in mineral oil) was washed once with hexane and suspended in dry DMF (50 mL). To this suspension cooled at 0° C. was added 17A (14.6 g, 0.10 mol) in dry DMF (100 mL). The reaction mixture was stirred at ambient temperature for 30 min. After cooling to 0° C., a solution of 4-methoxy benzylchloride (14.9 mL, 0.11 mol) in 50 mL of dry DMF was added, followed by n-Bu$_4$NI (7.38 g, 0.2 eq., 20 mmol). The mixture was stirred at room temperature for 2 h, then was heated at 60° C. for 2 h. The reaction mixture was partitioned between sat. NH$_4$Cl solution and EtOAc and extracted with EtOAc. The combined extracts were washed with water and dried over anhydrous Na$_2$SO$_4$. Concentration in vacuo gave a crude product as an off-white solid. Trituration with ether overnight gave, after filtration, 14.2 g of 17B as an off-white solid (first crop). The mother liquid was concentrated and chromatographed (hexane-EtOAc: 3:1 to 1:1) on silica gel to give an additional 5.51 g of 17B as an off-white solid (74% combined yield).

C. 5-[(4-Methoxyphenyl)methyl]imidazo[1,5-a]quinoxalin-4(5H)-one

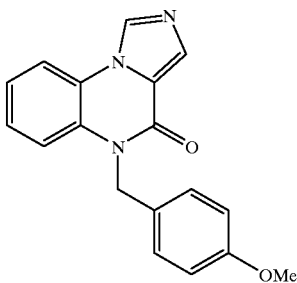

1.82 g of NaH (2.2 eq., 45.52 mmol, 60% in mineral oil) was washed once with hexane and suspended in dry THF (40 ml). To this suspension cooled at 0° C. was added a mixture of 17B (5.51 g, 20.7 mmol) and tosylmethyl isocyanide (4.44 g, 22.76 mmol) in dry THF (80 mL). The reaction mixture was stirred at 0° C. for 30 min, warmed to room temperature and stirred for an additional 1.0 h. The reaction mixture was poured onto a mixture of ice-water (1.5 L). The light beige-colored precipitate was collected by filtration and washed with water and dried under high vacuum. Trituration with MeOH and ether gave 5.72 g (94%) of 17C as a light beige solid.

D. Imidazo[1,5-a]quinoxalin-4(5H)-one

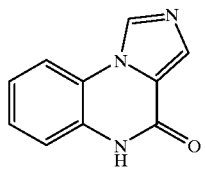

To a solution of 17C (7.69 g, 26.22 mmol) in 130 mL of trifluoroacetic acid was added 52 mL of anisole, followed by dropwise addition of 26 mL of trifluoromethane sulfonic acid. The mixture was stirred at room temperature overnight. Concentration in vacuo gave a residue which was added carefully via pipet to a mixture of cold saturated NaHCO$_3$. The resulting orange-yellow precipitate was collected by filtration and washed first with water, then ether to give 13.5 g of crude product after drying under high vacuum. This material was stirred in 1 L of MeOH overnight and the white precipitate was removed by filtration. The filtrate was concentrated in vacuo and the residue was again triturated with ether to give, after drying under high vacuum, 4.23 g (91%) of 17D as a light yellow solid.

17D was alternatively prepared as follows, employing as a starting material 17E(ii) prepared below:

To a solution of 17E(ii) (3.3 g, 16.1 mmol) in 30 m L dimethylacetamide was added K$_2$CO$_3$ (4.4 g, 32.16 mmol). The reaction mixture was heated to reflux for 18 h then the reaction was concentrated in vacuo and H$_2$O was added. The solid precipitate was filtered, rinsed with water, and dried under vacuum to give 2.49 g (84%) of 17D.

E. N-(2-Fluorophenyl)-1H-imidazole-4-carboxamide
(i) Imidazolecarbonyl Dimer

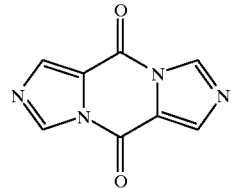

To 4-imidazolecarboxylic acid (5 g, 44.6 mmol) in toluene (100 mL) was added DMF (700 μL) followed by thionyl chloride (10 mL). The suspension was heated to reflux for 1.5 hours, then cooled to room temperature. The solid was filtered with toluene rinse, then supsended in 80 mL CHCl$_3$ followed by the addition of 12 mL triethylamine. The mixture was stirred for 2 hours at room temperature, then filtered with CHCl$_3$ rinse. The solid product was dried under vacuo to give 4.07 g (97%) of the title dimer 17E(i). 17E(i) can alsobe prepared by the method described in Kasina, S., Nematollahi, J., *Synthesis*, 162 (1975).

(ii) N-(2-Fluorophenyl)-1H-imidazole-4-carboxamide

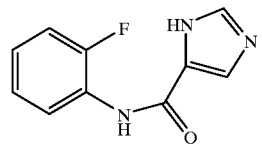

To a solution of 2-fluoroaniline (2.3 mL, 23.4 mmol) in 10 mL THF was added a solution of sodium bis(trimethylsilyl) amide (47 mL, 47 mmol) in THF. The mixture was heated to reflux for 0.5 h then cooled to room temperature. To the reaction mixture was added 17E(i) (2.2 g, 11.7 mmole) in 20 mL THF and heated to reflux for 2 h. The reaction mixture was cooled in ice quenched with acetic acid and condensed in vacuo. Water was added to the residue and neutralized with NaHCO$_3$. The resulting solid precipitate was filtered and washed with water followed by hexane. Drying in vacuo gave 3.5 g (80%) of 17E(ii).

F. 4-Chloroimidazo[1,5-a]quinoxaline

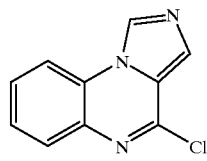

A mixture of 17D (2.16 g, 11.7 mmol) in 20 mL of phosphorus oxychloride was heated to reflux for 16 h. The reaction mixture was then concentrated in vacuo and azeotroped with toluene. The residue was then cooled in an ice bath and cold water was added. The aqueous layer was neutralized with NaHCO$_3$ and extracted with CH$_2$Cl$_2$. Concentration of the organic layer under reduced pressure gave 2.0 g (84%) of 17F.

G. N-(2-Chloro-6-methylphenyl)imidazo[1,5-a]quinoxalin-4-amine

To a solution of 2-chloro-6-methyl aniline (139 mg, 0.98 mmol) in 5 mL THF was added a solution of sodium bis(trimethylsilyl)amide (2.36 mL, 2.36 mmol) in THF. The reaction mixture was heated to reflux for 0.5 h then cooled to room temperature. To the reaction mixture was added a solution of 17F (200 mg, 0.98 mmol) in 10 mL THF, and the mixture was heated to reflux for 1 h. The reaction was cooled in an ice bath and quenched with acetic acid. The reaction was condensed in vacuo and partitioned between sat. NaHCO₃ and CH₂Cl₂. Concentration of the organic layer gave 227 mg (75%) of the title compound 17G. MS (M+H)⁺: 309. HPLC Retention time=2.68 minutes (HPLC conditions: "HPLC Method 2" described below).

EXAMPLE 18

Preparation of N-(2-Methoxyphenyl)imidazo[1,5-a] quinoxalin-4-amine

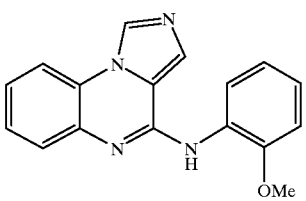

A. 1-(2-Nitrophenyl)-1H-imidazole

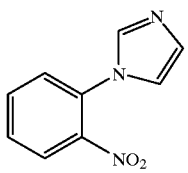

To a solution of 2-fluoronitrobenzene (12 g, 85 mmol) in 200 mL acetonitrile was added imidazole (8.6 g, 127 mmol) and potassium carbonate (23 g, 170 mmol). The reaction was heated to reflux for 18 h then cooled to room temperature and filtered through celite. The mixture was concentrated in vacuo followed by the addition of water. The aqueous solution was extracted with dichloromethane. Concentration of the organic layer gave a yellow solid which was refluxed in diethyl ether. The ether was cooled to room temperature and the solid filtered to give 14.39 g (89.9%) of 18A.

B. 2-(1H-Imidazol-1-yl)benzenamine

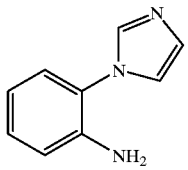

To a suspension of Pd/C (catalytic amount) in ethanol (30 mL) was added 18A (10 g, 52.9 mmol) in ethanol (70 mL). The mixture was degassed with hydrogen and stirred under a hydrogen atmosphere at room temperature for 18 h. The reaction mixture was then filtered through celite and condensed in vacuo. The residue was refluxed in diethyl ether then cooled to room temperature. The solid was collected by filtration to give 7.56 g (89.8%) of 18B.

C. N-[2-(1H-Imidazol-1-yl)phenyl]-N'-(2-methoxyphenyl) urea

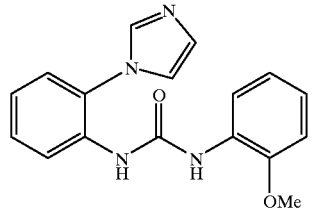

To a solution of 18B (250 mg, 1.57 mmol) in 2 mL of dry DMF was 2-methoxy aniline (1.1 eq., 1.73 mmol). The mixture was stirred at room temperature for 2 h. Ether (20 mL) was added and the mixture was stirred for additional 2 h. The white precipitate were collected by filtration and washed with water, then diethyl ether, and dried under high vacuum to give 205 mg of 18C.

D. N-(2-Methoxyphenyl)imidazo[1,5-a]quinoxalin-4-amine

To the mixture of 18C (202 mg, 0.655 mmol) in 3 mL of dry pyridine was added phosphorus oxychloride (3.0 eq., 0.183 mL, 1.965 mmol). The mixture was heated to reflux overnight. The reaction mixture was cooled to room temperature, 3 drops of water was added, and the mixture was heated to reflux for several hours. The mixture was cooled to room temperature and partitioned between water and EtOAc. The organic phase was washed with saturated NaHCO₃ and brine, and dried over anhydrous Na₂SO₄. Concentration in vacuo followed by flash chromatography (CH₂Cl₂-EtOAc: 9:1 to 1:1) on silica gel gave 20 mg of the title compound 18D as a tan solid. HPLC: 2.29 min (YMC ODS-A 6.0×150 mm, S-3 μm, 120A; 70–100% B linear gradient over 20 min; 1.5 ml/min; A: 90% H₂O-10% MeOH-0.2% H₃PO₄; B: 10% H₂O-90% MeOH-0.2% H₃PO₄).

EXAMPLE 19

Preparation of N-(2-Nitrophenyl)imidazo[1,5-a] quinoxalin-4-amine

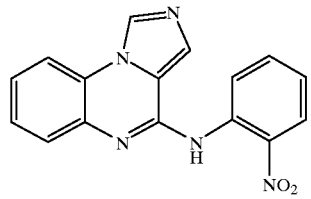

Analogous to the preparation of 18D using 2-nitro aniline. HPLC Ret Time=16.701 minutes (by HPLC Method 1 described following).

HPLC Method 1:

50% B to 100% B; 20 minute gradient; 10 minute hold; YMC ODS-A 6.0×150 mm; 1.5 mL/min; A: 90% H₂O-10% MeOH-0.2% H₃PO₄; B: 10% H₂O-90% MeOH-0.2% H₃PO₄.

EXAMPLE 20

Preparation of N-(2-Fluorophenyl)imidazo[1,5-a]quinoxalin-4-amine

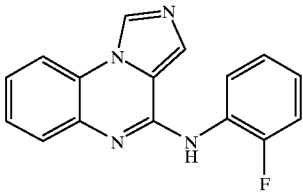

Analogous to the preparation of 18D using 2-fluoro aniline. HPLC Ret Time=5.858 minutes (by HPLC Method 1 without 10 minute hold).

EXAMPLES 21 TO 122

General Procedure

Compounds 21 to 122 were prepared by a route analogous to that used for the preparation of 17G, substituting with the required amine in place of 2-chloro-6-methyl aniline. The compounds of these examples have the structure:

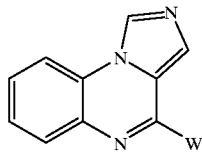

where W is shown in the following Table 1.

In Table 1, $X_1$ is the imidazoquinoxaline core structure to which W is bonded, i.e., the structure:

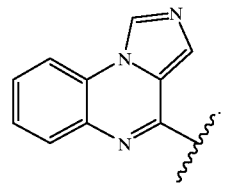

"HPLC Ret Time" is the HPLC retention time under the following conditions: 0% B to 100% B; 4 minute gradient; 2 minute hold; 4 mL/min; 254 nm; YMC S5 C18 Rapid Resolution column 4.6×50 mm; A: 90% $H_2O$-10% MeOH-0.2% $H_3PO_4$; B: 10% $H_2O$-90% MeOH-0.2% $H_3PO_4$. ("HPLC Method 2"). Unfilled valences on nitrogen indicate the presence of a hydrogen.

TABLE 1

| Ex. No. | W | Compound Name | HPLC Ret Time (min) |
|---|---|---|---|
| 21 | (2,6-dimethylbenzyl-N-$X_1$ structure with CH₃ groups) | N-(2,6-Diethylphenyl)-imidazo[1,5-a]quinoxalin-4-amine | 2.81 |
| 22 | ($X_1$-N-phenyl-C≡N) | 4-[(Imidazo[1,5-a]quinoxalin-4-yl)amino]benzonitrile | 3.73 |
| 23 | ($X_1$-N-indanyl) | N-(2,3-Dihydro-1H-inden-5-yl)imidazo[1,5-a]quinoxalin-4-amine | 3.13 |
| 24 | ($X_1$-N-phenyl-CF₃) | N-[3-(Trifluoromethyl)-phenyl]imidazo[1,5-a]quinoxalin-4-amine | 4.25 |

TABLE 1-continued

| Ex. No. | W | Compound Name | HPLC Ret Time (min) |
|---|---|---|---|
| 25 | (4-decylphenyl group) | N-(4-Decylphenyl)imidazo[1,5-a]quinoxalin-4-amine | 5.17 |
| 26 | (2,6-dimethylphenyl group) | N-(2,6-Dimethylphenyl)-imidazo[1,5-a]quinoxalin-4-amine | 2.43 |
| 27 | (2-methyl-6-isopropylphenyl group) | N-[2-Methyl-6-(1-methylethyl)-phenyl]imidazo[1,5-a]quinoxalin-4-amine | 2.88 |
| 28 | (biphenyl-3-yl group) | N-([1,1'-Biphenyl]-3-yl)imidazo-[1,5-a]quinoxalin-4-amine | 4.00 |
| 29 | (2,6-diisopropylphenyl group) | N-[2,6-Bis(1-methylethyl)-phenyl]imidazo[1,5-a]-quinoxalin-4-amine | 3.17 |
| 30 | (2,5-dimethylphenyl group) | N-(2,5-Dimethylphenyl)-imidazo[1,5-a]quinoxalin-4-amine | 2.57 |
| 31 | (2,3-dimethylphenyl group) | N-(2,3-Dimethylphenyl)-imidazo[1,5-a]quinoxalin-4-amine | 2.54 |

TABLE 1-continued

| Ex. No. | W | Compound Name | HPLC Ret Time (min) |
|---|---|---|---|
| 32 | (3-methyl-4-isopropylphenyl) | N-[3-Methyl-4-(1-methylethyl)-phenyl]imidazo[1,5-a]-quinoxalin-4-amine | 3.60 |
| 33 | (2,4-dimethylphenyl) | N-(2,4-Dimethylphenyl)-imidazo[1,5-a]quinoxalin-4-amine | 2.63 |
| 34 | ([1,1'-biphenyl]-4-yl) | N-([1,1'-Biphenyl]-4-yl)imidazo-[1,5-a]quinoxalin-4-amine | 4.05 |
| 35 | (2-benzylphenyl) | N-[2-(Phenylmethyl)-phenyl]imidazo[1,5-a]-quinoxalin-4-amine | 2.86 |
| 36 | (4-tert-butylphenyl) | N-[4-(1,1-Dimethylethyl)-phenyl]imidazo[1,5-a]-quinoxalin-4-amine | 3.75 |
| 37 | (2-propylphenyl) | N-(2-Propylphenyl)imidazo-[1,5-a]quinoxalin-4-amine | 2.84 |

TABLE 1-continued

| Ex. No. | W | Compound Name | HPLC Ret Time (min) |
|---|---|---|---|
| 38 | | N-[3,5-Bis(1,1-dimethylethyl)-phenyl]imidazo[1,5-a]-quinoxalin-4-amine | 4.50 |
| 39 | | N-(3-Ethylphenyl)imidazo-[1,5-a]quinoxalin-4-amine | 3.25 |
| 40 | | N-[3-(1,1-Dimethylethyl)-phenyl]imidazo[1,5-a]-quinoxalin-4-amine | 3.84 |
| 41 | | N-(4-Cyclohexyl-phenyl)imidazo[1,5-a]-quinoxalin-4-amine | 4.18 |
| 42 | | N-(2,6-Dimethoxyphenyl)-imidazo[1,5-a]quinoxalin-4-amine | 2.29 |
| 43 | | N-(3,4,5-Trimethoxy-phenyl)imidazo[1,5-a]-quinoxalin-4-amine | 2.80 |
| 44 | | N-(2-Methoxy-6-methylphenyl)-imidazo[1,5-a]quinoxalin-4-amine | 2.34 |

TABLE 1-continued

| Ex. No. | W | Compound Name | HPLC Ret Time (min) |
|---|---|---|---|
| 45 | 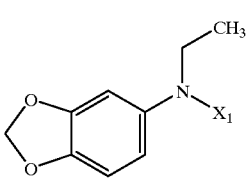 | N-(1,3-Benzodioxol-5-yl)-N-ethylimidazo[1,5-a]quinoxalin-4-amine | 3.07 |
| 46 | 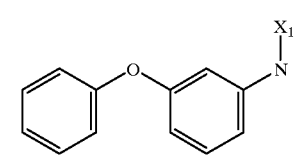 | N-(3-Phenoxyphenyl)-imidazo[1,5-a]quinoxalin-4-amine | 4.20 |
| 47 | 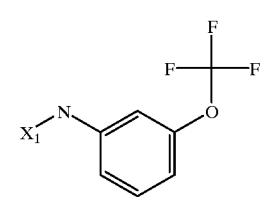 | N-[3-(Trifluoromethoxy)-phenyl]imidazo[1,5-a]-quinoxalin-4-amine | 4.35 |
| 48 | 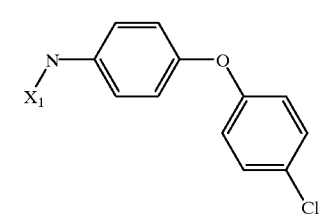 | N-[4-(4-Chlorophenoxy)-phenyl]imidazo[1,5-a]-quinoxalin-4-amine | 4.25 |
| 49 | 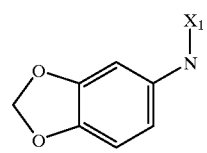 | N-(1,3-Benzodioxol-5-yl)imidazo[1,5-a]quinoxalin-4-amine | 2.43 |
| 50 | 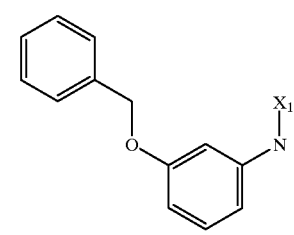 | N-[3-(Phenylmethoxy)-phenyl]imidazo[1,5-a]-quinoxalin-4-amine | 3.96 |
| 51 | 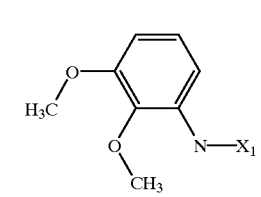 | N-(2,3-Dimethoxyphenyl)-imidazo[1,5-a]quinoxalin-4-amine | 2.59 |

TABLE 1-continued

| Ex. No. | W | Compound Name | HPLC Ret Time (min) |
|---|---|---|---|
| 52 | | N-[2-(Trifluoromethoxy)-phenyl]imidazo[1,5-a]-quinoxalin-4-amine | 3.33 |
| 53 | | N-(1,4-Benzodioxin-6-yl)-imidazo[1,5-a]quinoxalin-4-amine | 2.52 |
| 54 | | N-(4-Ethoxyphenyl)imidazo-[1,5-a]quinoxalin-4-amine | 2.78 |
| 55 | | N-(4-Phenoxyphenyl)-imidazo[1,5-a]quinoxalin-4-amine | 3.80 |
| 56 | | N-(4-Chlorophenyl)imidazo-[1,5-a]quinoxalin-4-amine | 3.79 |
| 57 | | N-[3-Methoxy-5-(trifluoromethyl)phenyl]-imidazo[1,5-a]quinoxalin-4-amine | 4.41 |
| 58 | | N-(2-Bromo-5-methoxyphenyl)imidazo-[1,5-a]quinoxalin-4-amine | 3.26 |

TABLE 1-continued

| Ex. No. | W | Compound Name | HPLC Ret Time (min) |
|---|---|---|---|
| 59 | 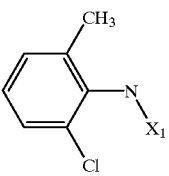 | N-(2-Chloro-6-methylphenyl)-imidazo[1,5-a]quinoxalin-4-amine (This compound prepared in Example 17 as 17G.) | 2.68 |
| 60 | 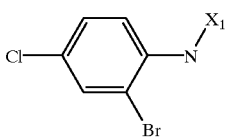 | N-(2-Bromo-4-chlorophenyl)-imidazo[1,5-a]quinoxalin-4-amine | 3.87 |
| 61 | 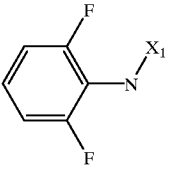 | N-(2,6-Difluorophenyl)-imidazo[1,5-a]quinoxalin-4-amine | 2.79 |
| 62 | 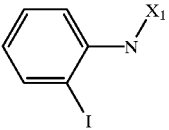 | N-(2-Iodophenyl)imidazo-[1,5-a]quinoxalin-4-amine | 2.86 |
| 63 | 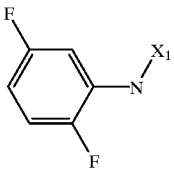 | N-(2,5-Difluorophenyl)-imidazo[1,5-a]quinoxalin-4-amine | 3.52 |
| 64 | 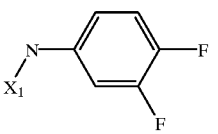 | N-(3,4-Difluorophenyl)-imidazo[1,5-a]quinoxalin-4-amine | 3.82 |
| 65 | 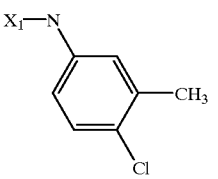 | N-(4-Chloro-3-methylphenyl)-imidazo[1,5-a]quinoxalin-4-amine | 4.00 |
| 66 | 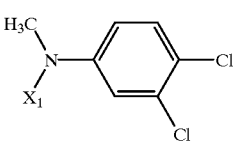 | N-(3,4-Dichlorophenyl)-N-methylimidazo[1,5-a]-quinoxalin-4-amine | 4.09 |

TABLE 1-continued

| Ex. No. | W | Compound Name | HPLC Ret Time (min) |
|---|---|---|---|
| 67 | (4-bromophenyl group with X$_1$-N) | N-(4-Bromophenyl)imidazo-[1,5-a]quinoxalin-4-amine | 3.99 |
| 68 | (2,4-dibromophenyl group with X$_1$-N) | N-(2,4-Dibromophenyl)-imidazo[1,5-a]quinoxalin-4-amine | 4.04 |
| 69 | (4-fluoro-3-methylphenyl group with X$_1$-N) | N-(4-Fluoro-3-methylphenyl)-imidazo[1,5-a]quinoxalin-4-amine | 3.09 |
| 70 | (2-chloro-5-methylphenyl group with X$_1$-N) | N-(2-Chloro-5-methylphenyl)-imidazo[1,5-a]quinoxalin-4-amine | 3.13 |
| 71 | (2,5-dibromophenyl group with X$_1$-N) | N-(2,5-Dibromophenyl)-imidazo[1,5-a]quinoxalin-4-amine | 4.16 |
| 72 | (3,5-dichlorophenyl group with X$_1$-N) | N-(3,5-Dichlorophenyl)-imidazo[1,5-a]quinoxalin-4-amine | 4.81 |
| 73 | (4-chlorophenyl group with X$_1$-N(CH$_3$)) | N-(4-Chlorophenyl)-N-methylimidazo[1,5-a]-quinoxalin-4-amine | 3.28 |
| 74 | (3,5-dibromo-4-methylphenyl group with X$_1$-N) | N-(3,5-Dibromo-4-methylphenyl)imidazo-[1,5-a]quinoxalin-4-amine | 5.05 |

TABLE 1-continued

| Ex. No. | W | Compound Name | HPLC Ret Time (min) |
|---|---|---|---|
| 75 | (4-chloro-1-naphthalenyl group attached via X₁—N) | N-(4-Chloro-1-naphthalenyl)-imidazo[1,5-a]quinoxalin-4-amine | 3.37 |
| 76 | (3,4,5-trichlorophenyl group attached via X₁—N) | N-(3,4,5-Trichlorophenyl)-imidazo[1,5-a]quinoxalin-4-amine | 5.09 |
| 77 | (4-morpholinylphenyl group attached via N—X₁) | N-[4-(4-Morpholinyl)-phenyl]imidazo[1,5-a]-quinoxalin-4-amine | 2.43 |
| 78 | (4-dimethylaminophenyl group attached via X₁—N) | N-[4-(Dimethylamino)-phenyl]imidazo[1,5-a]-quinoxalin-4-amine | 2.02 |
| 79 | (2-(1H-pyrrol-1-yl)phenyl group attached via X₁—N) | N-[2-(1H-Pyrrol-1-yl)phenyl]imidazo[1,5-a]-quinoxalin-4-amine | 2.89 |
| 80 | (4-(1-piperidinyl)phenyl group attached via N—X₁) | N-[4-(1-Piperidinyl)-phenyl]imidazo[1,5-a]-quinoxalin-4-amine | 2.22 |
| 81 | (2-(1-piperidinyl)phenyl group attached via N—X₁) | N-[2-(1-Piperidinyl)-phenyl]imidazo[1,5-a]quinoxalin-4-amine | 2.84 |

TABLE 1-continued

| Ex. No. | W | Compound Name | HPLC Ret Time (min) |
|---|---|---|---|
| 82 | quinolin-6-yl-N(X₁) | N-(6-Quinolinyl)imidazo[1,5-a]-quinoxalin-4-amine | 2.51 |
| 83 | pyridin-3-yl-N(X₁) | N-(3-Pyridinyl)imidazo[1,5-a]-quinoxalin-4-amine | 1.95 |
| 84 | 2-chlorophenyl-N(X₁) | N-(2-Chlorophenyl)imidazo-[1,5-a]quinoxalin-4-amine | 2.86 |
| 85 | 2-bromo-4-(trifluoromethoxy)phenyl-N(X₁) | N-[2-Bromo-4-(trifluoromethoxy)phenyl]imidazo[1,5-a]-quinoxalin-4-amine | 4.12 |
| 86 | 2,4-dichlorophenyl-N(X₁) | N-(2,4-Dichlorophenyl)-imidazo[1,5-a]quinoxalin-4-amine | 3.85 |
| 87 | 2-bromo-4-methylphenyl-N(X₁) | N-(2-Bromo-4-methylphenyl)-imidazo[1,5-a]quinoxalin-4-amine | 3.12 |
| 88 | 3-bromo-2-methylphenyl-N(X₁) | N-(3-Bromo-2-methylphenyl)-imidazo[1,5-a]quinoxalin-4-amine | 3.05 |
| 89 | 3-fluorophenyl-N(X₁) | N-(3-Fluorophenyl)imidazo-[1,5-a]quinoxalin-4-amine | 3.52 |
| 90 | 2-chlorophenyl-N(X₁)(CH₃) | N-(2-Chlorophenyl)-N-methylimidazo[1,5-a]-quinoxalin-4-amine | 3.47 |

TABLE 1-continued

| Ex. No. | W | Compound Name | HPLC Ret Time (min) |
|---|---|---|---|
| 91 | 3,5-dibromophenyl-N(X₁) | N-(3,5-Dibromophenyl)-imidazo[1,5-a]quinoxalin-4-amine | 4.91 |
| 92 | 4-benzoylphenyl-N(X₁) | N-(4-Benzoylphenyl)imidazo-[1,5-a]quinoxalin-4-amine | 4.27 |
| 93 | 4-pyridinyl-N(X₁) | N-(4-Pyridinyl)imidazo[1,5-a]-quinoxalin-4-amine | 2.11 |
| 94 | N-(phenylmethyl)-N-(2-pyridinyl)(X₁) | N-(Phenylmethyl)-N-(2-pyridinyl)imidazo[1,5-a]-quinoxalin-4-amine | 3.94 |
| 95 | 4-bromo-2,6-dimethylphenyl-N(X₁) | N-(4-Bromo-2,6-dimethyl-phenyl)imidazo[1,5-a]-quinoxalin-4-amine | 3.15 |
| 96 | 2-chloro-4-(1,1-dimethylethyl)phenyl-N(X₁) | N-[2-Chloro-4-(1,1-dimethyl-ethyl)phenyl]imidazo[1,5-a]-quinoxalin-4-amine | 4.02 |
| 97 | 2-ethyl-6-methylphenyl-N(X₁) | N-(2-Ethyl-6-methylphenyl)-imidazo[1,5-a]quinoxalin-4-amine | 2.72 |

TABLE 1-continued

| Ex. No. | W | Compound Name | HPLC Ret Time (min) |
|---|---|---|---|
| 98 | 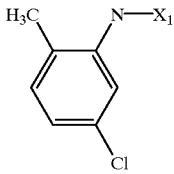 | N-(5-Chloro-2-methylphenyl)-imidazo[1,5-a]quinoxalin-4-amine | 3.06 |
| 99 | 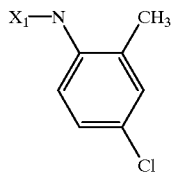 | N-(4-Chloro-2-methylphenyl)-imidazo[1,5-a]quinoxalin-4-amine | 2.99 |
| 100 | 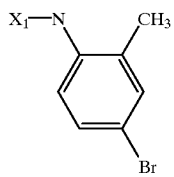 | N-(4-Bromo-2-methylphenyl)-imidazo[1,5-a]quinoxalin-4-amine | 3.14 |
| 101 | 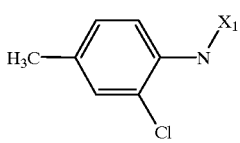 | N-(2-Chloro-4-methylphenyl)-imidazo[1,5-a]quinoxalin-4-amine | 3.17 |
| 102 | 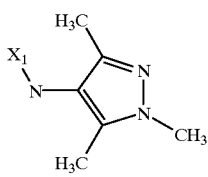 | N-(1,3,5-Trimethyl-1H-pyrazol-4-yl)imidazo[1,5-a]quinoxalin-4-amine | 1.82 |
| 103 | 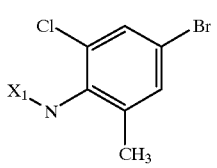 | N-(4-Bromo-2-chloro-6-methylphenyl)imidazo[1,5-a]-quinoxalin-4-amine | 3.67 |
| 104 | 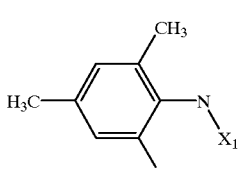 | N-(2-Chloro-4,6-dimethyl-phenyl)imidazo[1,5-a]-quinoxalin-4-amine | 3.02 |
| 105 | 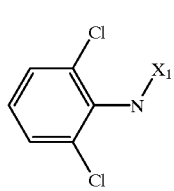 | N-(2,6-Dichlorophenyl)-imidazo[1,5-a]-quinoxalin-4-amine | 3.06 |

TABLE 1-continued

| Ex. No. | W | Compound Name | HPLC Ret Time (min) |
|---|---|---|---|
| 106 | 2,4,6-trichlorophenyl-N(X₁)- | N-(2,4,6-Trichlorophenyl)-imidazo[1,5-a]quinoxalin-4-amine | 3.93 |
| 107 | 2,6-dibromophenyl-N(X₁)- | N-(2,6-Dibromophenyl)-imidazo[1,5-a]quinoxalin-4-amine | 3.12 |
| 108 | 2,4,6-tribromophenyl-N(X₁)- | N-(2,4,6-Tribromophenyl)-imidazo[1,5-a]quinoxalin-4-amine | 4.06 |
| 109 | 3,5-dichloro-2-pyridinyl-N(X₁)- | N-(3,5-Dichloro-2-pyridinyl)imidazo[1,5-a]-quinoxalin-4-amine | 4.13 |
| 110 | 2,6-dibromo-4-methylphenyl-N(X₁)- | N-(2,6-Dibromo-4-methylphenyl)imidazo[1,5-a]-quinoxalin-4-amine | 3.35 |
| 111 | 2,6-dibromo-4-propylphenyl-N(X₁)- | N-(2,6-Dibromo-4-propylphenyl)imidazo[1,5-a]-quinoxalin-4-amine | 3.95 |
| 112 | 3-chloro-4-cyanophenyl-N(X₁)- | 3-Chloro-4-[[imidazo[1,5-a]quinoxalin-4-yl]amino]benzonitrile | 3.78 |
| 113 | 2,4,6-trimethylphenyl-N(X₁)- | N-(2,4,6-Trimethylphenyl)-imidazo[1,5-a]quinoxalin-4-amine | 2.805 |

TABLE 1-continued

| Ex. No. | W | Compound Name | HPLC Ret Time (min) |
|---|---|---|---|
| 114 | [structure: X₁-NH-phenyl-morpholine] | N-[2-(4-Morpholinyl)phenyl]-imidazo[1,5-a]quinoxalin-4-amine | 2.688 |
| 115 | [structure: X₁-indole-carbonitrile] | 1-(Imidazo[1,5-a]quinoxalin-4-yl)-1H-indole-5-carbonitrile | 4.043 |
| 116 | [structure: X₁-NH-phenyl-imidazole] | N-[2-(1H-Imidazol-1-yl)phenyl]imidazo[1,5-a]-quinoxalin-4-amine | 1.894 |
| 117 | [structure: X₁-NH-2,4-dimethoxyphenyl] | N-(2,4-Dimethoxyphenyl)-imidazo[1,5-a]quinoxalin-4-amine | 2.488 |
| 118 | [structure: X₁-NH-phenyl] | N-Phenylimidazo[1,5-a]-quinoxalin-4-amine | 2.642 |
| 119 | [structure: X₁-NH-phenyl-O-phenyl] | N-(2-Phenoxyphenyl)-imidazo[1,5-a]quinoxalin-4-amine | 3.402 |
| 120 | [structure: X₁-NH-2-tert-butylphenyl] | N-[2-(1,1-Dimethylethyl)phenyl]-imidazo[1,5-a]quinoxalin-4-amine | 2.962 |

TABLE 1-continued

| Ex. No. | W | Compound Name | HPLC Ret Time (min) |
|---|---|---|---|
| 121 | X₁–N(CH₃)–phenyl | N-Methyl-N-phenylimidazo-[1,5-a]quinoxalin-4-amine | 2.634 |
| 122 | X₁–NH–(2,3-dichlorophenyl) | N-(2,3-Dichlorophenyl)-imidazo[1,5-a]quinoxalin-4-amine | 3.841 |

EXAMPLES 123 TO 129

General Procedure

Compounds 123 to 129 were prepared by a route analogous to that used for the preparation of 17G, substituting 4-methoxy-1,2-phenylene diamine for 1,2-phenylene diamine, and using the required amine in place of 2-chloro-6-methyl aniline. The compounds of these examples have the structure:

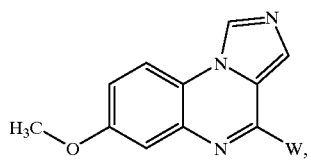

where W is shown in the following Table 2.

In Table 2, $X_1$ is the imidazoquinoxaline core structure to which W is bonded, i.e., the structure:

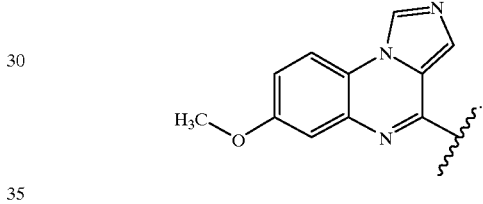

"HPLC Ret Time" is the HPLC retention time under the conditions of HPLC Method 2 described above. Unfilled valences on nitrogen indicate the presence of a hydrogen.

TABLE 2

| Ex. No. | W | Compound Name | HPLC Ret Time (min) |
|---|---|---|---|
| 123 | X₁–NH–(2-bromophenyl) | N-(2-Bromophenyl)-7-methoxyimidazo-[1,5-a]quinoxalin-4-amine | 3.20 |
| 124 | (2,6-dimethylphenyl)–N–X₁ | N-(2,6-Dimethylphenyl)-7-methoxy-imidazo[1,5-a]quinoxalin-4-amine | 2.78 |
| 125 | (2-chloro-6-methylphenyl)–N–X₁ | N-(2-Chloro-6-methylphenyl)-7-methoxyimidazo[1,5-a]quinoxalin-4-amine | 3.01 |

TABLE 2-continued

| Ex. No. | W | Compound Name | HPLC Ret Time (min) |
|---|---|---|---|
| 126 | ![structure] | N-(2,4-Dimethylphenyl)-7-methoxyimidazo[1,5-a]quinoxalin-4-amine | 2.95 |
| 127 | ![structure] | N-(2-Chlorophenyl)-7-methoxyimidazo-[1,5-a]quinoxalin-4-amine | 3.18 |
| 128 | ![structure] | N-(2,6-Dichlorophenyl)-7-methoxy-imidazo[1,5-a]quinoxalin-4-amine | 3.27 |
| 129 | ![structure] | N-(2-Chloro-4,6-dimethylphenyl)-7-methoxyimidazo[1,5-a]quinoxalin-4-amine | 3.26 |

EXAMPLE 130

Preparation of 7,8-Dimethoxy-N-(2,4,6-trimethylphenyl)imidazo[1,5-a]quinoxalin-4-amine

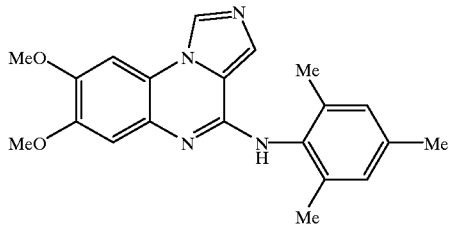

A. 4,5-Dimethoxy-1,2-benzenediamine

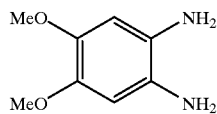

A mixture of 4,5-dimethoxy-1,2-diaminobenzene (16.4 g, 71.7 mmol) and 10% Pd-C (5.0 g) in 500 mL of dry MeOH was stirred under hydrogen atmosphere for 3 days. The catalyst was removed by filtration and the filtrate was concentrated in vacuo to give 11.98 g of 130A as a dark purple solid.

B. 6,7-Dimethoxy-2,3-quinoxalinediol

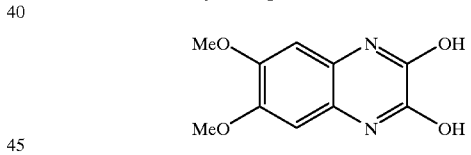

A mixture of crude 130A (11.98 g, 71.7 mmol) and ethyl glyoxylate (75 mL) was heated to reflux for 14 h. Upon cooling to room temperature, the resulting solid was collected by filtration and washed with anhydrous ether (ca. 500 mL) and dried under high vacuum to give 13.8 g of 130B as a dark brown solid.

C. 2,3-Dichloro-6,7-dimethoxyquinoxaline

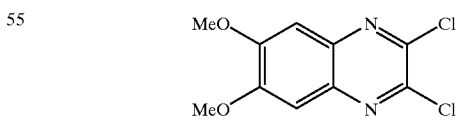

A mixture of crude 130B (8.0 g, 36.0 mmol) and phosphorus oxychoride (80 mL) was heated to reflux for 24 h. Upon cooling to room temperature, the excess phosphorus oxychoride was removed under reduced pressure and the residue was carefully poured into a mixture of ice-water. The resulting dark precipitate was collected by filtration and washed with additional water and dried under high vacumm.

Flash chromatography (CH$_2$Cl$_2$) on silica gel gave 6.47 g of 130C as a white crystalline material.

D. 4-Chloro-7,8-dimethoxyimidazo[1,5-a]quinoxaline

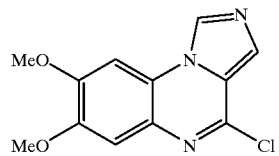

To a mixture of 130C (130 mg, 0.5 mmol), trimethylsilylmethyl isocyacyanide (57 mg, 0.5 mmol) in dry THF (2 mL) cooled at −78° C. was added a 1.0 M solution of sodium bis(trimethylsilyl)amide in THF (0.5 mL, 0.5 mmol). The mixture was stirred at −78° C. for 1 hr, then at ambient temperature for an additional 30 min. The reaction was quenched by addition of saturated NH$_4$Cl aq. solution. The reaction mixture was extracted with EtOAc, combined extracts were washed with saturated NaHCO$_3$ and brine, and dried over anhydrous Na$_2$SO$_4$. Concentration in vacuo followed by flash chromatography (hexane-EtOAc: 7:3 to 1:1) on silica gel gave 62 mg of 130D as a light-yellow solid.

Alternatively, 130D can be prepared by following route:

(i) 7,8-Dimethoxyimidazo[1,5-a]quinoxalin-4(5H)-one

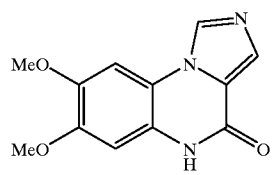

The title compound of this step was prepared from 130A by a method analogous to that used for the preparation of 1D. HPLC Retention time=1.911 min (HPLC Conditions: "HPLC Method 2").

(ii) 130D

To a suspension of 7,8-dimethoxyimidazo[1,5-a]quinoxalin-4(5H)-one (5.0 g, 20.4 mmol) in 80 mL of POCl$_3$ ("POCl$_3$"=Phosphorus oxychloride) was added triethylamine (5.7 mL, 40.8 mmol). The mixture was heated at reflux for 1.0 hr. An additional 20 mL of POCl$_3$ was added and the mixture was refluxed for another 1.0 hr. Another 20 mL of POCl$_3$ was added to the mixture and the mixture was refluxed again for 1.0 hr upon which time a homogeneous light yellow solution was obtained. The mixture was concentrated under reduced pressure and the residue was azeotropically evaporated several times with CH$_2$Cl$_2$-heptane. The residue was then suspended in CH$_2$Cl$_2$ and poured into a mixture of ice-sat'd NaHCO$_3$ and the resulting mixture was stirred vigorously at room temperature overnight. The organic layer was separated and the aqueous layer was extracted with more CH$_2$Cl$_2$ (×2). The combined organic extracts were washed with water and dried over anhydrous Na$_2$SO$_4$. Concentration in vacuo followed by flash chromatography (CH$_2$Cl$_2$-MeOH: 100:0 to 98:2) on silica gel gave, after further trituration with CH$_2$Cl$_2$-ether, 3.37 g of 130D as a light yellow solid.

E. 7,8-Dimethoxy-N-(2,4,6-trimethylphenyl)imidazo[1,5-a]quinoxalin-4-amine

Analogous to the preparation of 17G, replacing 2-chloro-6-methyl aniline with 2,4,6-trimethyl aniline. HPLC Ret Time: 3.019 minutes (by HPLC Method 2).

EXAMPLE 131

Preparation of N-(2,6-Dimethylphenyl)-7,8-dimethoxyimidazo[1,5-a]quinoxalin-4-amine

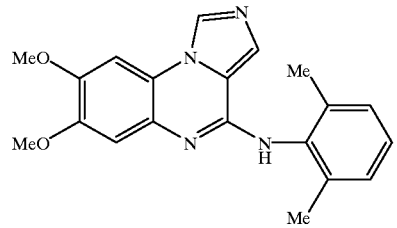

Analogous to the preparation of 17G, replacing 2-chloro-6-methyl aniline with 2,6-dimethyl aniline. HPLC Ret Time: 2.781 minutes (by HPLC Method 2).

EXAMPLES 132 TO 169

General Procedure

To a solution of 17F (15 mg, 0.074 mmol) in 0.8 mL dioxane was added the requisite amine (0.222 mmol). The reaction was heated to 125° C. for 18 h then cooled to room temperature. The reaction mixture was added to water and extracted with dichloromethane. The organic phase was concentrated under vacuum and the product crystallized from CH$_2$Cl$_2$/hexane to give the title compounds. The compounds of these examples have the structure:

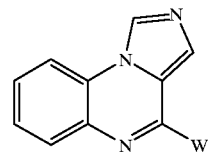

where W is shown in the following Table 3.

In Table 3, X$_1$ is the imidazoquinoxaline core structure to which W is bonded, i.e., the structure:

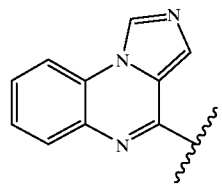

"HPLC Ret Time" is the HPLC retention time under the conditions of HPLC Method 2 described above. Unfilled valences on nitrogen indicate the presence of a hydrogen.

TABLE 3

| Ex. No. | W | Compound Name | HPLC Ret Time (min) |
|---|---|---|---|
| 132 | | N-[2-(3-Chlorophenyl)ethyl]-imidazo[1,5-a]quinoxalin-4-amine | 3.09 |
| 133 | | N-[2-[(Phenylmethyl)thio]ethyl]-imidazo[1,5-a]quinoxalin-4-amine | 2.99 |
| 134 | | N-[[2-[[2-(Hydroxymethyl)-phenyl]thio]phenyl]methyl]imidazo-[1,5-a]quinoxalin-4-amine | 2.97 |
| 135 | | N-[2-(1-Cyclohexen-1-yl)ethyl]-imidazo[1,5-a]quinoxalin-4-amine | 3.16 |
| 136 | | N-[2-[Ethyl(3-methylphenyl)-amino]ethyl]imidazo[1,5-a]-quinoxalin-4-amine | 2.54 |
| 137 | | N-Hexylimidazo[1,5-a]quinoxalin-4-amine | 3.08 |
| 138 | | N-[2-(4-Methylphenyl)-ethyl]imidazo[1,5-a]quinoxalin-4-amine | 3.00 |
| 139 | | N-[(2-Chlorophenyl)methyl]-imidazo[1,5-a]quinoxalin-4-amine | 3.00 |

TABLE 3-continued

| Ex. No. | W | Compound Name | HPLC Ret Time (min) |
|---|---|---|---|
| 140 | (2-methylpiperidinyl-propyl structure) | N-[3-(2-Methyl-1-piperidinyl)-propyl]imidazo[1,5-a]quinoxalin-4-amine | 1.26 |
| 141 | (2-pyridinyl-ethyl structure) | N-[2-(2-Pyridinyl)ethyl]imidazo-[1,5-a]quinoxalin-4-amine | 1.31 |
| 142 | (1-naphthalenyl-ethyl structure) | N-[1-(1-Naphthalenyl)-ethyl]imidazo[1,5-a]quinoxalin-4-amine | 3.46 |
| 143 | (tetrahydrofuranyl-methyl structure) | N-[(Tetrahydro-2-furanyl)methyl]imidazo-[1,5-a]quinoxalin-4-amine | 2.04 |
| 144 | (2,4-dichlorophenyl-ethyl structure) | N-[2-(2,4-Dichlorophenyl)-ethyl]imidazo[1,5-a]quinoxalin-4-amine | 3.47 |
| 145 | (2-aminophenyl-methyl structure) | N-[(2-Aminophenyl)-methyl]imidazo[1,5-a]quinoxalin-4-amine | 2.20 |
| 146 | (4-amino-1-piperidinecarboxylic acid ethyl ester structure) | 4-[(Imidazo[1,5-a]quinoxalin-4-yl)amino]-1-piperidinecarboxylic acid, ethyl ester | 2.53 |
| 147 | (4-phenylmethyl-1-piperazinyl structure) | 4-[4-(Phenylmethyl)-1-piperazinyl]imidazo[1,5-a]-quinoxaline | 2.37 |

TABLE 3-continued

| Ex. No. | W | Compound Name | HPLC Ret Time (min) |
|---|---|---|---|
| 148 | (4-trifluoromethyl-phenyl)methyl-NH-X₁ | N-[[4-(Trifluoromethyl)-phenyl]methyl]imidazo[1,5-a]-quinoxalin-4-amine | 3.38 |
| 149 | 4-(2-pyridinyl)piperazin-1-yl-X₁ | 4-[4-(2-Pyridinyl)-1-piperazinyl]imidazo[1,5-a]-quinoxaline | 1.32 |
| 150 | (S)-1-(phenylmethyl)pyrrolidin-3-yl-NH-X₁ | (S)-N-[1-(Phenylmethyl)-3-pyrrolidinyl]imidazo[1,5-a]-quinoxalin-4-amine | 2.15 |
| 151 | (2-chloro-6-phenoxyphenyl)methyl-NH-X₁ | N-[(2-Chloro-6-phenoxyphenyl)-methyl]imidazo[1,5-a]quinoxalin-4-amine | 3.36 |
| 152 | 4-[2-nitro-4-(trifluoromethyl)phenyl]piperazin-1-yl-X₁ | 4-[4-[2-Nitro-4-(trifluoromethyl)-phenyl]-1-piperazinyl]imidazo-[1,5-a]-quinoxaline | 3.95 |
| 153 | X₁-NH-CH₂CH₂CH₃ | N-Propylimidazo[1,5-a]quinoxalin-4-amine | 2.04 |
| 154 | X₁-NH-cyclopropyl | N-Cyclopropylimidazo[1,5-a]-quinoxalin-4-amine | 1.78 |
| 155 | X₁-NH-CH₂CH₂-(4-fluorophenyl) | N-[2-(4-Fluorophenyl)-ethyl]imidazo[1,5-a]quinoxalin-4-amine | 2.83 |

TABLE 3-continued

| Ex. No. | W | Compound Name | HPLC Ret Time (min) |
|---|---|---|---|
| 156 | (N-hexyl-N-methyl structure) | N-Hexyl-N-methylimidazo[1,5-a]-quinoxalin-4-amine | 3.05 |
| 157 | (N-methyl-N-benzyl structure) | N-Methyl-N-(phenylmethyl)imidazo[1,5-a]-quinoxalin-4-amine | 2.70 |
| 158 | (3-methoxypropyl structure) | N-(3-Methoxypropyl)imidazo[1,5-a]-quinoxalin-4-amine | 1.99 |
| 159 | (phenyl-propanediol structure) | [S-(R*,R*)]-2-[(Imidazo[1,5-a]-quinoxalin-4-yl)amino]-1-phenyl-1,3-propanediol | 2.25 |
| 160 | (2-methoxybenzyl structure) | N-[(2-Methoxyphenyl)-methyl]imidazo[1,5-a]quinoxalin-4-amine | 2.69 |
| 161 | (4-methylpiperazinyl structure) | N-(4-Methyl-1-piperazinyl)imidazo[1,5-a]-quinoxalin-4-amine | 1.19 |
| 162 | (2-furanylmethyl structure) | N-(2-Furanylmethyl)imidazo[1,5-a]-quinoxalin-4-amine | 2.30 |
| 163 | (morpholinyl structure) | N-(4-Morpholinyl)imidazo[1,5-a]-quinoxalin-4-amine | 1.75 |
| 164 | (2,4-difluorobenzyl structure) | N-[(2,4-Difluorophenyl)-methyl]imidazo[1,5-a]quinoxalin-4-amine | 2.90 |

TABLE 3-continued

| Ex. No. | W | Compound Name | HPLC Ret Time (min) |
|---|---|---|---|
| 165 | (3-pyridinylmethyl-N-X₁) | N-(3-Pyridinylmethyl)imidazo-[1,5-a]quinoxalin-4-amine | 1.03 |
| 166 | (X₁-N-CH₂-C(CH₃)₂-CH₃ with H₃C) | N-(3,3-Dimethylbutyl)imidazo-[1,5-a]quinoxalin-4-amine | 2.93 |
| 167 | (benzyl-N-X₁) | N-(Phenylmethyl)imidazo[1,5-a]-quinoxalin-4-amine | 2.63 |
| 168 | (cyclohexyl-N-X₁) | N-Cyclohexylimidazo[1,5-a]-quinoxalin-4-amine | 2.56 |
| 169 | (morpholinyl-X₁) | 4-(4-Morpholinyl)imidazo[1,5-a]-quinoxaline | 1.74 |

EXAMPLES 170 TO 222

Compounds 170 to 222 were prepared by the following procedure. Steps A and B were the same for all these examples; general and representative procedures (the latter demonstrating preparation of compound 170) are provided below for Steps C through F.

A. 2-Methoxy-4-Alkoxybenzyl Alcohol Resin[1-3]

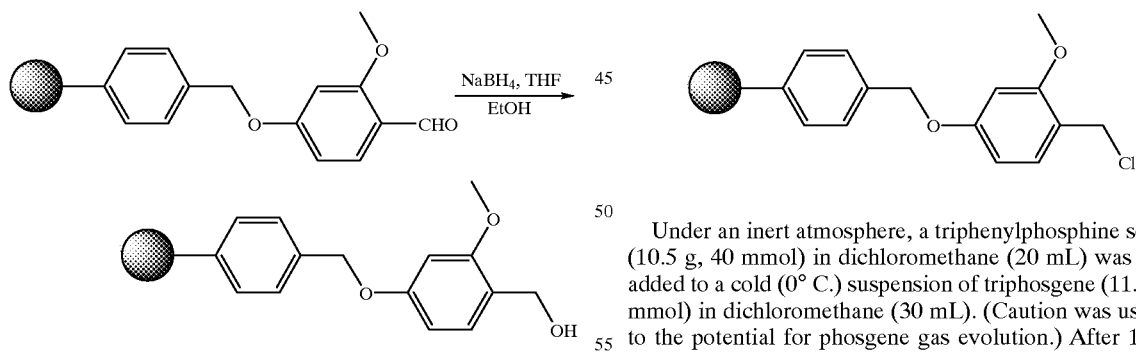

Sodium borohydride (1.51 g, 40 mmol) was added portionwise to a thanol (2/1, 120 mL) suspension of 2-methoxy-4-alkoxy-benzaldehyde resin (polystyrene resin, 2% crosslinked with 1,4-divinylbenzene, where approximately 10% of the polystyrene phenyl groups are functionalized as above) (20 g , ~20 meq.) in a peptide synthesis flask on a vortex shaker. The mixture was stirred for 2.5 h at 25° C. and the solvents were drained. A solution of acetic acid in THF (10%, 200 mL) was added and the resin was stirred for 15 min. The solvents were drained and the resin was washed succesively with THF and methanol. The resin was dried under reduced presure overnight to give ~20 g of the title free flowing colorless resin ("Resin A"). (Resin A is also available commercially as Sasrin®.)

1. *Journal of Organic Chemistry*, 60, 5742–5743 (1995).
2. *Tetrahedron Letters*, 29, 4005–4008 (1988).
3. *Tetrahedron Letters*, 29, 4009–4012 (1988).

B. 2-Methoxy-4-Alkoxybenzyl Chloride Resin[4,5]

Under an inert atmosphere, a triphenylphosphine solution (10.5 g, 40 mmol) in dichloromethane (20 mL) was slowly added to a cold (0° C.) suspension of triphosgene (11.9 g, 40 mmol) in dichloromethane (30 mL). (Caution was used due to the potential for phosgene gas evolution.) After 15 min. stirring at 0° C., the ice bath was removed and the solvent was removed under reduced pressure to give a white solid. The solid was suspended in dichloromethane (60 mL) and Resin A (10 g, ~10 meq.) was added. The mixture was stirred under nitrogen for 4 h, the solvent was drained and the resin was washed repeatedly with anhydrous dichloromethane. The resin was dried under reduced pressure overnight to give ~10.6 g of the title free flowing, colorless resin ("Resin B").

4. *Synthetic Communications*, 23, 711–714 (1993).
5. *Tetrahedron Letters*, 38, 973–976 (1997).

C. 2-Methoxy-4-Alkoxybenzylarylamine Resin

General Procedure

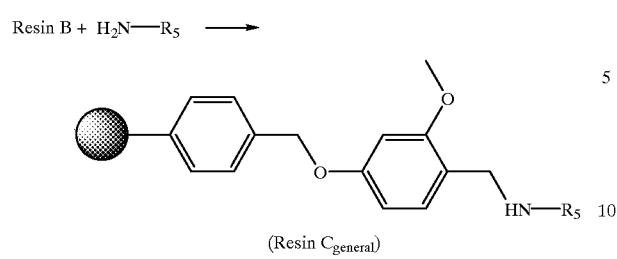

(Resin C$_{general}$)

Representative Procedure

2-Bromoaniline (1.1 g, 6.4 mmol) was added to a suspension of Resin B (1.5 g, ~1.6 meq.) and N,N-diisopropyl-N-ethylamine (280 µL, 1.6 mmol) in THF (15 mL) in a Teflon-lined capped 30 mL vial. The mixture was stirred at 70° C. for 20 h, cooled, filtered and washed with THF, methanol, and dichloromethane. The resin was dried under reduced pressure to give 1.78 g of the following faintly yellow resin ("Resin C"):

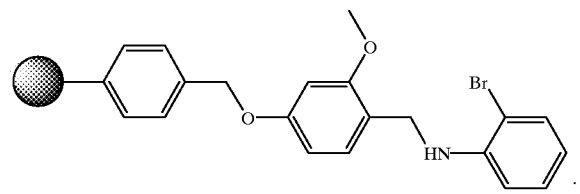

D. 2-Chloro-3-(2-Methoxy-4-Alkoxybenzylarylamino)-quinoxaline Resin

General Procedure

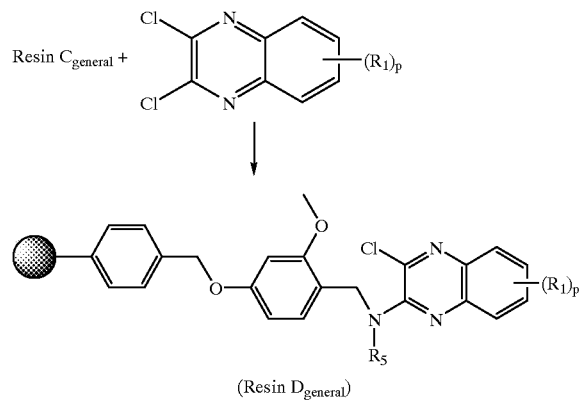

(Resin D$_{general}$)

Representative Procedure

A solution of potassium hexamethyldisilazane (0.5 M in THF, 1.2 mL, 0.6 mmol) was added to a suspension of Resin C (400 mg, ~0.37 meq.) in anhydrous THF (0.3 mL) and the suspension was stirred for 1 h. The solvents were drained, anhydrous THF (2 mL) was added followed by the addition of 2,3-dichloroquinoxaline (150 mg, 0.74 mmol) and the mixture was stirred for 12 h at 25° C. The solvents were drained and the resin was washed with a 10% acetic acid solution in THF, THF, and dichloromethane, and the resin was dried under reduced pressure to give 490 mg of the following yellow resin ("Resin D"):

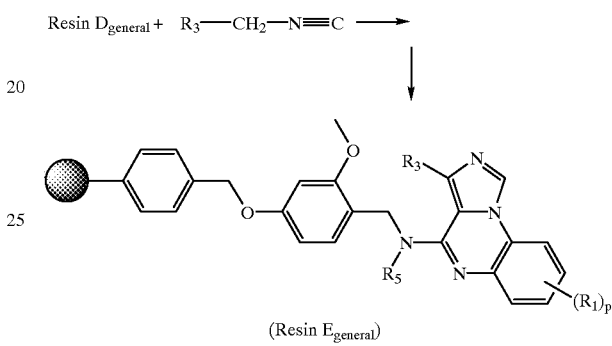

The resin was used as is for the next step.

E. 4-(Arylamino)-Imidazo[1,5-a]quinoxaline Resin

General Procedure

Resin D$_{general}$ + R$_3$—CH$_2$—N≡C ⟶

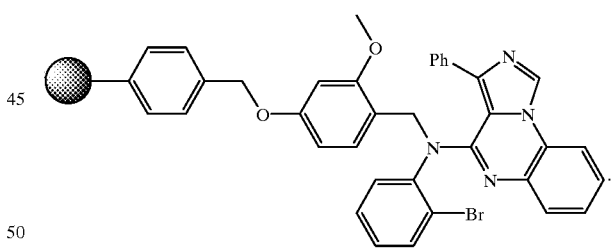

(Resin E$_{general}$)

Representative Procedure[6]

A solution of potassium hexamethyldisilazane (0.5 M in THF, 0.98 mL, 0.05 mmol) was added to a suspension of Resin D (50 mg, ~0.04 meq.) and benzylisocyanide (15 µL, 0.12 mmol) in THF (0.5 mL) at 0° C. The mixture was warmed to 25° C. overnight and a solution of acetic acid in THF (5%, 5 mL) was added. The solvents were drained and the resin was washed with THF/water (1/1), THF, methanol, and dichloromethane yielding the following resin ("Resin E"):

6. *Journal of Medicinal Chemistry*, 39, 3820–3836 (1996)

F. Release from 4-(Arylamino)-Imidazo[1,5-a]quinoxaline Resin

General Procedure

Resin E$_{general}$ + trifluoroacetic acid → Compound of formula I

Representative Procedure

TFA (1 mL) was added to Resin E and the suspension was stirred for 1 h. The TFA solution was collected, the resin was washed with dichloromethane and methanol and the combined washings were concentrated. The residue was dissolved in ethyl acetate and was washed with a solution of 5% aq. sodium bicarbonate. The organic layer was dryed with sodium sulfate and concentrated to give 3.4 mg (20%) of compound 170.

Compounds 170 to 222 prepared by the above procedure have the structure:

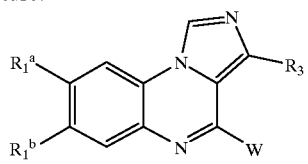

where W, $R_3$, $R_1^a$ and $R_1^b$ are shown in the following Table 4.

In Table 4, $X_1$, $X_2$, $X_3$ and $X_4$ are the imidazoquinoxaline core structures to which W, $R_3$, $R_1^a$ and $R_1^b$, respectively, are bonded, i.e., the respective structures:

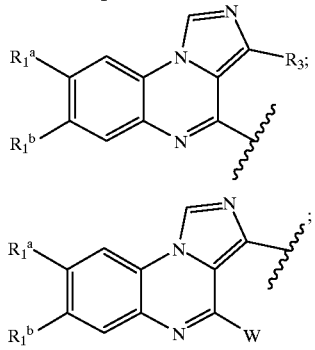

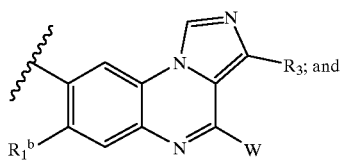

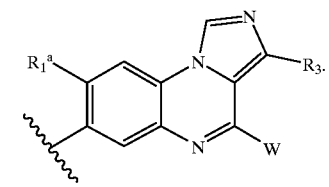

"HPLC Ret Time" is the HPLC retention time under the following conditions: Column: YMC 4.6×50mm; ODS 5 micron Reverse Phase; Flow: 4 ml/min; Solvent A=10% MeOH, 90% $H_2O$, 0.1% $H_3PO_4$; Solvent B=90% MeOH, 10% $H_2O$, 0.1% $H_3PO_4$; 4 minute gradient; 0% B to 100% B; 2 minute hold; UV 220 nm detection.

Unfilled valences on nitrogen indicate the presence of a hydrogen.

TABLE 4

| Ex. No. | W | $R_3$ | $R_1^b$ | $R_1^a$ | Compound Name | HPLC Ret Time (min) |
|---|---|---|---|---|---|---|
| 170 | $X_1$-NH-(2-Br-phenyl) | $X_2$-phenyl | H | H | N-(2-Bromo-phenyl)-3-phenylimidazo-[1,5-a]-quinoxalin-4-amine | 4.98 |
| 171 | $X_1$-NH-(2-Br-phenyl) | $X_2$-CH$_2$-morpholinyl | H | H | N-(2-Bromo-phenyl)-3-(4-morpholinyl-methyl)imidazo-[1,5-a]-quinoxalin-4-amine | 2.86 |
| 172 | $X_1$-NH-(2-Br-phenyl) | H | Cl-$X_4$ | H | N-(2-Bromo-phenyl)-7-chloro-imidazo[1,5-a]-quinoxalin-4-amine | 3.59 |
| 173 | $X_1$-NH-(2-Br-phenyl) | $X_2$-P(O)(OEt)$_2$ | Cl-$X_4$ | Cl-$X_3$ | [4-[(2-Bromo-phenyl)-amino]-7,8-dichloro-imidazo[1,5-a]-quinoxalin-3-yl]phosphonic acid, diethyl ester | 4.76 |

TABLE 4-continued

| Ex. No. | W | R$_3$ | R$_1$$^b$ | R$_1$$^a$ | Compound Name | HPLC Ret Time (min) |
|---|---|---|---|---|---|---|
| 174 | X$_1$-N-(2-bromophenyl) | H | (CH$_3$)$_3$C-X$_4$ | H | N-(2-Bromo-phenyl)-7-(1,1-dimethylethyl)-imidazo[1,5-a]-quinoxalin-4-amine | 3.71 |
| 175 | X$_1$-N-(2-bromophenyl) | X$_2$-P(=O)(OEt)$_2$ | (CH$_3$)$_3$C-X$_4$ | H | [4-[(2-Bromo-phenyl)amino]-7-(1,1-dimethyl-ethyl)imidazo-[1,5-a]quinoxalin-3-yl]phosphonic acid, diethyl ester | 4.47 |
| 176 | X$_1$-N-(2-chlorophenyl) | X$_2$-P(=O)(OMe)$_2$ | H | H | [4-[(2-Chloro-phenyl)amino]-imidazo[1,5-a]quinoxalin-3-yl]phosphonic acid, dimethyl ester | 2.86 |
| 177 | X$_1$-N-(2-chlorophenyl) | H | Cl-X$_4$ | H | 7-Chloro-N-(2-chlorophenyl)-imidazo[1,5-a]-quinoxalin-4-amine | 3.58 |
| 178 | X$_1$-N-(2-chlorophenyl) | H | Cl-X$_4$ | Cl-X$_3$ | 7,8-Dichloro-N-(2-chlorophenyl)-imidazo[1,5-a]-quinoxalin-4-amine | 4.38 |
| 179 | X$_1$-N-(2-chlorophenyl) | H | (CH$_3$)$_3$C-X$_4$ | H | N-(2-Chloro-phenyl)-7-(1,1-dimethylethyl)-imidazo[1,5-a]-quinoxalin-4-amine | 3.72 |
| 180 | X$_1$-N-(2-chlorophenyl) | X$_2$-CH$_2$-morpholinyl | (CH$_3$)$_3$C-X$_4$ | H | N-(2-Chloro-phenyl)-7-(1,1-dimethylethyl)-3-(4-morpholinyl-methyl)imidazo-[1,5-a]quinoxalin-4-amine | 3.62 |
| 181 | X$_1$-N-(2-chloro-6-methylphenyl) | X$_2$-P(=O)(OMe)$_2$ | H | H | [4-[(2-Chloro-6-methylphenyl)-amino]imidazo[1,5-a]-quinoxalin-3-yl]phosphonic acid, dimethyl ester | 2.94 |

TABLE 4-continued

| Ex. No. | W | R₃ | R₁ᵇ | R₁ᵃ | Compound Name | HPLC Ret Time (min) |
|---|---|---|---|---|---|---|
| 182 | 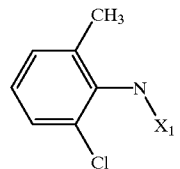 | 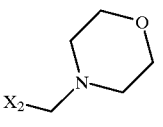 | H | H | N-(2-Chloro-6-methylphenyl)-3-(4-morpholinyl-methyl)imidazo-[1,5-a]quinoxalin-4-amine | 2.90 |
| 183 |  | H | 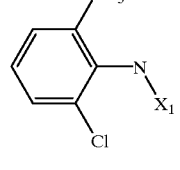 | H | 7-Chloro-N-(2-chloro-6-methylphenyl)-imidazo[1,5-a]-quinoxalin-4-amine | 3.54 |
| 184 |  | 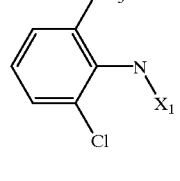 |  | H | [7-Chloro-4-[(2-chloro-6-methylphenyl)amino]-imidazo[1,5-a]-quinoxalin-3-yl]-phosphonic acid, diethyl ester | 4.45 |
| 185 |  | H | 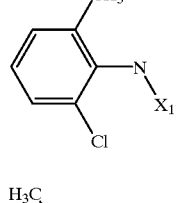 | 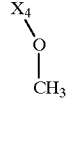 | 7,8-Dichloro-N-(2-chloro-6-methylphenyl)imidazo-[1,5-a]-quinoxalin-4-amine | 4.16 |
| 186 |  | H | 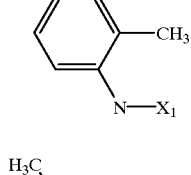 |  | N-(2-Chloro-6-methylphenyl)-7,8-dimethoxy-imidazo-[1,5-a]-quinoxalin-4-amine | 3.00 |
| 187 | 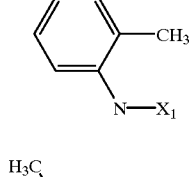 | H | 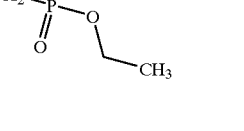 | H | 7-Chloro-N-(2,4-dimethylphenyl)imidazo-[1,5-a]-quinoxalin-4-amine | 3.33 |
| 188 |  |  | 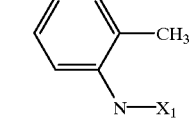 | 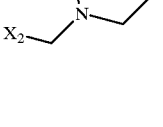 | [7,8-Dichloro-4-[(2,4-dimethyl-phenyl])amino]-imidazo[1,5-a]-quinoxalin-3-yl]phosphonic acid, diethyl ester | 4.86 |
| 189 |  |  | 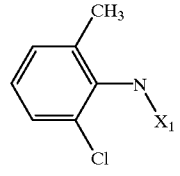 | 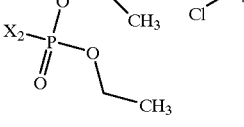 | 7,8-Dimethoxy-N-(2,4-dimethyl-phenyl)-3-(4-morpholinylmethyl)-imidazo[1,5-a]-quinoxalin-4-amine | 3.08 |

TABLE 4-continued

| Ex. No. | W | R₃ | R₁ᵇ | R₁ᵃ | Compound Name | HPLC Ret Time (min) |
|---|---|---|---|---|---|---|
| 190 | 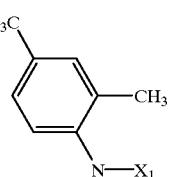 | H |  | H | 7-(1,1-Dimethyl-ethyl)-N-(2,4-dimethylphenyl)-imidazo[1,5-a]-quinoxalin-4-amine | 3.64 |
| 191 | 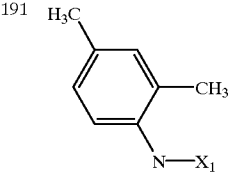 | 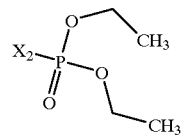 | 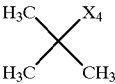 | H | [7-(1,1-Dimethyl-ethyl)-4-[(2,4-dimethylphenyl)-amino]imidazo[1,5-a]-quinoxalin-3-yl]phosphonic acid, diethyl ester | 4.30 |
| 192 | 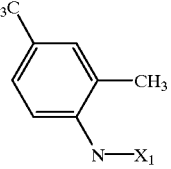 | 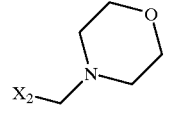 | 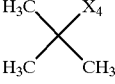 | H | 7-(1,1-Dimethyl-ethyl)-N-(2,4-dimethylphenyl])-3-(4-morpholinylmethyl)-imidazo[1,5-a]-quinoxalin-4-amine | 3.62 |
| 193 | 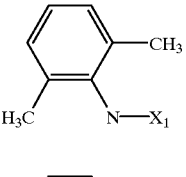 | 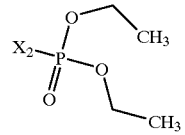 | H | H | [4-[(2,6-Dimethyl-phenyl)amino]-imidazol[1,5-a]-quinoxalin-3-yl]-phosphonic acid, diethyl ester | 3.59 |
| 194 | 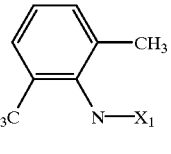 | H |  | H | 7-Chloro-N-(2,6-dimethylphenyl)-imidazo[1,5-a]-quinoxalin-4-amine | 3.18 |
| 195 | 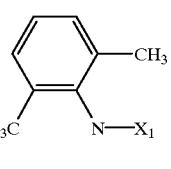 | 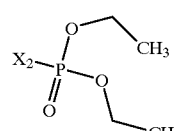 |  | H | [7-Chloro-4-[(2,6-dimethylphenyl)-amino]imidazo-[1,5-a]-quinoxalin-3-yl]-phosphonic acid, diethyl ester | 4.25 |
| 196 | 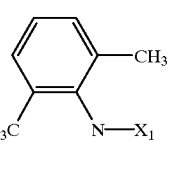 | H |  | H | 7-(1,1-Dimethyl-ethyl)-N-(2,6-dimethylphenyl)-imidazo[1,5-a]-quinoxalin-4-amine | 3.42 |
| 197 | 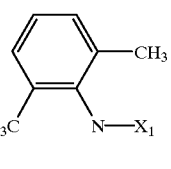 | 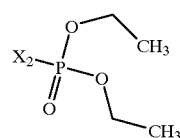 | 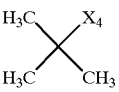 | H | [7-(1,1-Dimethyl-ethyl)-4-[(2,6-dimethylphenyl)-amino]imidazo[1,5-a]-quinoxalin-3-yl]-phosphonic acid, diethyl ester | 4.15 |
| 198 | 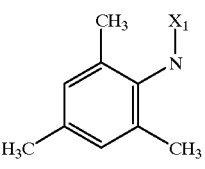 | 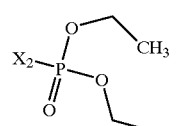 | H | H | [4-[(2,4,6-Trimethylphenyl)-amino]imidazo-[1,5-a]-quinoxalin-3-yl]-phosphonic acid, diethyl ester | 3.77 |

TABLE 4-continued

| Ex. No. | W | R₃ | R₁ᵇ | R₁ᵃ | Compound Name | HPLC Ret Time (min) |
|---|---|---|---|---|---|---|
| 199 | 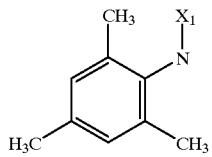 | H |  | H | 7-Chloro-N-(2,4,6-trimethylphenyl)-imidazo[1,5-a]-quinoxalin-4-amine | 3.41 |
| 200 | 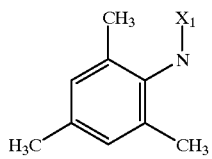 | 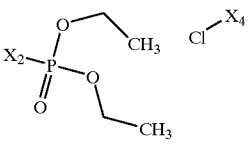 | 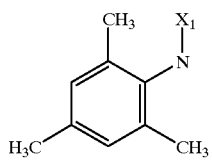 | H | [7-Chloro-4-[(2,4,6-trimethylphenyl)-amino]imidazo[1,5-a]-quinoxalin-3-yl]-phosphonic acid, diethyl ester | 4.35 |
| 201 |  | H |  | 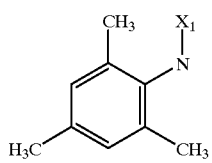 | 7,8-Dichloro-N-(2,4,6-trimethyl-phenyl)imidzo-[1,5-a]quinoxalin-4-amine | 3.95 |
| 202 | 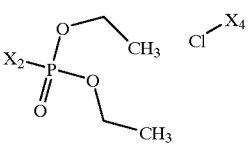 |  |  | 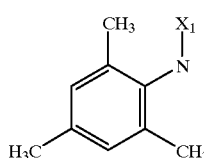 | [7,8-Dichloro-4-[(2,4,6-trimethyl-phenyl)amino]-imidazo[1,5-a]-quinoxalin-3-yl]-phosphonic acid, diethyl ester | 4.82 |
| 203 | 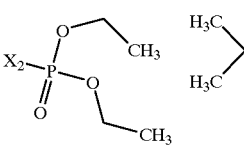 |  | 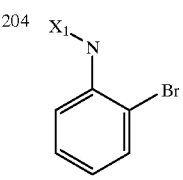 | H | [7-(1,1-Dimethyl-ethyl)-4-[(2,4,6-trimethylphenyl)-amino]imidazo-[1,5-a]quinoxalin-3-yl]-phosphonic acid, diethyl ester | 4.24 |
| 204 | 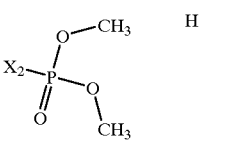 | 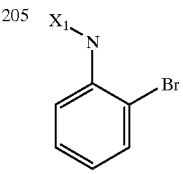 | H | H | [4-[(2-Bromo-phenyl)amino]imidazo-[1,5-a]-quinoxalin-3-yl]-phosphonic acid, dimethyl ester | 2.88 |
| 205 |  | H | H | 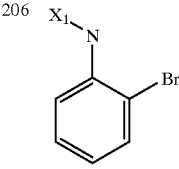 | [N-(2-Bromophenyl)-8-chloroimidazo[1,5-a]-quinoxalin-4-amine | 3.76 |
| 206 | 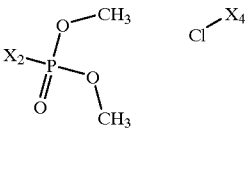 |  |  | Cl-X₃ | [4-[(2-Bromo-phenyl)amino]-7,8-dichloro-imidazo[1,5-a]-quinoxalin-3-yl]-phosphonic acid, dimethyl ester | 3.92 |

TABLE 4-continued

| Ex. No. | W | R$_3$ | R$_1$$^b$ | R$_1$$^a$ | Compound Name | HPLC Ret Time (min) |
|---|---|---|---|---|---|---|
| 207 |  | 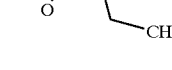 |  | H | [4-[(2-Bromo-phenyl)amino]-8-(1,1-dimethyl-ethyl)imidazo-[1,5-a]quinoxalin-3-yl]-phosphonic acid, diethyl ester | 4.54 |
| 208 |  | 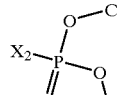 |  | H | [4-[(2-Bromo-phenyl)amino]-7-(1,1-dimethyl-ethyl)imidazo-[1,5-a]quinoxalin-3-yl]-phosphonic acid, dimethyl ester | 3.72 |
| 209 |  | H | H |  | 8-Chloro-N-(2-chlorophenyl)imidazo[1,5-a]-quinoxalin-4-amine | 3.75 |
| 210 |  | 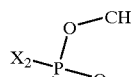 |  | H | [4-[(2-Chloro-phenyl)amino]-7-(1,1-dimethyl-ethyl)imidazo-[1,5-a]quinoxalin-3-yl]-phosphonic acid, dimethyl ester | 3.72 |
| 211 |  | 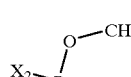 |  | H | [7-Chloro-4-[(2-chloro-6-methyl-phenyl)amino]imidazo[1,5-a]-quinoxalin-3-yl]-phosphonic acid, dimethyl ester | 3.33 |
| 212 |  |  |  | H | [7-Chloro-4-[(2,4-dimethylphenyl)amino]-imidazo-[1,5-a]-quinoxalin-3-yl]-phosphonic acid, dimethyl ester | 3.28 |
| 213 |  |  | H |  | [8-Chloro-4-[(2,4-dimethylphenyl)-amino]imidazo-[1,5-a]quinoxalin-3-yl]-phosphonic acid, dimethyl ester | 3.41 |
| 214 |  | 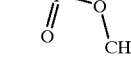 |  |  | [7,8-Dichloro-4-[(2,4-di-methylphenyl)amino-imidazo-[1,5-a]-quinoxalin-3-yl]-phosphonic acid, dimethyl ester | 3.76 |

TABLE 4-continued

| Ex. No. | W | R₃ | R₁ᵇ | R₁ᵃ | Compound Name | HPLC Ret Time (min) |
|---|---|---|---|---|---|---|
| 215 | 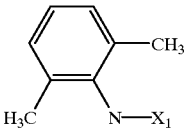 | 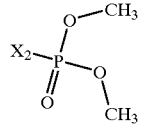 | H | H | [4-[(2,6-Dimethyl-phenyl)amino]imidazo-[1,5-a]quinoxalin-3-yl]-phosphonic acid, dimethyl ester | 2.81 |
| 216 | 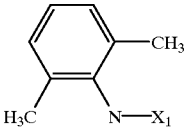 | 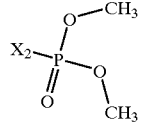 |  | H | [7-Chloro-4-[(2,6-dimethylphenyl)-amino]imidazo-[1,5-a]quinoxalin-3-yl]-phosphonic acid, dimethyl ester | 3.14/3.25 |
| 217 | 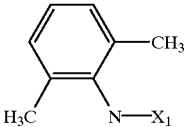 | 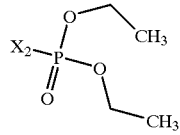 | H |  | [8-Chloro-4-[(2,4-dimethylphenyl)amino-imidazo[1,5-a]-quinoxalin-3-yl]-phosphonic acid, diethyl ester | 4.35 |
| 218 | 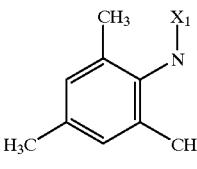 | 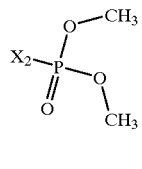 | H | H | [4-[(2,4,6-Trimethyl-phenyl)amino]imidazo[1,5-a]-quinoxalin-3-yl]-phosphonic acid, dimethyl ester | 3.13 |
| 219 | 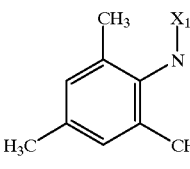 | 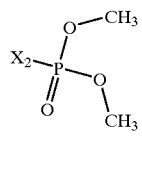 |  | H | [7-Chloro-4-[(2,4,6-trimethylphenyl)-amino]imidazo[1,5-a]-quinoxalin-3-yl]-phosphonic acid, dimethyl ester | 3.40/3.50 |
| 220 | 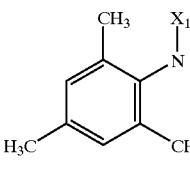 | 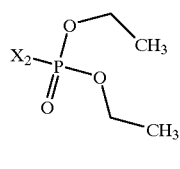 | H |  | [8-Chloro-4-[(2,4,6-trimethylphenyl)-amino]imidazo[1,5-a]-quinoxalin-3-yl]-phosphonic acid, diethyl ester | 4.47 |
| 221 | 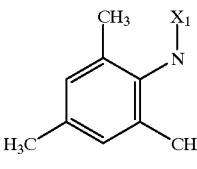 | 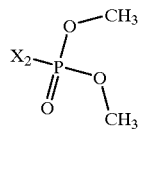 |  |  | [7,8-Dichloro-4-[(2,4,6-trimethylphenyl)-amino]imidazo-[1,5-a]quinoxalin-3-yl]-phosphonic acid, dimethyl ester | 3.83 |
| 222 | 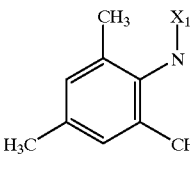 | 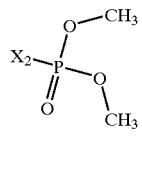 | 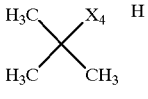 | H | [7-(1,1-Dimethyl-ethyl)-4-[(2,4,6-trimethylphenyl)-amino]imidazo[1,5-a]-quinoxalin-3-yl]-phosphonic acid, dimethyl ester | 3.95 |

EXAMPLES 223 TO 234

Compounds 223 to 234 were prepared by a route analogous to that used for the preparation of 130E, using the appropriate amine in place of 2,4,6-trimethylaniline. HPLC conditions for HPLC retention time: YMC C18 S-5 120 Å ODS column, 4.6×50 mm; 0% B–100% B, linear gradient over 4 min at 4.0 ml/min; then isocratic for 2 min at 100% B, Solvent A: 10% MeOH-90% $H_2O$-0.2% $H_3PO_4$, Solvent B: 90% MeOH-10% $H_2O$-0.2% $H_3PO_4$. Unfilled valences on nitrogen indicate the presence of a hydrogen.

TABLE 5

| Ex. No. | Structure | Compound Name | HPLC Ret Time (min) |
|---|---|---|---|
| 223 | 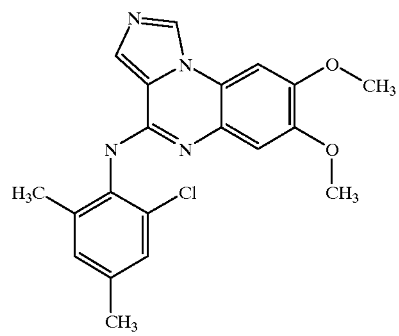 | N-(2-Chloro-4,6-dimethylphenyl)-7,8-dimethoxyimidazo[1,5-a]-quinoxalin-4-amine | 3.15 |
| 224 | 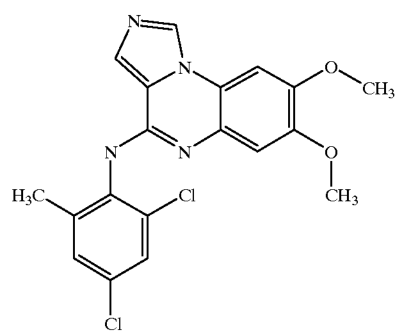 | N-(2,4-Dichloro-6-methylphenyl)-7,8-dimethoxyimidazo[1,5-a]-quinoxalin-4-amine | 3.49 |
| 225 | 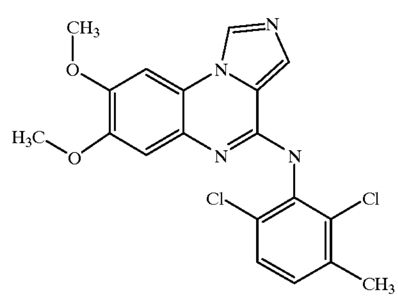 | N-(2,6-Dichloro-3-methylphenyl)-7,8-dimethoxyimidazo[1,5-a]-quinoxalin-4-amine | 3.26 |
| 226 | 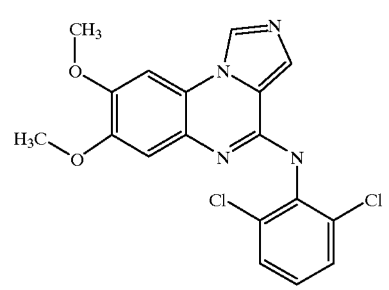 | N-(2,6-Dichlorophenyl)-7,8-dimethoxyimidazo[1,5-a]-quinoxalin-4-amine | 3.08 |

TABLE 5-continued

| Ex. No. | Structure | Compound Name | HPLC Ret Time (min) |
|---|---|---|---|
| 227 | 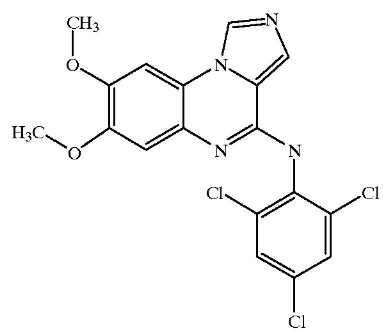 | 7,8-Dimethoxy-N-(2,4,6-trichlorophenyl)imidazo[1,5-a]quinoxalin-4-amine | 3.75 |
| 228 | 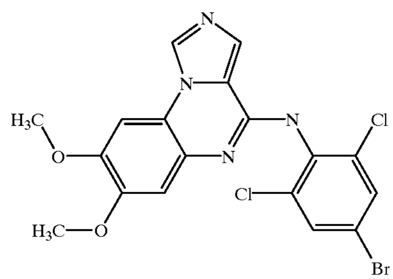 | N-(4-Bromo-2,6-dichlorophenyl)-7,8-dimethoxyimidazo[1,5-a]-quinoxalin-4-amine | 3.85 |
| 229 | 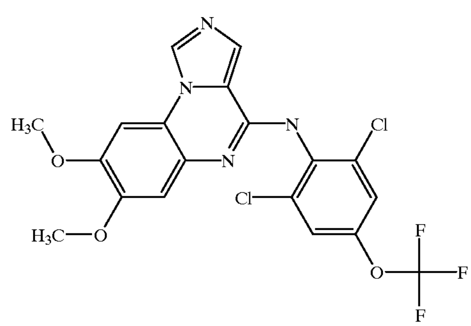 | N-[2,6-Dichloro-4-(trifluoromethoxy)phenyl]-7,8-dimethoxyimidazo[1,5-a]-quinoxalin-4-amine | 3.99 |
| 230 | 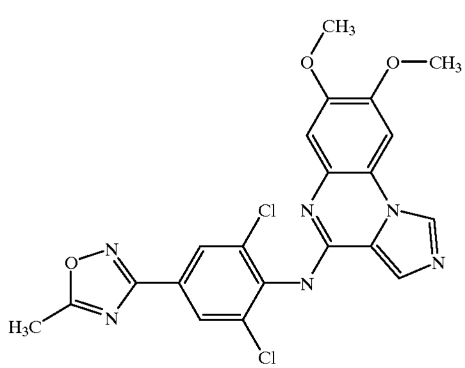 | N-[2,6-Dichloro-4-(5-methyl-1,2,4-oxadiazol-3-yl)phenyl]-7,8-dimethoxyimidazo[1,5-a]-quinoxalin-4-amine | 3.69 |

TABLE 5-continued

| Ex. No. | Structure | Compound Name | HPLC Ret Time (min) |
|---|---|---|---|
| 231 | 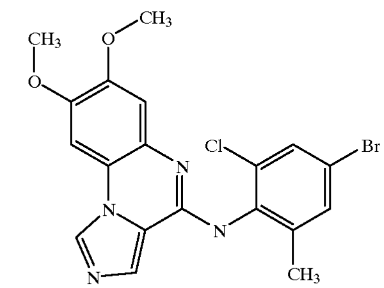 | N-(4-Bromo-2-cloro-6-methyl-phenyl)-7,8-dimethoxyimidazo[1,5-a]quinoxalin-4-amine | 3.6 |
| 232 | 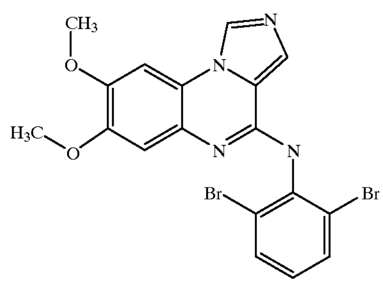 | N-(2,6-Dibromophenyl)-7,8-dimethoxyimidazo[1,5-a]-quinoxalin-4-amine | 3.11 |
| 233 | 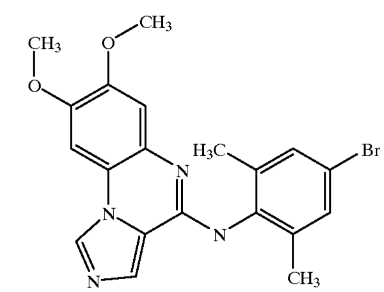 | N-(4-Bromo-2,6-dimethylphenyl)-7,8-dimethoxyimidazo[1,5-a]-quinoxalin-4-amine | 3.24 |
| 234 | 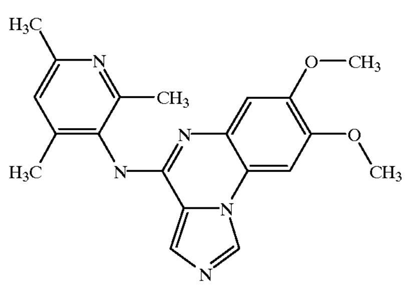 | 7,8-Dimethoxy-N-(2,4,6-trimethyl-3-pyridinyl)imidazo[1,5-a]quinoxalin-4-amine | 1.92 |

EXAMPLES 235 TO 258

Compounds 235 to 258 were prepared by a route analogous to that used for the preparation of 1F substituting 2-chloro-6-methyl aniline with the appropriate amines. HPLC conditions for HPLC retention time were the same as those used for Table 5. Unfilled valences on nitrogen indicate the presence of a hydrogen.

TABLE 6

| Ex. No. | Structure | Compound Name | HPLC Ret Time (min) |
|---|---|---|---|
| 235 | 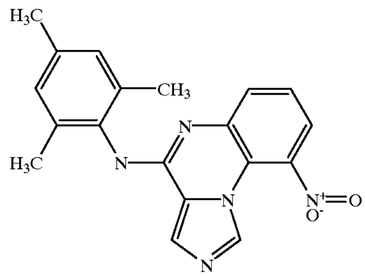 | 9-Nitro-N-(2,4,6-trimethylphenyl)imidazo[1,5-a]-quinoxalin-4-amine | 4.01 |
| 236 | 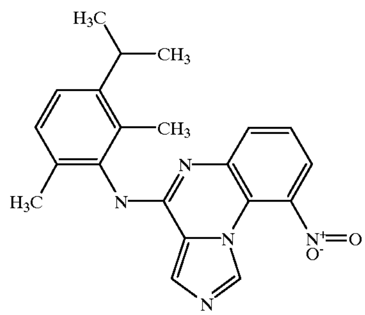 | N-[2,6-Dimethyl-3-(1-methylethyl)-phenyl]-9-nitroimidazo[1,5-a]-quinoxalin-4-amine | 4.36 |
| 237 | 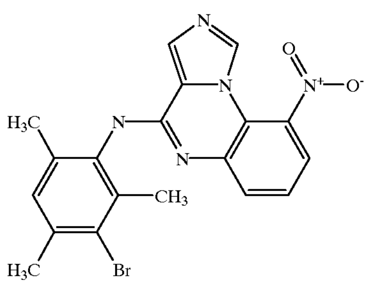 | N-(3-Bromo-2,4,6-trimethylphenyl)-9-nitroimidazo[1,5-a]quinoxalin-4-amine | 4.52 |
| 238 | 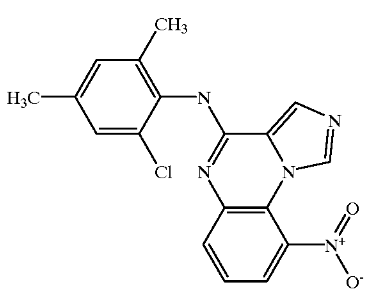 | N-(2-Chloro-4,6-dimethylphenyl)-9-nitroimidazo[1,5-a]quinoxalin-4-amine | 4.16 |
| 239 | 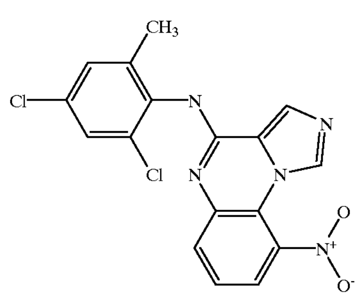 | N-(2,4-Dichloro-6-methylphenyl)-9-nitroimidazo[1,5-a]quinoxalin-4-amine | 4.41 |

TABLE 6-continued

| Ex. No. | Structure | Compound Name | HPLC Ret Time (min) |
|---|---|---|---|
| 240 | 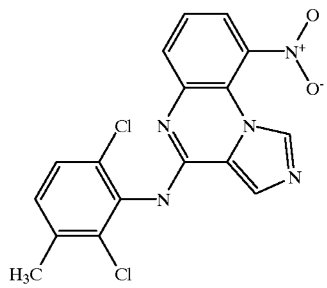 | N-(2,6-Dichloro-3-methylphenyl)-9-nitroimidazo[1,5-a]quinoxalin-4-amine | 4.14 |
| 241 | 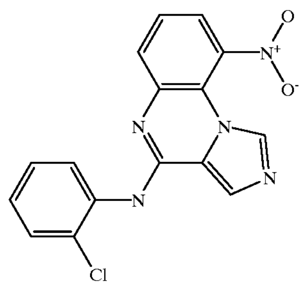 | N-(2-Chlorophenyl)-9-nitroimidazo[1,5-a]quinoxalin-4-amine | 4.04 |
| 242 | 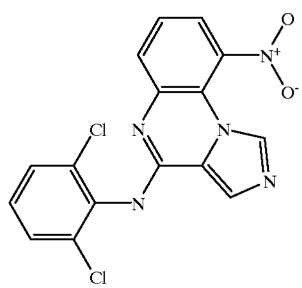 | N-(2,6-Dichlorophenyl)-9-nitroimidazo-[1,5-a]quinoxalin-4-amine | 3.97 |
| 243 | 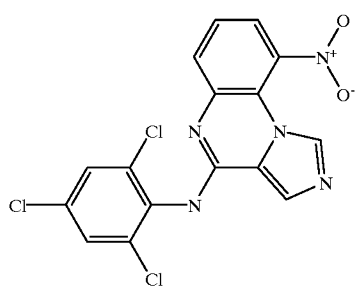 | 9-Nitro-N-(2,4,6-trichlorophenyl)imidazo[1,5-a]-quinoxalin-4-amine | 4.43 |
| 244 | 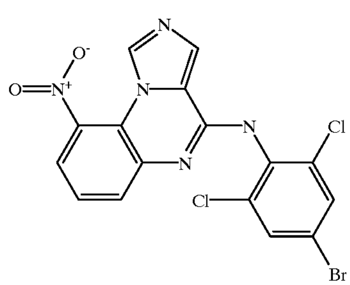 | N-(4-Bromo-2,6-dichlorophenyl)-9-nitroimidazo[1,5-a]quinoxalin-4-amine | 4.48 |

TABLE 6-continued

| Ex. No. | Structure | Compound Name | HPLC Ret Time (min) |
|---|---|---|---|
| 245 | 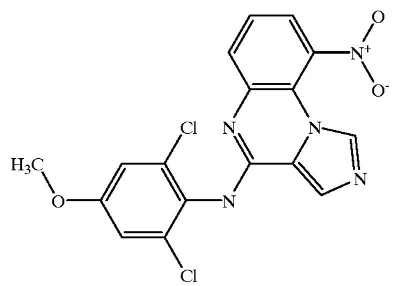 | N-(2,6-Dichloro-4-methoxyphenyl)-9-nitroimidazo[1,5-a]quinoxalin-4-amine | 4.07 |
| 246 | 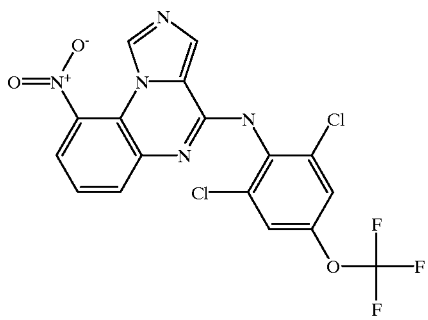 | N-[2,6-Dichloro-4-(trifluoromethoxy)-phenyl]-9-nitroimidazo[1,5-a]-quinoxalin-4-amine | 4.5 |
| 247 | 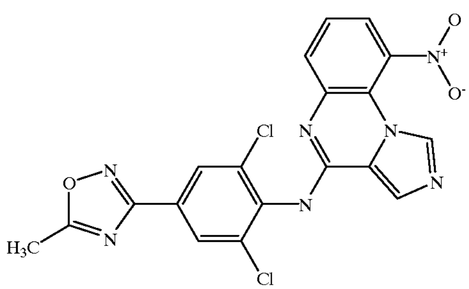 | N-[2,6-Dichloro-4-(5-methyl-1,2,4-oxadiazol-3-yl)phenyl]-9-nitroimidazo-[1,5-a]quinoxalin-4-amine | 4.29 |
| 248 | 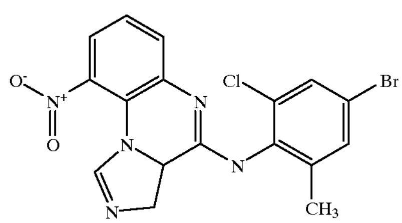 | N-(4-Bromo-2-chloro-6-methylphenyl)-9-nitroimidazo[1,5-a]quinoxalin-4-amine | 4.46 |
| 249 | 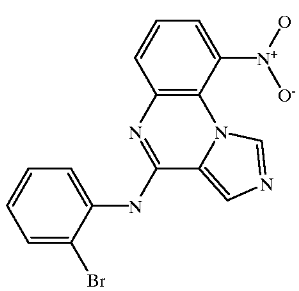 | N-(2-Bromophenyl)-9-nitroimidazo[1,5-a]quinoxalin-4-amine | 4.01 |

TABLE 6-continued

| Ex. No. | Structure | Compound Name | HPLC Ret Time (min) |
| --- | --- | --- | --- |
| 250 | 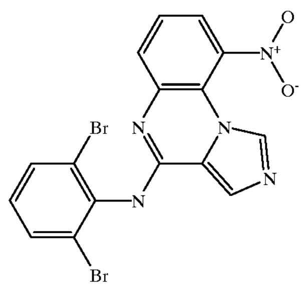 | N-(2,6-Dibromophenyl)-9-nitroimidazo-[1,5-a]quinoxalin-4-amine | 3.99 |
| 251 | 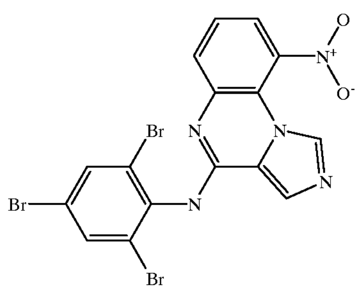 | N-(2,4,6-Tribromophenyl)-9-nitroimidazo[1,5-a]quinoxalin-4-amine | 4.5 |
| 252 | 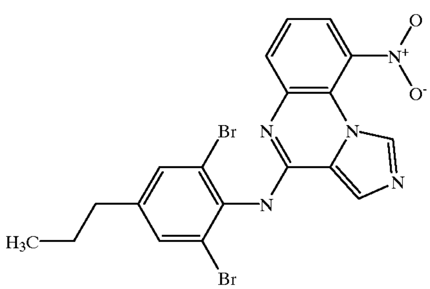 | N-(2,6-Dibromo-4-propylphenyl)-9-nitroimidazo[1,5-a]quinoxalin-4-amine | 4.56 |
| 253 | 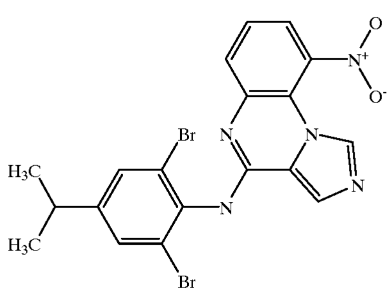 | N-[2,6-Dibromo-4-(1-methylethyl)-phenyl]-9-nitroimidazo[1,5-a]quinoxalin-4-amine | 4.52 |
| 254 | 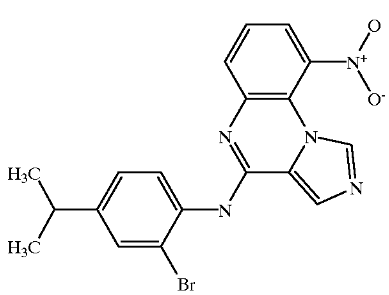 | N-[2-Bromo-4-(1-methylethyl)phenyl]-9-nitroimidazo[1,5-a]quinoxalin-4-amine | 4.48 |

TABLE 6-continued

| Ex. No. | Structure | Compound Name | HPLC Ret Time (min) |
|---|---|---|---|
| 255 | 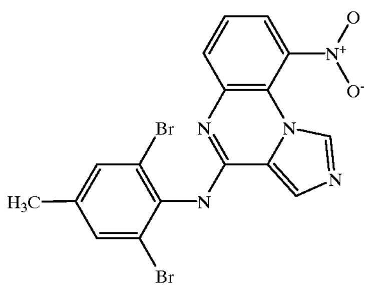 | N-(2,6-Dibromo-4-methylphenyl)-9-nitroimidazo[1,5-a]quinoxalin-4-amine | 4.22 |
| 256 | 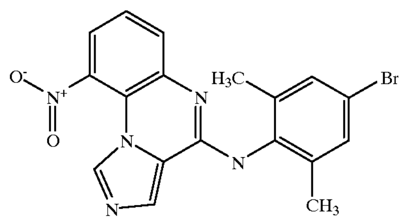 | N-(4-Bromo-2,6-dimethylphenyl)-9-nitroimidazo[1,5-a]quinoxalin-4-amine | 4.39 |
| 257 | 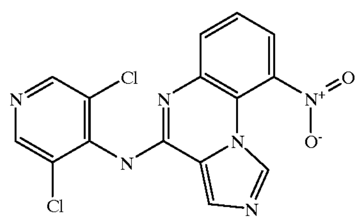 | N-(3,5-Dichloro-4-pyridinyl)-9-nitroimidazo[1,5-a]quinoxalin-4-amine | 3.71 |
| 258 | 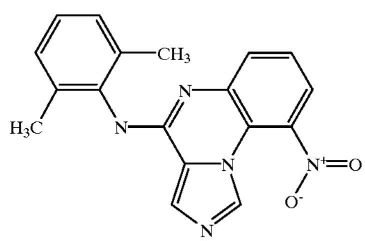 | N-(2,6-Dimethylphenyl)-9-nitroimidazo-[1,5-a]quinoxalin-4-amine | 3.77 |

EXAMPLE 259

Preparation of N-[4-[(2,6-Dimethylphenyl)amino]imidazo[1,5-a]quinoxalin-8-yl]-3-methoxypropanamide

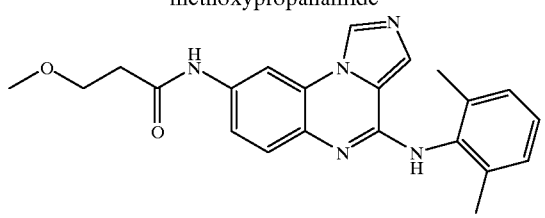

Analogous to the preparation of 3 using 3-methoxypropanoic acid to give the title compound. HPLC Ret time=28.16 min (HPLC conditions: Column: YMC, Inc. ODS 3 micron 6.0×150 mm; flow: 1.5 mL/min; solvents: A=10% MeOH, 90% $H_2O$ with 0.1% $H_3PO_4$ added, B=90% MeOH, 10% $H_2O$ with 0.1% $H_3PO_4$ added. A 30 minute gradient, 0% B to 100% B followed by 10 minutes at 100% B. Detection was by absorption at 217 or 254 nm.

EXAMPLE 260

Preparation of N-[4-[(2,6-Dimethylphenyl)amino]imidazo[1,5-a]quinoxalin-8-yl]-2-cyanoacetamide

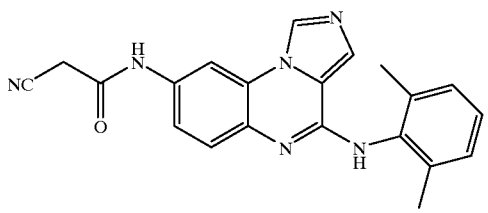

Analogous to the preparation of 3 using 2-cyanoacetic acid to give the title compound. HPLC Ret time=2.89 min (HPLC conditions: YMC C18 S-5 120 Å ODS column, 4.6×50 mm; 0% B–100% B, linear gradient over 4 min at 4.0 mmin; 2 min isocratic at 100% B, Solvent A: 10% MeOH-90% $H_2O$-0.2% $H_3PO_4$; Solvent B: 90% MeOH-10% $H_2O$-0.2% $H_3PO_4$.)

EXAMPLE 261

Preparation of $N^4$-(2,6-Dimethylphenyl)-$N^8,N^8$-dimethylimidazo[1,5-a]quinoxaline-4,8-diamine

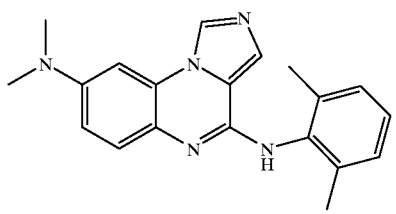

To 12 (17 mg, 0.056 mmol), sodium triacetoxyborohydride (95 mg, 0.448 mmol), and 1 mL dichloroethane, formaldehyde (37% wt. in water, 9 μL, 0.118 mmol) was added and the mixture stirred at room temperature for 40 min. The reaction was quenched with sat. sodium bicarbonate and extracted with ethyl acetate. The organic layer was washed with brine, dried over magnesium sulfate, filtered and concentrated in vacuo to give a brown oil (13 mg, 70%): MS $(M+H)^+$=332. HPLC Ret time=3.26 min (HPLC conditions: same as used for Example 260).

EXAMPLE 262

Preparation of $N^4$-(2,6-Dimethylphenyl)-$N^8,N^8$-diethylimidazo[1,5-a]quinoxaline-4,8-diamine

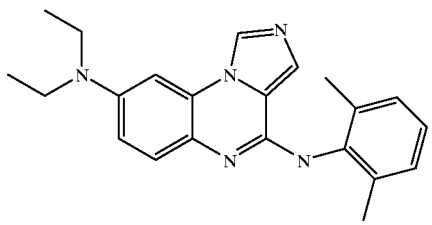

Analogous to the preparation of 261 using acetaldehyde. HPLC Ret time=3.20 min (HPLC conditions: same as used for Example 260).

EXAMPLE 263

Preparation of 4-[(2,6-Dimethylphenyl)amino]imidazo[1,5-a]quinoxaline-7,8-diol

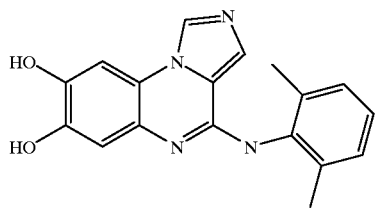

To 131 (17 mg, 0.056 mmol) and 0.5 mL dichloromethane at 0° C. was added borontribromide (15 μL, 0.157 mmol) in 0.3 mL dichloromethane and the mixture was stirred overnight. The reaction was quenched with water and extracted with ethyl acetate. The organic layer was dried over magnesium sulfate, filtered and concentrated in vacuo to give a crude brown solid. Recrystallization from MeOH/Hexane/Chloroform gave the title compound as a yellow solid (11 mg, 92%): MS $(M+H)^+$=321. HPLC Ret time=2.78 min (HPLC conditions: same as used for Example 260).

EXAMPLE 264

Preparation of N-[4-[(2-Chloro-6-methylphenyl)amino]imidazo[1,5-a]quinoxalin-8-yl]-2-thiophenebutanamide

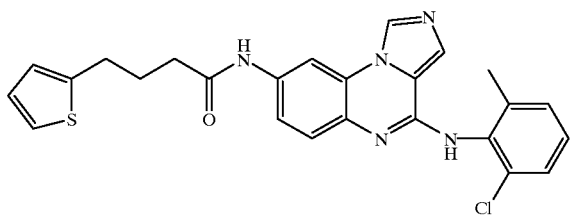

Analogous to the preparation of 3 using 2-thiophenebutyric acid to give the title compound as a tan solid: MS $(M+H)^+$=476; HPLC: Ret Time=27.43 min. (HPLC conditions: same as used for Example 259).

EXAMPLE 265 TO 270

Compounds 265 to 270 were prepared by a route analogous to that used for the preparation of 2, substituting 2-chloro-6-methyl aniline with the appropriate amines in step 1F.

TABLE 7

| Ex. No. | Structure[a] | Compound Name | HPLC retention time (min)[b] |
|---|---|---|---|
| 265 | | N[4]-(2,6-Dimethylphenyl)imidazo[1,5-a]quinoxaline-4,9-diamine | 2.43 |
| 266 | | N[4]-(2,4,6-Trimethylphenyl)imidazo[1,5-a]quinoxaline-4,9-diamine | 2.79 |
| 267 | | N[4]-[2,6-Dimethyl-3-(1-methylethyl)phenyl]imidazo[1,5-a]quinoxaline-4,9-diamine | 3.17 |
| 268 | | N[4]-(3-Bromo-2,4,6-trimethylphenyl)imidazo[1,5-a]quinoxaline-4,9-diamine | 3.18 |
| 269 | | N[4]-(2-Chloro-4,6-dimethylphenyl)imidazo[1,5-a]quinoxaline-4,9-diamine | 2.87 |

TABLE 7-continued

| Ex. No. | Structure[a] | Compound Name | HPLC retention time (min)[b] |
|---|---|---|---|
| 270 | | N[4]-(2,4-Dichloro-6-methylphenyl)imidazo[1,5-a]quinoxaline-4,9-diamine | 3.12 |

EXAMPLE 271

Preparation of N-(2-Chloro-6-methylphenyl)-8-iodoimidazo[1,5-a]quinoxalin-4-amine

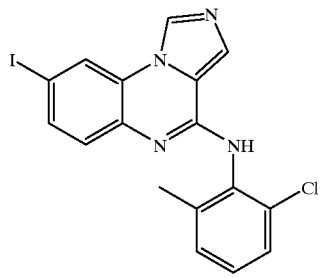

A. N-(2-Fluoro-4-iodophenyl)-1H-imidazole-5-carboxamide

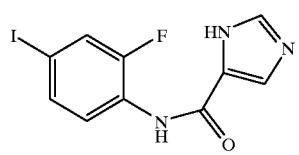

Compound 271A was prepared by a method analogous to that used for the preparation of 17E using 4-iodo-2-fluoroaniline.

B. 8-Iodoimidazo[1,5-a]quinoxalin-4(5H)-one

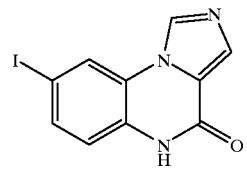

Compound 271B was prepared from 271A by a method analogous to the alternative method for the preparation of 17D described above.

C. N-(2-Chloro-6-methylphenyl)-8-iodoimidazo[1,5-a]quinoxalin-4-amine

Compound 271C was prepared from 271B by a method analogous to that used for the preparation of 17G. HPLC Retention time=3.86 min (HPLC Conditions: "HPLC Method 2").

EXAMPLE 272

Preparation of N-(2-Chloro-6-methylphenyl)-8-fluoroimidazo[1,5-a]quinoxalin-4-amine

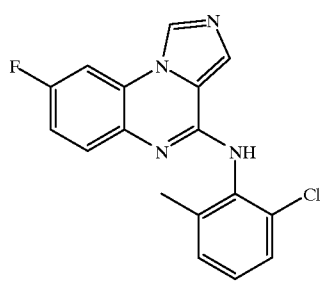

A. N-(2,4-Difluorophenyl)-1H-imidazole-5-carboxamide

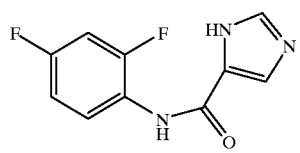

Compound 272A was prepared by a method analogous to that used for the preparation of 17E using 4-fluoro-2-fluoroaniline.

B. 8-Fluoroimidazo[1,5-a]quinoxalin-4(5H)-one

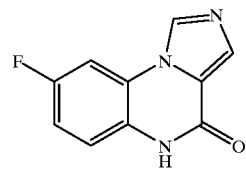

Compound 272B was prepared from 272A by a method analogous to the alternative method for the preparation of 17D described above.

C. N-(2-Chloro-6-methylphenyl)-8-fluoroimidazo[1,5-a]quinoxalin-4-amine

Compound 272C was prepared from 272B by a method analogous to that used for the preparation of 17G. HPLC Retention time=3.08 min (HPLC Conditions: "HPLC Method 2").

EXAMPLE 273

This Example demonstrates preparation of compound 273C, and compounds 274 to 277 prepared by an analogous procedure (Examples 274 to 277).

A. 8-Methoxyimidazo[1,5-a]quinoxalin-4(5H)-one

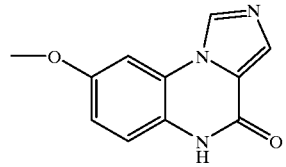

To a solution of 271B (700 mg, 2.25 mmol) in MeOH (6 mL) and DMSO (7 mL) was added 60% NaH (270 mg, 6.75 mmol). The mixture was stirred for 10 min at room temperature. To the mixture was then added CuBr (162 mg, 1.125 mmol) and the reaction heated in a sealed tube to 200° C. for 4 hours. The mixture was cooled to room temperature, quenched with acetic acid and concentrated under vacuo. Water and NaHCO₃ were added and the crude product filtered, then dried under vacuo.

B. 4-Chloro-8-methoxyimidazo[1,5-a]quinoxaline

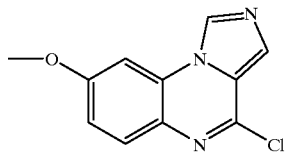

Compound 273B was prepared from 273A by a method analogous to that used for the preparation of 17F.

Compounds 273C and 274 to 277 were prepared from 273B by a route analogous to that used for the preparation of 17G. These compounds have the structure:

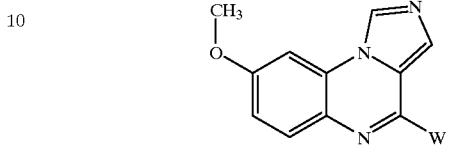

where W is shown in the following Table 8.

In Table 8, $X_1$ is the imidazoquinoxaline core structure to which W is bonded, i.e., the structure:

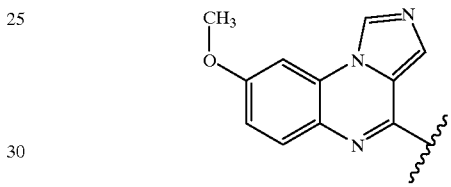

TABLE 8

| Ex. No. | Wᵃ | Compound Name | HPLC retention time (min)ᵇ |
|---|---|---|---|
| 273C | ![X₁-N-(2-Cl-6-Me-phenyl)] | N-(2-Chloro-6-methylphenyl)-8-methoxyimidazo[1,5-a]quinoxalin-4-amine | 2.941 |
| 274 | ![X₁-N-(2,6-diMe-phenyl)] | N-(2,6-Dimethylphenyl)-8-methoxyimidazo[1,5-a]quinoxalin-4-amine | 2.744 |
| 275 | ![X₁-N-(2,6-diCl-phenyl)] | N-(2,6-Dichlorophenyl)-8-methoxyimidazo[1,5-a]quinoxalin-4-amine | 3.201 |

TABLE 8-continued

| Ex. No. | W[a] | Compound Name | HPLC retention time (min)[b] |
|---|---|---|---|
| 276 | 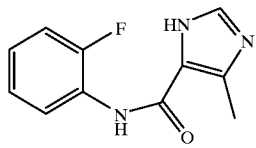 | N-(2,4,6-Trimethylphenyl)-8-methoxyimidazo[1,5-a]quinoxalin-4-amine | 3.007 |
| 277 | 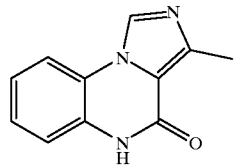 | N-(2-Chlorophenyl)-8-methoxyimidazo[1,5-a]quinoxalin-4-amine | 3.205 |

[a]. Unfilled valences on nitrogen indicate the presence of a hydrogen.
[b]. HPLC Conditions: "HPLC Method 2".

EXAMPLE 278

This Example demonstrates preparation of compound 278D, and compounds 279 and 280 prepared by an analogous method (Examples 279 and 280).

A. N-(2-Fluorophenyl)-5-methyl-1H-imidazole-4-carboxamide

To ethyl-4-methyl-5-imidazolecarboxylate (5 g, 32.4 mmol) was added 20 mL of 2-fluoroaniline and potassium carbonate (8.9 g, 64.8 mmol). The reaction mixture was heated to reflux for 18 h then cooled to room temperature and concentrated in vacuo. Water and hexane were added and the precipitate filtered to give the crude product.

B. 3-Methylimidazo[1,5-a]quinoxalin-4(5H)-one

Compound 278B was prepared from 278A by a method analogous to the alternative method for the preparation of 17D described above.

C. 4-Chloro-3-methylimidazo[1,5-a]quinoxaline

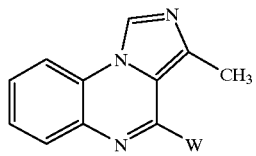

Compound 278C was prepared from 278B by a method analogous to that used for the preparation of 17F.

Compounds 278D, 279 and 280 were prepared from 278C by a method analogous to that used for the preparation of 17G. These compounds have the structure:

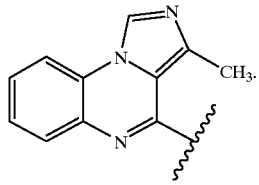

where W is shown in the following Table 9.

In Table 9, $X_1$ is the imidazoquinoxaline core structure to which W is bonded, i.e., the structure:

TABLE 9

| Ex. No. | W[a] | Compound Name | HPLC retention time[b] (min) |
|---|---|---|---|
| 278D | ![structure] | N-(2-Chloro-6-methylphenyl)-3-methylimidazo[1,5-a]quinoxalin-4-amine | 2.983 |
| 279 | ![structure] | N-(2,6-Dimethylphenyl)-3-methylimidazo[1,5-a]quinoxalin-4-amine | 2.500 |
| 280 | ![structure] | N-(2-Chlorophenyl)-3-methylimidazo[1,5-a]quinoxalin-4-amine | 4.009 |

[a]. Unfilled valences on nitrogen indicate the presence of a hydrogen.
[b]. HPLC Conditions: "HPLC Method 2".

EXAMPLE 281

Preparation of N-(2-Chloro-6-methylphenyl)-8-(4-methyl-1-piperazinyl)imidazo[1,5-a]quinoxalin-4-amine

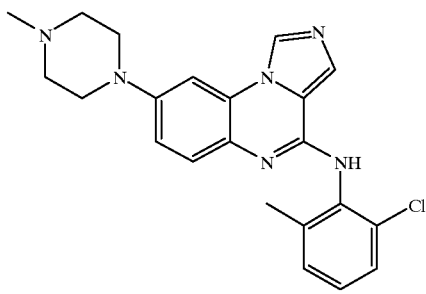

A mixture of 272C (50 mg) and 1-methylpiperazine (1 mL) was heated in a sealed tube at 300° C. for 18 h. The mixture was cooled to room temperature and water was added. The crude product was filtered and dried under vacuo. HPLC Retention time=2.00 min. (HPLC Conditions: "HPLC Method 2").

EXAMPLE 282

Preparation of N-(2-Chloro-6-methylphenyl)-8-phenylimidazo[1,5-a]quinoxalin-4-amine

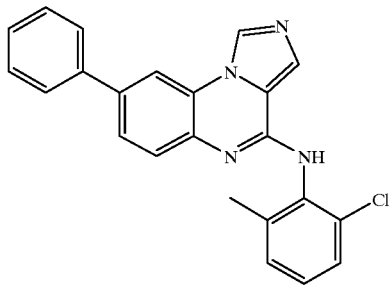

To 271C (50 mg, 0.115 mmol) was added phenylboronic acid (21.1 mg, 0.173 mmol), toluene (1 mL), ethanol (0.8 mL), 2M $Na_2CO_3$ (0.7 mL) and catalytic tetrakis (triphenylphosphine)palladium(0). The mixture was heated to 80° C. for 2 h then cooled to room temperature and extracted with $CH_2Cl_2$. The organic layer was concentrated and the crude material subjected to column chromatography purification. HPLC retention time=3.88 min (HPLC conditions: "HPLC Method 2").

EXAMPLE 283

Preparation of N-(2-Chloro-6-methylphenyl)-8-(4-methoxyphenyl)imidazo[1,5-a]quinoxalin-4-amine

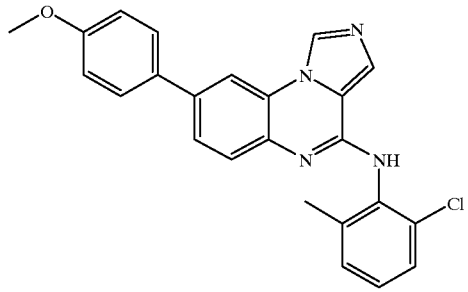

Compound 283 was prepared by a method analogous to that used for the preparation of 282 using 4-methoxyphenyl boronic acid. HPLC retention time=3.84 min (HPLC conditions: "HPLC Method 2").

EXAMPLE 284

Preparation of $N^4$-(2-Chloro-6-methylphenyl)-$N^8$-ethylimidazo[1,5-a]quinoxaline-4,8-diamine

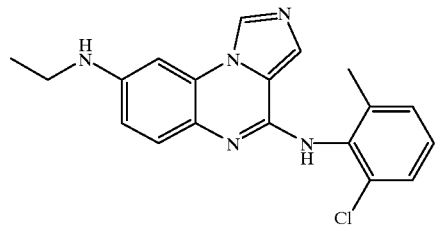

A one dram vial was charged with 2 (12 mg, 0.037 mmol), 2 mg of acetaldehyde and 0.5 mL methanol, and stirred under argon for 2 hours. Sodium borohydride (10 mg, 0.264 mmol) was added in one portion and stirred at room temperature for 2 hours. The reaction was quenched with sat. sodium bicarbonate, and extracted with methylene chloride. The organic layer was washed with brine, dried over magnesium sulfate, filtered and concentrated in vacuo to give a red solid (12.9 mg, 99%): MS $(M+H)^+$=352. HPLC retention time=3.26 min. (HPLC Conditions: YMC C18 S-5 120 Å ODS column, 4.6×50 mm; 0% B–100% B, linear gradient over 4 min at 4.0 mmin; 2 min isocratic at 100% B. Solvent A: 10% MeOH-90% $H_2O$-0.2% $H_3PO_4$; Solvent B: 90% MeOH-10% $H_2O$-0.2% $H_3PO_4$.)

EXAMPLE 285

Preparation of $N^4$-(2-Chloro-6-methylphenyl)-$N^8$-methylimidazo[1,5-a]quinoxaline-4,8-diamine

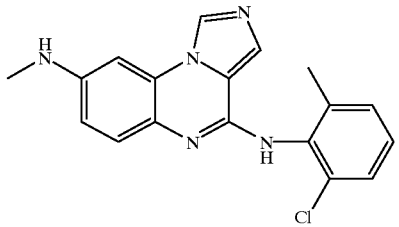

Analogous to preparation of 284. MS $(M+H)^+$=352. HPLC retention time (by the method of Example 284)=2.96 min.

EXAMPLE 286

Preparation of $N^4$-(2-Chloro-6-methylphenyl)-$N^8$-(1-methylethyl)imidazo[1,5-a]quinoxaline-4,8-diamine

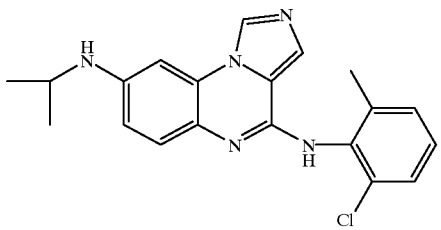

A one dram vial was charged with 2 (9.5 mg, 0.0293 mmol), acetone (6.6 μL, 0.0879 mmol), acetic acid (3.4 μL, 0.0586 mmol) and sodium triacetoxyborohydride (27 mg, 0.123 mmol), and 0.5 mL dichloroethane, and stirred under argon at room temperature for 3 days. Formaldehyde (37% wt. in water, 9 μL, 0.118 mmol) was added and stirred at room temperature for 40 min. The reaction was quenched with sat. sodium bicarbonate, and extracted with ethyl acetate. The organic layer was washed with brine, dried over magnesium sulfate, filtered and concentrated in vacuo to give a brown oil (13 mg, 70%): MS $(M+H)^+0$=332. The reaction was quenched with sat. sodium bicarbonate, and extracted with methylene chloride. The organic layer was washed with brine, dried over magnesium sulfate, filtered and concentrated in vacuo to give a crude red solid, which was purified by silica gel (40:1 $CH_2Cl_2$:MeOH) to give a red solid (7.2 mg, 67%): MS $(M+H)^+$=366. HPLC retention time (by the method of Example 284)=3.39 min.

The following compounds of Examples 287 to 293 were made by procedures analogous to one or more of those described above.

EXAMPLE 287

Preparation of N-(2,6-Dichlorophenyl)-8-fluoroimidazo[1,5-a]quinoxalin-4-amine

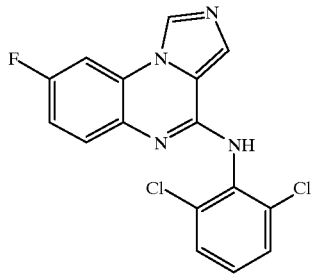

HPLC ret. time: 3.467 min (S5 C18 Rapid Resolution Column 4.6×50 mm. 0 to 100% B over 4 min gradient with 2 min hold time. Flow rate 4 mL/min.)

EXAMPLE 288

Preparation of N-(2-Chloro-6-methylphenyl)-8-(1-piperazinyl)imidazo[1,5-a]quinoxalin-4-amine

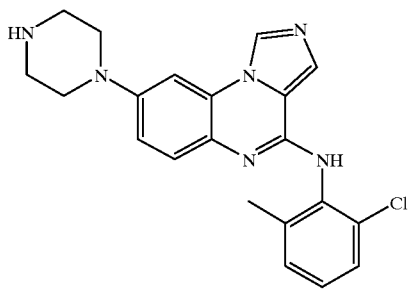

HPLC ret time: 2.05 min (same conditions as in Example 287).

EXAMPLE 289

Preparation of N-(2-Chloro-6-methylphenyl)-7-nitroimidazo[1,5-a]quinoxalin-4-amine

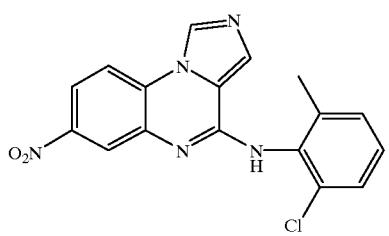

HPLC retention time=4.11 minutes; MS (M+H)=354. HPLC conditions: 0–100% linear gradient of 10–90% aqueous methanol containing 0.2% $H_3PO_4$, 4 min., 2.5 mL/min., detected at 217 nm, YMC S-5 (ODS-A), 4.6×50 mm.

EXAMPLE 290

Preparation of $N^4$-(2-Chloro-6-methylphenyl)imidazo[1,5-a]quinoxaline-4,7-diamine

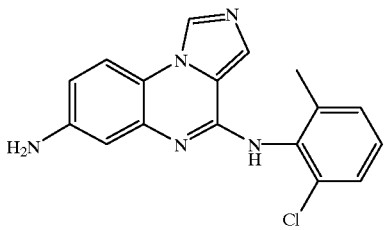

HPLC retention time=2.41 minutes; MS (M+H)=324. HPLC conditions: same as for Example 289.

EXAMPLE 291

Preparation of N-[4-[(2-Chloro-6-methylphenyl)amino]imidazo[1,5-a]quinoxalin-7-yl]hexanamide

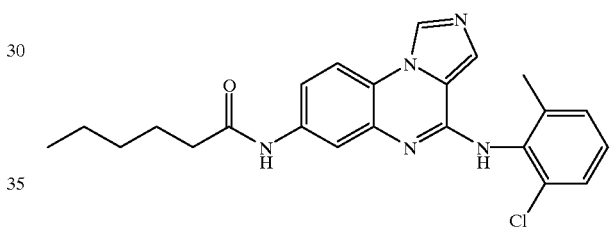

HPLC retention time=3.93 minutes; MS (M+H)=422. HPLC conditions: same as for Example 289.

EXAMPLE 292

Preparation of $N^4$-(2-Chloro-6-methylphenyl)-$N^8$,$N^8$-diethylimidazo[1,5-a]quinoxaline-4,8-diamine

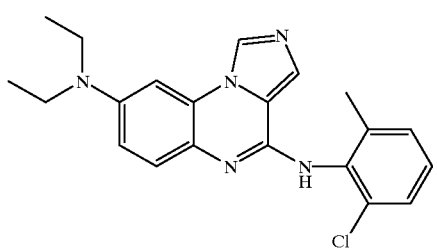

HPLC retention time=3.25 minutes; MS (M+H)=380. HPLC conditions: YMC C18 S-5 120 Å ODS column, 4.6×50 mm; 0% B–100% B, linear gradient over 4 min at 4.0 mvmin; 2 min isocratic at 100% B. Solvent A: 10% MeOH-90% $H_2O$-0.2% $H_3PO_4$; Solvent B: 90% MeOH-10% $H_2O$-0.2% $H_3PO_4$.

EXAMPLE 293

Preparation of N⁴-(2-Chloro-6-methylphenyl)-N⁸, N⁸-dimethylimidazo[1,5-a]quinoxaline-4,8-diamine

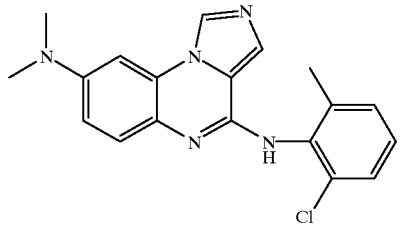

HPLC retention time=3.25 minutes; MS (M+H)=380. HPLC conditions: same as for Example 292.

EXAMPLE 294

Preparation of 1-Acetyl-4-[4-[(2-chloro-6-methylphenyl)amino]imidazo[1,5-a]quinoxalin-8-yl]piperazine

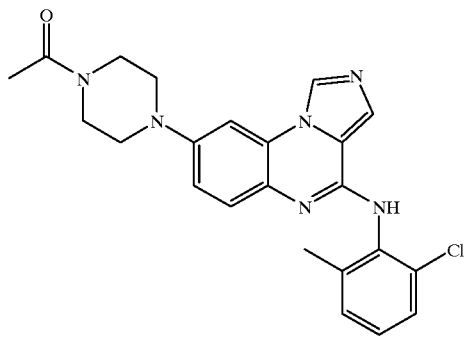

To a mixture of 288 (5 mg, 0.0127 mmol), dichloromethane (300 μL) and excess triethylamine was added acetic anhydride (1.32 μL, 0.014 mmol) at room temperature. The mixture was stirred for 15 min then concentrated in vacuo. Water was added to the residue and the solid was filtered, rinsed with water and dried under vacuo to give the desired product. HPLC ret time: 2.914 min (same conditions as Example 287).

EXAMPLE 295

Preparation of N⁴-(2-Chloro-6-methylphenyl)-N⁸-(cyclopropylmethyl)imidazo[1,5-a]quinoxaline-4,8-diamine

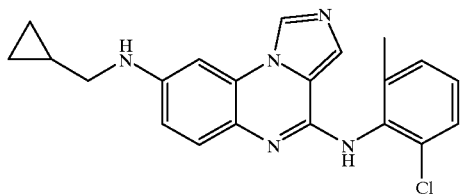

A. 8-Bromo-N-(2-chloro-6-methylphenyl)imidazo[1,5-a]quinoxalin-4-amine

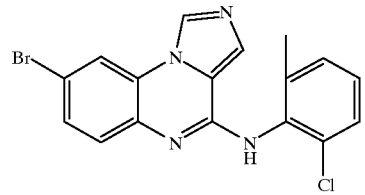

The title compound of this step was prepared from 4-bromo-2-fluoroaniline by a method analogous to that used for the preparation of 272C. HPLC Retention time=3.736 min (HPLC Conditions: "HPLC Method 2").

B. 8-Bromo-N-(2-chloro-6-methylphenyl)-N-[(1,1-dimethylethoxy)carbonyl]imidazo[1,5-a]quinoxalin-4-amine

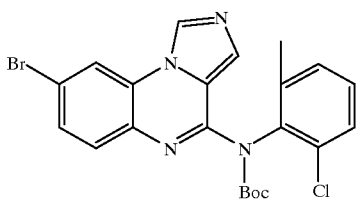

To a solution of compound 295A (1.18 g, 3.04 mmol) in 6 mL of dry THF was added a 1.0 M solution of sodium bis(trimethylsilyl)amide (3.4 mL, 3.4 mmol) in THF, followed by a solution of di-tert-butyl dicarbonate (0.8 g, 3.65 mmol) in 5 mL of dry THF. Finally, 4-dimethylaminopyridine (186 mg, 1.52 mmol) was added and the mixture was stirred at 70° C. for 1.5 hr. After cooling to room temperature, water was added and the reaction mixture was extracted with ethyl acetate (×2). The combined organic extracts were washed once with brine and dried over anhydrous $Na_2SO_4$. Concentration in vacuo followed by flash chromatography ($CH_2Cl_2$-EtOAc: 100:0 to 95:5) on silica gel gave, after an ether-hexane trituration, 986 mg of the title compound of this step as an off-white solid.

C. N⁴-(2-Chloro-6-methylphenyl)-N⁸-(cyclopropylmethyl)imidazo[1,5-a]quinoxaline-4,8-diamine A mixture of 295B (39 mg, 0.08 mmol), sodium tert-butoxide (22 mg, 0.224 mmol), cyclopropyl methylamine (13.7 mg, 0.192 mmol), palladium bis(dibenzylidene acetate) (2.3 mg, 5 mol %) and R-(−)-BINAP (5.0 mg, 10 mol %; "BINAP"=2,2'-bis(diphenylphosphino)-1,1'-binaphthyl) in 0.5 mL of dry toluene was heated at 80° C. for 3.5 hrs. Upon cooling, the reaction mixture was concentrated under reduced pressure and the residue was taken into a mixture of $CH_2Cl_2$-TFA (1.2 mL, 1:3 ratio). After stirring for 2 hrs, the reaction mixture was again concentrated under reduced pressure and purified by preparative HPLC (YMC S5 ODS, 20×100 mm, flow rate: 20 mL/min, 10 min gradient at 254 nM) to give 28 mg of the title compound of this Example. HPLC Retention time=3.100 min (HPLC Conditions: "HPLC Method 2").

EXAMPLES 296 TO 313

General Procedure

Compounds 296 to 313 were prepared from 295B by a route analogous to that used for the preparation of 295C, substituting with the required amine in place of cyclopropyl methylamine (HPLC Conditions: "HPLC Method 2"). The compounds of these examples have the structure:

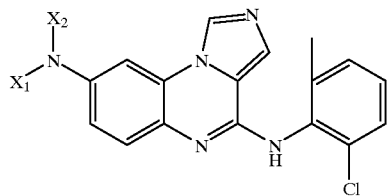

| Ex. No. | $X_1X_2N$ | Compound name | HPLC Ret Time (min) |
|---|---|---|---|
| 296 | cyclohexylmethyl-NH | $N^4$-(2-Chloro-6-methylphenyl)-$N^8$-(cyclohexylmethyl)imidazo[1,5-a]quinoxaline-4,8-diamine | 3.775 |
| 297 | cyclopentyl-NH | $N^4$-(2-Chloro-6-methylphenyl)-$N^8$-(cyclopentyl)imidazo[1,5-a]quinoxaline-4,8-diamine | 3.314 |
| 298 | AcHN-CH2CH2-NH | N-[2-[[4-[(2-Chloro-6-methylphenyl)amino]imidazo[1,5-a]quinoxalin-8-yl]amino]ethyl]acetamide | 3.129 |
| 299 | 2-oxopyrrolidin-1-yl-propyl-NH | 1-[3-[[4-[(2-Chloro-6-methylphenyl)amino]imidazo[1,5-a]quinoxalin-8-yl]amino]propyl]-2-pyrrolidinone | 2.859 |
| 300 | (CH3)2N-CH2CH2-NH | $N^4$-(2-Chloro-6-methylphenyl)-$N^8$-[2-(dimethylamino)ethyl]imidazo[1,5-a]quinoxaline-4,8-diamine | 2.307 |
| 301 | 1-methyl-2-pyrrolidinyl-ethyl-NH | $N^4$-(2-Chloro-6-methylphenyl)-$N^8$-[2-(1-methyl-2-pyrrolidinyl)ethyl]imidazo[1,5-a]quinoxaline-4,8-diamine | 2.487 |
| 302 | morpholinyl-ethyl-NH | $N^4$-(2-Chloro-6-methylphenyl)-$N^8$-[2-(4-morpholinyl)ethyl]imidazo[1,5-a]quinoxaline-4,8-diamine | 2.341 |
| 303 | 2-pyridinyl-ethyl-NH | $N^4$-(2-Chloro-6-methylphenyl)-$N^8$-[2-(2-pyridinyl)ethyl]imidazo[1,5-a]quinoxaline-4,8-diamine | 2.436 |
| 304 | imidazol-1-yl-propyl-NH | $N^4$-(2-Chloro-6-methylphenyl)-$N^8$-(3-1H-imidazol-1-ylpropyl)imidazo[1,5-a]quinoxaline-4,8-diamine | 2.443 |
| 305 | morpholinyl-propyl-NH | $N^4$-(2-Chloro-6-methylphenyl)-$N^8$-[3-(4-morpholinyl)propyl]imidazo[1,5-a]quinoxaline-4,8-diamine | 2.423 |

-continued

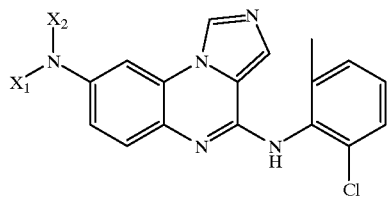

| Ex. No. | X₁X₂N | Compound name | HPLC Ret Time (min) |
|---|---|---|---|
| 306 | (2-pyridinyl)piperazinyl | N-(2-Chloro-6-methylphenyl)-8-[4-(2-pyridinyl)-1-piperazinyl]imidazo[1,5-a]quinoxalin-4-amine | 2.593 |
| 307 | 4-ethylpiperazinyl | N-(2-Chloro-6-methylphenyl)-8-(4-ethyl-1-piperazinyl)imidazo[1,5-a]quinoxalin-4-amine | 2.316 |
| 308 | EtO₂C-piperazinyl | 4-[4-[(2-Chloro-6-methylphenyl)amino]imidazo[1,5-a]quinoxalin-8-yl]-1-piperazinecarboxylic acid ethyl ester | 3.236 |
| 309 | 3,5-dimethylpiperazinyl | N-(2-Chloro-6-methylphenyl)-8-(3,5-dimethyl-1-piperazinyl)imidazo[1,5-a]quinoxalin-4-amine | 2.431 |
| 310 | CHO-piperazinyl | 4-[4-[(2-Chloro-6-methylphenyl)amino]imidazo[1,5-a]quinoxalin-8-yl]-1-piperazinecarboxaldehyde | 2.706 |
| 311 | piperidinyl | N-(2-Chloro-6-methylphenyl)-8-(1-piperidinyl)imidazo[1,5-a]quinoxalin-4-amine | 3.088 |
| 312 | morpholinyl | N-(2-Chloro-6-methylphenyl)-8-(4-morpholinyl)imidazo[1,5-a]quinoxalin-4-amine | 3.019 |
| 313 | (tetrahydrofuranyl)methyl-NH | $N^4$-(2-Chloro-6-methylphenyl)-$N^8$-[(tetrahydro-2-furanyl)methyl]imidazo[1,5-a]quinoxaline-4,8-diamine | 3.126 |

EXAMPLE 314

Preparation of 4-[(2-Chloro-6-methylphenyl) amino]-7,8-dimethoxyimidazo[1,5-a]quinoxaline-1-methanol

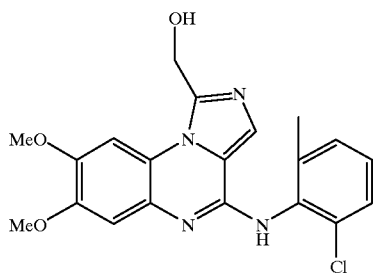

A mixture of 186 (36 mg, 0.1 mmol) in 1 mL of 37% formaldehyde aqueous solution in a closed vial was heated to 150° C. overnight. After cooling to room temperature, the reaction mixture was concentrated in vacuo and purified by preparative HPLC (YMC S5 ODS, 20×100 mm, flow rate: 20 ml/min, 10 min gradient at 254 nM). The fractions eluted from HPLC containing the desired product were concentrated under reduced pressure to a small volume, neutralized with saturated NaHCO$_3$, extracted with CH$_2$Cl$_2$ (×2) and the combined extracts were dried over anhydrous Na$_2$SO$_4$. Concentration in vacuo gave 9 mg of the title compound of this Example as a white solid. HPLC Retention time=2.817 min (HPLC Conditions: "HPLC Method 2").

EXAMPLE 315

Preparation of N-(3,5-Dimethyl[1,1'-biphenyl]-4-yl)-7,8-dimethoxyimidazo[1,5-a]quinoxalin-4-amine

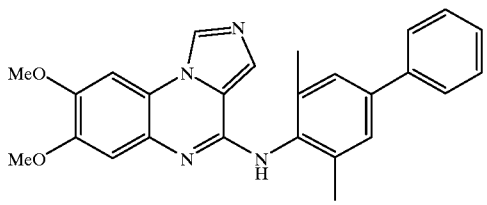

The title compound of this Example was prepared from 130D by a method analogous to that used for the preparation of 130E, using 4-phenyl-2,6-dimethylaniline in place of 2,4,6-trimethylaniline. HPLC Retention time=3.545 min (HPLC Conditions: "HPLC Method 2").

EXAMPLE 316

Preparation of N-(2-Chloro-6-methylphenyl)-8-(phenylmethoxy)imidazo[1,5-a]quinoxalin-4-amine

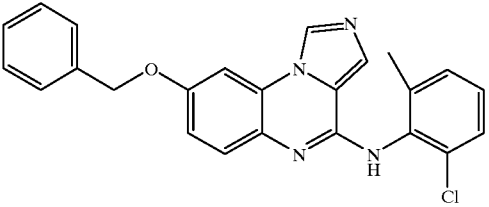

To a solution of benzylalcohol (0.2 mL) in DMSO (0.3 mL) was added NaH (60% dispersion in mineral oil, 19 mg, 0.46 mmol). The mixture was stirred at room temperature for 0.5 hr. A solution of 271C (50 mg, 0.115 mmol) in DMSO (0.3 mL) was then added followed by CuI (22 mg, 0.115 mmol). The reaction was heated to 100° C. for 5 hr, then cooled to room temperature. The product was isolated by preparative HPLC to give 17 mg of the title compound of this Example. HPLC Retention time=3.787 min (HPLC Conditions: "HPLC Method 2").

EXAMPLE 317

Preparation of 6-Bromo-N-(2-chloro-6-methylphenyl)-8-fluoroimidazo[1,5-a]quinoxalin-4-amine

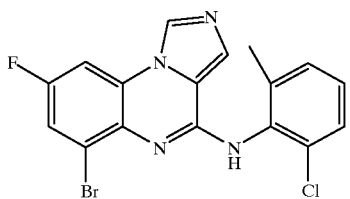

The title compound of this Example was prepared from 2,4-difluoro-6-bromoaniline by a method analogous to that used for the preparation of 271C. HPLC Retention time= 4.432 min (HPLC Conditions: "HPLC Method 2").

EXAMPLE 318

Preparation of 6-Bromo-N-(2-chloro-6-methylphenyl)-8-(4-methyl-1-piperazinyl)imidazo[1,5-a]quinoxalin-4-amine

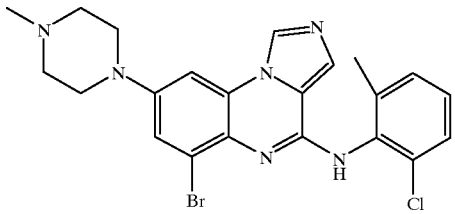

The title compound of this Example was prepared from 317 by a method analogous to that used for the preparation of 281. HPLC Retention time=3.229 min (HPLC Conditions: "HPLC Method 2").

EXAMPLE 319

Preparation of N-(2-Chloro-6-methylphenyl)-8-fluoro-6-(4-methyl-1-piperazinyl)imidazo[1,5-a]quinoxalin-4-amine

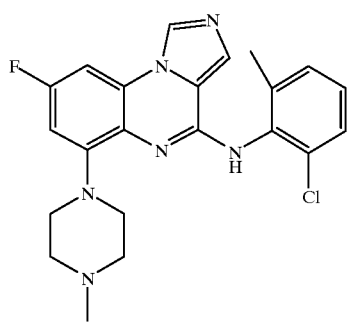

The title compound of this Example was isolated under the reaction conditions used for the preparation of 318. HPLC Retention time=2.431 mmn (HPLC Conditions: "HPLC Method 2").

EXAMPLE 320

Preparation of N-(2-Chloro-6-methylphenyl)-6,8-bis(1-piperazinyl)imidazo[1,5-a]quinoxalin-4-amine

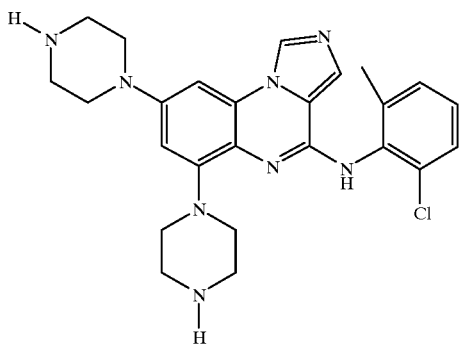

The title compound of this Example was prepared from 317 by a method analogous to that used for the preparation of 281. HPLC Retention time=1.723 min (HPLC Conditions: "HPLC Method 2").

EXAMPLE 321

Preparation of 6,8-Bis(4-acetyl-1-piperazinyl)-N-(2-chloro-6-methylphenyl)imidazo[1,5-a]quinoxalin-4-amine

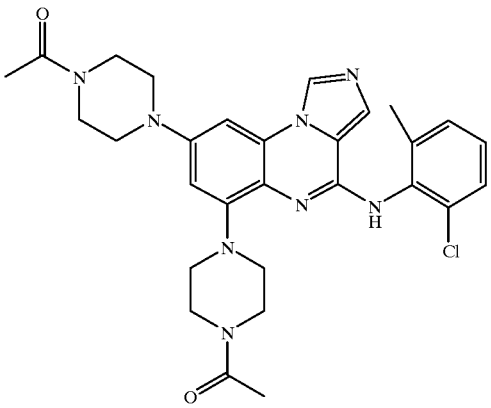

The title compound of this Example was prepared from 320 by a method analogous to that used for the preparation of 294. HPLC Retention time=3.112 min (HPLC Conditions: "HPLC Method 2").

EXAMPLE 322

Preparation of $N^4$-(2-Chloro-6-methylphenyl)-$N^7$,$N^7$-dimethylimidazo[1,5-a]quinoxaline-4,7-diamine

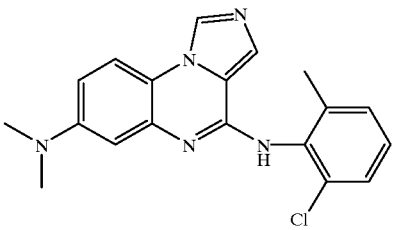

Analogous to the preparation of 293 using 290 gave the title compound of this Example as a tan solid: MS $(M+H)^+$= 352. HPLC (by the method of Example 289): Retention time=3.29 min.

EXAMPLE 323

Preparation of [4-[[4-[(2-Chloro-6-methylphenyl)amino]imidazo[1,5-a]quinoxalin-7-yl]amino]-4-oxobutyl]carbamic acid 1,1-dimethylethyl ester

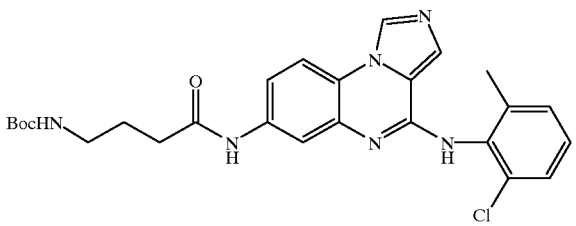

Analogous to the preparation of 291 using 290 and N-Boc butyric acid gave the title compound of this Example as a tan solid: MS (M+H)$^+$=509. HPLC (by the method of Example 289): Retention time=3.79 min.

EXAMPLE 324

Preparation of N$^4$-(2-Chloro-6-methylphenyl)-N$^7$, N$^7$-diethylimidazo[1,5-a]quinoxaline-4,7-diamine

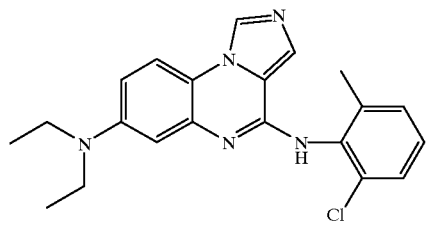

Analogous to the preparation of 292 using 290 gave the title compound of this Example as a tan solid: MS (M+H)$^+$=380. HPLC (by the method of Example 289): Retention time=3.23 min.

EXAMPLE 325

Preparation of N-[4-[(2-Chloro-6-methylphenyl) amino]imidazo[1,5-a]quinoxalin-7-yl]acetamide

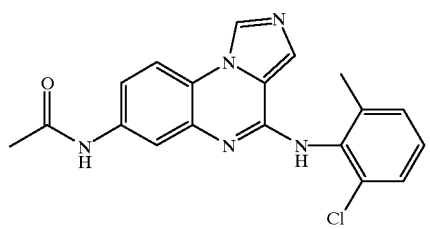

Analogous to the preparation of 291 using 290 and acetic acid gave the title compound of this Example as a tan solid: MS (M+H)$^+$=366. HPLC (by the method of Example 289): Retention time=3.09 min.

EXAMPLE 326

Preparation of N-[4-[(2-Chloro-6-methylphenyl) amino]imidazo[1,5-a]quinoxalin-7-yl] benzeneacetamide

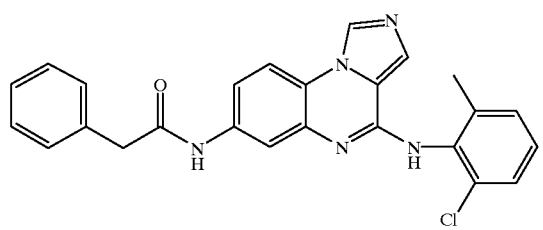

Analogous to the preparation of 291 using 290 and phenylacetic acid gave the title compound of this Example as a tan solid: MS (M+H)$^+$=442. HPLC (by the method of Example 289): Retention time=3.76 min.

EXAMPLE 327

Preparation of N$^4$-(2-Chloro-6-methylphenyl)-N$^7$-methylimidazo[1,5-a]quinoxaline-4,7-diamine

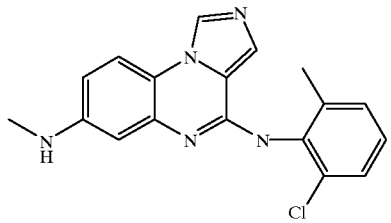

Analogous to the preparation of 285 using 290 gave the title compound of this Example as a brown solid: MS (M+H)$^+$=338. HPLC (by the method of Example 289): Retention time=2.96 min.

EXAMPLE 328

Preparation of 4-Amino-N-[4-[(2-chloro-6-methylphenyl)amino]imidazo[1,5-a]quinoxalin-7-yl] butanamide dihydrochloride

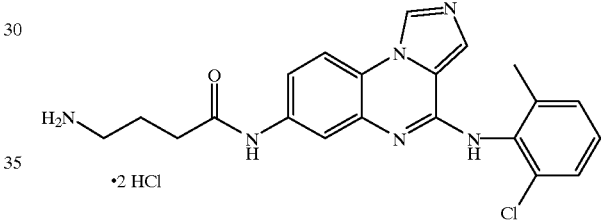

323 (0.010 g, 0.02 mmol) and 4 N HCl/dioxane (0.05 mL, 0.2 mmol) were stirred under nitrogen at 0° C. for 2 h. The reaction mixture was concentrated in vacuo to give 0.0095 g (99%) of the title compound of this Example as a red-brown solid: MS (M+H)$^+$=409. HPLC (by the method of Example 289): Retention time=2.49 min.

EXAMPLE 329

Preparation of N$^4$-(2-Chloro-6-methylphenyl)-N$^7$-ethylimidazo[1,5-a]quinoxaline-4,7-diamine

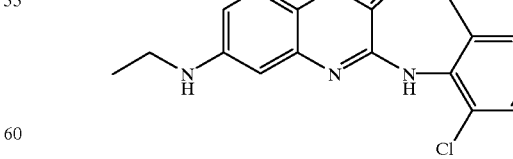

Analogous to the preparation of 284 using 290 gave the title compound of this Example as a tan solid: MS (M+H)$^+$=352. HPLC (by the method of Example 289): Retention time=2.91 min.

EXAMPLE 330

Preparation of N$^4$-(2-Chloro-6-methylphenyl)-N$^7$-(phenylmethyl)imidazo[1,5-a]quinoxaline-4,7-diamine

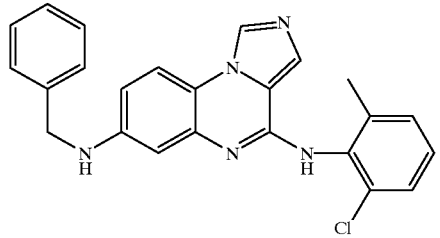

Analogous to the preparation of 284 using 290 and benzaldehyde gave the title compound of this Example as a tan solid: MS (M+H)$^+$=414. HPLC (by the method of Example 289): Retention time=3.53 min.

EXAMPLE 331

Preparation of N-[4-[(2-Chloro-6-methylphenyl)amino]imidazo[1,5-a]quinoxalin-8-yl]-3-hydroxy-3-methylbutanamide

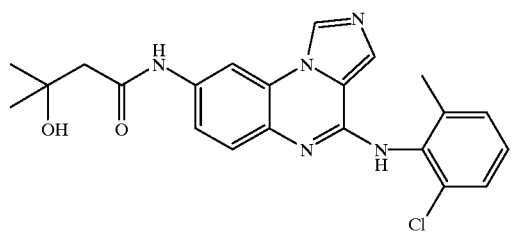

Analogous to the preparation of 3 using 3-hydroxy-3-methylbutanoic acid gave the title compound of this Example as a brown solid: MS (M+H)$^+$=424. HPLC (by the method of Example 289): Retention time=3.15 min.

EXAMPLE 332

Preparation of N-(2-Chloro-6-methylphenyl)-9-methoxyimidazo[1,5-a]quinoxalin-4-amine

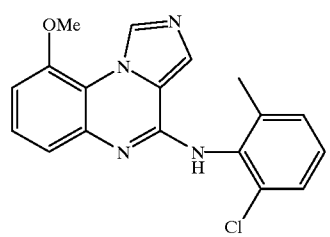

Analogous to the preparation of 1F, substituting 3-methoxy-1,2-diaminobenzene for 4-nitro-1,2-diaminobenzene gave the title compound of this Example as a brown solid: MS (M+H)$^+$=339. HPLC (by the method of Example 289): Retention time=3.15 min.

EXAMPLE 333

Preparation of N-(2,6-Dichlorophenyl)-8-nitroimidazo[1,5-a]quinoxalin-4-amine

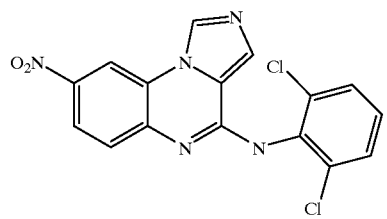

Analogous to the preparation of 1F. MS (M+H)$^+$=374. HPLC Ret time (by the method of Example 284)=4.47 min.

EXAMPLE 334

Preparation of N$^4$-(2,6-Dichlorophenyl)imidazo[1,5-a]quinoxaline-4,8-diamine

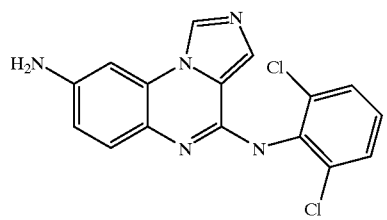

Analogous to the preparation of 2. MS (M+H)$^+$=344. HPLC Ret time (by the method of Example 284)=2.70 min.

EXAMPLE 335

Preparation of N-(2-Chloro-6-methylphenyl)-7,8-dihydroxyimidazo[1,5-a]quinoxalin-4-amine

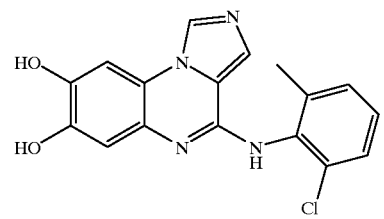

Analogous to the preparation of 263. MS (M+H)$^+$=341. HPLC Ret time (by the method of Example 284)=2.85 min.

EXAMPLE 336

Preparation of N-(2-Chloro-6-methylphenyl)[1,3]dioxolo[4,5-g]imidazo[1,5-a]quinoxalin-4-amine

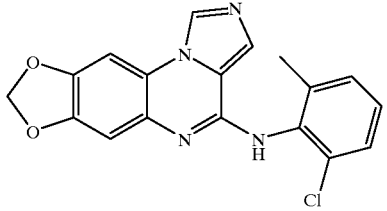

To 335 (TFA salt, 15 mg, 0.033 mmol) was added $Cs_2CO_3$ (43 mg, 0.132 mmol), 0.5 mL DMF, and bromochloromethane (3.2 gL, 0.050 mmol), and the mixture flushed with argon and heated to 110° C. for 2 hours. The reaction was quenched with saturated $NH_4Cl$, extracted with ethyl acetate, the organic layer washed with brine and concentrated in vacuo. Chromatography of the crude product gave 3 mg of the title compound of this Example as a white solid (yield: 20%). MS $(M+H)^+=353$. HPLC Ret time (by the method of Example 284)=3.47 min.

EXAMPLE 337

Preparation of N-(2-Chloro-6-methylphenyl)-2,3-dihydro-1,4-dioxino[2,3-g]imidazo[1,5-a]quinoxalin-7-amine

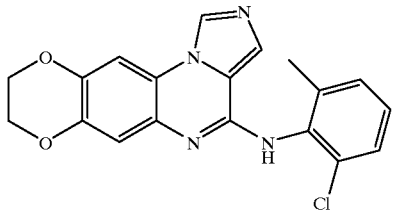

To 1,2 dibromoethane (7.0 μL, 0.080 mmol), Triton-B (N-benzyltrimethylammonium hydroxide; 4.2 mg) and 1 mL water heated to reflux was added a solution of 335 (TFA salt, 26 mg, 0.057 mmol), KOH (13 mg, 0.240 mmol) and 1 mL $H_2O$ over a 2 hour period. The mixture was allowed to reflux for 18 hr. The reaction mixture was quenched with saturated $NH_4Cl$, extracted with ethyl acetate, the organic layer washed with brine and concentrated in vacuo. Chromatography of the crude product gave 3 mg of the title compound of this Example as a yellow solid (yield: 10%). MS $(M+H)^+=367$. HPLC Ret time (by the method of Example 284)=3.29 min.

EXAMPLE 338

Preparation of N-[2,6-Dimethyl-4-[2-(dimethylamino)ethoxy]phenyl]-7,8-dimethoxyimidazo[1,5-a]quinoxalin-4-amine

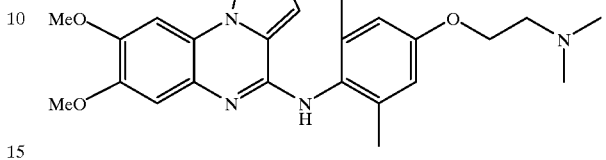

A. 3,5-Dimethyl-4-nitrophenol

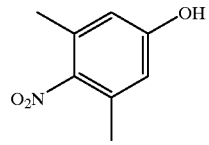

The bi-phasic mixture of 3,5-dimethylphenol (25 g, 0.20 mol) and sodium nitrate (17.4 g, 0.20 mol) in a 1:1 mixture of ether-water (800 ml) containing 40 ml of concentrated HCl was vigorously stirred for several hours. n-$Bu_4NHSO_4$ (3.4 g, 0.01 mol) and additional conc. HCl (40 ml) were added and stirring continued for 60 hrs. The reaction mixture was extracted with ether (×2). The combined ether extracts were washed with 1.0N HCl, brine and dried over anhydrous $Na_2SO_4$. Concentration in vacuo followed by flash chromatography (hexane-EtOAc: 99:1 to 40:60) on silica gel gave, after trituration with hexane, 12.3 g of the title compound of this step as a yellow solid.

B. N,N-Dimethyl-2-(3,5-dimethyl-4-nitrophenoxy)ethanamine

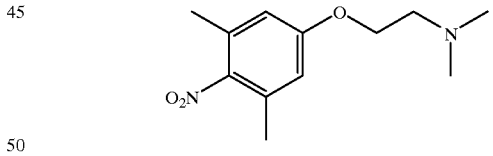

To a suspension of 1-chloro-2-dimethyl-aminoethane hydrochloride (0.77 g, 5.38 mmol) in 12 ml of dry DMF was added NaH (0.14 g, 5.9 mmol) and the mixture was stirred for 1.0 hr. To this mixture was then added 338A (0.6 g, 3.59 mmol), followed by NaH (0.09 g, 3.95 mmol). After being stirred for 1.0 hr at room temperature, additional NaH (0.05 g, 2.08 mmol) was added and the reaction mixture was heated to 90° C. for an additional 2.0 hrs. After being cooled to 0° C., sat'd $NH_4Cl$ was added slowly to the reaction mixture to quench the reaction. The mixture was diluted with water and extracted with EtOAc (×2). The combined organic layers were washed with sat'd $NH_4Cl$ (×2) and dried over anhydrous $Na_2SO_4$. Concentration in vacuo followed by trituration with hexane gave 0.71 g of the title compound of this step as a tan oil.

C. 2,6-Dimethyl-4-[2-(dimethylamino)ethoxy]benzenamine

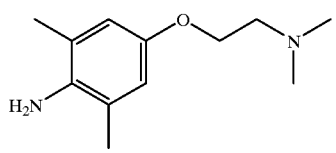

A mixture of 338B (0.71 g, 2.98 mmol) and 0.07 g of 10% Pd-C in 170 ml of EtOH was stirred under hydrogen atmosphere for 16 hrs. The catalyst was removed by filtration and the filtrate was concentrated in vacuo to give 0.63 g of the title compound of this step as a light yellow oil.

D. N-[2,6-Dimethyl-4-[2-(dimethylamino)ethoxy]phenyl]-7,8-dimethoxyimidazo[1,5-a]quinoxalin-4-amine The title compound of this Example was prepared from 130D by a method analogous to that used for the preparation of 130E, using 338C in place of 2,4,6-trimethylaniline. HPLC Retention time=2.022 min (HPLC Conditions: "HPLC Method 2").

EXAMPLE 339

Preparation of N-[2,6-Dimethyl-4-[2-(4-morpholinyl)ethoxy]phenyl]-7,8-dimethoxyimidazo[1,5-a]quinoxalin-4-amine

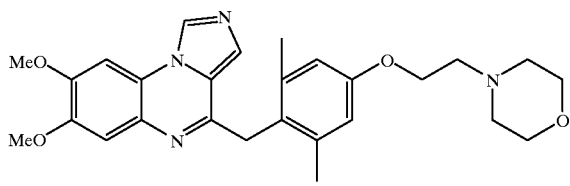

A. 4-[2-(3,5-Dimethyl-4-nitrophenoxy)ethyl]morpholine

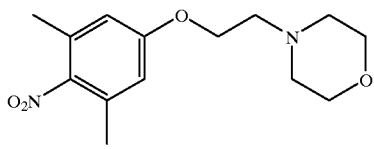

The title compound of this step was prepared from 338A by a method analogous to that used for the preparation of 338B, using 4-(2-chloroethyl)morpholine in place of 1-chloro-2-dimethyl-aminoethane hydrochloride. 0.74 g of the title compound of this step was obtained as a golden crystalline material.

B. 2,6-Dimethyl-4-[2-(4-morpholinyl)ethoxy]benzenamine

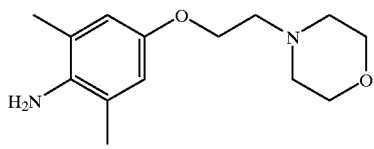

The title compound of this step was prepared from 339A by a method analogous to that used for the preparation of 338C. 0.60 g of the title compound of this step was obtained as a red-brown viscous oil.

C. N-[2,6-Dimethyl-4-[2-(4-morpholinyl)ethoxy]phenyl]-7,8-dimethoxyimidazo[1,5-a]quinoxalin-4-amine The title compound of this Example was prepared from 130D by a method analogous to that used for the preparation of 130E, using 339B in place of 2,4,6-trimethylaniline. HPLC Retention time=2.080 min (HPLC Conditions: "HPLC Method 2").

EXAMPLE 340

Preparation of 4-[(2-Chloro-6-methylphenyl)amino]imidazo[1,5-a]quinoxaline-7-carboxylic acid methyl ester

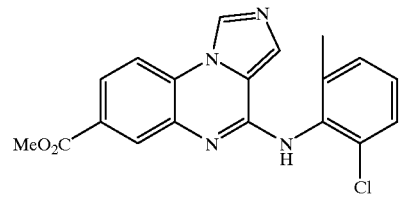

A. 4-Chloroimidazo[1,5-a]quinoxaline-6-carboxylic acid methyl ester, mixture with 4-chloroimidazo[1,5-a]quinoxaline-7-carboxylic acid methyl ester (mixture of 6 and 7 regioisomers)

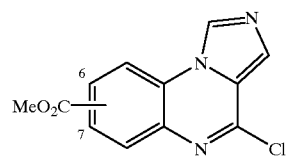

The title mixture of this step was prepared from methyl 3,4-diaminobenzoate by a method analogous to that used for the preparation of 1E.

B. 4-[(2-Chloro-6-methylphenyl)amino]imidazo[1,5-a]quinoxaline-7-carboxylic acid methyl ester (7-isomer only)

The title compound of this Example was prepared from 340A by a method analogous to that used for the preparation of 1F. MS (M+H)$^+$=367. HPLC Retention time=3.565 min (HPLC Conditions: "HPLC Method 2").

EXAMPLE 341

Preparation of 4-[(2-Chloro-6-methylphenyl)amino]imidazo[1,5-a]quinoxaline-7-carboxylic acid

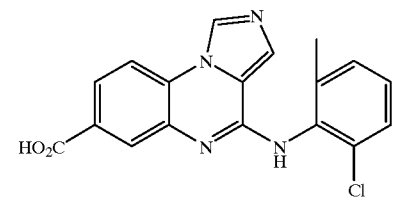

A mixture of 340 (15.0 mg, 0.041 mmol) and 2.0N KOH (0.2 ml) in 0.11 mL of THF and 0.17 mL of methanol was stirred for 2.0 hrs at room temperature. The reaction mixture was cooled to 0° C. and acidified with 2.0N HCl. This mixture was concentrated under reduced pressure and the residue was taken in water. The solid was collected by filtration and washed with water and ether. 7.3 mg of the title compound of this Example was obtained as a light tan solid.

EXAMPLE 342

Preparation of 4-[(2-Chloro-6-methylphenyl)amino]imidazo[1,5-a]quinoxaline-7-carboxamide

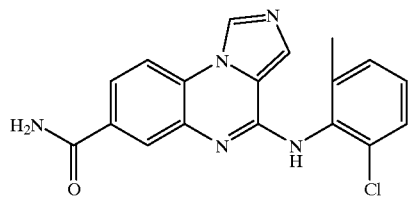

NH$_3$ gas was bubbled into a solution of 340 (50 mg) in 4.0 mL of dry MeOH cooled at 0° C. After 10 min, the reaction vessel was sealed and heated at 60° C. for 34 hrs and then stored at room temperature for 3 days. The mixture was concentrated in vacuo and the residue was triturated with ether to give 8.0 mg of the title compound of this Example as a tan solid. MS (M−H)$^-$=350. HPLC Retention time=2.630 min (HPLC Conditions: "HPLC Method 2").

EXAMPLE 343

Preparation of N-(2-Chloro-6-methylphenyl)-8-(2,6-dimethylphenyl)imidazo[1,5-a]quinoxalin-4-amine

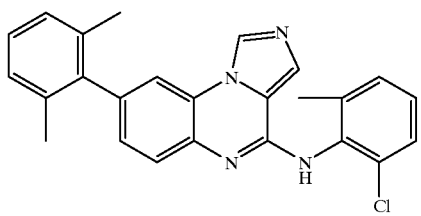

A. 2,6-Dimethylphenylboronic acid

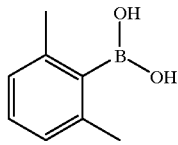

A 1.0 M solution of 2,6-dimethylphenylmagnesium bromide in THF (20 ml; 20 mmol) was added over 5 minutes to a solution of trimethylborate (4.5 ml; 40 mmol) in 50 ml of THF at −78° C. The reaction mixture was allowed to warm to room temperature and stir 18 hr. Mter cooling to 0° C., 50 ml of 2 N HCl was added and the resulting mixture was stirred 30 minutes at 0° C. The mixture was partitioned between water (100 ml) and CH$_2$Cl$_2$ (100 ml). The aqueous layer was extracted with CH$_2$Cl$_2$ (2×100 ml) and the combined organic layers were dried (MgSO$_4$) and concentrated to afford a quantitative recovery of the crude title compound of this step. This material was used in the next step without further purification.

B. N-(2-Chloro-6-methylphenyl)-8-(2,6-dimethylphenyl)imidazo[1,5-a]quinoxalin-4-amine A mixture of 271 (100 mg; 0.23 mmol), 343A (180 mg; 1.20 mmol), tetrakistriphenylphosphine palladium (20 mg), ethanol (1.6 ml), toluene (2 ml) and 2M sodium carbonate (1.4 ml) was stirred briskly at 85° C. for 18 hrs. An additional amount of 343A (180 mg; 1.20 mmol) and tetrakistriphenylphosphine palladium (20 mg) was added and the reaction was stirred briskly at 85° C. for 8 hr. An additional amount of 343A (180 mg; 1.20 mmol) and tetrakistriphenylphosphine palladium (20 mg) was added and the reaction was stirred briskly at 85° C. for 18 hr. After cooling to room temperature, the reaction mixture was partitioned between EtOAc (25 ml) and water (25 ml). The organic layer was washed with 1N NaOH (3×25 ml), brine (25 ml), dried (MgSO$_4$) and concentrated to a yellow oil. The residue was chromatographed on a 2.5×15 cm silica gel column, using 500 ml each of 20% EtOAc/Hex to 50% EtOAc/Hex in 10% increments, as the mobile phase. The pure fractions were concentrated to a residue that was subsequently recrystallized from EtOAc/Hex to afford 76 mg (80%) of the title compound of this Example as a yellow crystalline solid. [mp 140–150° C.; HPLC: Retention time= 19.71 min., (UV 254 nM); YMC S-3 ODS (C-18) 6.0×150 mm; 50% B:A-100% B (A=90% H$_2$O/MeOH+0.2% H$_3$PO$_4$; B=90% MeOH/H$_2$O+0.2% H$_3$PO$_4$) linear gradient over 25 minutes.]

EXAMPLE 344

Preparation of N-(2-Chloro-6-methylphenyl)-8-methoxy-7-[2-(4-morpholinyl)ethoxy]imidazo[1,5-a]quinoxalin-4-amine

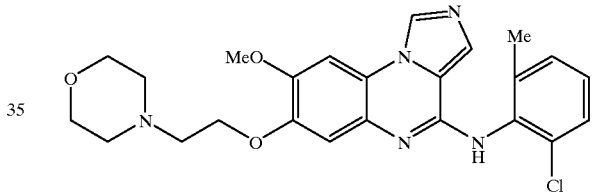

A. 4-[(2-Chloro-6-methylphenyl)amino]imidazo[1,5-a]quinoxaline-7,8-diol, hydrobromide (1:2)

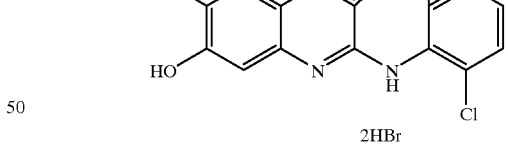

To a suspension of 186 (1.98 g, 5.37 mmol) in 25 mL of dry CH$_2$Cl$_2$ cooled at 0° C. was added BBr$_3$ (2.54 mL, 26.84 mmol) via a syringe. The resulting thick paste was diluted with 50 mL of dry CH$_2$Cl$_2$ and stirring continued at ambient temperature for 2.0 hrs. The reaction mixture was cooled to 0° C. and MeOH (ca. 30 mL) was added to give a clear solution. The mixture was stirred for 30 min. and concentration in vacuo followed by azeotropic evaporation with CH$_2$Cl$_2$-MeOH gave 2.374 g of 344A (HBr salt) as a yellow-orange solid.

B. 4-[(2-Chloro-6-methylphenyl)amino]-8-[[tris(1-methylethyl)silyl]oxy]imidazo[1,5-a]quinoxalin-7-one, mixture with 4-[(2-Chloro-6-methylphenyl)amino]-7-[[tris(1-methylethyl)silyl]oxy]imidazo[1,5-a]quinoxalin-8-ol

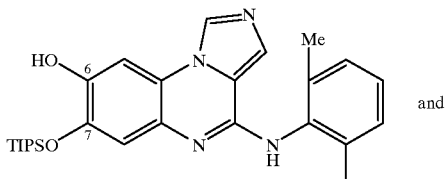

and

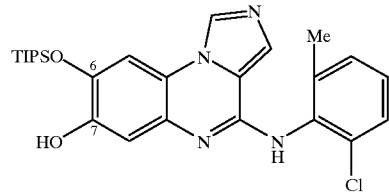

To the mixture of 344A (2.374 g, 5.37 mmol theoretical) and imidazole (1.92 g, 28.15 mmol) in 20 mL of dry DMF was added triisopropylsilyl chloride (TIPS-Cl) (3.6 mL, 16.89 mmol). The mixture was stirred at room temperature overnight. The reaction mixture was cooled to 0° C. and diluted with water. The mixture was extracted with EtOAc (×2) and the combined organic extracts were washed with water and dried over anhydrous $Na_2SO_4$. Concentration in vacuo followed by $CH_2Cl_2$-hexane trituration gave 1.61 g of 344B as a light tan solid. Further purification by flash chromatography ($CH_2Cl_2$-MeOH: 98:2) on silica gel gave, after trituration with $CH_2Cl_2$-hexane, 1.30 g of 344B as an off-white solid (mixture of 6- and 7-regioisomers).

C. N-(2-Chloro-6-methylphenyl)-7-methoxy-8-[[tris(1-methylethyl)silyl]oxy]imidazo[1,5-a]quinoxalin-4-amine (344C(1))

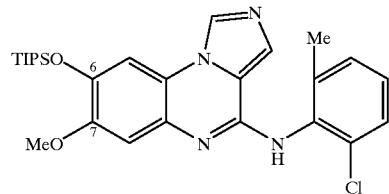

and
N-(2-Chloro-6-methylphenyl)-8-methoxy-7-[[tris(1-methylethyl)silyl]oxy]imidazo[1,5-a]quinoxalin-4-amine (344C(2))

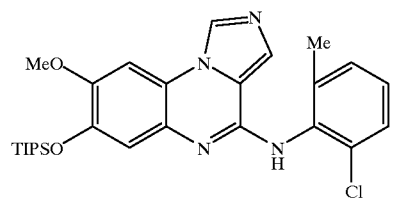

To the mixture of 344B (0.5 g, 1.0 mmol), $Ph_3P$ (0.53 g, 2.0 mmol) in 6 mL of dry THF at 0° C. was added dry MeOH (0.1 mL, 2.5 mmol), followed by DEAD (0.32 mL, 2.0 mmol). The mixture was stirred at ambient temperature for 1.0 hr. Concentration in vacuo and purification by flash chromatography (hexane-EtOAc: 7:3) on silica gel gave 220 mg of 344C(1) as a colorless oil and 459 mg of 344C(2) as a white solid.

D. 4-[(2-Chloro-6-methylphenyl)amino]-8-methoxyimidazo[1,5-a]quinoxalin-7-ol

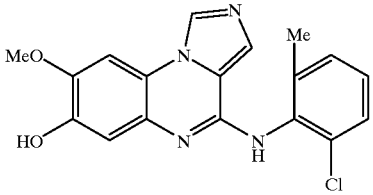

The mixture of 344C(2) (450 mg, 0.88 mmol) and TBAF n$H_2O$ (690 mg, 2.64 mmol) in 10 mL of THF was stirred overnight. The mixture was then concentrated in vacuo, and the residue partitioned between EtOAc and water. The organic extracts were washed with water and dried over anhydrous $Na_2SO_4$. Concentration in vacuo followed by recrystallization from $CH_2Cl_2$ gave 210 mg of 344D as an off-white solid. The mother liquid was concentrated in vacuo and triturated with hexane-ether to give an additional 147 mg of 344D as an off-white solid.

E. N-(2-Chloro-6-methylphenyl)-8-methoxy-7-[2-(4-morpholinyl)ethoxy]imidazo[1,5-a]quinoxalin-4-amine To the mixture of 344D (25 mg, 0.07 mmol), $Ph_3P$ (37 mg, 0.14 mmol) and 4-(2-hydroxyethyl)morpholine (0.017 mL, 0.14 mmol) in 0.5 mL of dry THF at 0° C. was added DEAD (0.022 mL, 0.14 mmol). The mixture was stirred at ambient temperature for 1.0 hr. Concentration in vacuo followed by flash chromatography ($CH_2Cl_2$-MeOH-$NH_4OH$: 98:2:0.2 to 96:4:0.4) on silica gel gave 27.4 mg of the title compound 344E as a white solid. HPLC Ret time: 2.389 min (by HPLC Method 2).

EXAMPLES 345 TO 355

General Procedure

Compounds 345 to 355 were prepared from 344D by a route analogous to that used for the preparation of 344E, substituting with the required alcohol in place of 4-(2-hydroxyethyl)morpholine (HPLC Conditions: "HPLC Method 2"). The compounds of these examples have the structure:

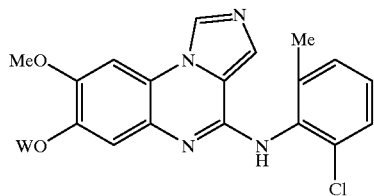

| Ex. No | W | Compound name | HPLC Ret. Time (min) |
|---|---|---|---|
| 345 | morpholinyl-propyl | N-(2-Chloro-6-methylphenyl)-8-methoxy-7-[3-(4-morpholinyl)propoxy]imidazo[1,5-a]quinoxalin-4-amine | 2.389 |
| 346 | (CH₃)₂N-propyl | N-(2-Chloro-6-methylphenyl)-7-[3-(dimethylamino)propoxy]-8-methoxyimidazo[1,5-a]quinoxalin-4-amine | 2.526 |
| 347 | (CH₃)₂N-ethyl | N-(2-Chloro-6-methylphenyl)-7-[2-(dimethylamino)ethoxy]-8-methoxyimidazo[1,5-a]quinoxalin-4-amine | 2.357 |
| 348 | CH₃O-ethyl | N-(2-Chloro-6-methylphenyl)-8-methoxy-7-(2-methoxyethoxy)imidazo[1,5-a]quinoxalin-4-amine | 3.021 |
| 349 | AcO-ethyl | 7-[2-(Acetyloxy)ethoxy]-N-(2-chloro-6-methylphenyl)-8-methoxyimidazo[1,5-a]quinoxalin-4-amine | 3.058 |
| 350 | HO-ethyl | N-(2-Chloro-6-methylphenyl)-7-(2-hydroxyethoxy)-8-methoxyimidazo[1,5-a]quinoxalin-4-amine | 2.856 |
| 351 | (tetrahydro-2-furanyl)methyl | N-(2-Chloro-6-methylphenyl)-8-methoxy-7-[(tetrahydro-2-furanyl)methoxy]imidazo[1,5-a]quinoxalin-4-amine | 3.275 |
| 352 | (tetrahydro-3-furanyl)methyl | N-(2-Chloro-6-methylphenyl)-8-methoxy-7-[(tetrahydro-3-furanyl)methoxy]imidazo[1,5-a]quinoxalin-4-amine | 3.195 |
| 353 | tetrahydro-3-furanyl | N-(2-Chloro-6-methylphenyl)-8-methoxy-7-[(tetrahydro-3-furanyl)oxy]imidazo[1,5-a]quinoxalin-4-amine | 3.010 |
| 354 | 1-methyl-2-pyrrolidinyl-ethyl | N-(2-Chloro-6-methylphenyl)-8-methoxy-7-[2-(1-methyl-2-pyrrolidinyl)ethoxy]imidazo[1,5-a]quinoxalin-4-amine | 2.645 |

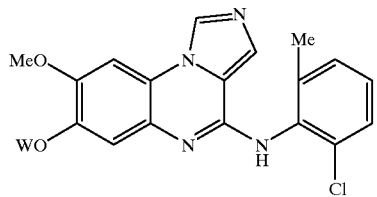

| Ex. No | W | Compound name | HPLC Ret. Time (min) |
|---|---|---|---|
| 355 | N-methylpyrrolidinyl group | N-(2-Chloro-6-methylphenyl)-8-methoxy-7-[(1-methyl-3-pyrrolidinyl)oxy]imidazo[1,5-a]quinoxalin-4-amine | 2.429 |

EXAMPLE 356

Preparation of N-(2-Chloro-6-fluorophenyl)-7,8-dimethoxyimidazo[1,5-a]quinoxalin-4-amine

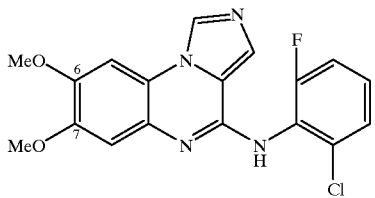

Analogous to the preparation of 17G, replacing 2-chloro-6-methylaniline with 2-chloro-6-fluoroaniline; 356 was prepared from 130D. HPLC Ret time: 2.921 min (by HPLC Method 2).

EXAMPLES 357 TO 360

General Procedure

Compounds 357 to 360 were prepared from 356 by a route analogous to that used for the preparation of 344E, substituting with the required alcohol in place of 4-(2-hydroxyethyl)morpholine (HPLC Conditions: "HPLC Method 2"). The compounds of these examples have the structure:

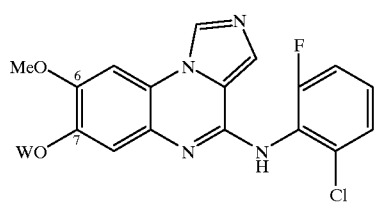

| Ex. No | W | Compound name | HPLC Ret. Time (min) |
|---|---|---|---|
| 357 | morpholinylethyl | N-(2-Chloro-6-fluorophenyl)-8-methoxy-7-[2-(4-morpholinyl)ethoxy]imidazo[1,5-a]quinoxalin-4-amine | 2.360 |
| 358 | morpholinylpropyl | N-(2-Chloro-6-fluorophenyl)-8-methoxy-7-[3-(4-morpholinyl)propoxy]imidazo[1,5-a]quinoxalin-4-amine | 2.489 |
| 359 | dimethylaminoethyl | N-(2-Chloro-6-fluorophenyl)-7-[2-(dimethylamino)ethoxy]-8-methoxyimidazo[1,5-a]quinoxalin-4-amine | 2.337 |

-continued

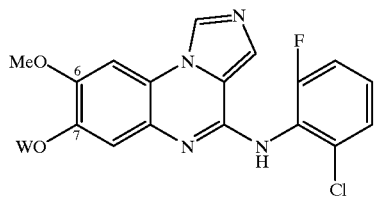

| Ex. No | W | Compound name | HPLC Ret. Time (min) |
|---|---|---|---|
| 360 | (dimethylamino)propyl | N-(2-Chloro-6-fluorophenyl)-7-[3-(dimethylamino)propoxy]-8-methoxyimidazo[1,5-a]quinoxalin-4-amine | 2.472 |

EXAMPLES 361 TO 365

General Procedure

Compounds 361 to 365 were prepared by a route analogous to that used for the preparation of 344E (HPLC Conditions: "HPLC Method 2"). The compounds of these examples have the structure:

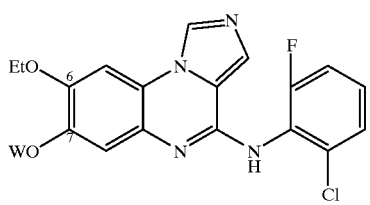

| Ex. No | W | Compound name | HPLC Ret. Time (min) |
|---|---|---|---|
| 361 | (4-morpholinyl)ethyl | N-(2-Chloro-6-fluorophenyl)-8-ethoxy-7-[2-(4-morpholinyl)ethoxy]imidazo[1,5-a]quinoxalin-4-amine | 2.829 |
| 362 | (4-morpholinyl)propyl | N-(2-Chloro-6-fluorophenyl)-8-ethoxy-7-[3-(4-morpholinyl)propoxy]imidazo[1,5-a]quinoxalin-4-amine | 2.901 |
| 363 | (dimethylamino)ethyl | N-(2-Chloro-6-fluorophenyl)-7-[2-(dimethylamino)ethoxy]-8-ethoxyimidazo[1,5-a]quinoxalin-4-amine | 2.807 |
| 364 | (dimethylamino)propyl | N-(2-Chloro-6-fluorophenyl)-7-[3-(dimethylamino)propoxy]-8-ethoxyimidazo[1,5-a]quinoxalin-4-amine | 2.914 |

-continued

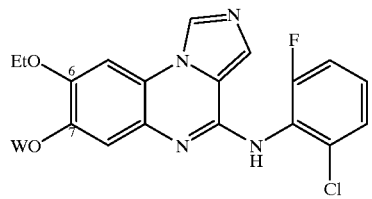

| Ex. No | W | Compound name | HPLC Ret. Time (min) |
|---|---|---|---|
| 365 | (tetrahydrofuran-3-yl) | N-(2-Chloro-6-fluorophenyl)-8-ethoxy-7-[(tetrahydro-3-furanyl)oxy]imidazo[1,5-a]quinoxalin-4-amine | 3.809 |

EXAMPLES 366 TO 368
General Procedure

Compounds 366 to 368 were prepared from 344B by a route analogous to that used for the preparation of 344E (HPLC Conditions: "HPLC Method 2"). The compounds of these examples have the structure:

EXAMPLES 369 TO 389
General Procedure

Compounds 369 to 389 were prepared from 130D by a route analogous to that used for the preparation of 356 (HPLC Conditions: "HPLC Method 2"). The compounds of these examples have the structure:

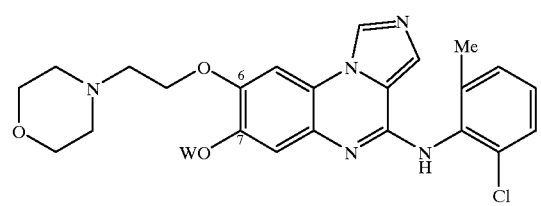

| Ex. No | W | Compound name | HPLC Ret. Time (min) |
|---|---|---|---|
| 366 | Me | N-(2-Chloro-6-methylphenyl)-7-methoxy-8-[2-(4-morpholinyl)ethoxy]imidazo[1,5-a]quinoxalin-4-amine | 2.615 |
| 367 | Et | N-(2-Chloro-6-methylphenyl)-7-ethoxy-8-[2-(4-morpholinyl)ethoxy]imidazo[1,5-a]quinoxalin-4-amine | 2.680 |
| 368 | (tetrahydrofuran-3-yl) | N-(2-Chloro-6-methylphenyl)-8-[2-(4-morpholinyl)ethoxy]-7-[(tetrahydro-3-furanyl)oxy]imidazo[1,5-a]quinoxalin-4-amine | 2.626 |

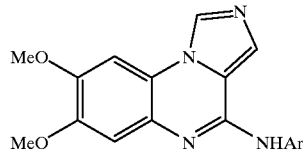

| Ex. No | Ar | Compound name | HPLC Ret. Time (min) |
|---|---|---|---|
| 369 | 3,5-dichloro-4-(N-cyclopropylcarbamoyl)phenyl | 3,5-Dichloro-N-cyclopropyl-4-[(7,8-dimethoxyimidazo[1,5-a]quinoxalin-4-yl)amino]benzamide | 3.255 |
| 370 | 2-bromo-4,6-difluorophenyl | N-(2-Bromo-4,6-difluorophenyl)-7,8-dimethoxyimidazo[1,5-a]quinoxalin-4-amine | 3.333 |
| 371 | 3,5-dichloro-4-carboxyphenyl | 3,5-Dichloro-4-[(7,8-dimethoxyimidazo[1,5-a]quinoxalin-4-yl)amino]benzoic acid | 3.288 |
| 372 | 2,4-dibromo-6-fluorophenyl | N-(2,4-Dibromo-6-fluorophenyl)-7,8-dimethoxyimidazo[1,5-a]quinoxalin-4-amine | 3.831 |
| 373 | 3,5-dichloro-4-sulfamoylphenyl | 3,5-Dichloro-4-[(7,8-dimethoxyimidazo[1,5-a]quinoxalin-4-yl)amino]benzenesulfonamide | 2.912 |
| 374 | 3-chloro-5-methyl-4-sulfophenyl | 3-Chloro-4-[(7,8-dimethoxyimidazo[1,5-a]quinoxalin-4-yl)amino]-5-methylbenzenesulfonic acid | 3.607 |
| 375 | 2,6-dichloro-4-(trifluoromethyl)phenyl | N-[2,6-Dichloro-4-(trifluoromethyl)phenyl]-7,8-dimethoxyimidazo[1,5-a]quinoxalin-4-amine | 4.076 |

-continued

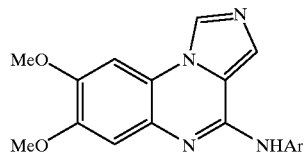

| Ex. No | Ar | Compound name | HPLC Ret. Time (min) |
|---|---|---|---|
| 376 | 2,6-dibromo-4-methylphenyl | N-(2,6-Dibromo-4-methylphenyl)-7,8-dimethoxyimidazo[1,5-a]quinoxalin-4-amine | 3.373 |
| 377 | 2,4-dichloro-6-(trifluoromethyl)phenyl | N-[2,4-Dichloro-6-(trifluoromethyl)phenyl]-7,8-dimethoxyimidazo[1,5-a]quinoxalin-4-amine | 3.840 |
| 378 | 2,6-dichloro-4-methoxyphenyl | N-(2,6-Dichloro-4-methoxyphenyl)-7,8-dimethoxyimidazo[1,5-a]quinoxalin-4-amine | 3.182 |
| 379 | 2-fluoro-6-(trifluoromethyl)phenyl | N-[2-Fluoro-6-(trifluoromethyl)phenyl]-7,8-dimethoxyimidazo[1,5-a]quinoxalin-4-amine | 3.265 |
| 380 | 2-bromo-6-chloro-4-fluorophenyl | N-(2-Bromo-6-chloro-4-fluorophenyl)-7,8-dimethoxyimidazo[1,5-a]quinoxalin-4-amine | 3.240 |
| 381 | 2,6-dibromo-4-fluorophenyl | N-(2,6-Dibromo-4-fluorophenyl)-7,8-dimethoxyimidazo[1,5-a]quinoxalin-4-amine | 3.250 |
| 382 | 2-bromo-4,6-dimethylphenyl | N-(2-Bromo-4,6-dimethylphenyl)-7,8-dimethoxyimidazo[1,5-a]quinoxalin-4-amine | 3.260 |

-continued

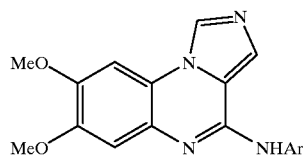

| Ex. No | Ar | Compound name | HPLC Ret. Time (min) |
|---|---|---|---|
| 383 | 2-Br, 4-Cl, 6-F phenyl | N-(2-Bromo-4-chloro-6-fluorophenyl)-7,8-dimethoxyimidazo[1,5-a]quinoxalin-4-amine | 3.560 |
| 384 | 2,6-diF phenyl | N-(2,6-Difluorophenyl)-7,8-dimethoxyimidazo[1,5-a]quinoxalin-4-amine | 2.850 |
| 385 | 2,4,6-triF phenyl | N-(2,4,6-Trifluorophenyl)-7,8-dimethoxyimidazo[1,5-a]quinoxalin-4-amine | 3.150 |
| 386 | 3-Cl, 5-Me, 4-CN phenyl | 3-Chloro-4-[(7,8-dimethoxyimidazo[1,5-a]quinoxalin-4-yl)amino]-5-methylbenzonitrile | 3.178 |
| 387 | 3-Cl, 5-Me, 4-C(O)NH₂ phenyl | 3-Chloro-4-[(7,8-dimethoxyimidazo[1,5-a]quinoxalin-4-yl)amino]-5-methylbenzamide | 2.578 |
| 388 | 2-Cl, 3,6-diMe phenyl | N-(2-Chloro-3,6-dimethylphenyl) 7,8-dimethoxyimidazo[1,5-a]quinoxalin-4-amine | 3.130 |
| 389 | 2-Cl, 5,6-diMe phenyl | N-(2-Chloro-5,6-dimethylphenyl)-7,8-dimethoxyimidazo[1,5-a]quinoxalin-4-amine | 3.630 |

The aniline:

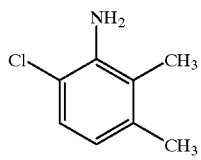

used in the preparation of 389 was prepared as follows: N-Chlorosuccinimide (1.00 g; 8.2 mmol) was added to a solution of 2,3-dimethylaniline (1 ml; 8.2 mmol) in 20 ml of DMF in the dark. After stirring 1 hr. in the dark, the reaction mixture was partitioned between EtOAc (100 ml) and water (100 ml). The organic layer was washed with 1N NaOH (100 ml), water (100 ml) and brine (50 ml). Drying (MgSO$_4$) and concentration afforded 1.25 g (99%) of 2,3-dimethyl-6-chloroaniline as a deep red liquid.

The aniline:

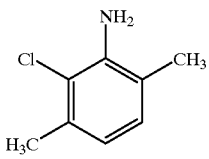

used in the preparation of 388 was prepared in the same manner as described in Godfrey, K. E. and Thrift, R. I., *J. Chem. Soc.* (C), 1967; p 400.

EXAMPLE 390

Preparation of N-(2-Chloro-6-methylphenyl)-6-methoxyimidazo[1,5-a]quinoxalin-4-amine

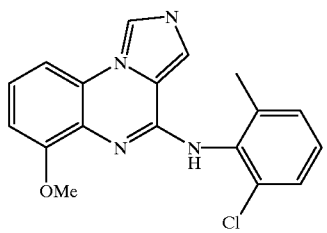

390 was prepared by a route analogous to that used for the preparation of 1F, substituting 3-methoxy-1,2-diaminobenzene for 4-nitro-1,2-diaminobenzene which gave the title compound of this Example as a brown solid. HPLC Ret time: 3.18 min (by HPLC Method 2).

EXAMPLE 391

Preparation of N-(2-Chloro-6-methylphenyl)-9-(phenylmethoxy)imidazo[1,5-a]quinoxalin-4-amine

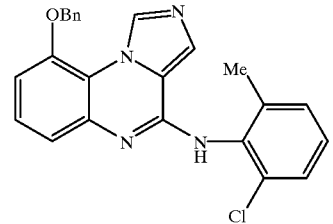

A. 4-[(2-Chloro-6-methylphenyl)amino]imidazo[1,5-a]quinoxalin-9-ol

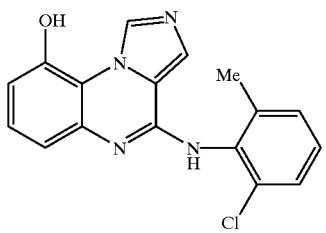

To a solution of 332 (0.0236 g, 0.07 mmol) in dichloromethane (0.23 mL) under nitrogen at −78° C. was added boron tribromide (1 M in dichloromethane, 0.31 mL). After 1 hr at −78° C., the reaction mixture was stirred for 2.5 hr at ambient temperature. The reaction mixture was re-cooled to −78° C., and more boron tribromide (1 M in dichloromethane, 1 mL) was added. The reaction was stirred at ambient temperature overnight. At 0° C., water and dichloromethane were added; the layers were separated, and the aqueous layer was extracted with dichloromethane (3×) and ethyl acetate (2×). The combined organic extracts were dried over magnesium sulfate, filtered and concentrated in vacuo to give 391A.

B. N-(2-Chloro-6-methylphenyl)-9-(phenylmethoxy) imidazo[1,5-a]quinoxalin-4-amine To a mixture of 391A (0.07 mmol) and potassium carbonate (0.040 g, 0.29 mmol) in dimethyl formamide (0.14 mL) was added benzyl bromide (0.0076 mL, 0.07 mmol). After 1.5 h, ethyl acetate and water were added; the layers were separated, and the aqueous layer was extracted with ethyl acetate (2×). The organic layers were combined, dried over sodium sulfate, filtered and concentrated in vacuo and purified by flash chromatography on silica gel (13×240 mm; hexane:ethyl acetate v/v 3/1) to give 13.0 mg of 391B as a light tan solid. MS (M+H)$^+$=415. HPLC: Ret. Time=3.52 min. (by HPLC Method 2).

EXAMPLES 392 TO 397

General Procedure

Compounds 392 to 397 were prepared from 391A by a route analogous to that used for the preparation of 391B (HPLC Conditions: "HPLC Method 2"). The compounds of these examples have the structure:

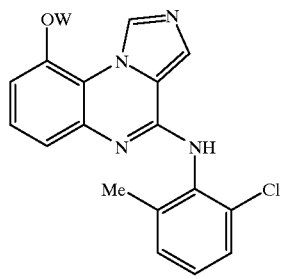

| Ex. No | W | Compound name | HPLC Ret. Time (min) |
|---|---|---|---|
| 392 | HO⁀⁀ | N-(2-Chloro-6-methylphenyl)-9-(2-hydroxyethoxy)imidazo[1,5-a]quinoxalin-4-amine | 3.212 |
| 393 | Me₂N⁀⁀ | N-(2-Chloro-6-methylphenyl)-9-[2-(dimethylamino)ethoxy]imidazo[1,5-a]quinoxalin-4-amine | 2.051 |
| 394 | HO⁀⁀⁀ | N-(2-Chloro-6-methylphenyl)-9-(3-hydroxypropoxy)imidazo[1,5-a]quinoxalin-4-amine | 3.027 |
| 395 | MeO⁀⁀ | N-(2-Chloro-6-methylphenyl)-9-(2-methoxyethoxy)imidazo[1,5-a]quinoxalin-4-amine | 3.147 |
| 396 | (tetrahydropyran-4-yl) | N-(2-Chloro-6-methylphenyl)-9-[(tetrahydro-2H-pyran-4-yl)oxy]imidazo[1,5-a]quinoxalin-4-amine | 3.567 |
| 397 | morpholinylethyl | N-(2-Chloro-6-methylphenyl)-9-[2-(4-morpholinyl)ethoxy]imidazo[1,5-a]quinoxalin-4-amine | 2.045 |

EXAMPLE 398

Preparation of 8-Bromo-N-(2-chloro-6-fluorophenyl)imidazo[1,5-a]quinoxalin-4-amine

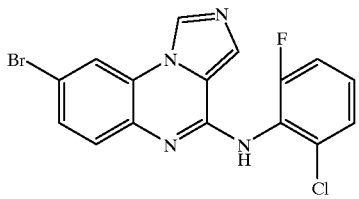

398 was prepared by a route analogous to that used for the preparation of 295A, replacing 2-chloro-6-methylaniline with 2-chloro-6-fluoroaniline. HPLC Ret time: 3.608 min (by HPLC Method 2).

EXAMPLES 399 TO 414

General Procedure

Compounds 399 to 414 were prepared from 398 by a route analogous to that used for the preparation of 295C, substituting with the required amine in place of cyclopropyl methylamine (HPLC Conditions: "HPLC Method 2"). The compounds of these examples have the structure:

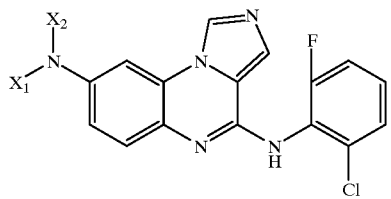

| Ex. No | X₁X₂N | Compound name | HPLC Ret. Time (min) |
|---|---|---|---|
| 399 | (3,5-dimethylpiperazinyl) | N-(2-Chloro-6-fluorophenyl)-8-(3,5-dimethyl-1-piperazinyl)imidazo[1,5-a]quinoxalin-4-amine | 2.459 |
| 400 | (4-methylpiperazinyl) | N-(2-Chloro-6-fluorophenyl)-8-(4-methyl-1-piperazinyl)imidazo[1,5-a]quinoxalin-4-amine | 2.080 |
| 401 | (2-(2-pyridinyl)ethyl)amino | N-(2-Chloro-6-fluorophenyl)-8-[[2-(2-pyridinyl)ethyl]amino]imidazo[1,5-a]quinoxalin-4-amine | 2.469 |
| 402 | (tetrahydro-2-furanyl)methylamino | $N^4$-(2-Chloro-6-fluorophenyl)-$N^8$-[(tetrahydro-2-furanyl)methyl]imidazo[1,5-a]quinoxaline-4,8-diamine | 3.130 |
| 403 | 2-aminoethylamino | $N^8$-(2-Aminoethyl)-$N^4$-(2-chloro-6-fluorophenyl)imidazo[1,5-a]quinoxaline-4,8-diamine | 2.252 |
| 404 | 3-(4-methylpiperazinyl)propylamino | $N^4$-(2-Chloro-6-fluorophenyl)-$N^8$-[3-(4-methyl-1-piperazinyl)propyl]imidazo[1,5-a]quinoxaline-4,8-diamine | 2.349 |
| 405 | 2-(1-methyl-2-pyrrolidinyl)ethylamino | $N^4$-(2-Chloro-6-fluorophenyl)-$N^8$-[2-(1-methyl-2-pyrrolidinyl)ethyl]imidazo[1,5-a]quinoxaline-4,8-diamine | 2.479 |
| 406 | 2-(4-morpholinyl)ethylamino | $N^4$-(2-Chloro-6-fluorophenyl)-$N^8$-[2-(4-morpholinyl)ethyl]imidazo[1,5-a]quinoxaline-4,8-diamine | 2.286 |
| 407 | 6-(dimethylamino)hexylamino | $N^4$-(2-Chloro-6-fluorophenyl)-$N^8$-[6-(dimethylamine)hexyl]imidazo[1,5-a]quinoxaline-4,8-diamine | 2.703 |

-continued

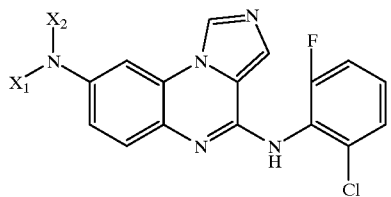

| Ex. No | X₁X₂N | Compound name | HPLC Ret. Time (min) |
|---|---|---|---|
| 408 | (structure) | $N^4$-(2-Chloro-6-fluorophenyl)-$N^8$-[4-(dimethylamino)butyl]imidazo[1,5-a]quinoxaline-4,8-diamine | 2.449 |
| 409 | (structure) | $N^4$-(2-Chloro-6-fluorophenyl)-$N^8$-[3-(dimethylamino)propyl]imidazo[1,5-a]quinoxaline-4,8-diamine | 2.376 |
| 410 | (structure) | $N^4$-(2-Chloro-6-fluorophenyl)-$N^8$-[2-(dimethylamino)ethyl]imidazo[1,5-a]quinoxaline-4,8-diamine | 2.244 |
| 411 | (structure) | 1-[3-[[4-(2-Chloro-6-fluorophenyl)imidazo[1,5-a]quinoxalin-8-yl]amino]propyl]-2-pyrrolidinone | 2.956 |
| 412 | (structure) | $N^4$-(2-Chloro-6-fluorophenyl)-$N^8$-[2-(4-pyridinyl)ethyl]imidazo[1,5-a]quinoxaline-4,8-diamine | 2.462 |
| 413 | (structure) | $N^4$-(2-Chloro-6-fluorophenyl)-$N^8$-[3-(4-morpholinyl)propyl]imidazo[1,5-a]quinoxaline-4,8-diamine | 2.396 |
| 414 | (structure) | $N^4$-(2-Chloro-6-fluorophenyl)-$N^8$-(cyclopropylmethyl)imidazo[1,5-a]quinoxaline-4,8-diamine | 3.137 |

EXAMPLE 415

Preparation of 7-Bromo-N-(2-chloro-6-methylphenyl)imidazo[1,5-a]quinoxalin-4-amine

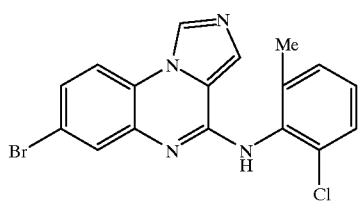

The title compound was prepared from 5-bromo-2-fluoroaniline, obtained by $SnCl_2$ reduction of commercially available 5-bromo-2-fluoronitrobenzene, by a method analogous to that used for the preparation of 272C. HPLC retention time=3.521 min (by HPLC Method 2).

EXAMPLE 416 TO 440

General Procedure

Compounds 416 to 440 were prepared from 415 by a route analogous to that used for the preparation of 295C, substituting with the required amine in place of cyclopropyl methylamine (HPLC Conditions: "HPLC Method 2"). The compounds of these examples have the structure:

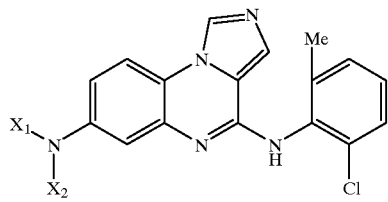

| Ex. No | X₁X₂N | Compound name | HPLC Ret. Time (min) |
|---|---|---|---|
| 416 | (dimethylamino-butyl-NH) | $N^4$-(2-Chloro-6-methylphenyl)-$N^7$-[4-(dimethylamino)butyl]imidazo[1,5-a]quinoxaline-4,7-diamine | 2.577 |
| 417 | (dimethylamino-hexyl-HN) | $N^4$-(2-Chloro-6-methylphenyl)-$N^7$-[6-(dimethylamino)hexyl]imidazo[1,5-a]quinoxaline-4,7-diamine | 2.764 |
| 418 | (4-methylpiperazinyl-propyl-NH) | $N^4$-(2-Chloro-6-methylphenyl)-$N^7$-[3-(4-methyl-1-piperazinyl)propyl]imidazo[1,5-a]quinoxaline-4,7-diamine | 2.459 |
| 419 | (cyclopropyl-NH) | $N^4$-(2-Chloro-6-methylphenyl)-$N^7$-cyclopropylimidazo[1,5-a]quinoxaline-4,7-diamine | 3.178 |
| 420 | (1-benzylpiperidin-4-yl-NH) | $N^4$-(2-Chloro-6-methylphenyl)-$N^7$-[1-(phenylmethyl)-4-piperidinyl]imidazo[1,5-a]quinoxaline-4,7-diamine | 2.908 |
| 421 | (N-methyl-N-phenylamino-propyl-NH) | $N^4$-(2-Chloro-6-methylphenyl)-$N^7$-[3-(methylphenylamino)propyl]imidazo[1,5-a]quinoxaline-4,7-diamine | 2.844 |
| 422 | (2-aminobenzyl-NH) | $N^7$-[(2-Aminophenyl)methyl]-$N^4$-(2-chloro-6-methylphenyl)imidazo[1,5-a]quinoxaline-4,7-diamine | 2.885 |
| 423 | (morpholinyl) | N-(2-Chloro-6-methylphenyl)-7-(4-morpholinyl)imidazo[1,5-a]quinoxalin-4-amine | 3.000 |

-continued

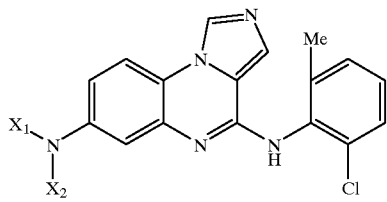

| Ex. No | X₁X₂N | Compound name | HPLC Ret. Time (min) |
|---|---|---|---|
| 424 | 4-methylpiperazin-1-yl | N-(2-Chloro-6-methylphenyl)-7-(4-methyl-1-piperazinyl)imidazo[1,5-a]quinoxalin-4-amine | 2.345 |
| 425 | piperazin-1-yl | N-(2-Chloro-6-methylphenyl)-7-(1-piperazinyl)imidazo[1,5-a]quinoxalin-4-amine | 2.346 |
| 426 | 3,5-dimethylpiperazin-1-yl | N-(2-Chloro-6-methylphenyl)-7-(3,5-dimethyl-1-piperazinyl)imidazo[1,5-a]quinoxalin-4-amine | 2.505 |
| 427 | 4-[2-(dimethylamino)ethyl]piperazin-1-yl | N-(2-Chloro-6-methylphenyl)-7-[4-[2-(dimethylamino)ethyl]-1-piperazinyl]imidazo[1,5-a]quinoxalin-4-amine | 2.351 |
| 428 | 4-[3-(dimethylamino)propyl]piperazin-1-yl | N-(2-Chloro-6-methylphenyl)-7-[4-[3-(dimethylamino)propyl]-1-piperazinyl]imidazo[1,5-a]quinoxalin-4-amine | 2.315 |
| 429 | (S)-3-methylpiperazin-1-yl | (S)-N-(2-Chloro-6-methylphenyl)-7-(3-methyl-1-piperazinyl)imidazo[1,5-a]quinoxalin-4-amine | 2.455 |
| 430 | [2-(dimethylamino)ethyl]amino | $N^4$-(2-Chloro-6-methylphenyl)-$N^7$-[2-(dimethylamino)ethyl]imidazo[1,5-a]quinoxaline-4,7-diamine | 2.369 |
| 431 | [3-(dimethylamino)propyl]amino | $N^4$-(2-Chloro-6-methylphenyl)-$N^7$-[3-(dimethylamino)propyl]imidazo[1,5-a]quinoxaline-4,7-diamine | 2.497 |

-continued

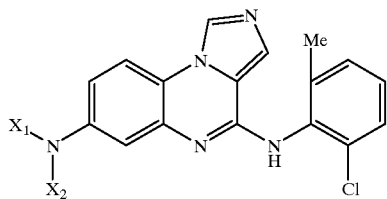

| Ex. No | X₁X₂N | Compound name | HPLC Ret. Time (min) |
|---|---|---|---|
| 432 | (2-thienylmethyl)NH | $N^4$-(2-Chloro-6-methylphenyl)-$N^7$-(2-thienylmethyl)imidazo[1,5-a]quinoxaline-4,7-diamine | 3.176 |
| 433 | (2,3-dihydro-1,4-benzodioxin-2-ylmethyl)NH | $N^4$-(2-Chloro-6-methylphenyl)-$N^7$-[(2,3-dihydro-1,4-benzodioxin-2-yl)methyl]imidazo[1,5-a]quinoxaline-4,7-diamine | 3.628 |
| 434 | 2-(2-thienyl)ethyl NH | $N^4$-(2-Chloro-6-methylphenyl)-$N^7$-[2-(2-thienyl)ethyl]imidazo[1,5-a]quinoxaline-4,7-diamine | 3.545 |
| 435 | (R)-3-methylpiperazin-1-yl | (R)-N-(2-Chloro-6-methylphenyl)-7-(3-methyl-1-piperazinyl)imidazo[1,5-a]quinoxalin-4-amine | 2.454 |
| 436 | 4-(1,3-benzodioxol-5-ylmethyl)piperazin-1-yl | 7-[4-(1,3-Benzodioxol-5-ylmethyl)-1-piperazinyl]-N-(2-chloro-6-methylphenyl)imidazo[1,5-a]quinoxalin-4-amine | 2.774 |
| 437 | 4-[2-(isopropylamino)-2-oxoethyl]piperazin-1-yl | 4-[4-[(2-Chloro-6-methylphenyl)amino]imidazo[1,5-a]quinoxalin-7-yl]-N-(1-methylethyl)-1-piperazineacetamide | 2.595 |
| 438 | 4-phenylpiperazin-1-yl | N-(2-Chloro-6-methylphenyl)-7-(4-phenyl-1-piperazinyl)imidazo[1,5-a]quinoxalin-4-amine | 3.362 |
| 439 | 4-(2-furanylcarbonyl)piperazin-1-yl | 1-[4-[(2-Chloro-6-methylphenyl)amino]imidazo[1,5-a]quinoxalin-7-yl]-4-(2-furanylcarbonyl)piperazine | 3.209 |

-continued

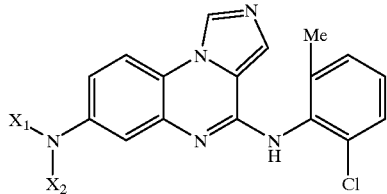

| Ex. No | X₁X₂N | Compound name | HPLC Ret. Time (min) |
|---|---|---|---|
| 440 | 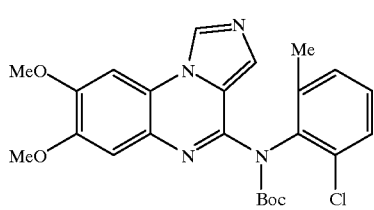 | N-(2-Chloro-6-methylphenyl)-7-[4-(2-methoxyethyl)-1-piperazinyl]imidazo[1,5-a]quinoxalin-4-amine | 2.436 |

EXAMPLE 441

Preparation of 4-[(2-Chloro-6-methylphenyl)amino]-7,8-dimethoxyimidazo[1,5-a]quinoxaline-1-carboxaldehyde

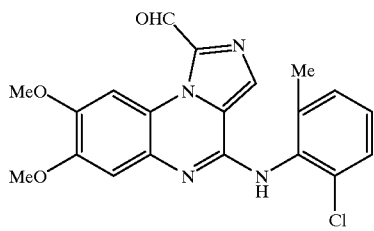

A. (2-Chloro-6-methylphenyl)(7,8-dimethoxyimidazo[1,5-a]quinoxalin-4-yl)carbamic acid 1,1-dimethylethyl ester 441A was prepared from 186 by a method analogous to that used for the preparation of 295B.

B. (2-Chloro-6-methylphenyl)(1-formyl-7,8-dimethoxyimidazo[1,5-a]quinoxalin-4-yl)carbamic acid 1,1-dimethylethyl ester

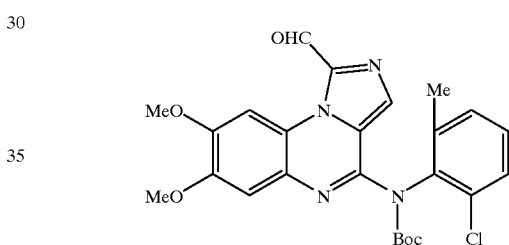

To a solution of 441A (56 mg, 0.12 mmol) in 0.5 mL of dry THF cooled at −78° C. was added a solution of 20M LDA in THF (0.09 mL, 0.18 mmol). After 15 min, dry DMF (0.047 mL, 0.6 mmol) was added and the mixture was stirred at −78° C. for 1.0 hr and −40° C. overnight. Sat'd NH₄Cl was added to the reaction mixture and extracted with EtOAc (×2). The combined organic extracts were washed with water, brine and dried over anhydrous Na₂SO₄. Concentration in vacuo followed by flash chromatography (CH₂Cl₂-EtOAc: 100:0 to 4:1) on silica gel gave 50.6 mg of 441B as a yellow solid.

C. 4-[(2-Chloro-6-methylphenyl)amino]-7,8-dimethoxyimidazo[1,5-a]quinoxaline-1-carboxaldehyde The mixture of 441B (20 mg) in 3:1 TFA- CH₂Cl₂ (2.0 mL) was stirred for 5.0 hrs. Concentration in vacuo followed by flash chromatography (hexane-EtOAc: 4:1) on silica gel gave 13.3 mg of the title compound 441C as a yellow solid. HPLC Ret time: 3.050 min (by HPLC Method 2).

EXAMPLE 442

Preparation of 4-[(2-Chloro-6-methylphenyl)amino]-7,8-dimethoxyimidazo[1,5-a]quinoxaline-1-carboxaldehyde oxime

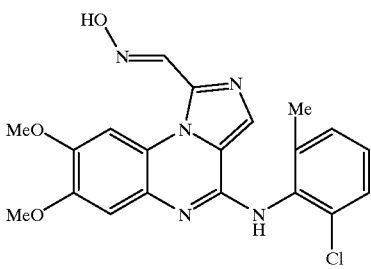

A. (2-Chloro-6-methylphenyl)[1-[(hydroxyimino)methyl]-7,8-dimethoxyimidazo[1,5-a]quinoxalin-4-yl]carbamic acid 1,1-dimethylethyl ester

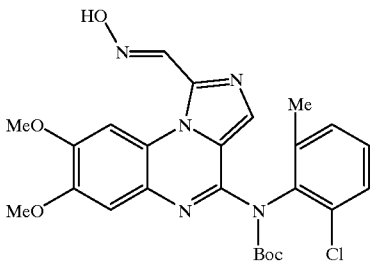

The mixture of 441B (20 mg, 0.04 mmol), hydroxylamine hydrochloride salt (13.3 mg, 0.192 mmol) and triethylamine (0.032 mL, 0.228 mmol) in 0.5 mL of EtOH was heated at 90° C. in a sealed vial for 5.0 hrs. The reaction mixture was cooled to room temperature, and concentrated under reduced pressure. The residue was taken into 5 mL of water and glacial AcOH was added. The mixture was extracted with EtOAc (x2) and washed with brine, and dried over anhydrous $Na_2SO_4$. Concentration in vacuo and trituration with ether gave 442A.

B. 4-[(2-Chloro-6-methylphenyl)amino]-7,8-dimethoxyimidazo[1,5-a]quinoxaline-1-carboxaldehyde oxime The mixture of 442A in 4:1 TFA- $CH_2Cl_2$ (1.0 mL) was stirred for 5.0 hrs. Concentration in vacuo followed by recrystallization from ether gave 17.8 mg of the title compound 442B as a yellow solid (a 20:80 mixture of Z/E isomers). HPLC Ret time: 2.945 and 3.244 min (by HPLC Method 2).

EXAMPLE 443

Preparation of 4-[(2-Chloro-6-methylphenyl)amino]-8-methoxyimidazo[1,5-a]quinoxalin-7-ol

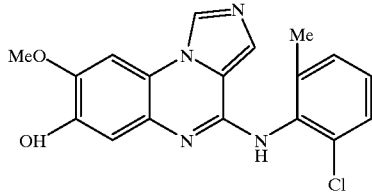

The title compound, prepared previously as 344D forms part of the present invention. HPLC Ret. Time=2.930 min. (HPLC Conditions: "HPLC Method 2").

EXAMPLE 444

Preparation of 2-[[4-[(2-Chloro-6-methylphenyl)amino]-7-hydroxyimidazo[1,5-a]quinoxalin-8-yl]oxy]-2-propenenitrile

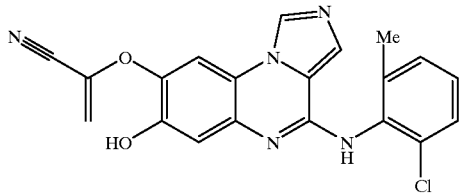

The mixture of 344A (50 mg), cesium carbonate (243 mg) and chloroacrylonitrile (0.05 mL) in 1 mL of DMF was heated to 80° C. for 1.0 hr. The reaction mixture was cooled to room temperature and the title compound was isolated by preparative HPLC. HPLC Retention time=3.410 min (HPLC Conditions: "HPLC Method 2").

EXAMPLES 445 TO 447

General Procedure

Compounds 445 to 447 were prepared from 344A by a method analogous to that used for the preparation of 444, substituting with the appropriate halide in place of chloroacrylonitrile (HPLC Conditions: "HPLC Method 2"). The compounds of these examples have the structure:

| Ex. No | W | Compound name | HPLC Ret. Time (min) |
|---|---|---|---|
| 445 | 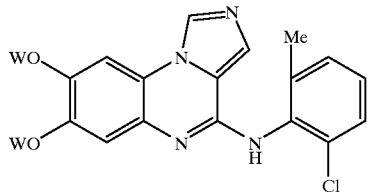 | 7-[(2-Chloro-6-methylphenyl)amino]-2,3-dihydro-1,4-dioxino[2,3-g]imidazo[1,5-a]quinoxaline-2-carbonitrile | 3.200 |
| 446 | | N-(2-Chloro-6-methylphenyl)-7,8-bis[3-(dimethylamino)-propoxy]imidazo[1,5-a]-quinoxalin-4-amine | 2.160 |
| 447 | | N-(2-Chloro-6-methylphenyl)-7,8-bis[2-(4-morpholinyl)-ethoxy]imidazo[1,5-a]-quinoxalin-4-amine | 1.780 |

EXAMPLE 448

Preparation of N-Cyclohexyl-7,8-dimethoxyimidazo[1,5-a]quinoxaline-4-amine

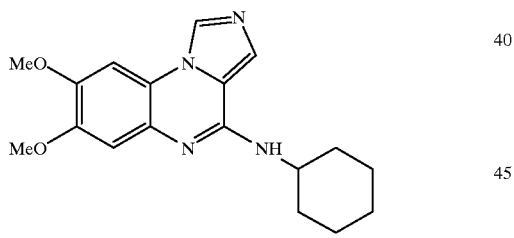

The mixture of 130D (67 mg, 0.254 mmol) and cyclohexylamine (0.076 mL, 0.763 mmol) in 0.5 mL of anhydrous 1,4-dioxane was heated in a sealed tube at 120° C. for 36 hrs. Upon cooling, the volatiles were removed under reduced pressure and the residue was taken into a mixture of water-sat'd sodium bicarbonate-EtOAc. The organic layer was dried over anhydrous Na$_2$SO$_4$. Concentration in vacuo followed by trituration with hexane gave 74.6 mg of the title compound as a light brown solid. HPLC Ret. Time=5.224 min. (HPLC Conditions: "HPLC Method 3": HPLC Conditions for Method 3: YMS C18 S-3 120 Å ODS column, 4.6×50 mm; 0%–100% B, linear gradient over 8 min at 2.5 mL/min; then isocratic for 3 min at 100% B; Solvent A: 10% MeOH-90% H$_2$O-0.2% H$_3$PO$_4$, solvent B: 90% MeOH-10% H$_2$O-0.2% H$_3$PO$_4$.)

EXAMPLE 449

Preparation of 1-Chloro-N-(2-chloro-6-methylphenyl)-7,8-dimethoxyimidazo[1,5-a]quinoxalin-4-amine

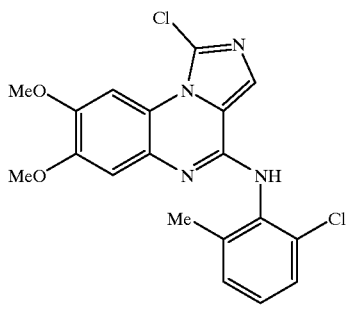

A. (1-Chloro-7,8-dimethoxyimidazo[1,5-a]quinoxalin-4-yl)(2-chloro-6-methylphenyl)carbamic acid 1,1-dimethylethyl ester

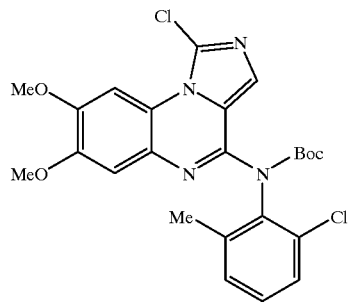

A solution of 2.0 M LDA in THF (1.5 mL; 3.0 mmol) was added dropwise over 5 min to a solution of 441A (530 mg; 1.14 mmol) in 18 mL of THF at −78° C. After stirring at −78° C. for 20 min, a solution of N-chlorosuccinimide (500 mg; 3.75 mmol) in 10 mL of THF was added in one portion. The reaction was stirred at −78° C. for 1.0 hr. and allowed to stand at −40° C. for 18 hrs. The reaction mixture was partitioned between saturated ammonium chloride solution (50 mL) and EtOAc (50 mL). The organic layer was washed with water and brine, and dried over anhydrous $MgSO_4$. Concentration in vacuo followed by flash chromatography (EtOAc-Hex: 1:3) on silica gel afforded 330 mg of 449A as a light yellow solid.

B. 1-Chloro-N-(2-chloro-6-methylphenyl)-7,8-dimethoxyimidazo[1,5-a]quinoxalin-4-amine A mixture of 449A (325 mg; 0.64 mmol) and TFA (5 mL) was stirred 1.5 hr at room temperature. Concentration in vacuo followed by azeotropic evaporation from EtOAc/Heptane gave a residue which was partitioned between $CHCl_3$ and saturated $NaHCO_3$ solution. The organic layer was dried over anhydrous $MgSO_4$ and concentrated under reduced pressure to afford 257 mg of 449B as a yellow solid. HPLC Ret time: 3.34 min (by HPLC Method 2).

EXAMPLE 450

Preparation of N-(2-Chloro-6-methylphenyl)-1,7,8-trimethoxyimidazo[1,5-a]quinoxalin-4-amine

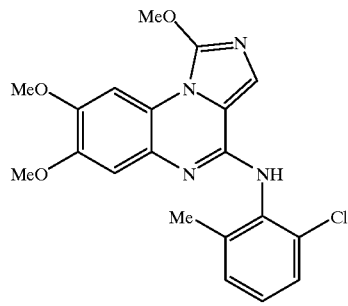

A mixture of 449B (40 mg; 0.1 mmol) and 2 mL of 1M sodium methoxide (2 mmol) in 2 mL of MeOH and 1 mL of DMF was heated to 120° C. in a pressure tube for 5 hrs. After cooling to room temperature, the reaction mixture was partitioned between EtOAc and water. The organic layer was washed with water and brine. After drying over anhydrous $MgSO_4$ and concentration, the residue was chromatographed ($CH_2Cl_2$-MeOH: 100:0 to 96:4) on silica gel. Recrystallization with $CH_2Cl_2$-hexane afforded 25 mg of 450 as a yellow powder. MS (ESI): 399+ (M+H)+ (compound unstable to HPLC conditions).

EXAMPLE 451

Preparation of $N^4$-(2-Chloro-6-methylphenyl)-7,8-dimethoxy-$N^1$-[(4-methoxyphenyl)methyl]imidazo[1,5-a]quinoxaline-1,4-diamine

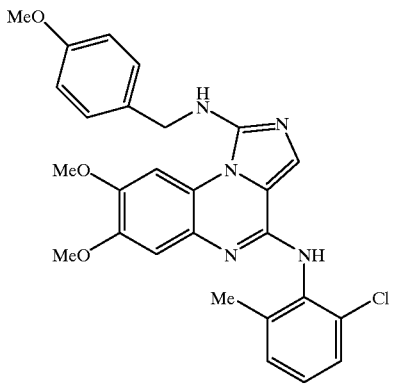

A mixture of 449B (120 mg; 0.30 mmol) and p-methoxybenzylamine (3 mL) was heated at 160° C. for 2 days. The reaction mixture was partitioned between EtOAc and water. The organic layer was washed with saturated ammonium chloride solution (×3), water and brine. After drying ($MgSO_4$) and concentration, the residue was purified by flash chromatography on a 2.5×15 cm silica gel column using EtOAc:Hex, 1:1 as the mobile phase. Concentration in vacuo afforded 95 mg of 451 as a yellow solid. HPLC Ret time: 3.70 min (by HPLC Method 2).

EXAMPLE 452

Preparation of N-[4-[(2-Chloro-6-methylphenyl)amino]-7,8-dimethoxyimidazo[1,5-a]quinoxalin-1-yl]-N-[(4-methoxyphenyl)methyl]acetamide

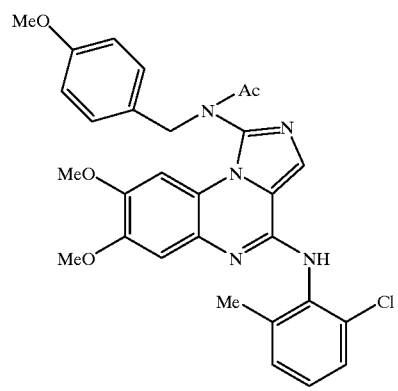

Acetic anhydride (0.008 mL; 0.072 mmol) was added to a solution of 451 (30 mg; 0.059 mmol) in 0.5 mL of pyridine. After stirring for 24 hrs. at room temperature, the volatiles were removed in vacuo and the residue was triturated with ethyl ether to afford 30 mg of 452 as a light yellow powder. HPLC Ret. time: 3.770 min (by HPLC Method 2).

EXAMPLE 453

Preparation of N-[4-[(2-Chloro-6-methylphenyl)amino]-7,8-dimethoxyimidazo[1,5-a]quinoxalin-1-yl acetamide

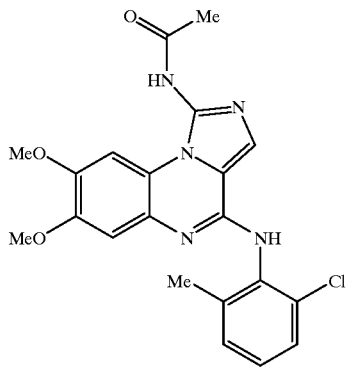

A mixture of 452 (27 mg; 0.049 mmol) in 1 mL of TFA was stirred for 3 days at room temperature. After concentrating, the residue was coevaporated from heptane and partitioned between EtOAc and 1N NaOH. The organic layer was washed with brine and dried over anhydrous MgSO$_4$. Concentration in vacuo was conducted and the residue was crystallized from CH$_2$Cl$_2$/hexane to afford 16 mg 453 as a canary yellow powder. HPLC Ret time: 3.15 min (by HPLC Method 2).

EXAMPLE 454

Preparation of N$^4$-(2-Chloro-6-methylphenyl)-7,8-dimethoxyimidazo[1,5-a]quinoxaline-1,4-diamine, dihydrochloride

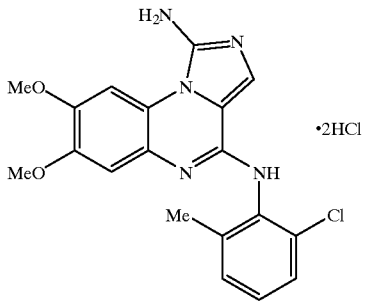

A mixture of 451 (20 mg; 0.04 mmol) in TFA was heated to 50° C. for 18 hrs. The volatiles were removed in vacuo and the residue was coevaporated from heptane. The residue was suspended in MeOH (2 mL) and 0.25 mL of 2N HCl was added. The mixture was concentrated and the HCl treatment was repeated. The residue was coevaporated from EtOH several times and the resulting solid was triturated with ethyl ether to afford 16 mg of 454 as a yellow powder. HPLC Ret time: 2.92 min (by HPLC Method 2).

EXAMPLE 455

Preparation of 3-Chloro-N-(2-chloro-6-methylphenyl)imidazo[1,5-a]quinoxalin-4-amine

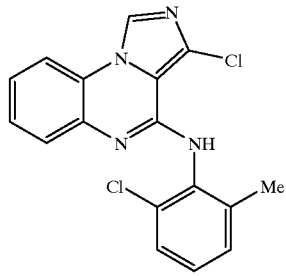

A. 3,4-Dichloroimidazo[1,5-a]quinoxaline

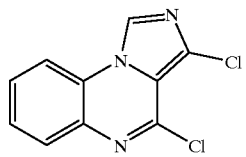

A mixture of 17D (1.75 g; 9.46 mmol), N-chlorosuccinimide (1.45 g; 10.5 mmol) and NaOAc (ca. 10 mg) in 50 mL of AcOH was stirred for 18 hrs at 50° C. The reaction mixture was poured into a stirred biphasic mixture of 200 mL of water and 200 mL of EtOAc. The pH of the water layer was adjusted to ca. 8 by careful addition of solid sodium bicarbonate. The layers were separated and the organic layer was dried over anhydrous MgSO$_4$ and concentrated under reduced pressure. The residue was chromatographed on a 5×15 cm silica gel column, using 40% EtOAc/Hex followed by 60% EtOAc/Hex as the mobile phase. Concentration of appropriate fractions afforded 1.18 g of a partially purified product. A portion of this material (290 mg) was refluxed in 7 mL of phosphorusoxy-chloride for 1 hr. The volatiles were removed in vacuo and the residue was coevaporated from toluene. The residue was partitioned between CHCl$_3$ (50 ml) and saturated sodium bicarbonate solution (50 ml). The organic layer was dried over anhydrous MgSO$_4$ and concentrated to afford a residue that was chromatographed on a 2.5×15 cm silica gel column using 20% EtOAc/Hex as the mobile phase. The pure fractions were concentrated to afford 94 mg of 455A as a tan solid.

B. 3-Chloro-N-(2-chloro-6-methylphenyl)imidazo[1,5-a]quinoxalin-4-amine

A 1.0M sodium hexamethyldisilizane solution in THF (0.75 mL; 0.75 mmol) was added to a solution of 2-methyl-6-chloroaniline in 1 mL of THF. After heating to 70° C. for 15 min, 455A (71 mg; 0.29 mmol) was added and the reaction mixture was stirred for 3 hrs at room temperature. AcOH (0.2 mL) was added and the solvents were removed in vacuo. The residue was partitioned between EtOAc (20 ml) and saturated sodium bicarbonate solution (20 ml). The organic layer was washed with brine (20 ml), dried (MgSO$_4$) and concentrated. The residue was crystalled from CH$_2$Cl$_2$/hexane to afford 33 mg of 455B as a tan solid. HPLC Ret time: 3.67 min (by HPLC Method 2).

EXAMPLE 456

Preparation of 4-[(2-Chloro-6-methylphenyl)amino]imidazo[1,5-a]quinoxaline-8-carbonitrile

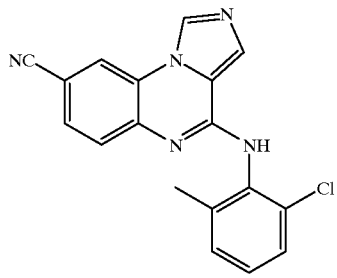

A. (2-Chloro-6-methylphenyl)(8-iodoimidazo[1,5-a]quinoxalin-4-yl)carbamic acid 1,1-dimethylethyl ester

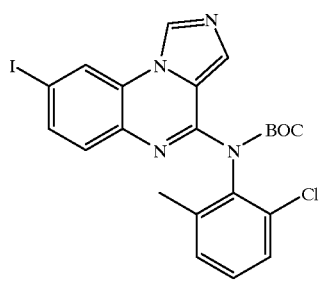

Compound 456A was prepared from 271C by a method analogous to that used for the preparation of 295B.

B. 4-[(2-Chloro-6-methylphenyl)amino]imidazo[1,5-a]quinoxaline-8-carbonitrile

To a solution of 456A (64.8 mg, 0.121 mmol) in DMF (0.5 mL) was added CuCN (32.5 mg, 0.363 mmol). The mixture was heated to reflux. When complete the title compound 456B was purified by prep HPLC. HPLC Ret time: 3.593 min (by HPLC Method 2).

EXAMPLE 457

Preparation of 4-[(2-Chloro-6-methylphenyl)amino]imidazo[1,5-a]quinoxaline-8-carboxamide

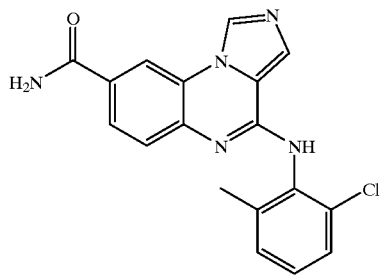

A suspension of 456B (15.0 mg, 0.045 mmol) in 85% aqueous sulfuric acid (1.0 mL) was heated at 80° C. for 1 hr. The reaction mixture was poured into 10.0 mL of ice water, and the pH was raised to 8.5 with saturated aqueous $KHCO_3$ solution. The mixture was extracted with $CH_2Cl_2$ (×3); the combined organic layers were washed with saturated aqueous $KHCO_3$ solution, dried ($Na_2SO_4$), and concentrated under vacuum. The solid was collected by filtration, rinsed with water and ether, and combined with the organic extracts. Trituration with ether yielded 6.5 mg of 457 as a light tan solid. HPLC Ret time: 2.760 min (by HPLC Method 2).

EXAMPLE 458

Preparation of 4-[(2-Chloro-6-methylphenyl)amino]imidazo[1,5-a]quinoxaline-8-carboxylic acid

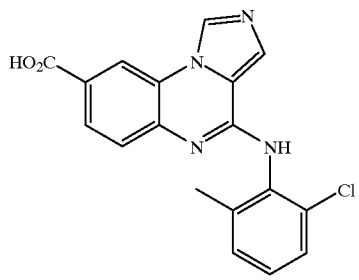

A suspension of 456B (50.0 mg, 0.150 mmol) with NaOH (12.0 mg, 0.30 mmol) in ethylene glycol (0.30 mL) and water (24.0 mL) was heated at 95° C. for 2.5 hrs then at 105° C. for 6.0 hrs. After the addition of more NaOH (12.0 mg) and ethylene glycol (0.10 mL), heating at 105° C. was continued for 16 hrs. The solvents were removed under vacuum. The oily product was solidified with MeOH and ether, collected by filtration, and rinsed with ether. The crude product was purified by flash chromatography on reversed-phase silica gel, eluting with a mixture of MeOH-$H_2$O-TFA to yield 18.8 mg of 458 as an off-white solid. HPLC Ret time: 2.95 min (by HPLC Method 2); MS: 353+(M+H)$^+$.

EXAMPLE 459

Preparation of 4-[(2-Chloro-6-methylphenyl)amino]imidazo[1,5-a]quinoxaline-8-carboxylic acid methyl ester

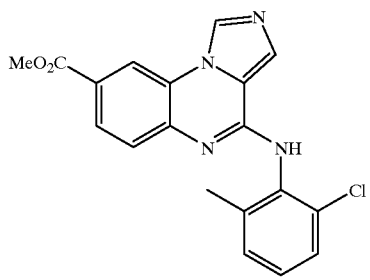

A stirred solution of 458 (8.2 mg, 0.023 mmol) in MeOH (2.0 mL) at 0° C. was saturated wth HCl gas for 10 min. The reaction vessel was sealed; after 16 hrs, the solvent was evaporated. Trituration with ether yielded 5.4 mg of 459 as an off-white solid. HPLC Ret time: 3.61 min (by HPLC Method 2); MS: 367+(M+H)$^+$.

EXAMPLE 460

Preparation of 4-[(2-Chloro-6-methylphenyl)amino]imidazo[1,5-a]quinoxalin-8-ol

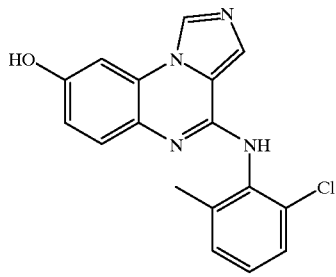

460 was prepared from 273C by a method analogous to that used for the preparation of 263. HPLC Ret time: 2.700 min (by HPLC Method 2).

EXAMPLE 461

Preparation of N-[2-Chloro-6-methyl-4-(4-morpholinyl)phenyl]-7,8-dimethoxyimidazo[1,5-a]quinoxalin-4-amine

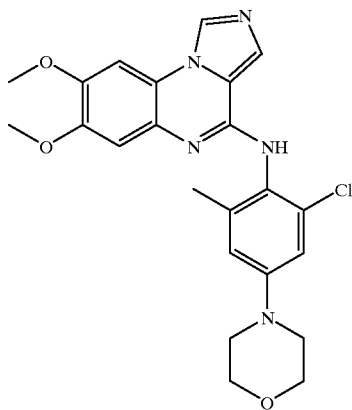

A. (4-Bromo-2-chloro-6-methylphenyl)(7,8-dimethoxyimidazo[1,5-a]quinoxalin-4-yl)carbamic acid 1,1-dimethylethyl ester

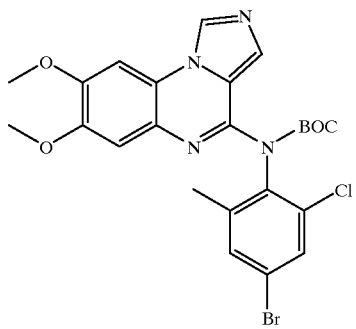

461A was prepared from 231 by a method analogous to that used for the preparation of 295B.
B. N-[2-Chloro-6-methyl-4-(4-morpholinyl)phenyl]-7,8-dimethoxyimidazo[1,5-a]quinoxalin-4-amine
461B was prepared from 461A by a method analogous to that used for the preparation of 312. HPLC Ret time: 2.989 min (by HPLC Method 2).

EXAMPLE 462

Preparation of N-(2-Chloro-6-methylphenyl)-8-(hexahydro-4-methyl-1H-1,4-diazepin-1-yl)imidazo[1,5-a]quinoxalin-4-amine

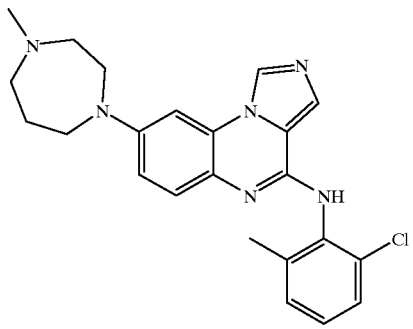

462 was prepared from 295B by a method analogous to that used for the preparation of 295. HPLC Ret time: 2.123 min (by HPLC Method 2).

EXAMPLE 463

Preparation of N-(2-Chloro-6-fluorophenyl)-8-(1H-imidazol-1-yl)imidazo[1,5-a]quinoxalin-4-amine

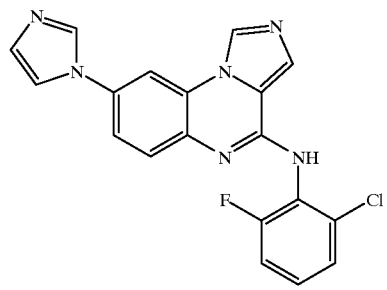

A. 8-(1H-Imidazol-1-yl)imidazo[1,5-a]quinoxalin-4(5H)-one

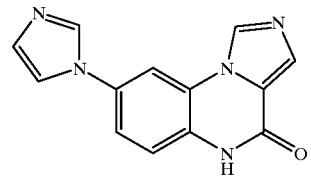

A mixture of 272B (400 mg, 1.97 mmol) and excess imidazole were heated under nitrogen in a sealed vessel to 280° C. for 1 hr. The reaction was cooled to room temperature and the title compound 463A was precipitated with water and isolated by filtration.

B. 4-Chloro-8-(1H-imidazol-1-yl)imidazo[1,5-a]quinoxaline

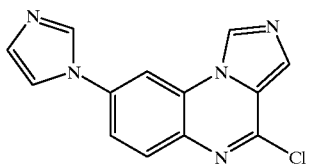

463B was prepared from 463A by a method analogous to that used for the preparation of 17F.

C. N-(2-Chloro-6-fluorophenyl)-8-(1H-imidazol-1-yl)imidazo[1,5-a]quinoxalin-4-amine 463C was prepared from 463B by a method analogous to that used for the preparation of 17G, substituting with the required aniline. HPLC Ret time: 2.317 min (by HPLC Method 2).

EXAMPLE 464

Preparation of N-(2-Chloro-6-methylphenyl)-7,9-dimethoxyimidazo[1,5-a]quinoxalin-4-amine

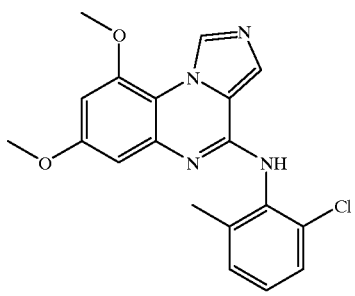

A. N-(3,5-Dimethoxyphenyl)acetamide

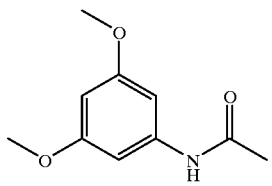

To a solution of 3,5-dimethoxyaniline (7.13 g, 46.5 mmol) in acetic acid (30 mL) and water (10 mL) was added acetic anhydride (4.61 mL, 48.9 mmol) at room temperature. The reaction was heated gently on a steam bath then cooled to room temperature. Excess water was added and the title compound 464A was collected by filtration.

B. N-(3,5-Dimethoxy-2-nitrophenyl)acetamide

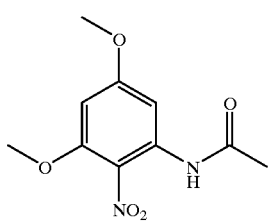

To a solution of 464A (14.86 g, 76.2 mmol) in $CH_2Cl_2$ (150 mL) was added silver nitrate (13.59 g, 80.0 mmol) followed by trifluoroacetic anhydride (37.7 mL, 266.7 mmol). When complete the reaction was poured into saturated sodium bicarbonate solution and extracted with $CH_2Cl_2$. The title compound 464B was recrystallized from $CH_2Cl_2$-hexane to give pure 464B.

C. 3,5-Dimethoxy-2-nitrobenzenamine

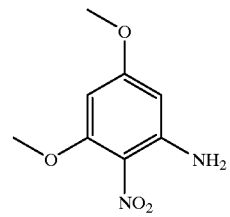

A solution of 464B (13.65 g) in Claisen Alkalie (100 mL) was heated to reflux for 1 hr. The reaction was then cooled in an ice bath and the title compound 464C was collected by filtration. Trituration with water gave pure 464C.

D. 3,5-Dimethoxy-1,2-benzenediamine

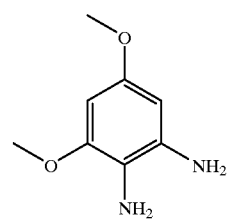

A solution of 464C (10.59 g) in MeOH (400 mL) and THF (50 mL) was stirred with Pd/C 10% (1 g) under hydrogen atmosphere. When completed the catalyst was removed by filtration and the filtrate was concentrated in vacuo to give 464D.

E. 5,7-Dimethoxy-2(1H)-quinazolinone mixture with 6,8-Dimethoxy-2(1H)-quinazolinone

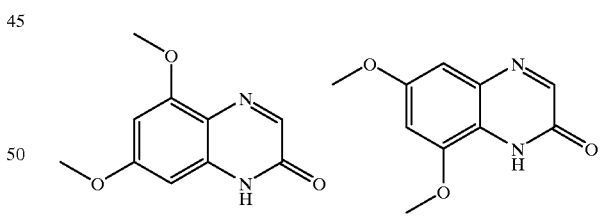

To a solution of 464D (8.49 g, 50.5 mmol) in EtOH (200 mL) was added a 50% ethyl glyoxylate solution in toluene (10 mL, 50.5 mmol) and the reaction mixture was heated to reflux. When complete the reaction was cooled to room temperature and the title compound 464E was collected by filtration (464E exists as a mixture of regioisomers).

F. N-(2-Chloro-6-methylphenyl)-7,9-dimethoxyimidazo[1,5-a]quinoxalin-4-amine 464F was prepared from 464E by a route analogous to that used for the preparation of 131. HPLC Ret time: 3.161 min (by HPLC Method 2).

EXAMPLE 465

Preparation of N-(2-Chloro-6-fluorophenyl)-7,9-dimethoxyimidazo[1,5-a]quinoxalin-4-amine

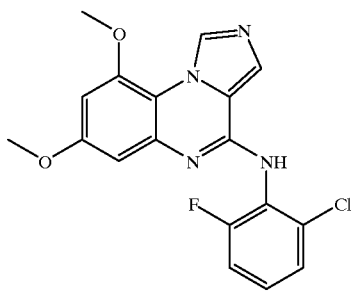

465 was prepared from 464E by a route analogous to that used for the preparation of 131. HPLC Ret time: 3.238 min (by HPLC Method 2).

EXAMPLE 466

Preparation of N-(2-Chloro-6-fluorophenyl)-6,8-dimethoxyimidazo[1,5-a]quinoxalin-4-amine

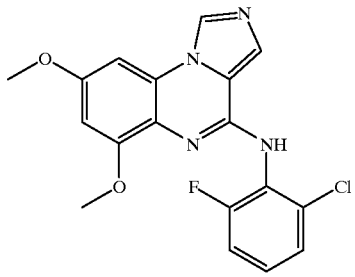

466 was prepared from 464E by a route analogous to that used for the preparation of 131. HPLC Ret time: 3.109 min (by HPLC Method 2).

EXAMPLE 467

Preparation of N-(2-Chloro-6-methylphenyl)-8-[4-[[[3-(dimethylamino)propyl]amino]methyl]phenyl]imidazo[1,5-a]quinoxalin-4-amine

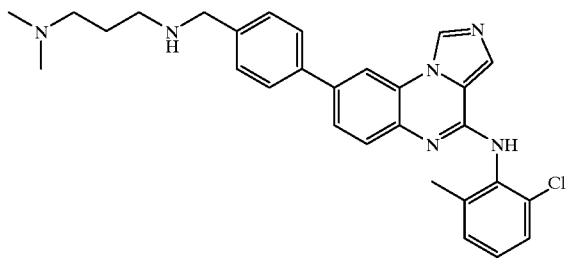

A. (2-Chloro-6-methylphenyl)[8-(4-formylphenyl)imidazo[1,5-a]quinoxalin-4-yl]carbamic acid 1,1-dimethylethyl ester

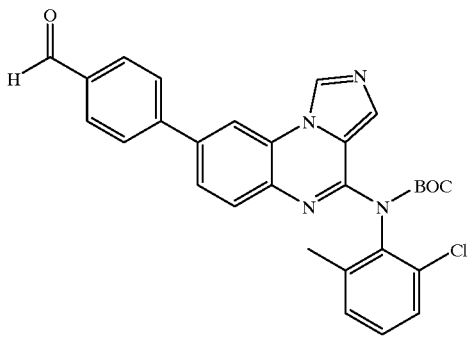

467A was prepared from 456A by a method analogous to that used for the preparation of 282, substituting with the appropriate boronic acid.

B. N-(2-Chloro-6-methylphenyl)-8-[4-[[[3-(dimethylamino)propyl]amino]methyl]phenyl]imidazo[1,5-a]quinoxalin-4-amine To a solution of 467A in $CH_2Cl_2$ (2 mL) was added two drops of acetic acid followed by excess N,N-dimethyl-1,3-propanediamine and excess sodium triacetoxyborohydride. When complete the title compound 467B was purified by prep HPLC. HPLC Ret time: 2.357 min (by HPLC Method 2).

EXAMPLE 468

Preparation of N-(2-Chloro-6-methylphenyl)-7-methoxy-8-(1-piperazinyl)imidazo[1,5-a]quinoxalin-4-amine

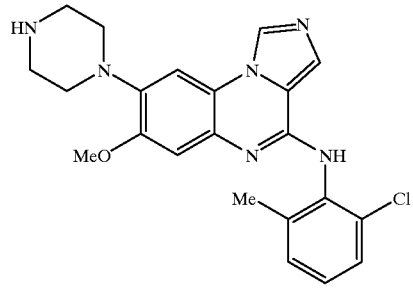

A. 4-Bromo-2,5-difluorobenzenamine

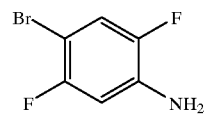

To a solution of 2,5-difluoro-4-bromo-nitrobenzene (10 g, 42 mmol) in MeOH (200 mL) and conc. HCl (11 mL) was added tin(II)chloride dihydrate (38 g, 168 mmol) at room temperature. When complete the MeOH was distilled off under vacuum then water and celite were added. The mixture was neutralized with NaOH (50%) and filtered to remove the tin residue. The mixture was extracted with $CH_2Cl_2$ and the title compound 468A crystallized from $CH_2Cl_2$/hexane.

B. N-(4-Bromo-2,5-difluorophenyl)-1H-imidazole-4-carboxamide

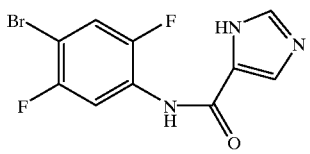

468B was prepared from 468A by a method analogous to that used for the preparation of 17E.

C. 8-Bromo-7-fluoroimidazo[1,5-a]quinoxalin-4(5H)-one

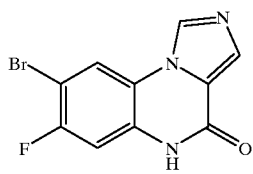

468C was prepared from 468B by a method analogous to that used for the preparation of 17D.

D. 8-Bromo-7-methoxyimidazo[1,5-a]quinoxalin-4(5H)-one

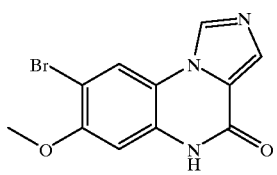

To a solution of 468C (1 g) in anhydrous DMSO (13 mL) and MeOH (5 mL) was added a 25% solution of NaOMe in MeOH (10 mL). The mixture was heated to 120° C. in a sealed vessel under nitrogen. When complete the reaction mixture was neutralized with acetic acid and the title compound 468D was precipitated with water, and collected by filtration with water rinses.

E. 8-Bromo-4-chloro-7-methoxyimidazo[1,5-a]quinoxaline

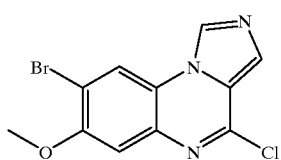

468E was prepared from 468D by a method analogous to that used for the preparation of 17F.

F. (8-Bromo-7-methoxyimidazo[1,5-a]quinoxalin-4-yl)(2-chloro-6-methylphenyl)carbamic acid 1,1-dimethylethyl ester

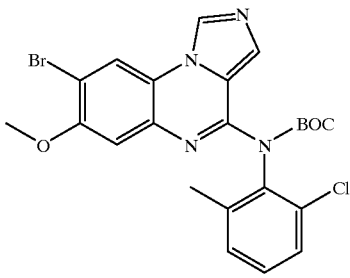

To 2-chloro-6-methylaniline (0.213 mL, 1.73 mmol) was added THF (15 mL) followed by a 1M solution of sodium bistrimethylsilylamide in THF (3.46 mL, 3.46 mmol). To this mixture was added 468E (490 mg, 1.57 mmol) dissolved in THF (15 mL). The reaction was stirred for 10 min at room temperature then a solution of di-t-butyl dicarbonate (1.13 g, 5.19 mmol) in THF (5 mL) was added, followed by DMAP (105 mg, 0.85 mmol). The reaction was heated to reflux for 1 hr then cooled to room temperature and quenched with acetic acid. The THF was distilled off under vacuum and the residue was partitioned between saturated sodium bicarbonate and $CH_2Cl_2$. The title compound 468F was purified by flash chromatography on silica gel.

G. N-(2-Chloro-6-methylphenyl)-7-methoxy-8-(1-piperazinyl)imidazo[1,5-a]quinoxalin-4-amine The title compound 468G was prepared from 468F by a route analogous to that used for the preparation of 295, substituting with the t-butyl 1-piperazine carboxylate in place of cyclopropyl methylamine. HPLC Ret time: 2.263 min (by HPLC Method 2).

EXAMPLES 469 TO 472

General Procedure

Compounds 469 to 472 were prepared from 468F by a route analogous to that used for the preparation of 295, substituting with the appropriate amine in place of cyclopropyl methylamine (HPLC Conditions: "HPLC Method 2"). The compounds of these examples have the structure:

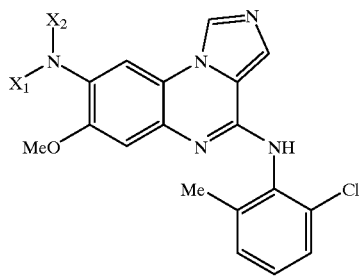

| Ex. No | X₁X₂N | Compound name | HPLC Ret. Time (min) |
|---|---|---|---|
| 469 | | cis-N-(2-Chloro-6-methylphenyl)-8-(3,5-dimethyl-1-piperazinyl)-7-methoxyimidazo[1,5-a]quinoxalin-4-amine | 2.409 |
| 470 | | $N^4$-(2-Chloro-6-methylphenyl)-7-methoxy-$N^8$-[3-(4-morpholinyl)propyl]imidazo[1,5-a]quinoxaline-4,8-diamine | 2.435 |
| 471 | | N-(2-Chloro-6-methylphenyl)-8-(hexahydro-1H-1,4-diazepin-1-yl)-7-methoxyimidazo[1,5-a]quinoxalin-4-amine | 2.317 |
| 472 | | N-(2-Chloro-6-methylphenyl)-8-(hexahydro-4-methyl-1H-1,4-diazepin-1-yl)-7-methoxyimidazo[1,5-a]quinoxalin-4-amine | 2.294 |

EXAMPLE 473

Preparation of N-(2-Chloro-6-methylphenyl)-7-[2-(4-morpholinyl)ethox]-8-(1-piperazinyl)imidazo]1,5-a]quinoxalin-4-amine

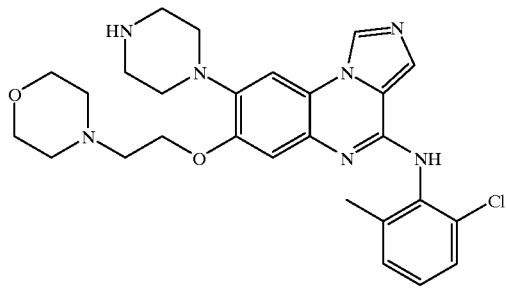

A. 8-Bromo-7-[2-(4-morpholinyl)ethoxy]imidazo[1,5-a]quinoxalin-4(5H)-one

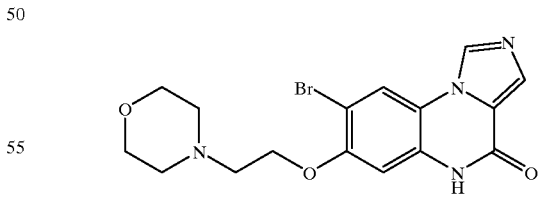

To a solution of 468C (1 g) in anhydrous DMSO (10 mL) was added 4-(2-hydroxyethyl)morpholine (8.6 mL) followed by the slow addition of sodium hydride 60% dispersion in mineral oil (0.86 g, 21.3 mmol). The mixture was heated to 120° C. in a sealed vessel under nitrogen. When complete the reaction was neutralized with acetic acid and the title compound 473A was precipitated with water, and collected by filtration with water rinses.

B. 8-Bromo-4-chloro-7-[2-(4-morpholinyl)ethoxy]imidazo[1,5-a]quinoxaline

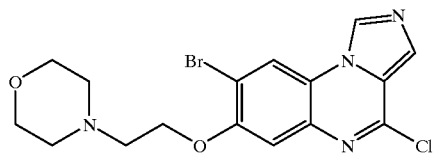

473B was prepared from 473A by a method analogous to that used for the preparation of 468E.

C. [8-Bromo-7-[2-(4-morpholinyl)ethoxy]imidazo[1,5-a]quinoxalin-4-yl](2-chloro-6-methylphenyl)carbamic acid 1,1-dimethylethyl ester

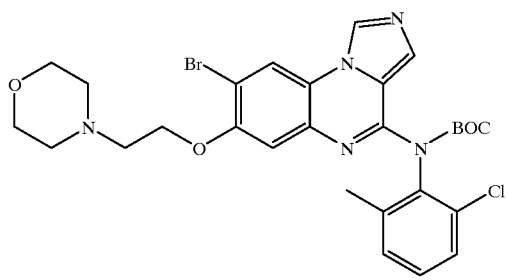

473C was prepared from 473B by a method analogous to that used for the preparation of 468F.

D. N-(2-Chloro-6-methylphenyl)-7-[2-(4-morpholinyl)ethoxy]-8-(1-piperazinyl)imidazo[1,5-a]quinoxalin-4-amine 473D was prepared from 473C by a method analogous to that used for the preparation of 468G, substituting with the t-butyl 1-piperazine carboxylate in place of cyclopropyl methylamine. HPLC Ret time: 1.653 min (by HPLC Method 2).

EXAMPLES 474 TO 481

General Procedure

Compounds 474 to 481 were prepared from 473C by a route analogous to that used for the preparation of 295, substituting with the required amine in place of cyclopropyl methylamine (HPLC Conditions: "HPLC Method 2"). The compounds of these examples have the structure:

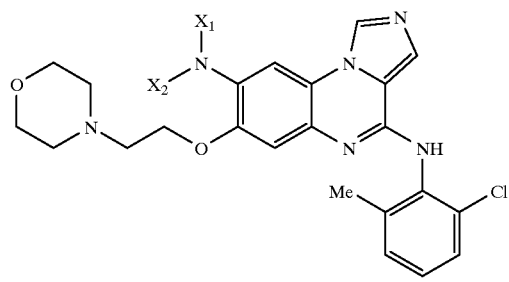

| Ex. No | $X_1X_2N$ | Compound name | HPLC Ret. Time (min) |
|---|---|---|---|
| 474 | | cis-N-(2-Chloro-6-methylphenyl)-8-(3,5-dimethyl-1-piperazinyl)-7-[2-(4-morpholinyl)ethoxy]imidazo[1,5-a]quinoxalin-4-amine | 1.825 |
| 475 | | $N^4$-(2-Chloro-6-methylphenyl)-7-[2-(4-morpholinyl)ethoxy]-$N^8$-[3-(4-morpholinyl)propyl]imidazo[1,5-a]quinoxaline-4,8-diamine | 1.780 |
| 476 | | $N^4$-(2-Chloro-6-methylphenyl)-$N^8$-[2-(dimethylamino)ethyl]-7-[2-(4-morpholinyl)ethoxy]imidazo[1,5-a]quinoxaline-4,8-diamine | 1.609 |

-continued

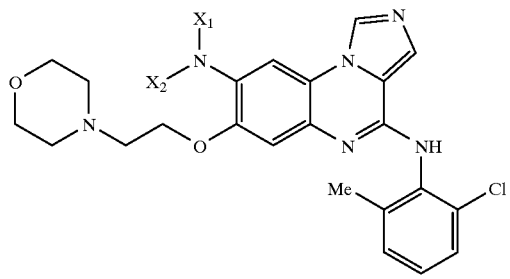

| Ex. No | X₁X₂N | Compound name | HPLC Ret. Time (min) |
|---|---|---|---|
| 477 | (dimethylaminoethyl-methylamino) | $N^4$-(2-Chloro-6-methylphenyl)-$N^8$-[3-(dimethylamino)propyl]-7-[2-(4-morpholinyl)ethoxy]imidazo[1,5-a]quinoxaline-4,8-diamine | 1.680 |
| 478 | (dimethylaminobutyl-methylamino) | $N^4$-(2-Chloro-6-methylphenyl)-$N^8$-[4-(dimethylamino)butyl]-7-[2-(4-morpholinyl)ethoxy]imidazo[1,5-a]quinoxaline-4,8-diamine | 1.766 |
| 479 | (3-acetamidopyrrolidinyl) | N-[1-[4-[(2-Chloro-6-methylphenyl)amino]-7-[2-(4-morpholinyl)ethoxy]imidazo[1,5-a]quinoxalin-8-yl]-3-pyrrolidinyl]acetamide | 2.254 |
| 480 | (4-acetylpiperazinyl) | 1-Acetyl-4-[4-[(2-Chloro-6-methylphenyl)amino]-7-[2-(4-morpholinyl)ethoxy]imidazo[1,5-a]quinoxalin-8-yl]piperazine | 2.262 |
| 481 | (4-methyl-1,4-diazepanyl) | N-(2-Chloro-6-methylphenyl)-8-(hexahydro-4-methyl-1H-1,4-diazepin-1-yl)-7-[2-(4-morpholinyl)ethoxy]imidazo[1,5-a]quinoxalin-4-amine | 1.617 |

EXAMPLE 482

Preparation of N-(2-Chloro-6-methylphenyl)-7-[2-(4-morpholinyl)ethoxy]-8-phenylimidazo[1,5-a]quinoxalin-4-amine

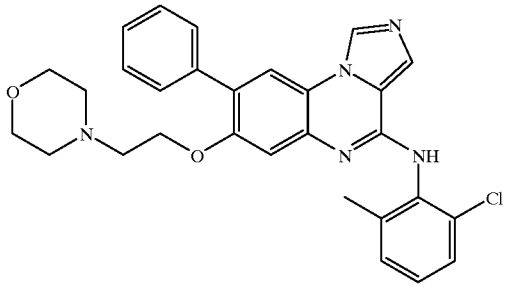

482 was prepared from 473C by a method analogous to that used for the preparation of 282. HPLC Ret time: 2.863 min (by HPLC Method 2).

EXAMPLE 483

Preparation of $N^4$-(2-Chloro-6-methylphenyl)-$N^1$,$N^1$-dimethyl-7,8-dimethoxyimidazo[1,5-a]quinoxaline-1,4-diamine

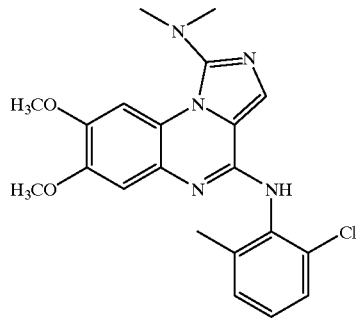

A mixture of 449B (25 mg; 62 gmol), dimethylamine (2 ml; 40% in water) in 2 ml of DMF was heated to 120° C. for 24 hrs. in a pressure tube. Upon cooling to room temperature, the reaction mixture was partitioned between EtOAc (25 ml) and water (25 ml). The organic layer was washed with saturated ammonium chloride solution (3×25 ml), water (25 ml) and brine (25 ml). After drying (MgSO$_4$) and concentration under reduced pressure, the residue was recrystallized from CH$_2$Cl$_2$/hexane to afford 19 mg of 483b as a beige crystalline solid. HPLC Retention time=3.19 min (by HPLC Method 2).

EXAMPLE 484

N-(2-Chloro-6-methylphenyl)-8-[4-[[[3-(dimethylamino)propyl]amino]methyl]phenyl-7-[2-(4-morpholinyl)ethoxy]imidazo[1,5-a]quinoxalin-4-amine

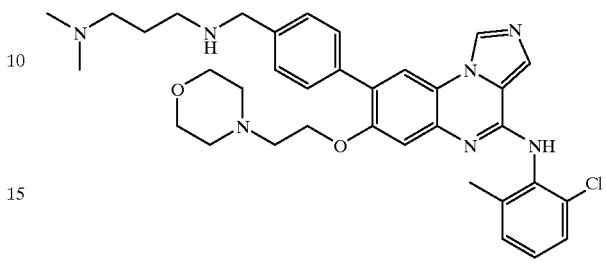

A. (2-Chloro-6-methylphenyl)[8-(4-formylphenyl)-7-[2-(4-morpholinyl)ethoxy]imidazo[1,5-a]quinoxalin-4-yl] carbamic acid 1,1-dimethylethyl ester

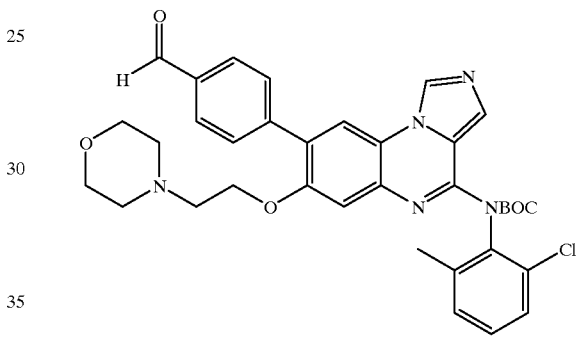

484A was prepared from 473C by a method analogous to that used for the preparation of 467A. HPLC Ret. time= 3.647 min. (by HPLC Method 2).

B. N-(2-Chloro-6-methylphenyl)-8-[4-[[[3-(dimethylamino)propyl]amino]methyl]phenyl]-7-[2-(4-morpholinyl])ethoxy]imidazo[1,5-a]quinoxalin-4-amine 484B was prepared from 484A by a method analogous to that used for the preparation of 467B. HPLC Ret time: 2.171 min (by HPLC Method 2).

EXAMPLE 485

Preparation of $N^4$-(2-Chloro-6-methylphenyl)-8-methoxy-$N^7$-[2-(4-morpholinyl)ethyl]imidazo[1,5-a]quinoxaline-4,7-diamine

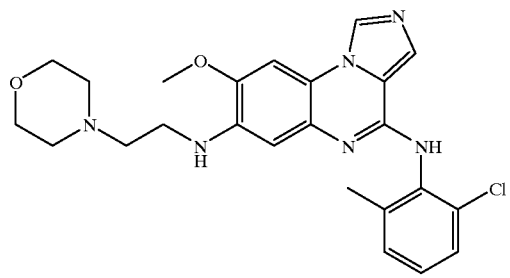

A. 1-Bromo-2,4-difluoro-5-nitrobenzene

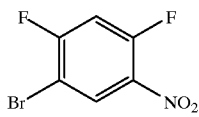

To 2,4-difluorobromobenzene (10 mL, 85.5 mmol) in conc. sulfuric acid (50 mL) was added 90% $HNO_3$ (4.57 mL, 97.3 mmol) dissolved in conc. sulfuric acid (10 mL) at room temperature. The reaction was stirred for 1 h then slowly poured over ice water. The mixture was extracted with $CH_2Cl_2$ and washed with saturated bicarbonate solution. The solvent was removed in vacuo to give title compound 485A.

B. 5-Bromo-2,4-difluorobenzenamine

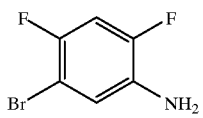

485B was prepared from 485A by a method analogous to that used for the preparation of 468A.

C. (7-Bromo-8-methoxyimidazo[1,5-a]quinoxalin-4-yl)(2-Chloro-6-methylphenyl)carbamic acid 1,1-dimethylethyl ester

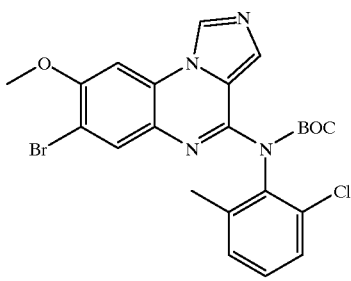

485C was prepared from 485B by a method analogous to that used for the preparation of 468F.

D. $N^4$-(2-Chloro-6-methylphenyl)-8-methoxy-$N^7$-[2-(4-morpholinyl)ethyl]imidazo[1,5-a]quinoxaline-4,7-diamine 485D was prepared from 485C by a method analogous to that used for the preparation of 295, substituting with the 4-(2-aminoethyl)morpholine in place of cyclopropyl methylamine. HPLC Ret time: 2.067 min (by HPLC Method 2).

EXAMPLES 486 TO 488

General Procedure

Compounds 486 to 488 were prepared from 485C by a route analogous to that used for the preparation of 295, substituting with the appropriate amine in place of cyclopropyl methylamine (HPLC Conditions: "HPLC Method 2"). The compounds of these examples have the structure:

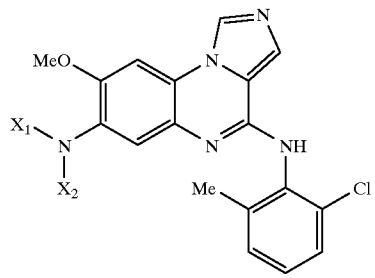

| Ex. No | $NX_1X_2$ | Compound name | HPLC Ret. Time (min) |
|---|---|---|---|
| 486 | ![dimethylaminoethylamino] | $N^4$-(2-Chloro-6-methylphenyl)-$N^7$-[2-(dimethylamino)ethyl]-8-methoxyimidazo[1,5-a]quinoxaline-4,7-diamine | 2.063 |
| 487 | ![cis-3,5-dimethylpiperazinyl] | cis-N-(2-Chloro-6-methylphenyl)-7-(3,5-dimethyl-1-piperazinyl)-8-methoxyimidazo[1,5-a]quinoxalin-4-amine | 2.225 |

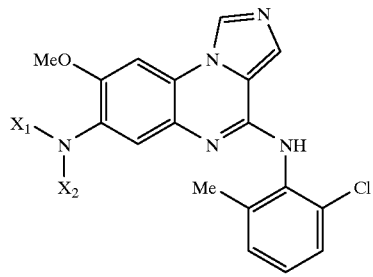

| Ex. No | NX₁X₂ | Compound name | HPLC Ret. Time (min) |
|---|---|---|---|
| 488 | 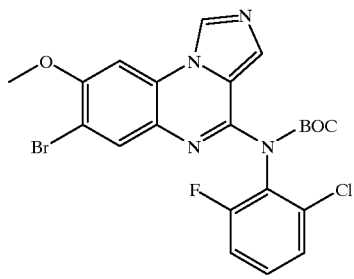 | N-(2-Chloro-6-methylphenyl)-7-[4-[2-(dimethylamino)ethyl]-1-piperazinyl]-8-methoxyimidazo[1,5-a]quinoxalin-4-amine | 1.667 |

EXAMPLE 489

Preparation of $N^4$-(2-Chloro-6-fluorophenyl)-8-methoxy-$N^7$-[2-(4-morpholinyl)ethyl]imidazo[1,5-a]quinoxaline-4,7-diamine

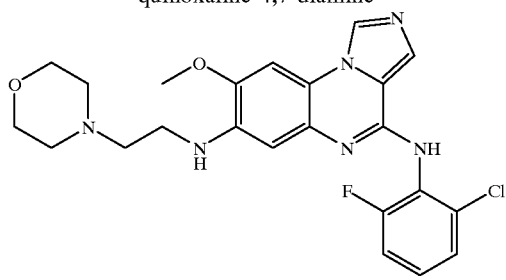

A. (7-Bromo-8-methoxyimidazo[1,5-a]quinoxalin-4-yl)(2-chloro-6-fluorophenyl)carbamic acid 1,1-dimethylethyl ester 489A was prepared from 485B by a method analogous to that used for the preparation of 468F.

B. $N^4$-(2-Chloro-6-fluorophenyl)-8-methoxy-$N^7$-[2-(4-morpholinyl)ethyl]imidazo[1,5-a]quinoxaline-4,7-diamine 489B was prepared from 489A by a method analogous to that used for the preparation of 295, substituting with the 4-(2-aminoethyl)morpholine in place of cyclopropyl methylamine. HPLC Ret time: 2.018 min (by HPLC Method 2).

EXAMPLES 490 TO 491

General Procedure

Compounds 490 to 491 were prepared from 489A by a route analogous to that used for the preparation of 295, substituting with the appropriate amine in place of cyclopropyl methylamine (HPLC Conditions: "HPLC Method 2"). The compounds of these examples have the structure:

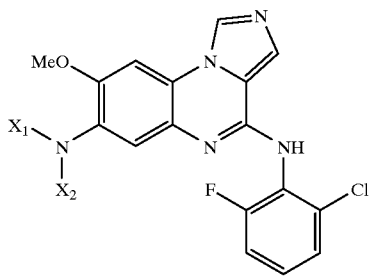

| Ex. No | NX₁X₂ | Compound name | HPLC Ret. Time (min) |
|---|---|---|---|
| 490 | (dimethylaminoethyl-methylamino group) | $N^4$-(2-Chloro-6-fluorophenyl)-$N^7$-[2-(dimethylamino)ethyl]-8-methoxyimidazo[1,5-a]quinoxaline-4,7-diamine | 1.997 |
| 491 | (cis-3,5-dimethylpiperazinyl group) | cis-N-(2-Chloro-6-fluorophenyl)-7-(3,5-dimethyl-1-piperazinyl)-8-methoxyimidazo[1,5-a]quinoxalin-4-amine | 2.298 |

EXAMPLE 492

Preparation of 4-Amino-N-(2-chloro-6-methylphenyl)imidazo[1,5-a]quinoxaline-7-carboxamide

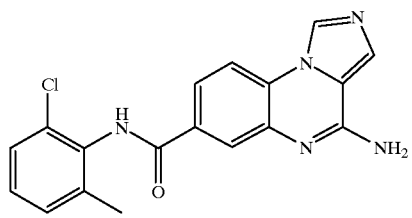

A. 4,5-Dihydro-4-oxoimidazo[1,5-a]quinoxaline-7-carboxylic acid methyl ester

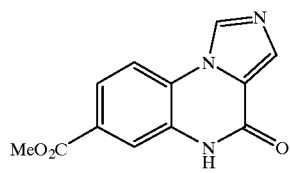

492A was prepared from commercially available 3-nitro-4-fluorobenzoic acid by a method analogous to that used for the preparation of 272B.

B. 4,5-Dihydro-4-oxoimidazo[1,5-a]quinoxaline-5,7-dicarboxylic acid methyl 1,1-dimethylethyl ester

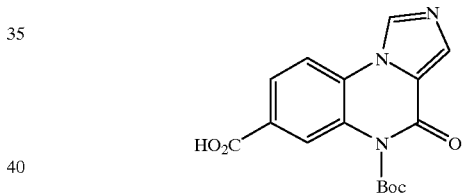

4-Dimethylaminopyridine (0.23 g, 1.87 mmol) was added to a mixture of 492A (2.27 g, 9.33 mmol) and di-tert-butyl dicarbonate (4.08 g, 18.7 mmol) in DMF (75 mL). After stirring for several hours, more di-tert-butyl dicarbonate (5.72 g, 19.51 mmol) and 4-dimethylaminopyridine (0.23 g, 1.87 mmol) were added and stirring was continued until no starting material was left. The reaction mixture was diluted with EtOAc and washed with 1N HCl; the aqueous layer was extracted with EtOAc (×2), the combined EtOAc layers were washed with 1N HCl (×3) and brine, dried over anhydrous $Na_2SO_4$, and concentrated under reduced pressure to yield, after silica gel chromatography with hexane-EtOAc, 0.87 g of N-Boc methyl ester as an off-white solid. LC-MS: Rt=3.60 min; $(M+H)^+$=344.

492B was prepared by hydrolysis of the above N-Boc methyl ester with 1N aqueous NaOH in 2:1 THF-MeOH, and isolated by precipitation with aqueous 1N HCl. LC-MS: Rt=2.10 min; $(M+H)^+$=292.

C. 4-Chloroimidazo[1,5-a]quinoxaline-7-carboxylic acid

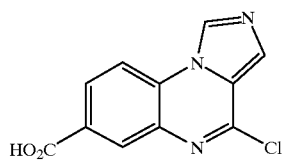

A suspension of 492B (0.46 g, 1.34 mmol) in POCl$_3$ (26.0 mL) was refluxed for 2.5 hours. POCl$_3$ was removed under vacuum, azeotropic evaporation was conducted with toluene, and then with ether (×2). The crude residue was stirred with saturated aqueous KHCO$_3$ solution for 10 minutes at 0° C. followed by 30 minutes at ambient temperature. After acidification to pH 2.5 with 1.0 M HCl at 0° C., the precipitate was collected by filtration and washed with water. Drying under vacuum gave 0.31 g of 492C as a light tan solid. LC/MS: Rt=2.87 min, (M+H)$^+$=248.

D. 4-Chloro-N-(2-chloro-6-methylphenyl)imidazo[1,5-a]quinoxaline-7-carboxamide

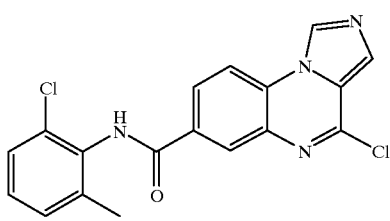

Oxalyl chloride (0.095 mL, 1.09 mmol) was added to a suspension of 492C (90.0 mg, 0.36 mmol) in THF (9.0 mL). After the addition of DMF (20.0 mL), the reaction mixture was stirred for 1.5 hrs. 2-Chloro-6-methylaniline was added (0.35 mL, 2.88 mmol), followed by diisopropylethylamine (0.50 mL, 2.88 mmol), and the reaction mixture was stirred for 16 hrs. The volatiles was removed under reduced pressure and the residue was purified by silica gel chromatography, eluting with CH$_2$Cl$_2$-MeOH, to yield 65.3 mg of 492D as a light tan solid. LC/MS: Rt=3.48 min, (M+H)$^+$=371.

E. 4-Amino-N-(2-chloro-6-methylphenyl)imidazo[1,5-a]quinoxaline-7-carboxamide

NH$_3$ gas was condensed into a stirred solution of 492D (65.0 mg, 0.18 mmol) in isopropanol (26.0 mL) in a pressure tube. The tube was sealed and the reaction mixture was stirred for 3 days at ambient temperature. Isopropanol and NH$_3$ were evaporated. Trituration with ether followed by flash chromatography on reversed-phase silica gel, eluting with a MeOH-H$_2$O-TFA solvent gradient gave 18.5 mg of 492E as a light yellow solid. LC/MS: Rt=2.60 min; (M+H)$^+$=352.

EXAMPLE 493

Preparation of 4-Amino-N-(2,4,6-trimethylphenyl)imidazo[1,5-a]quinoxaline-7-carboxamide

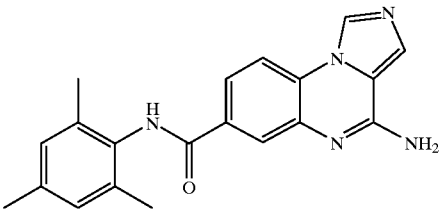

493 was prepared from 492C by a method analogous to that used for the preparation of 492E, substituting with the 2,4,6-trimethylaniline in place of 2-chloro-6-methylaniline. LC/MS: Rt=2.96 min; (M+H)$^+$=346$^+$.

EXAMPLE 494

Preparation of 4-[(2-Chloro-6-methylphenyl)amino]-7,8-dimethoxy-(α-methylimidazo[1,5-a]quinoxaline-1-methanol

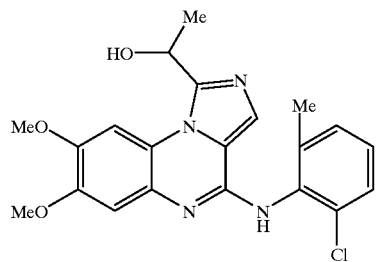

A. (2-Chloro-6-methylphenyl)[1-(1-hydroxyethyl)-7,8-dimethoxy-imidazo[1,5-a]quinoxalin-4-yl]carbamic acid, 1,1-dimethylethyl ester

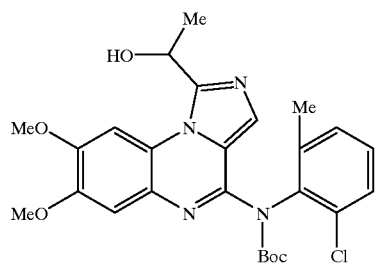

To the suspension of 441B (20 mg, 0.04 mmol) in dry 0.5 mL of Et$_2$O at 0° C. was added methylmagnesium bromide (3.0M in ether, 0.017 mL, 0.05 mmol), followed by 0.5 mL of dry THF. The reaction mixture was stirred at 0° C. for 30 min, then room temperature for 1.0 hr. The reaction mixture was partitioned between water-EtOAc, extracted with EtOAc (×2), washed with brine and dried over anhydrous Na$_2$SO$_4$. It was then concentrated in vacuo and the residue, 494A, was directly used in the next reaction without further purification.

B. 4-[(2-Chloro-6-methylphenyl)amino]-7,8-dimethoxy-α-methylimidazo[1,5-a]quinoxaline-1-methanol The mixture of 494A in 3:1 TFA- CH$_2$Cl$_2$ (4 mL) was stirred for 3.0 hrs. Concentration in vacuo followed by recrystallization from ether gave 15.8 mg of 494B as a yellow solid. HPLC Ret time: 3.022 min (by HPLC Method 2).

EXAMPLES 495 TO 496

General Procedure

Compounds 495 to 496 were prepared from 441B by a route analogous to that used for the preparation of 494B, substituting with the appropriate ethylmagnesium bromide or isopropylmagnesium chloride in place of methylmagnesium bromide (HPLC Conditions: "HPLC Method 2"). The compounds of these examples have the structure:

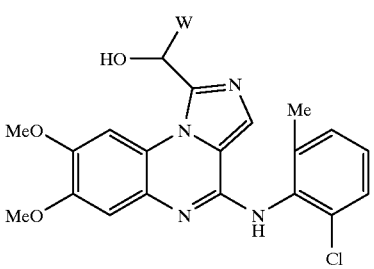

| Ex. No | W | Compound name | HPLC Ret. Time (min) |
|---|---|---|---|
| 495 | Et | 4-[(2-Chloro-6-methylphenyl)amino]-α-ethyl-7,8-dimethoxyimidazo[1,5-a]quinoxaline-1-methanol | 6.078 |
| 496 | i-Pr | 4-[(2-Chloro-6-methylphenyl)amino]-7,8-dimethoxy-α-(1-methylethyl)imidazo[1,5-a]quinoxaline-1-methanol | 6.505 |

EXAMPLE 497

Preparation of 4-[(2-Chloro-6-methylphenyl)amino]-N-ethyl-7,8-dimethoxyimidazo[1,5-a]quinoxaline-1-carboxamide

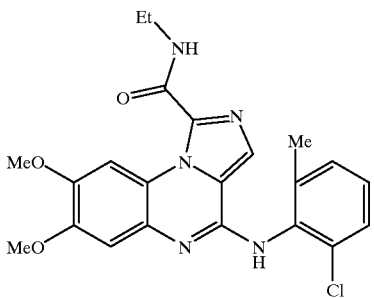

A. 4-[(2-Chloro-6-methylphenyl)[(1,1-dimethylethoxy)carbonyl]amino]-N-ethyl-7,8-dimethoxyimidazo[1,5-a]quinoxaline-1-carboxamide

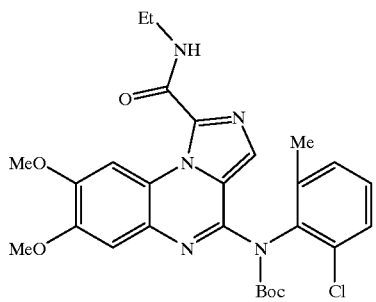

To a solution of 441A (47 mg, 0.10 mmol) in 0.5 mL of dry THF cooled at −78° C. was added a solution of 2.0M LDA in THF (0.075 mL, 0.15 mmol). After 15 min, ethyl isocyanate (0.040 mL, 0.5 mmol) was added and the mixture was stirred at −78° C. for 2.0 hr and ambient temperature overnight. Sat'd $NH_4Cl$ was added to the reaction mixture and extracted with EtOAc (×2). The combined organic extracts were washed with water, brine and dried over anhydrous $Na_2SO_4$. Concentration in vacuo and the residue, 497A, was directly used in next reaction without further purification.

B. 4-[(2-Chloro-6-methylphenyl)amino]-N-ethyl-7,8-dimethoxyimidazo[1,5-a]quinoxaline-1-carboxamide The mixture of 497A (crude) in a 3:1 $TFA-CH_2Cl_2$ (2.0 mL) was stirred for 1.0 hrs. Concentration in vacuo followed by preparative HPLC gave 55.4 mg of 497B as a pale-yellow solid. HPLC Ret time: 3.302 min (by HPLC Method 2).

EXAMPLES 498 TO 505

General Procedure

Compounds 498 to 505 were prepared from 441A by a route analogous to that used for the preparation of 497, substituting with the appropriate alkyl isocyanate in place of ethyl isocyanate (HPLC Conditions: "HPLC Method 2"). The compounds of these examples have the structure:

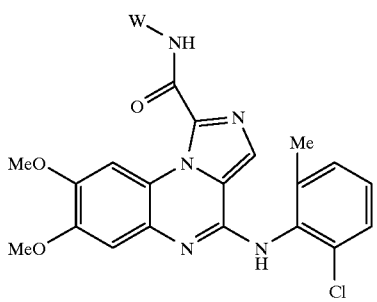

| Ex. No | W | Compound name | HPLC Ret. Time (min) |
|---|---|---|---|
| 498 | t-Bu | 4-[(2-Chloro-6-methylphenyl)amino]-N-(1,1-dimethylethyl)-7,8-dimethoxyimidazo[1,5-a]quinoxaline-1-carboxamide | 3.645 |
| 499 | benzyl | 4-[(2-Chloro-6-methylphenyl)amino]-7,8-dimethoxy-N-(phenylmethyl)imidazo[1,5-a]quinoxaline-1-carboxamide | 3.830 |
| 500 | CH(Me)(COOEt) | N-[[4-[(2-Chloro-6-methylphenyl)amino]-7,8-dimethoxyimidazo[1,5-a]quinoxalin-1-yl]carbonyl]alanine ethyl ester | 3.656 |
| 501 | n-pentyl | 4-[(2-Chloro-6-methylphenyl)amino]-7,8-dimethoxy-N-pentylimidazo[1,5-a]quinoxaline-1-carboxamide | 4.020 |
| 502 | CH2COOEt | N-[[4-[(2-Chloro-6-methylphenyl)amino]-7,8-dimethoxyimidazo[1,5-a]quinoxalin-1-yl]carbonyl]glycine ethyl ester | 3.455 |
| 503 | CH(Me)(Ph) | (S)-4-[(2-Chloro-6-methylphenyl)amino]-7,8-dimethoxy-N-(1-phenylethyl)imidazo[1,5-a]quinoxaline-1-carboxamide | 4.036 |
| 504 | cyclohexyl | 4-[(2-Chloro-6-methylphenyl)amino]-N-cyclohexyl-7,8-dimethoxyimidazo[1,5-a]quinoxaline-1-carboxamide | 3.969 |
| 505 | i-Pr | 4-[(2-Chloro-6-methylphenyl)amino]-7,8-dimethoxy-N-(1-methylethyl)imidazo[1,5-a]quinoxaline-1-carboxamide | 3.473 |

EXAMPLE 506

Preparation of N-[(2-Chloro-6-methylphenyl)amino]-7,8-dimethoxyimidazo[1,5-a]quinoxaline-1-propanol

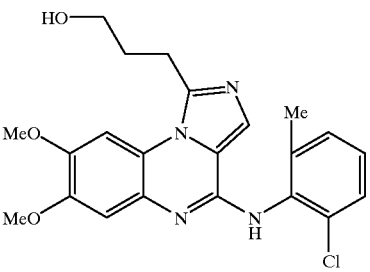

A. (E)-3-[4-[(2-Chloro-6-methylphenyl)[(1,1-dimethylethoxy)carbonyl]amino]-7,8-dimethoxyimidazo[1,5-a]quinoxalin-1-yl]-2-propenoic acid ethyl ester

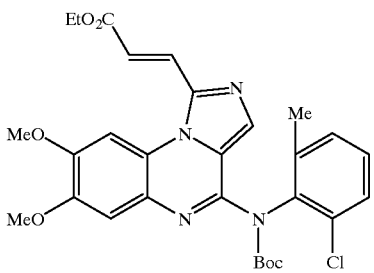

(EtO)$_2$P(=O)CH$_2$CO$_2$Et (27 mg, 0.12 mmol) was added to a suspension of NaH (4.4 mg, 0.11 mmol, 60% in mineral oil, washed once with hexane) in 0.2 mL of dry THF at 0° C. After being stirred at ambient temperature for 20 min, a solution of 441B (50 mg, 0.10 mmol) in 0.4 mL of dry THF was added and the mixture was stirred at room temperature for 1.0 hr. Water was added and the reaction mixture was extracted with EtOAc (×2), washed with brine and dried over anhydrous Na$_2$SO$_4$. Concentration in vacuo followed by flash chromatography (hexane-EtOAc: 10:1) on silica gel gave 58 mg of 506A as an off-white solid.

B. 4-[(2-Chloro-6-methylphenyl)[(1,1-dimethylethoxy)carbonyl]amino]-7,8-dimethoxyimidazo[1,5-a]quinoxaline-1-propanoic acid ethyl ester

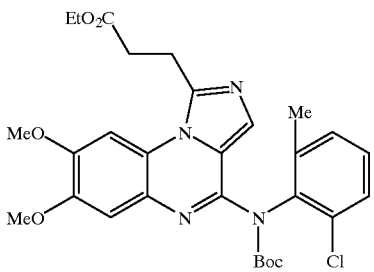

The mixture of 506A (50 mg, 0.088 mmol) and 10% Pd-C (5 mg) in a 1:1 EtOAc-EtOH (5.0 mL) was stirred under hydrogen atmosphere for 6.0 hrs. The catalyst was removed by filtration and the filtrate was concentrated in vacuo. Flash chromatography (hexane-EtOAc: 7:3 to 1:1) on silica gel gave 28.1 mg of 506B as a white solid.

C. (2-Chloro-6-methylphenyl)[1-(3-hydroxypropyl)-7,8-dimethoxyimidazo[1,5-a]quinoxalin-4-yl]carbamic acid 1,1-dimethyethyl ester

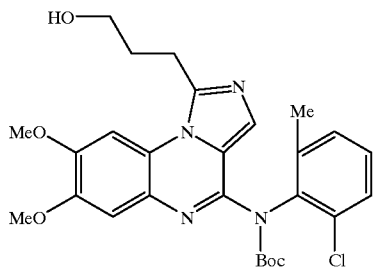

A solution of LAH (1.0M in THF, 0.08 mL, 0.08 mmol) was added to the solution of 506B (28 mg, 0.049 mmol) in dry THF (1.0 mL) at 0° C. After 2.0 hr, water was added and the mixture was diluted with EtOAc. The mixture was filtered through a pad of Celite, and the organic phase was washed once with brine, and dried over anhydrous Na$_2$SO$_4$. Concentration in vacuo gave 27 mg of 506C as a yellow solid.

D. N-[(2-Chloro-6-methylphenyl)amino]-7,8-dimethoxyimidazo[1,5-a]qufinoxaline-1-propanol The mixture of 506C (27 mg) in a 3:1 TFA-CH$_2$Cl$_2$ (2.0 mL) was stirred overnight. Concentration in vacuo followed by preparative HPLC gave 10.3 mg of 506D as a pale-yellow solid. HPLC Ret time: 2.965 min (by HPLC Method 2).

EXAMPLE 507

Preparation of 4-[(2-Chloro-6-methylphenyl)amino]imidazo[1,5-a]quinoxalin-9-ol

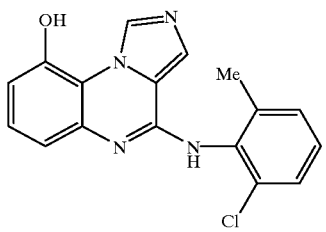

The title compound, prepared previously as 391A, forms part of the present invention. MS: 324$^+$ (m+H)$^+$; HPLC Ret. time: 2.943 min. (by HPLC Method 2).

EXAMPLE 508 TO 509

Compounds 508 to 509 were prepared by the general procedure of, and have the structure shown for, Examples 345 to 355 where W is defined as follows.

| Ex. No | W | Compound name | HPLC Ret. time (min) |
|---|---|---|---|
| 508 | 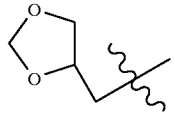 | N-(2-Chloro-6-methylphenyl)-7-(1,3-dioxolan-4-ylmethoxy)-8-methoxyimidazo[1,5-a]quinoxalin-4-amine | 2.920 |
| 509 | 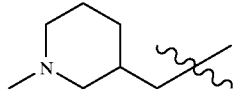 | N-(2-Chloro-6-methylphenyl)-8-methoxy-7-[(1-methyl-3-piperidinyl)methoxy]imidazo[1,5-a]quinoxalin-4-amine | 2.450 |

EXAMPLE 510

Preparation of N-(2-Chloro-6-methylphenyl)-7,8-dimethoxy-1-methylimidazo[1,5-a]quinoxalin-4-amine

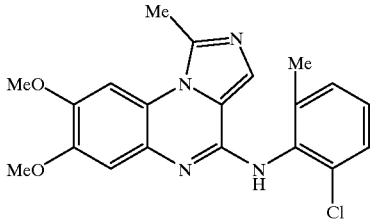

A. (2-Chloro-6-methylphenyl)(7,8-dimethoxy-1-methylimidazo[1,5-a]quinoxalin-4-yl)carbamic acid 1,1-dimethylethyl ester

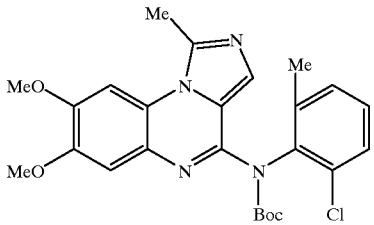

To a solution of 441A (125 mg, 0.27 mmol) in 3.0 mL of dry THF cooled at −78° C. was added a solution of LDA (2.0M in THF, 0.35 mL, 0.675 mmol). After 30 min, methyl iodide (0.12 mL) was added and the reaction mixture was stirred for 1.0 hr at −78° C., then room temperature for 2.0 hrs. The reaction mixture was partitioned between water and EtOAc. The mixture was extracted with EtOAc (×2) and the organic layers were washed with brine and dried over anhydrous $Na_2SO_4$. Concentration in vacuo followed by flash chromatography (EtOAc) on silica gel gave 90 mg of 510A as a yellow solid.

B. N-(2-Chloro-6-methylphenyl)-7,8-dimethoxy-1-methylimidazo[1,5-a]quinoxalin-4-amine The above obtained 510A in neat TFA (2 mL) was stirred for 1.0 hr. The mixture was concentrated in vacuo and the residue was partitioned between 1.0N NaOH and EtOAc. The mixture was extracted with EtOAc (×2) and the organic layers were washed with brine and dried over anhydrous $Na_2SO_4$. The crude product was purified by recrystallization from $CH_2Cl_2$ and hexane to give 60 mg of 510B as a crystalline material. HPLC Ret time: 2.98 min (by HPLC Method 2).

What is claimed is:

1. An imidazoquinoxaline compound of the following formula I or a salt thereof:

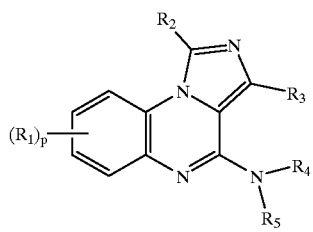

(I)

where p is 0, 1, 2, 3 or 4;

each $R_1$, and $R_2$ and $R_3$, are independently selected from:
(1) hydrogen or $R_6$,
where $R_6$ is alkyl, alkenyl, alkynyl, cycloalkyl, cycloalkylalkyl, cycloalkenyl, cycloalkenylalkyl, aryl, aralkyl, heterocyclo, or heterocycloalkyl, each of which is unsubstituted or substituted with $Z_1$, $Z_2$ and one or more groups $Z_3$;
(2) —OH or —OR$_6$;
(3) —SH or —SR$_6$;
(4) —C(O)$_q$H, —C(O)$_q$R$_6$ or —O—C(O)$_q$R$_6$, where q is 1 or 2;
(5) —SO$_3$H or —S(O)$_q$R$_6$;
(6) halo;
(7) cyano;
(8) nitro;
(9) —Z$_4$—NR$_7$R$_8$;
(10) —Z$_4$—N(R$_9$)—Z$_5$—NR$_{10}$R$_{11}$;
(11) —Z$_4$—N(R$_{12}$)—Z$_5$—R$_6$;
(12) —SiR$_{13}$R$_{14}$R$_{15}$;
(13) —P(O)(OR$_6$)$_2$;
(14) —CH=N—OR$_6$;
(15) any two groups $R_1$ may together be alkylene or alkenylene completing a 3- to 8-membered saturated or unsaturated ring together with the carbon atoms to which they are attached, which ring is unsubstituted or substituted with $Z_1$, $Z_2$ and $Z_3$; or
(16) any two groups $R_1$ may, together with the carbons to which they are attached, form a hetcrocyclo group, which group is unsubstituted or substituted with $Z_1$, $Z_2$ and $Z_3$;

$R_4$ and $R_5$:
(1) are each independently hydrogen, $R_6$, or —C(O)R$_6$; or (2) together with the nitrogen atom to which they are attached complete a 3- to 8-membered saturated or unsaturated heterocyclic ring which is unsubstituted or substituted with $Z_1$, $Z_2$ and $Z_3$, which heterocyclic ring may optionally have fused to it a benzene ring itself unsubstituted or substituted with $Z_1$, $Z_2$ and $Z_3$;

$R_7$, $R_8$, $R_9$, $R_{10}$, $R_{11}$ and $R_{12}$:
  (1) are each independently hydrogen or $R_6$;
  (2) $R_7$ and $R_8$ may together be alkylene or alkenylene, completing a 3- to 8-membered saturated or unsaturated ring with the nitrogen atom to which they are attached, which ring is unsubstituted or substituted with $Z_1$, $Z_2$ and $Z_3$; or
  (3) any two of $R_9$, $R_{10}$ and $R_{11}$ may together be alkylene or alkenylene completing a 3- to 8-membered saturated or unsaturated ring together with the nitrogen atoms to which they are attached, which ring is unsubstituted or substituted with $Z_1$, $Z_2$ and $Z_3$;

$R_{13}$, $R_{14}$ and $R_{15}$ are each independently:
  (1) alkyl; or
  (2) phenyl;

$Z_1$, $Z_2$ and $Z_3$ are each independently:
  (1) hydrogen or $Z_6$, where $Z_6$ is (i) alkyl, alkenyl, alkynyl, cycloalkyl, cycloalkylalkyl, cycloalkenyl, cycloalkenylalkyl, aryl, aralkyl, alkylaryl, cycloalkylaryl, heterocyclo, or heterocycloalkyl; (ii) a group (i) which is itself substituted by one or more of the same or different groups (i); or (iii) a group (i) or (ii) which is substituted by one or more of the following groups (2) to (16) of the definition of $Z_1$, $Z_2$ and $Z_3$;
  (2) —OH or —$OZ_6$;
  (3) —SH or —$SZ_6$;
  (4) —C(O)$_q$H, —C(O)$_q$$Z_6$ or —O—C(O)$_q$$Z_6$;
  (5) —$SO_3H$ or —$S(O)_q Z_6$;
  (6) halo;
  (7) cyano;
  (8) nitro;
  (9) —$Z_4$—$NZ_7Z_8$;
  (10) —$Z_4$—N($Z_9$)—$Z_5$—$NZ_7Z_8$;
  (11) —$Z_4$—N($Z_{10}$)—$Z_5$—$Z_6$;
  (12) —$Z_4$—N($Z_{10}$)—$Z_5$—H;
  (13) oxo;
  (14) —O—C(O)—$Z_6$;
  (15) any two of $Z_1$, $Z_2$, and $Z_3$ may together be alkylene or alkenylene completing a 3- to 8-membered saturated or unsaturated ring together with the atoms to which they are attached; or
  (16) any two of $Z_1$, $Z_2$, and $Z_3$ may together be —O—$(CH_2)_q$—O—;

$Z_4$ and $Z_5$ are each independently:
  (1) a single bond;
  (2) —$Z_{11}$—S(O)$_q$—$Z_{12}$—;
  (3) —$Z_{11}$—C(O)—$Z_{12}$—;
  (4) —$Z_{11}$—C(S)—$Z_{12}$—;
  (5) —$Z_{11}$—O—$Z_{12}$—;
  (6) —$Z_{11}$—S—$Z_{12}$—;
  (7) —$Z_{11}$—O—C(O)—$Z_{12}$—; or
  (8) —$Z_{11}$—C(O)—O—$Z_{12}$—;

$Z_7$, $Z_8$, $Z_9$ and $Z_{10}$:
  (1) are each independently hydrogen or $Z_6$;
  (2) $Z_7$ and $Z_8$, or $Z_6$ and $Z_{10}$, may together be alkylene or alkenylene, completing a 3- to 8-membered saturated or unsaturated ring together with the atoms to which they are attached, which ring is unsubstituted or substituted with $Z_1$, $Z_2$ and $Z_3$; or
  (3) $Z_7$ or $Z_8$, together with $Z_9$, may be alkylene or alkenylene completing a 3- to 8-membered saturated or unsaturated ring together with the nitrogen atoms to which they are attached, which ring is unsubstituted or substituted with $Z_1$, $Z_2$ and $Z_3$; and $Z_{11}$ and $Z_{12}$ are each independently:
  (1) a single bond;
  (2) alkylene;
  (3) alkenylene; or
  (4) alkynylene;

with the proviso that said compound is not selected from the group of compounds consisting of
  4-amino-7-trifluoromethylimidazo[1,5-a]quinoxaline-3-carboxylic acid ethyl ester;
  1-ethyl-3-methylimidazo[1,5-a]quinoxalin-4-amine;
  3-(5-Cyclopropyl-1,2,4-oxadiazol-3-yl)imidazo[1,5-a]quinoxalin-4-amine;
  3-(5-Cyclopropyl-1,2,4-oxadiazol-3-yl)-N,N-dimethylimidazo[1,5-a]quinoxalin-4-amine hydrochloride;
  3-(3-Cyclopropyl-1,2,4-oxadiazol-5-yl)-N,N-dimethylimidazo[1,5-a]quinoxalin-4-amine;
  3-(3-Cyclopropyl-1,2,4-oxadiazol-5-yl)-N-ethyl-N-methylimidazo[1,5-a]quinoxalin-4-amine;
  3-(3-Cyclopropyl-1,2,4-oxadiazol-5-yl)-N-methylimidazo[1,5-a]quinoxalin-4-amine;
  3-(5-Cyclopropyl-1,2,4-oxadiazol-3-yl)-4-(4-morpholinyl)imidazo[1,5-a]quinoxaline;
  3-(5-Cyclopropyl-1,2,4-oxadiazol-3-yl)-N-ethyl-N-methylimidazo[1,5-a]quinoxalin-4-amine hydrochloride;
  4-(N-Ethyl-N-methylamino)imidazo[1,5-a]quinoxaline-3-carboxylic acid ethyl ester;
  1-Phenylimidazo[1,5-a]quinoxalin-4-amine; and
  N-Cyclopentyl-1-phenylimidazo[1,5-a]quinoxalin-4-amine.

2. A compound of claim 1, wherein p is 0, 1 or 2.

3. A compound of claim 1, wherein each $R_1$ is independently selected from hydrogen, alkyl, alkoxy, nitro, aryl, halo, heterocyclo, —$Z_4$—$NR_7R_8$ or —$Z_4$—N($R_{12}$)—$Z_5$—$R_6$.

4. A compound of claim 1, wherein $R_2$ is hydrogen or alkyl.

5. A compound of claim 1, wherein $R_3$ is hydrogen or alkyl.

6. A compound of claim 1, wherein one of $R_4$ or $R_5$ is hydrogen or alkyl, and the other is aryl, or heteroaryl, either of which is substituted with $Z_1$, $Z_2$ and one or two groups $Z_3$.

7. A compound of claim 1, wherein said compound is substantially free of the corresponding 1,2-regioisomer.

8. A compound of claim 1, which compound of the formula I or salt thereof is selected from the group consisting of:
  N-(2-Chloro-6-methylphenyl)-8-nitroimidazo[1,5-a]quinoxalin-4-amine;
  $N^4$-(2-Chloro-6-methylphenyl)imidazo[1,5-a]quinoxaline-4,8-diamine;
  N-[4-[(2-Chloro-6-methylphenyl)amino]imidazo[1,5-a]quinoxalin-8-yl]acetamide;
  N-[4-[(2-Chloro-6-methylphenyl)amino]imidazo[1,5-a]quinoxalin-8-yl]hexanamide;
  N-[4-[(2-Chloro-6-methylphenyl)amino]imidazo[1,5-a]quinoxalin-8-yl]-3-methoxypropanamide;
  N-[4-[(2-Chloro-6-methylphenyl)amino]imidazo[1,5-a]quinoxalin-8-yl]-N'-ethylurea;
  N-(2-Bromophenyl)-8-methylimidazo[1,5-a]quinoxalin-4-amine;

N-(2-Bromophenyl)-7-methylimidazo[1,5-a]quinoxalin-4-amine;
N-(2-Bromophenyl)-1-methylimidazo[1,5-a]quinoxalin-4-amine;
N-(2-Bromophenyl)-1-(phenylthio)imidazo[1,5-a]quinoxalin-4-amine;
N-(2,6-Dimethylphenyl)-8-nitroimidazo[1,5-a]quinoxalin-4-amine;
$N^4$-(2,6-Dimethylphenyl)imidazo[1,5-a]quinoxalin-4,8-diamine;
N-[4-[(2,6-Dimethylphenyl)amino]imidazo[1,5-a]quinoxalin-8-yl]acetamide;
N-[4-[(2,6-Dimethylphenyl)amino]imidazo[1,5-a]quinoxalin-8-yl]hexanamide;
N-[4-[(2,6-Dimethylphenyl)amino]imidazo[1,5-a]quinoxalin-8-yl]benzeneacetamide;
[2-[[4-[(2,6-Dimethylphenyl)amino]imidazo[1,5-a]quinoxalin-8-yl]amino]-2-oxoethyl]carbamic acid, 1,1-dimethylethyl ester;
N-(2-Chloro-6-methylphenyl)imidazo[1,5-a]quinoxalin-4-amine;
N-(2-Methoxyphenyl)imidazo[1,5-a]quinoxalin-4-amine;
N-(2-Nitrophenyl)imidazo[1,5-a]quinoxalin-4-amine;
N-(2-Fluorophenyl)imidazo[1,5-a]quinoxalin-4-amine;
N-(2,6-Diethylphenyl)imidazo[1,5-a]quinoxalin-4-amine;
4-[(Imidazo[1,5-a]quinoxalin-4-yl)amino]benzonitrile;
N-(2,3-Dihydro-1H-inden-5-yl)imidazo[1,5-a]quinoxalin-4-amine;
N-[3-(Trifluoromethyl)phenyl]imidazo[1,5-a]quinoxalin-4-amine;
N-(4-Decylphenyl)imidazo[1,5-a]quinoxalin-4-amine;
N-(2,6-Dimethylphenyl)imidazo[1,5-a]quinoxalin-4-amine;
N-[2-Methyl-6-(1-methylethyl)phenyl]imidazo[1,5-a]quinoxalin-4-amine;
N-([1,1'-Biphenyl]-3-yl)imidazo[1,5-a]quinoxalin-4-amine;
N-[2,6-Bis(1-methylethyl)phenyl]imidazo[1,5-a]quinoxalin-4-amine;
N-(2,5-Dimethylphenyl)imidazo[1,5-a]quinoxalin-4-amine;
N-(2,3-Dimethylphenyl)imidazo[1,5-a]quinoxalin-4-amine;
N-[3-Methyl-4-(1-methylethyl)phenyl]imidazo[1,5-a]quinoxalin-4-amine;
N-(2,4-Dimethylphenyl)imidazo[1,5-a]quinoxalin-4-amine;
N-([1,1'-Biphenyl]-4-yl)imidazo[1,5-a]quinoxalin-4-amine;
N-[2-(Phenylmethyl)phenyl]imidazo[1,5-a]quinoxalin-4-amine;
N-[4-(1,1-Dimethylethyl)phenyl]imidazo[1,5-a]quinoxalin-4-amine;
N-(2-Propylphenyl)imidazo[1,5-a]quinoxalin-4-amine;
N-[3,5-Bis(1,1-dimethylethyl)phenyl]imidazo[1,5-a]quinoxalin-4-amine;
N-(3-Ethylphenyl)imidazo[1,5-a]quinoxalin-4-amine;
N-[3-(1,1-Dimethylethyl)phenyl]imidazo[1,5-a]quinoxalin-4-amine;
N-(4-Cyclohexylphenyl)imidazo[1,5-a]quinoxalin-4-amine;
N-(2,6-Dimethoxyphenyl)imidazo[1,5-a]quinoxalin-4-amine;
N-(3,4,5-Trimethoxyphenyl)imidazo[1,5-a]quinoxalin-4-amine;
N-(2-Methoxy-6-methylphenyl)imidazo[1,5-a]quinoxalin-4-amine;
N-(1,3-Benzodioxol-5-yl)-N-ethylimidazo[1,5-a]quinoxalin-4-amine;
N-(3-Phenoxyphenyl)imidazo[1,5-a]quinoxalin-4-amine;
N-[3-(Trifluoromethoxy)phenyl]imidazo[1,5-a]quinoxalin-4-amine;
N-[4-(4-Chlorophenoxy)phenyl]imidazo[1,5-a]quinoxalin-4-amine;
N-(1,3-Benzodioxol-5-yl)imidazo[1,5-a]quinoxalin-4-amine;
N-[3-(Phenylmethoxy)phenyl]imidazo[1,5-a]quinoxalin-4-amine;
N-(2,3-Dimethoxyphenyl)imidazo[1,5-a]quinoxalin-4-amine;
N-[2-(Trifluoromethoxy)phenyl]imidazo[1,5-a]quinoxalin-4-amine;
N-(1,4-Benzodioxin-6-yl)imidazo[1,5-a]quinoxalin-4-amine;
N-(4-Ethoxyphenyl)imidazo[1,5-a]quinoxalin-4-amine;
N-(4-Phenoxyphenyl)imidazo[1,5-a]quinoxalin-4-amine;
N-(4-Chlorophenyl)imidazo[1,5-a]quinoxalin-4-amine;
N-[3-Methoxy-5-(trifluoromethyl)phenyl]imidazo[1,5-a]quinoxalin-4-amine;
N-(2-Bromo-5-methoxyphenyl)imidazo[1,5-a]quinoxalin-4-amine;
N-(2-Chloro-6-methylphenyl)imidazo [1,5-a]quinoxalin-4-amine;
N-(2-Bromo-4-chlorophenyl)imidazo[1,5-a]quinoxalin-4-amine;
N-(2,6-Difluorophenyl)imidazo[1,5-a]quinoxalin-4-amine;
N-(2-Iodophenyl)imidazo[1,5-a]quinoxalin-4-amine;
N-(2,5-Difluorophenyl)imidazo[1,5-a]quinoxalin-4-amine;
N-(3,4-Difluorophenyl)imidazo[1,5-a]quinoxalin-4-amine;
N-(4-Chloro-3-methylphenyl)imidazo[1,5-a]quinoxalin-4-amine;
N-(3,4-Dichlorophenyl)-N-methylimidazo[1,5-a]quinoxalin-4-amine;
N-(4-Bromophenyl)imidazo[1,5-a]quinoxalin-4-amine;
N-(2,4-Dibromophenyl)imidazo[1,5-a]quinoxalin-4-amine;
N-(4-Fluoro-3-methylphenyl)imidazo[1,5-a]quinoxalin-4-amine;
N-(2-Chloro-5-methylphenyl)imidazo[1,5-a]quinoxalin-4-amine;
N-(2,5-Dibromophenyl)imidazo[1,5-a]quinoxalin-4-amine;
N-(3,5-Dichlorophenyl)imidazo[1,5-a]quinoxalin-4-amine;
N-(4-Chlorophenyl)-N-methylimidazo[1,5-a]quinoxalin-4-amine;
N-(3,5-Dibromo-4-methylphenyl)imidazo[1,5-a]quinoxalin-4-amine;
N-(4-Chloro-1-naphthalenyl)imidazo[1,5-a]quinoxalin-4-amine;

N-(3,4,5-Trichlorophenyl)imidazo[1,5-a]quinoxalin-4-amine;
N-[4-(4-Morpholinyl)phenyl]imidazo[1,5-a]quinoxalin-4-amine;
N-[4-(Dimethylamino)phenyl]imidazo[1,5-a]quinoxalin-4-amine;
N-[2-(1H-Pyrrol-1-yl)phenyl]imidazo[1,5-a]quinoxalin-4-amine;
N-[4-(1-Piperidinyl)phenyl]imidazo[1,5-a]quinoxalin-4-amine;
N-[2-(1-Piperidinyl)phenyl]imidazo[1,5-a]quinoxalin-4-amine;
N-(6-Quinolinyl)imidazo[1,5-a]quinoxalin-4-amine;
N-(3-Pyridinyl)imidazo[1,5-a]quinoxalin-4-amine;
N-(2-Chlorophenyl)imidazo[1,5-a]quinoxalin-4-amine;
N-[2-Bromo-4-(trifluoromethoxy)phenyl]imidazo[1,5-a]quinoxalin-4-amine;
N-(2,4-Dichlorophenyl)imidazo [1,5-a]quinoxalin-4-amine;
N-(2-Bromo-4-methylphenyl)imidazo[1,5-a]quinoxalin-4-amine;
N-(3-Bromo-2-methylphenyl)imidazo[1,5-a]quinoxalin-4-amine;
N-(3-Fluorophenyl)imidazo[1,5-a]quinoxalin-4-amine;
N-(2-Chlorophenyl)-N-methylimidazo[1,5-a]quinoxalin-4-amine;
N-(3,5-Dibromophenyl)imidazo[1,5-a]quinoxalin-4-amine;
N-(4-Benzoylphenyl)imidazo[1,5-a]quinoxalin-4-amine;
N-(4-Pyridinyl)imidazo[1,5-a]quinoxalin-4-amine;
N-(Phenylmethyl)-N-(2-pyridinyl)imidazo[1,5-a]quinoxalin-4-amine;
N-(4-Bromo-2,6-dimethylphenyl)imidazo[1,5-a]quinoxalin-4-amine;
N-[2-Chloro-4-(1,1-dimethylethyl)phenyl]imidazo[1,5-a]quinoxalin-4-amine;
N-(2-Ethyl-6-methylphenyl)imidazo[1,5-a]quinoxalin-4-amine;
N-(5-Chloro-2-methylphenyl)imidazo[1,5-a]quinoxalin-4-amine;
N-(4-Chloro-2-methylphenyl)imidazo[1,5-a]quinoxalin-4-amine;
N-(4-Bromo-2-methylphenyl)imidazo[1,5-a]quinoxalin-4-amine;
N-(2-Chloro-4-methylphenyl)imidazo[1,5-a]quinoxalin-4-amine;
N-(1,3,5-Trimethyl-1H-pyrazol-4-yl)imidazo[1,5-a]quinoxalin-4-amine;
N-(4-Bromo-2-chloro-6-methylphenyl)imidazo[1,5-a]quinoxalin-4-amine;
N-(2-Chloro-4,6-dimethylphenyl)imidazo[1,5-a]quinoxalin-4-amine;
N-(2,6-Dichlorophenyl)imidazo[1,5-a]quinoxalin-4-amine;
N-(2,4,6-Trichlorophenyl)imidazo[1,5-a]quinoxalin-4-amine;
N-(2,6-Dibromophenyl)imidazo[1,5-a]quinoxalin-4-amine;
N-(2,4,6-Tribromophenyl)imidazo[1,5-a]quinoxalin-4-amine;
N-(3,5-Dichloro-2-pyridinyl)imidazo[1,5-a]quinoxalin-4-amine;
N-(2,6-Dibromo-4-methylphenyl)imidazo[1,5-a]quinoxalin-4-amine;
N-(2,6-Dibromo-4-propylphenyl)imidazo[1,5-a]quinoxalin-4-amine;
3-Chloro-4-[[imidazo[1,5-a]quinoxalin-4-yl]amino]benzonitrile;
N-(2,4,6-Trimethylphenyl)imidazo[1,5-a]quinoxalin-4-amine;
N-[2-(4-Morpholinyl)phenyl]imidazo[1,5-a]quinoxalin-4-amine;
1-(Imidazo[1,5-a]quinoxalin-4-yl)-1H-indole-5-carbonitrile;
N-[2-(1H-Imidazol-1-yl)phenyl]imidazo[1,5-a]quinoxalin-4-amine;
N-(2,4-Dimethoxyphenyl)imidazo[1,5-a]quinoxalin-4-amine;
N-Phenylimidazo[1,5-a]quinoxalin-4-amine;
N-(2-Phenoxyphenyl)imidazo[1,5-a]quinoxalin-4-amine;
N-[2-(1,1-Dimethylethyl)phenyl]imidazo[1,5-a]quinoxalin-4-amine;
N-Methyl-N-phenylimidazo[1,5-a]quinoxalin-4-amine;
N-(2,3-Dichlorophenyl)imidazo[1,5-a]quinoxalin-4-amine;
N-(2-Bromophenyl)-7-methoxyimidazo[1,5-a]quinoxalin-4-amine;
N-(2,6-Dimethylphenyl)-7-methoxyimidazo[1,5-a]quinoxalin-4-amine;
N-(2-Chloro-6-methylphenyl)-7-methoxyimidazo[1,5-a]quinoxalin-4-amine;
N-(2,4-Dimethylphenyl)-7-methoxyimidazo[1,5-a]quinoxalin-4-amine;
N-(2-Chlorophenyl)-7-methoxyimidazo[1,5-a]quinoxalin-4-amine;
N-(2,6-Dichlorophenyl)-7-methoxyimidazo[1,5-a]quinoxalin-4-amine;
N-(2-Chloro-4,6-dimethylphenyl)-7-methoxyimidazo[1,5-a]quinoxalin-4-amine;
7,8-Dimethoxy-N-(2,4,6-trimethylphenyl)imidazo[1,5-a]quinoxalin-4-amine;
N-(2,6-Dimethylphenyl)-7,8-dimethoxyimidazo[1,5-a]quinoxalin-4-amine;
N-[2-(3-Chlorophenyl)ethyl]imidazo[1,5-a]quinoxalin-4-amine;
N-[2-[(Phenylmethyl)thio]ethyl]imidazo[1,5-a]quinoxalin-4-amine;
N-[[2-[[2-(Hydroxymethyl)phenyl]thio]phenyl]methyl]imidazo[1,5-a]quinoxalin-4-amine;
N-[2-(1-Cyclohexen-1-yl)ethyl]imidazo[1,5-a]quinoxalin-4-amine;
N-[2-[Ethyl(3-methylphenyl)amino]ethyl]imidazo[1,5-a]quinoxalin-4-amine;
N-Hexylimidazo[1,5-a]quinoxalin-4-amine;
N-[2-(4-Methylphenyl)ethyl]imidazo[1,5-a]quinoxalin-4-amine;
N-[(2-Chlorophenyl)methyl]imidazo[1,5-a]quinoxalin-4-amine;
N-[3-(2-Methyl-1-piperidinyl)propyl]imidazo[1,5-a]quinoxalin-4-amine;
N-[2-(2-Pyridinyl)ethyl]imidazo[1,5-a]quinoxalin-4-amine;
N-[1-(1-Naphthalenyl)ethyl]imidazo[1,5-a]quinoxalin-4-amine;

N-[(Tetrahydro-2-furanyl)methyl]imidazo[1,5-a]quinoxalin-4-amine;
N-[2-(2,4-Dichlorophenyl)ethyl]imidazo[1,5-a]quinoxalin-4-amine;
N-[(2-Aminophenyl)methyl]imidazo[1,5-a]quinoxalin-4-amine;
4-[(Imidazo[1,5-a]quinoxalin-4-yl)amino]-1-piperidinecarboxylic acid, ethyl ester;
4-[4-(Phenylmethyl)-1-piperazinyl]imidazo[1,5-a]quinoxaline;
N-[[4-(Trifluoromethyl)phenyl]methyl]imidazo[1,5-a]quinoxalin-4-amine;
4-[4-(2-Pyridinyl)-1-piperazinyl]imidazo[1,5-a]quinoxaline;
(S)-N-[1-(Phenylmethyl)-3-pyrrolidinyl]imidazo[1,5-a]quinoxalin-4-amine;
N-[(2-Chloro-6-phenoxyphenyl)methyl]imidazo[1,5-a]quinoxalin-4-amine;
4-[4-[2-Nitro-4-(trifluoromethyl)phenyl]-1-piperazinyl]imidazo[1,5-a]quinoxaline;
N-Propylimidazo[1,5-a]quinoxalin-4-amine;
N-Cyclopropylimidazo[1,5-a]quinoxalin-4-amine;
N-[2-(4-Fluorophenyl)ethyl]imidazo[1,5-a]quinoxalin-4-amine;
N-Hexyl-N-methylimidazo[1,5-a]quinoxalin-4-amine;
N-Methyl-N-(phenylmethyl)imidazo[1,5-a]quinoxalin-4-amine;
N-(3-Methoxypropyl)imidazo[1,5-a]quinoxalin-4-amine;
[S-(R*,R*)]-2-[(Imidazo[1,5-a]quinoxalin-4-yl)amino]-1-phenyl-1,3-propanediol;
N-[(2-Methoxyphenyl)methyl]imidazo[1,5-a]quinoxalin-4-amine;
N-(4-Methyl-1-piperazinyl)imidazo[1,5-a]quinoxalin-4-amine;
N-(2-Furanylmethyl)imidazo[1,5-a]quinoxalin-4-amine;
N-(4-Morpholinyl)imidazo[1,5-a]quinoxalin-4-amine;
N-[(2,4-Difluorophenyl)methyl]imidazo[1,5-a]quinoxalin-4-amine;
N-(3-Pyridinylmethyl)imidazo[1,5-a]quinoxalin-4-amine;
N-(3,3-Dimethylbutyl)imidazo[1,5-a]quinoxalin-4-amine;
N-(Phenylmethyl)imidazo[1,5-a]quinoxalin-4-amine;
N-Cyclohexylimidazo[1,5-a]quinoxalin-4-amine;
4-(4-Morpholinyl)imidazo[1,5-a]quinoxaline;
N-(2-Bromophenyl)-3-phenylimidazo[1,5-a]quinoxalin-4-amine;
N-(2-Bromophenyl)-3-(4-morpholinylmethyl)imidazo[1,5-a]quinoxalin-4-amine;
N-(2-Bromophenyl)-7-chloroimidazo[1,5-a]quinoxalin-4-amine;
[4-[(2-Bromophenyl)amino]-7,8-dichloroimidazo[1,5-a]quinoxalin-3-yl]phosphonic acid, diethyl ester;
N-(2-Bromophenyl)-7-(1,1-dimethylethyl)imidazo[1,5-a]quinoxalin-4-amine;
[4-[(2-Bromophenyl)amino]-7-(1,1-dimethylethyl)imidazo[1,5-a]quinoxalin-3-yl]phosphonic acid, diethyl ester;
[4-[(2-Chlorophenyl)amino]imidazo[1,5-a]quinoxalin-3-yl]phosphonic acid, dimethyl ester;
7-Chloro-N-(2-chlorophenyl)imidazo[1,5-a]quinoxalin-4-amine;
7,8-Dichloro-N-(2-chlorophenyl)imidazo[1,5-a]quinoxalin-4-amine;
N-(2-Chlorophenyl)-7-(1,1-dimethylethyl)imidazo[1,5-a]quinoxalin-4-amine;
N-(2-Chlorophenyl)-7-(1,1-dimethylethyl)-3-(4-morpholinylmethyl)imidazo[1,5-a]quinoxalin-4-amine;
[4-[(2-Chloro-6-methylphenyl)amino]imidazo[1,5-a]quinoxalin-3-yl]phosphonic acid, dimethyl ester;
N-(2-Chloro-6-methylphenyl)-3-(4-morpholinylmethyl)imidazo[1,5-a]quinoxalin-4-amine;
7-Chloro-N-(2-chloro-6-methylphenyl)imidazo[1,5-a]quinoxalin-4-amine;
[7-Chloro-4-[(2-chloro-6-methylphenyl)amino]imidazo[1,5-a]quinoxalin-3-yl]phosphonic acid, diethyl ester;
7,8-Dichloro-N-(2-chloro-6-methylphenyl)imidazo[1,5-a]quinoxalin-4-amine;
N-(2-Chloro-6-methylphenyl)-7,8-dimethoxyimidazo[1,5-a]quinoxalin-4-amine;
7-Chloro-N-(2,4-dimethylphenyl)imidazo[1,5-a]quinoxalin-4-amine;
[7,8-Dichloro-4-[(2,4-dimethylphenyl)amino]imidazo[1,5-a]quinoxalin-3-yl]phosphonic acid, diethyl ester;
7,8-Dimethoxy-N-(2,4-dimethylphenyl)-3-(4-morpholinylmethyl)imidazo[1,5-a]quinoxalin-4-amine;
7-(1,1-Dimethylethyl)-N-(2,4-dimethylphenyl)imidazo[1,5-a]quinoxalin-4-amine;
[7-(1,1-Dimethylethyl)-4-[(2,4-dimethylphenyl)amino]imidazo[1,5-a]quinoxalin-3-yl]phosphonic acid, diethyl ester;
7-(1,1-Dimethylethyl)-N-(2,4-dimethylphenyl)-3-(4-morpholinylmethyl)imidazo[1,5-a]quinoxalin-4-amine;
[4-[(2,6-Dimethylphenyl)amino]imidazo[1,5-a]quinoxalin-3-yl]phosphonic acid, diethyl ester;
7-Chloro-N-(2,6-dimethylphenyl)imidazo[1,5-a]quinoxalin-4-amine;
[7-Chloro-4-[(2,6-dimethylphenyl)amino]imidazo[1,5-a]quinoxalin-3-yl]phosphonic acid, diethyl ester;
7-(1,1-Dimethylethyl)-N-(2,6-dimethylphenyl)imidazo[1,5-a]quinoxalin-4-amine;
[7-(1,1-Dimethylethyl)-4-[(2,6-dimethylphenyl)amino]imidazo[1,5-a]quinoxalin-3-yl]phosphonic acid, diethyl ester;
[4-[(2,4,6-Trimethylphenyl)amino]imidazo[1,5-a]quinoxalin-3-yl]phosphonic acid, diethyl ester;
7-Chloro-N-(2,4,6-trimethylphenyl)imidazo[1,5-a]quinoxalin-4-amine;
[7-Chloro-4-[(2,4,6-trimethylphenyl)amino]imidazo[1,5-a]quinoxalin-3-yl]phosphonic acid, diethyl ester;
7,8-Dichloro-N-(2,4,6-trimethylphenyl)imidazo[1,5-a]quinoxalin-4-amine;
[7,8-Dichloro-4-[(2,4,6-trimethylphenyl)amino]imidazo[1,5-a]quinoxalin-3-yl]phosphonic acid, diethyl ester;
[7-(1,1-Dimethylethyl)-4-[(2,4,6-trimethylphenyl)amino]imidazo[1,5-a]quinoxalin-3-yl]phosphonic acid, diethyl ester;
[4-[(2-Bromophenyl)amino]imidazo[1,5-a]quinoxalin-3-yl]phosphonic acid, dimethyl ester;
N-(2-Bromophenyl)-8-chloroimidazo[1,5-a]quinoxalin-4-amine;

[4-[(2-Bromophenyl)amino]-7,8-dichloroimidazo[1,5-a]quinoxalin-3-yl]phosphonic acid, dimethyl ester;

[4-[(2-Bromophenyl)amino]-8-(1,1-dimethylethyl)imidazo[1,5-a]quinoxalin-3-yl]phosphonic acid, diethyl ester;

[4-[(2-Bromophenyl)amino]-7-(1,1-dimethylethyl)imidazo[1,5-a]quinoxalin-3-yl]phosphonic acid, dimethyl ester;

8-Chloro-N-(2-chlorophenyl)imidazo[1,5-a]quinoxalin-4-amine;

[4-[(2-Chlorophenyl)amino]-7-(1,1-dimethylethyl)imidazo[1,5-a]quinoxalin-3-yl]phosphonic acid, dimethyl ester;

[7-Chloro-4-[(2-chloro-6-methylphenyl)amino]imidazo[1,5-a]quinoxalin-3-yl]phosphonic acid, dimethyl ester;

[7-Chloro-4-[(2,4-dimethylphenyl)amino]imidazo[1,5-a]quinoxalin-3-yl]phosphonic acid, dimethyl ester;

[8-Chloro-4-[(2,4-dimethylphenyl)amino]imidazo[1,5-a]quinoxalin-3-yl]phosphonic acid, dimethyl ester;

[7,8-Dichloro-4-[(2,4-dimethylphenyl)amino]imidazo[1,5-a]quinoxalin-3-yl]phosphonic acid, dimethyl ester;

[4-[(2,6-Dimethylphenyl)amino]imidazo[1,5-a]quinoxalin-3-yl]phosphonic acid, dimethyl ester;

[7-Chloro-4-[(2,6-dimethylphenyl)amino]imidazo[1,5-a]quinoxalin-3-yl]phosphonic acid, dimethyl ester;

[8-Chloro-4-[(2,4-dimethylphenyl)amino]imidazo[1,5-a]quinoxalin-3-yl]phosphonic acid, diethyl ester;

[4-[(2,4,6-Trimethylphenyl)amino]imidazo[1,5-a]quinoxalin-3-yl]phosphonic acid, dimethyl ester;

[7-Chloro-4-[(2,4,6-trimethylphenyl)amino]imidazo[1,5-a]quinoxalin-3-yl]phosphonic acid, dimethyl ester;

[8-Chloro-4-[(2,4,6-trimethylphenyl)amino]imidazo[1,5-a]quinoxalin-3-yl]phosphonic acid, diethyl ester;

[7,8-Dichloro-4-[(2,4,6-trimethylphenyl)amino]imidazo[1,5-a]quinoxalin-3-yl]phosphonic acid, dimethyl ester;

[7-(1,1-Dimethylethyl)-4-[(2,4,6-trimethylphenyl)amino]-imidazo[1,5-a]quinoxalin-3-yl]phosphonic acid, dimethyl ester;

N-(2-Chloro-4,6-dimethylphenyl)-7,8-dimethoxyimidazo[1,5-a]quinoxalin-4-amine;

N-(2,4-Dichloro-6-methylphenyl)-7,8-dimethoxyimidazo[1,5-a]quinoxalin-4-amine;

N-(2,6-Dichloro-3-methylphenyl)-7,8-dimethoxyimidazo[1,5-a]quinoxalin-4-amine;

N-(2,6-Dichlorophenyl)-7,8-dimethoxyimidazo[1,5-a]quinoxalin-4-amine;

7,8-Dimethoxy-N-(2,4,6-trichlorophenyl)imidazo[1,5-a]quinoxalin-4-amine;

N-(4-Bromo-2,6-dichlorophenyl)-7,8-dimethoxyimidazo[1,5-a]quinoxalin-4-amine;

N-[2,6-Dichloro-4-(trifluoromethoxy)phenyl]-7,8-dimethoxyimidazo[1,5-a]-quinoxalin-4-amine;

N-[2,6-Dichloro-4-(5-methyl-1,2,4-oxadiazol-3-yl)phenyl]-7,8-dimethoxyimidazo[1,5-a]-quinoxalin-4-amine;

N-(4-Bromo-2-chloro-6-methylphenyl)-7,8-dimethoxyimidazo[1,5-a]quinoxalin-4-amine;

N-(2,6-Dibromophenyl)-7,8-dimethoxyimidazo[1,5-a]-quinoxalin-4-amine;

N-(4-Bromo-2,6-dimethylphenyl)-7,8-dimethoxyimidazo[1,5-a]quinoxalin-4-amine;

7,8-Dimethoxy-N-(2,4,6-trimethyl-3-pyridinyl)imidazo[1,5-a]quinoxalin-4-amine;

9-Nitro-N-(2,4,6-trimethylphenyl)imidazo[1,5-a]quinoxalin-4-amine;

N-[2,6-Dimethyl-3-(1-methylethyl)phenyl]-9-nitroimidazo[1,5-a]quinoxalin-4-amine;

N-(3-Bromo-2,4,6-trimethylphenyl)-9-nitroimidazo[1,5-a]quinoxalin-4-amine;

N-(2-Chloro-4,6-dimethylphenyl)-9-nitroimidazo[1,5-a]quinoxalin-4-amine;

N-(2,4-Dichloro-6-methylphenyl)-9-nitroimidazo[1,5-a]quinoxalin-4-amine;

N-(2,6-Dichloro-3-methylphenyl)-9-nitroimidazo[1,5-a]quinoxalin-4-amine;

N-(2-Chlorophenyl)-9-nitroimidazo[1,5-a]quinoxalin-4-amine;

N-(2,6-Dichlorophenyl)-9-nitroimidazo[1,5-a]quinoxalin-4-amine;

9-Nitro-N-(2,4,6-trichlorophenyl)imidazo[1,5-a]quinoxalin-4-amine;

N-(4-Bromo-2,6-dichlorophenyl)-9-nitroimidazo[1,5-a]quinoxalin-4-amine;

N-(2,6-Dichloro-4-methoxyphenyl)-9-nitroimidazo[1,5-a]quinoxalin-4-amine;

N-[2,6-Dichloro-4-(trifluoromethoxy)-phenyl]-9-nitroimidazo[1,5-a]quinoxalin-4-amine;

N-[2,6-Dichloro-4-(5-methyl-1,2,4-oxadiazol-3-yl)phenyl]-9-nitroimidazo[1,5-a]quinoxalin-4-amine;

N-(4-Bromo-2-chloro-6-methylphenyl)-9-nitroimidazo[1,5-a]quinoxalin-4-amine;

N-(2-Bromophenyl)-9-nitroimidazo[1,5-a]quinoxalin-4-amine;

N-(2,6-Dibromophenyl)-9-nitroimidazo[1,5-a]quinoxalin-4-amine;

N-(2,4,6-Tribromophenyl)-9-nitroimidazo[1,5-a]quinoxalin-4-amine;

N-(2,6-Dibromo-4-propylphenyl)-9-nitroimidazo[1,5-a]quinoxalin-4-amine;

N-[2,6-Dibromo-4-(1-methylethyl)phenyl]-9-nitroimidazo[1,5-a]quinoxalin-4-amine;

N-[2-Bromo-4-(1-methylethyl)phenyl]-9-nitroimidazo[1,5-a]quinoxalin-4-amine;

N-(2,6-Dibromo-4-methylphenyl)-9-nitroimidazo[1,5-a]quinoxalin-4-amine;

N-(4-Bromo-2,6-dimethylphenyl)-9-nitroimidazo[1,5-a]quinoxalin-4-amine;

N-(3,5-Dichloro-4-pyridinyl)-9-nitroimidazo[1,5-a]quinoxalin-4-amine;

N-(2,6-Dimethylphenyl)-9-nitroimidazo-[1,5-a]quinoxalin-4-amine;

N-[4-[(2,6-Dimethylphenyl)amino]imidazo[1,5-a]quinoxalin-8-yl]-3-methoxypropanamide;

N-[4-[(2,6-Dimethylphenyl)amino]imidazo[1,5-a]quinoxalin-8-yl]-2-cyanoacetamide;

$N^4$-(2,6-Dimethylphenyl)-$N^8$,$N^8$-dimethylimidazo[1,5-a]quinoxaline-4,8-diamine;

$N^4$-(2,6-Dimethylphenyl)-$N^8$,$N^8$-diethylimidazo[1,5-a]quinoxaline-4,8-diamine;

4-[(2,6-Dimethylphenyl)amino]imidazo[1,5-a]quinoxaline-7,8-diol;

N-[4-[(2-Chloro-6-methylphenyl)amino]imidazo[1,5-a]quinoxalin-8-yl]-2-thiophenebutanamide;

$N^4$-(2,6-Dimethylphenyl)imidazo[1,5-a]quinoxaline-4,9-diamine;

$N^4$-(2,4,6-Trimethylphenyl)imidazo[1,5-a]quinoxaline-4,9-diamine;

$N^4$-[2,6-Dimethyl-3-(1-methylethyl)phenyl]imidazo[1,5-a]quinoxaline-4,9-diamine;

$N^4$-(3-Bromo-2,4,6-trimethylphenyl)imidazo[1,5-a]quinoxaline-4,9-diamine;

$N^4$-(2-Chloro-4,6-dimethylphenyl)imidazo[1,5-a]quinoxaline-4,9-diamine;

$N^4$-(2,4-Dichloro-6-methylphenyl)imidazo[1,5-a]quinoxaline-4,9-diamine;

N-(2-Chloro-6-methylphenyl)-8-iodoimidazo[1,5-a]quinoxalin-4-amine;

N-(2-Chloro-6-methylphenyl)-8-fluoroimidazo[1,5-a]quinoxalin-4-amine;

N-(2-Chloro-6-methylphenyl)-8-methoxyimidazo[1,5-a]quinoxalin-4-amine;

N-(2,6-Dimethylphenyl)-8-methoxyimidazo[1,5-a]quinoxalin-4-amine;

N-(2,6-Dichlorophenyl)-8-methoxyimidazo[1,5-a]quinoxalin-4-amine;

N-(2,4,6-Trimethylphenyl)-8-methoxyimidazo[1,5-a]quinoxalin-4-amine;

N-(2-Chlorophenyl)-8-methoxyimidazo[1,5-a]quinoxalin-4-amine;

N-(2-Chloro-6-methylphenyl)-3-methylimidazo[1,5-a]quinoxalin-4-amine;

N-(2,6-Dimethylphenyl)-3-methylimidazo[1,5-a]quinoxalin-4-amine;

N-(2-Chlorophenyl)-3-methylimidazo[1,5-a]quinoxalin-4-amine;

N-(2-Chloro-6-methylphenyl)-8-(4-methyl-1-piperazinyl)imidazo[1,5-a]quinoxalin-4-amine;

N-(2-Chloro-6-methylphenyl)-8-phenylimidazo[1,5-a]quinoxalin-4-amine;

N-(2-Chloro-6-methylphenyl)-8-(4-methoxyphenyl)imidazo[1,5-a]quinoxalin-4-amine;

$N^4$-(2-Chloro-6-methylphenyl)-$N^8$-ethylimidazo[1,5-a]quinoxaline-4,8-diamine;

$N^4$-(2-Chloro-6-methylphenyl)-$N^8$-methylimidazo[1,5-a]quinoxaline-4,8-diamine;

$N^4$-(2-Chloro-6-methylphenyl)-$N^8$-(1-methylethyl)imidazo[1,5-a]quinoxaline-4,8-diamine;

N-(2,6-Dichlorophenyl)-8-fluoroimidazo[1,5-a]quinoxalin-4-amine;

N-(2-Chloro-6-methylphenyl)-8-(1-piperazinyl)imidazo[1,5-a]quinoxalin-4-amine;

N-(2-Chloro-6-methylphenyl)-7-nitroimidazo[1,5-a]quinoxalin-4-amine;

$N^4$-(2-Chloro-6-methylphenyl)imidazo[1,5-a]quinoxaline-4,7-diamine;

N-[4-[(2-Chloro-6-methylphenyl)amino]imidazo[1,5-a]quinoxalin-7-yl]hexanamide;

$N^4$-(2-Chloro-6-methylphenyl)-$N^8$,$N^8$-diethylimidazo[1,5-a]quinoxaline-4,8-diamine;

$N^4$-(2-Chloro-6-methylphenyl)-$N^8$,$N^8$-dimethylimidazo[1,5-a]quinoxaline-4,8-diamine;

1-Acetyl-4-[4-[(2-chloro-6-methylphenyl)amino]imidazo[1,5-a]quinoxalin-8-yl]piperazine;

$N^4$-(2-Chloro-6-methylphenyl)-$N^8$-(cyclopropylmethyl)imidazo[1,5-a]quinoxaline-4,8-diamine;

$N^4$-(2-Chloro-6-methylphenyl)-$N^8$-(cyclohexylmethyl)imidazo[1,5-a]quinoxaline-4,8-diamine;

$N^4$-(2-Chloro-6-methylphenyl)-$N^8$-(cyclopentyl)imidazo[1,5-a]quinoxaline-4,8-diamine;

N-[2-[[4-[(2-Chloro-6-methylphenyl)amino]imidazo[1,5-a]quinoxalin-8-yl]amino]ethyl]acetamide;

1-[3-[[4-[(2-Chloro-6-methylphenyl)amino]imidazo[1,5-a]quinoxalin-8-yl]amino]propyl]-2-pyrrolidinone;

$N^4$-(2-Chloro-6-methylphenyl)-$N^8$-[2-(dimethylamino)ethyl]imidazo[1,5-a]quinoxaline-4,8-diamine;

$N^4$-(2-Chloro-6-methylphenyl)-$N^8$-[2-(1-methyl-2-pyrrolidinyl)ethyl]imidazo[1,5-a]quinoxaline-4,8-diamine;

$N^4$-(2-Chloro-6-methylphenyl)-$N^8$-[2-(4-morpholinyl)ethyl]imidazo[1,5-a]quinoxaline-4,8-diamine;

$N^4$-(2-Chloro-6-methylphenyl)-$N^8$-[2-(2-pyridinyl)ethyl]imidazo[1,5-a]quinoxaline-4,8-diamine;

$N^4$-(2-Chloro-6-methylphenyl)-$N^8$-(3-1H-imidazol-1-ylpropyl)imidazo[1,5-a]quinoxaline-4,8-diamine;

$N^4$-(2-Chloro-6-methylphenyl)-$N^8$-[3-(4-morpholinyl)propyl]imidazo[1,5-a]quinoxaline-4,8-diamine;

N-(2-Chloro-6-methylphenyl)-8-[4-(2-pyridinyl)-1-piperazinyl]imidazo[1,5-a]quinoxalin-4-amine;

N-(2-Chloro-6-methylphenyl)-8-(4-ethyl-1-piperazinyl)imidazo[1,5-a]quinoxalin-4-amine;

4-[4-[(2-Chloro-6-methylphenyl)amino]imidazo[1,5-a]quinoxalin-8-yl]-1-piperazinecarboxylic acid ethyl ester;

N-(2-Chloro-6-methylphenyl)-8-(3,5-dimethyl-1-piperazinyl)imidazo[1,5-a]quinoxalin-4-amine;

4-[4-[(2-Chloro-6-methylphenyl)amino]imidazo[1,5-a]quinoxalin-8-yl]-1-piperazinecarboxaldehyde;

N-(2-Chloro-6-methylphenyl)-8-(1-piperidinyl)imidazo[1,5-a]quinoxalin-4-amine;

N-(2-Chloro-6-methylphenyl)-8-(4-morpholinyl)imidazo[1,5-a]quinoxalin-4-amine;

$N^4$-(2-Chloro-6-methylphenyl)-$N^8$-[(tetrahydro-2-furanyl)methyl]imidazo[1,5-a]quinoxaline-4,8-diamine;

4-[(2-Chloro-6-methylphenyl)amino]-7,8-dimethoxyimidazo[1,5-a]quinoxaline-1-methanol;

N-(3,5-Dimethyl[1,1'-biphenyl]-4-yl)-7,8-dimethoxyimidazo[1,5-a]quinoxalin-4-amine;

N-(2-Chloro-6-methylphenyl)-8-(phenylmethoxy)imidazo[1,5-a]quinoxalin-4-amine;

6-Bromo-N-(2-chloro-6-methylphenyl)-8-fluoroimidazo[1,5-a]quinoxalin-4-amine;

6-Bromo-N-(2-chloro-6-methylphenyl)-8-(4-methyl-1-piperazinyl)imidazo[1,5-a]quinoxalin-4-amine;

N-(2-Chloro-6-methylphenyl)-8-fluoro-6-(4-methyl-1-piperazinyl)imidazo[1,5-a]quinoxalin-4-amine;

N-(2-Chloro-6-methylphenyl)-6,8-bis(1-piperazinyl)imidazo[1,5-a]quinoxalin-4-amine;

6,8-Bis(4-acetyl-1-piperazinyl)-N-(2-chloro-6-methylphenyl)imidazo[1,5-a]quinoxalin-4-amine;

$N^4$-(2-Chloro-6-methylphenyl)-$N^7$,$N^7$-dimethylimidazo[1,5-a]quinoxaline-4,7-diamine;

[4-[[4-[(2-Chloro-6-methylphenyl)amino]imidazo[1,5-a]quinoxalin-7-yl]amino]-4-oxobutyl]carbamic acid 1,1-dimethylethyl ester;

$N^4$-(2-Chloro-6-methylphenyl)-$N^7$,$N^7$-diethylimidazo[1,5-a]quinoxaline-4,7-diamine;

N-[4-[(2-Chloro-6-methylphenyl)amino]imidazo[1,5-a]
quinoxalin-7-yl]acetamide;

N-[4-[(2-Chloro-6-methylphenyl)amino]imidazo[1,5-a]
quinoxalin-7-yl]benzeneacetamide;

$N^4$-(2-Chloro-6-methylphenyl)-$N^7$-methylimidazo[1,5-a]
quinoxaline-4,7-diamine;

4-Amino-N-[4-[(2-chloro-6-methylphenyl)amino]
imidazo[1,5-a]quinoxalin-7-yl]butanamide dihydrochloride;

$N^4$-(2-Chloro-6-methylphenyl)-$N^7$-ethylimidazo[1,5-a]
quinoxaline-4,7-diamine;

$N^4$-(2-Chloro-6-methylphenyl)-$N^7$-(phenylmethyl)
imidazo[1,5-a]quinoxaline-4,7-diamine;

N-[4-[(2-Chloro-6-methylphenyl)amino]imidazo[1,5-a]
quinoxalin-8-yl]-3-hydroxy-3-methylbutanamide;

N-(2-Chloro-6-methylphenyl)-9-methoxyimidazo[1,5-a]
quinoxalin-4-amine;

N-(2,6-Dichlorophenyl)-8-nitroimidazo[1,5-a]
quinoxalin-4-amine;

$N^4$-(2,6-Dichlorophenyl)imidazo[1,5-a]quinoxaline-4,8-diamine;

N-(2-Chloro-6-methylphenyl)-7,8-dihydroxyimidazo[1,5-a]quinoxalin-4-amine;

N-(2-Chloro-6-methylphenyl)[1,3]dioxolo[4,5-g]imidazo
[1,5-a]quinoxalin-4-amine;

N-(2-Chloro-6-methylphenyl)-2,3-dihydro-1,4-dioxino
[2,3-g]imidazo[1,5-a]quinoxalin-7-amine;

N-[2,6-Dimethyl-4-[2-(dimethylamino)ethoxy]phenyl]-7,
8-dimethoxyimidazo[1,5-a]quinoxalin-4-amine;

N-[2,6-Dimethyl-4-[2-(4-morpholinyl)ethoxy]phenyl]-7,
8-dimethoxyimidazo[1,5-a]quinoxalin-4-amine;

4-[(2-Chloro-6-methylphenyl)amino]imidazo[1,5-a]
quinoxaline-7-carboxylic acid methyl ester;

4-[(2-Chloro-6-methylphenyl)amino]imidazo[1,5-a]
quinoxaline-7-carboxylic acid;

4-[(2-Chloro-6-methylphenyl)amino]imidazo[1,5-a]
quinoxaline-7-carboxamide;

N-(2-Chloro-6-methylphenyl)-8-(2,6-dimethylphenyl)
imidazo[1,5-a]quinoxalin-4-amine;

N-(2-Chloro-6-methylphenyl)-8-methoxy-7-[2-(4-morpholinyl)ethoxy]imidazo[1,5-a]quinoxalin-4-amine;

N-(2-Chloro-6-methylphenyl)-8-methoxy-7-[3-(4-morpholinyl)propoxy]imidazo[1,5-a]quinoxalin-4-amine;

N-(2-Chloro-6-methylphenyl)-7-[3-(dimethylamino)
propoxy]-8-methoxyimidazo[1,5-a]quinoxalin-4-amine;

N-(2-Chloro-6-methylphenyl)-7-[2-(dimethylamino)
ethoxy]-8-methoxyimidazo[1,5-a]quinoxalin-4-amine;

N-(2-Chloro-6-methylphenyl)-8-methoxy-7-(2-methoxyethoxy)imidazo[1,5-a]quinoxalin-4-amine;

7-[2-(Acetyloxy)ethoxy]-N-(2-chloro-6-methylphenyl)-
8-methoxyimidazo[1,5-a]quinoxalin-4-amine;

N-(2-Chloro-6-methylphenyl)-7-(2-hydroxyethoxy)-8-methoxyimidazo[1,5-a]quinoxalin-4-amine;

N-(2-Chloro-6-methylphenyl)-8-methoxy-7-[(tetrahydro-2-furanyl)methoxy]imidazo[1,5-a]quinoxalin-4-amine;

N-(2-Chloro-6-methylphenyl)-8-methoxy-7-[(tetrahydro-3-furanyl)methoxy]imidazo[1,5-a]quinoxalin-4-amine;

N-(2-Chloro-6-methylphenyl)-8-methoxy-7-[(tetrahydro-3-furanyl)oxy]imidazo[1,5-a]quinoxalin-4-amine;

N-(2-Chloro-6-methylphenyl)-8-methoxy-7-[2-(1-methyl-2-pyrrolidinyl)ethoxy]imidazo[1,5-a]
quinoxalin-4-amine;

N-(2-Chloro-6-methylphenyl)-8-methoxy-7-[(1-methyl-3-pyrrolidinyl)oxy]imidazo[1,5-a]quinoxalin-4-amine;

N-(2-Chloro-6-fluorophenyl)-7,8-dimethoxyimidazo[1,5-
a]quinoxalin-4-amine;

N-(2-Chloro-6-fluorophenyl)-8-methoxy-7-[2-(4-morpholinyl)ethoxy]imidazo[1,5-a]quinoxalin-4-amine;

N-(2-Chloro-6-fluorophenyl)-8-methoxy-7-[3-(4-morpholinyl)propoxy]imidazo[1,5-a]quinoxalin-4-amine;

N-(2-Chloro-6-fluorophenyl)-7-[2-(dimethylamino)
ethoxy]-8-methoxyimidazo[1,5-a]quinoxalin-4-amine;

N-(2-Chloro-6-fluorophenyl)-7-[3-(dimethylamino)
propoxy]-8-methoxyimidazo[1,5-a]quinoxalin-4-amine;

N-(2-Chloro-6-fluorophenyl)-8-ethoxy-7-[2-(4-morpholinyl)ethoxy]imidazo[1,5-a]quinoxalin-4-amine;

N-(2-Chloro-6-fluorophenyl)-8-ethoxy-7-[3-(4-morpholinyl)propoxy]imidazo[1,5-a]quinoxalin-4-amine;

N-(2-Chloro-6-fluorophenyl)-7-[2-(dimethylamino)
ethoxy]-8-ethoxyimidazo[1,5-a]quinoxalin-4-amine;

N-(2-Chloro-6-fluorophenyl)-7-[3-(dimethylamino)
propoxy]-8-ethoxyimidazo[1,5-a]quinoxalin-4-amine;

N-(2-Chloro-6-fluorophenyl)-8-ethoxy-7-[(tetrahydro-3-furanyl)oxy]imidazo[1,5-a]quinoxalin-4-amine;

N-(2-Chloro-6-methylphenyl)-7-methoxy-8-[2-(4-morpholinyl)ethoxy]imidazo[1,5-a]quinoxalin-4-amine;

N-(2-Chloro-6-methylphenyl)-7-ethoxy-8-[2-(4-morpholinyl)ethoxy]imidazo[1,5-a]quinoxalin-4-amine;

N-(2-Chloro-6-methylphenyl)-8-[2-(4-morpholinyl)
ethoxy]-7-[(tetrahydro-3-furanyl)oxy]imidazo[1,5-a]
quinoxalin-4-amine;

3,5-Dichloro-N-cyclopropyl-4-[(7,8-dimethoxyimidazo
[1,5-a]quinoxalin-4-yl)amino]benzamide;

N-(2-Bromo-4,6-difluorophenyl)-7,8-dimethoxyimidazo
[1,5-a]quinoxalin-4-amine;

3,5-Dichloro-4-[(7,8-dimethoxyimidazo[1,5-a]
quinoxalin-4-yl)amino]benzoic acid;

N-(2,4-Dibromo-6-fluorophenyl)-7,8-dimethoxyimidazo
[1,5-a]quinoxalin-4-amine;

3,5-Dichloro-4-[(7,8-dimethoxyimidazo[1,5-a]
quinoxalin-4-yl)amino]benzenesulfonamide;

3-Chloro-4-[(7,8-dimethoxyimidazo[1,5-a]quinoxalin-4-
yl)amino]-5-methylbenzenesulfonic acid;

N-[2,6-Dichloro-4-(trifluoromethyl)phenyl]-7,8-dimethoxyimidazo[1,5-a]quinoxalin-4-amine;

N-(2,6-Dibromo-4-methylphenyl)-7,8-dimethoxyimidazo
[1,5-a]quinoxalin-4-amine;

N-[2,4-Dichloro-6-(trifluoromethyl)phenyl]-7,8-dimethoxyimidazo[1,5-a]quinoxalin-4-amine;

N-(2,6-Dichloro-4-methoxyphenyl)-7,8-dimethoxyimidazo[1,5-a]quinoxalin-4-amine;

N-[2-Fluoro-6-(trifluoromethyl)phenyl]-7,8-dimethoxyimidazo[1,5-a]quinoxalin-4-amine;

N-(2-Bromo-6-chloro-4-fluorophenyl)-7,8-dimethoxyimidazo[1,5-a]quinoxalin-4-amine;

N-(2,6-Dibromo-4-fluorophenyl)-7,8-dimethoxyimidazo[1,5-a]quinoxalin-4-amine;

N-(2-Bromo-4,6-dimethylphenyl)-7,8-dimethoxyimidazo[1,5-a]quinoxalin-4-amine;

N-(2-Bromo-4-chloro-6-fluorophenyl)-7,8-dimethoxyimidazo[1,5-a]quinoxalin-4-amine;

N-(2,6-Difluorophenyl)-7,8-dimethoxyimidazo[1,5-a]quinoxalin-4-amine;

N-(2,4,6-Trifluorophenyl)-7,8-dimethoxyimidazo[1,5-a]quinoxalin-4-amine;

3-Chloro-4-[(7,8-dimethoxyimidazo[1,5-a]quinoxalin-4-yl)amino]-5-methylbenzonitrile;

3-Chloro-4-[(7,8-dimethoxyimidazo[1,5-a]quinoxalin-4-yl)amino]-5-methylbenzamide;

N-(2-Chloro-3,6-dimethylphenyl)-7,8-dimethoxyimidazo[1,5-a]quinoxalin-4-amine;

N-(2-Chloro-5,6-dimethylphenyl)-7,8-dimethoxyimidazo[1,5-a]quinoxalin-4-amine;

N-(2-Chloro-6-methylphenyl)-6-methoxyimidazo[1,5-a]quinoxalin-4-amine;

N-(2-Chloro-6-methylphenyl)-9-(phenylmethoxy)imidazo[1,5-a]quinoxalin-4-amine;

N-(2-Chloro-6-methylphenyl)-9-(2-hydroxyethoxy)imidazo[1,5-a]quinoxalin-4-amine;

N-(2-Chloro-6-methylphenyl)-9-[2-(dimethylamino)ethoxy]imidazo[1,5-a]quinoxalin-4-amine;

N-(2-Chloro-6-methylphenyl)-9-(3-hydroxypropoxy)imidazo[1,5-a]quinoxalin-4-amine;

N-(2-Chloro-6-methylphenyl)-9-(2-methoxyethoxy)imidazo[1,5-a]quinoxalin-4-amine;

N-(2-Chloro-6-methylphenyl)-9-[(tetrahydro-2H-pyran-4-yl)oxy]imidazo[1,5-a]quinoxalin-4-amine;

N-(2-Chloro-6-methylphenyl)-9-[2-(4-morpholinyl)ethoxy]imidazo[1,5-a]quinoxalin-4-amine;

8-Bromo-N-(2-chloro-6-fluorophenyl)imidazo[1,5-a]quinoxalin-4-amine;

N-(2-Chloro-6-fluorophenyl)-8-(3,5-dimethyl-1-piperazinyl)imidazo[1,5-a]quinoxalin-4-amine;

N-(2-Chloro-6-fluorophenyl)-8-(4-methyl-1-piperazinyl)imidazo[1,5-a]quinoxalin-4-amine;

N-(2-Chloro-6-fluorophenyl)-8-[[2-(2-pyridinyl)ethyl]amino]imidazo[1,5-a]quinoxalin-4-amine;

$N^4$-(2-Chloro-6-fluorophenyl)-$N^8$-[(tetrahydro-2-furanyl)methyl]imidazo[1,5-a]quinoxaline-4,8-diamine;

$N^8$-(2-Aminoethyl)-$N^4$-(2-chloro-6-fluorophenyl)imidazo[1,5-a]quinoxaline-4,8-diamine;

$N^4$-(2-Chloro-6-fluorophenyl)-$N^8$-[3-(4-methyl-1-piperazinyl)propyl]imidazo[1,5-a]quinoxaline-4,8-diamine;

$N^4$-(2-Chloro-6-fluorophenyl)-$N^8$-[2-(1-methyl-2-pyrrolidinyl)ethyl]imidazo[1,5-a]quinoxaline-4,8-diamine;

$N^4$-(2-Chloro-6-fluorophenyl)-$N^8$-[2-(4-morpholinyl)ethyl]imidazo[1,5-a]quinoxaline-4,8-diamine;

$N^4$-(2-Chloro-6-fluorophenyl)-$N^8$-[6-(dimethylamino)hexyl]imidazo[1,5-a]quinoxaline-4,8-diamine;

$N^4$-(2-Chloro-6-fluorophenyl)-$N^8$-[4-(dimethylamino)butyl]imidazo[1,5-a]quinoxaline-4,8-diamine;

$N^4$-(2-Chloro-6-fluorophenyl)-$N^8$-[3-(dimethylamino)propyl]imidazo[1,5-a]quinoxaline-4,8-diamine;

$N^4$-(2-Chloro-6-fluorophenyl)-$N^8$-[2-(dimethylamino)ethyl]imidazo[1,5-a]quinoxaline-4,8-diamine;

1-[3-[[4-(2-Chloro-6-fluorophenyl)imidazo[1,5-a]quinoxalin-8-yl]amino]propyl]-2-pyrrolidinone;

$N^4$-(2-Chloro-6-fluorophenyl)-$N^8$-[2-(4-pyridinyl)ethyl]imidazo[1,5-a]quinoxaline-4,8-diamine;

$N^4$-(2-Chloro-6-fluorophenyl)-$N^8$-[3-(4-morpholinyl)propyl]imidazo[1,5-a]quinoxaline-4,8-diamine;

$N^4$-(2-Chloro-6-fluorophenyl)-$N^8$-(cyclopropylmethyl)imidazo[1,5-a]quinoxaline-4,8-diamine;

7-Bromo-N-(2-chloro-6-methylphenyl)imidazo[1,5-a]quinoxalin-4-amine;

$N^4$-(2-Chloro-6-methylphenyl)-$N^7$-[4-(dimethylamino)butyl]imidazo[1,5-a]quinoxaline-4,7-diamine;

$N^4$-(2-Chloro-6-methylphenyl)-$N^7$-[6-(dimethylamino)hexyl]imidazo[1,5-a]quinoxaline-4,7-diamine;

$N^4$-(2-Chloro-6-methylphenyl)-$N^7$-[3-(4-methyl-1-piperazinyl)propyl]imidazo[1,5-a]quinoxaline-4,7-diamine;

$N^4$-(2-Chloro-6-methylphenyl)-$N^7$-cyclopropylimidazo[1,5-a]quinoxaline-4,7-diamine;

$N^4$-(2-Chloro-6-methylphenyl)-$N^7$-[1-(phenylmethyl)-4-piperidinyl]imidazo[1,5-a]quinoxaline-4,7-diamine;

$N^4$-(2-Chloro-6-methylphenyl)-$N^7$-[3-(methylphenylamino)propyl]imidazo[1,5-a]quinoxaline-4,7-diamine;

$N^7$-[(2-Aminophenyl)methyl]-$N^4$-(2-chloro-6-methylphenyl)imidazo[1,5-a]quinoxaline-4,7-diamine;

N-(2-Chloro-6-methylphenyl)-7-(4-morpholinyl)imidazo[1,5-a]quinoxalin-4-amine;

N-(2-Chloro-6-methylphenyl)-7-(4-methyl-1-piperazinyl)imidazo[1,5-a]quinoxalin-4-amine;

N-(2-Chloro-6-methylphenyl)-7-(1-piperazinyl)imidazo[1,5-a]quinoxalin-4-amine;

N-(2-Chloro-6-methylphenyl)-7-(3,5-dimethyl-1-piperazinyl)imidazo[1,5-a]quinoxalin-4-amine;

N-(2-Chloro-6-methylphenyl)-7-[4-[2-(dimethylamino)ethyl]-1-piperazinyl]imidazo[1,5-a]quinoxalin-4-amine;

N-(2-Chloro-6-methylphenyl)-7-[4-[3-(dimethylamino)propyl]-1-piperazinyl]imidazo[1,5-a]quinoxalin-4-amine;

(S)-N-(2-Chloro-6-methylphenyl)-7-(3-methyl-1-piperazinyl)imidazo[1,5-a]quinoxalin-4-amine;

$N^4$-(2-Chloro-6-methylphenyl)-$N^7$-[2-(dimethylamino)ethyl]imidazo[1,5-a]quinoxaline-4,7-diamine;

$N^4$-(2-Chloro-6-methylphenyl)-$N^7$-[3-(dimethylamino)propyl]imidazo[1,5-a]quinoxaline-4,7-diamine;

$N^4$-(2-Chloro-6-methylphenyl)-$N^7$-(2-thienylmethyl)imidazo[1,5-a]quinoxaline-4,7-diamine;

$N^4$-(2-Chloro-6-methylphenyl)-$N^7$-[(2,3-dihydro-1,4-benzodioxin-2-yl)methyl]imidazo[1,5-a]quinoxaline-4,7-diamine;

$N^4$-(2-Chloro-6-methylphenyl)-$N^7$-[2-(2-thienyl)ethyl]imidazo[1,5-a]quinoxaline-4,7-diamine;

(R)-N-(2-Chloro-6-methylphenyl)-7-(3-methyl-1-piperazinyl)imidazo[1,5-a]quinoxalin-4-amine;

7-[4-(1,3-Benzodioxol-5-ylmethyl)-1-piperazinyl]-N-(2-chloro-6-methylphenyl)imidazo[1,5-a]quinoxalin-4-amine;

4-[4-[(2-Chloro-6-methylphenyl)amino]imidazo[1,5-a]quinoxalin-7-yl]-N-(1-methylethyl)-1-piperazineacetamide;

N-(2-Chloro-6-methylphenyl)-7-(4-phenyl-1-piperazinyl)imidazo[1,5-a]quinoxalin-4-amine;

1-[4-[(2-Chloro-6-methylphenyl)amino]imidazo[1,5-a]quinoxalin-7-yl]-4-(2-furanylcarbonyl)piperazine;

N-(2-Chloro-6-methylphenyl)-7-[4-(2-methoxyethyl)-1-piperazinyl]imidazo[1,5-a]quinoxalin-4-amine;

4-[(2-Chloro-6-methylphenyl)amino]-7,8-dimethoxyimidazo[1,5-a]quinoxaline-1-carboxaldehyde;

4-[(2-Chloro-6-methylphenyl)amino]-7,8-dimethoxyimidazo[1,5-a]quinoxaline-1-carboxaldehyde oxime;

4-[(2-Chloro-6-methylphenyl)amino]-8-methoxyimidazo[1,5-a]quinoxalin-7-ol;

2-[[4-[(2-Chloro-6-methylphenyl)amino]-7-hydroxyimidazo[1,5-a]quinoxalin-8-yl]oxy]-2-propenenitrile;

7-[(2-Chloro-6-methylphenyl)amino]-2,3-dihydro-1,4-dioxino[2,3-g]imidazo[1,5-a]quinoxaline-2-carbonitrile;

N-(2-Chloro-6-methylphenyl)-7,8-bis[3-(dimethylamino)propoxy]imidazo[1,5-a]quinoxalin-4-amine;

N-(2-Chloro-6-methylphenyl)-7,8-bis[2-(4-morpholinyl)ethoxy]imidazo[1,5-a]quinoxalin-4-amine;

N-Cyclohexyl-7,8-dimethoxyimidazo[1,5-a]quinoxaline-4-amine;

1-Chloro-N-(2-chloro-6-methylphenyl)-7,8-dimethoxyimidazo[1,5-a]quinoxalin-4-amine;

N-(2-Chloro-6-methylphenyl)-1,7,8-trimethoxyimidazo[1,5-a]quinoxalin-4-amine;

$N^4$-(2-Chloro-6-methylphenyl)-7,8-dimethoxy-N'-[(4-methoxyphenyl)methyl]imidazo[1,5-a]quinoxaline-1,4-diamine;

N-[4-[(2-Chloro-6-methylphenyl)amino]-7,8-dimethoxyimidazo[1,5-a]quinoxalin-1-yl]-N-[(4-methoxyphenyl)methyl]acetamide;

N-[4-[(2-Chloro-6-methylphenyl)amino]-7,8-dimethoxyimidazo[1,5-a]quinoxalin-1-yl]acetamide;

$N^4$-(2-Chloro-6-methylphenyl)-7,8-dimethoxyimidazo[1,5-a]quinoxaline-1,4-diamine, dihydrochloride;

3-Chloro-N-(2-chloro-6-methylphenyl)imidazo[1,5-a]quinoxalin-4-amine;

4-[(2-Chloro-6-methylphenyl)amino]imidazo[1,5-a]quinoxaline-8-carbonitrile;

4-[(2-Chloro-6-methylphenyl)amino]imidazo[1,5-a]quinoxaline-8-carboxamide;

4-[(2-Chloro-6-methylphenyl)amino]imidazo[1,5-a]quinoxaline-8-carboxylic acid;

4-[(2-Chloro-6-methylphenyl)amino]imidazo[1,5-a]quinoxaline-8-carboxylic acid methyl ester;

4-[(2-Chloro-6-methylphenyl)amino]imidazo[1,5-a]quinoxalin-8-ol;

N-[2-Chloro-6-methyl-4-(4-morpholinyl)phenyl]-7,8-dimethoxyimidazo[1,5-a]quinoxalin-4-amine;

N-(2-Chloro-6-methylphenyl)-8-(hexahydro-4-methyl-1H-1,4-diazepin-1-yl)imidazo[1,5-a]quinoxalin-4-amine;

N-(2-Chloro-6-fluorophenyl)-8-(1H-imidazol-1-yl)imidazo[1,5-a]quinoxalin-4-amine;

N-(2-Chloro-6-methylphenyl)-7,9-dimethoxyimidazo[1,5-a]quinoxalin-4-amine;

N-(2-Chloro-6-fluorophenyl)-7,9-dimethoxyimidazo[1,5-a]quinoxalin-4-amine;

N-(2-Chloro-6-fluorophenyl)-6,8-dimethoxyimidazo[1,5-a]quinoxalin-4-amine;

N-(2-Chloro-6-methylphenyl)-8-[4-[[[3-(dimethylamino)propyl]amino]methyl]phenyl]imidazo[1,5-a]quinoxalin-4-amine;

N-(2-Chloro-6-methylphenyl)-7-methoxy-8-(1-piperazinyl)imidazo[1,5-a]quinoxalin-4-amine;

cis-N-(2-Chloro-6-methylphenyl)-8-(3,5-dimethyl-1-piperazinyl)-7-methoxyimidazo[1,5-a]quinoxalin-4-amine;

$N^4$-(2-Chloro-6-methylphenyl)-7-methoxy-$N^8$-[3-(4-morpholinyl)propyl]imidazo[1,5-a]quinoxaline-4,8-diamine;

N-(2-Chloro-6-methylphenyl)-8-(hexahydro-1H-1,4-diazepin-1-yl)-7-methoxyimidazo[1,5-a]quinoxalin-4-amine;

N-(2-Chloro-6-methylphenyl)-8-(hexahydro-4-methyl-1H-1,4-diazepin-1-yl)-7-methoxyimidazo[1,5-a]quinoxalin-4-amine;

N-(2-Chloro-6-methylphenyl)-7-[2-(4-morpholinyl)ethoxy]-8-(1-piperazinyl)imidazo[1,5-a]quinoxalin-4-amine;

cis-N-(2-Chloro-6-methylphenyl)-8-(3,5-dimethyl-1-piperazinyl)-7-[2-(4-morpholinyl)ethoxy]imidazo[1,5-a]quinoxalin-4-amine;

$N^4$-(2-Chloro-6-methylphenyl)-7-[2-(4-morpholinyl)ethoxy]-$N^8$-[3-(4-morpholinyl)propyl]imidazo[1,5-a]quinoxaline-4,8-diamine;

$N^4$-(2-Chloro-6-methylphenyl)-$N^8$-[2-(dimethylamino)ethyl]-7-[2-(4-morpholinyl)ethoxy]imidazo[1,5-a]quinoxaline-4,8-diamine;

$N^4$-(2-Chloro-6-methylphenyl)-$N^8$-[3-(dimethylamino)propyl]-7-[2-(4-morpholinyl)ethoxy]imidazo[1,5-a]quinoxaline-4,8-diamine;

$N^4$-(2-Chloro-6-methylphenyl)-$N^8$-[4-(dimethylamino)butyl]-7-[2-(4-morpholinyl)ethoxy]imidazo[1,5-a]quinoxaline-4,8-diamine;

N-[1-[4-[(2-Chloro-6-methylphenyl)amino]-7-[2-(4-morpholinyl)ethoxy]imidazo[1,5-a]quinoxalin-8-yl]-3-pyrrolidinyl]acetamide;

1-Acetyl-4-[4-[(2-Chloro-6-methylphenyl)amino]-7-[2-(4-morpholinyl)ethoxy]imidazo[1,5-a]quinoxalin-8-yl]piperazine;

N-(2-Chloro-6-methylphenyl)-8-(hexahydro-4-methyl-1H-1,4-diazepin-1-yl)-7-[2-(4-morpholinyl)ethoxy]imidazo[1,5-a]quinoxalin-4-amine;

N-(2-Chloro-6-methylphenyl)-7-[2-(4-morpholinyl)ethoxy]-8-phenylimidazo[1,5-a]quinoxalin-4-amine;

$N^4$-(2-Chloro-6-methylphenyl)-$N^1$,$N^1$-dimethyl-7,8-dimethoxyimidazo[1,5-a]quinoxaline-1,4-diamine;

N-(2-Chloro-6-methylphenyl)-8-[4-[[[3-(dimethylamino)propyl]amino]methyl]phenyl]-7-[2-(4-morpholinyl)ethoxy]imidazo[1,5-a]quinoxalin-4-amine;

$N^4$-(2-Chloro-6-methylphenyl)-8-methoxy-$N^7$-[2-(4-morpholinyl)ethyl]imidazo[1,5-a]quinoxaline-4,7-diamine;

$N^4$-(2-Chloro-6-methylphenyl)-$N^7$-[2-(dimethylamino)ethyl]-8-methoxyimidazo[1,5-a]quinoxaline-4,7-diamine;

cis-N-(2-Chloro-6-methylphenyl)-7-(3,5-dimethyl-1-piperazinyl)-8-methoxyimidazo[1,5-a]quinoxalin-4-amine;

N-(2-Chloro-6-methylphenyl)-7-[4-[2-(dimethylamino)ethyl]-1-piperazinyl]-8-methoxyimidazo[1,5-a]quinoxalin-4-amine;

N⁴-(2-Chloro-6-fluorophenyl)-8-methoxy-N⁷-[2-(4-morpholinyl)ethyl]imidazo[1,5-a]quinoxaline-4,7-diamine;

N⁴-(2-Chloro-6-fluorophenyl)-N⁷-[2-(dimethylamino)ethyl]-8-methoxyimidazo[1,5-a]quinoxaline-4,7-diamine;

cis-N-(2-Chloro-6-fluorophenyl)-7-(3,5-dimethyl-1-piperazinyl)-8-methoxyimidazo[1,5-a]quinoxalin-4-amine;

4-Amino-N-(2-chloro-6-methylphenyl)imidazo[1,5-a]quinoxaline-7-carboxamide;

4-Amino-N-(2,4,6-trimethylphenyl)imidazo[1,5-a]quinoxaline-7-carboxamide;

4-[(2-Chloro-6-methylphenyl)amino]-7,8-dimethoxy-α-methylimidazo[1,5-a]quinoxaline-1-methanol;

4-[(2-Chloro-6-methylphenyl)amino]-α-ethyl-7,8-dimethoxyimidazo[1,5-a]quinoxaline-1-methanol;

4-[(2-Chloro-6-methylphenyl)amino]-7,8-dimethoxy-α-(1-methylethyl)imidazo[1,5-a]quinoxaline-1-methanol;

4-[(2-Chloro-6-methylphenyl)amino]-N-ethyl-7,8-dimethoxyimidazo[1,5-a]quinoxaline-1-carboxamide;

4-[(2-Chloro-6-methylphenyl)amino]-N-(1,1-dimethylethyl)-7,8-dimethoxyimidazo[1,5-a]quinoxaline-1-carboxamide;

4-[(2-Chloro-6-methylphenyl)amino]-7,8-dimethoxy-N-(phenylmethyl)imidazo[1,5-a]quinoxaline-1-carboxamide;

N-[[4-[(2-Chloro-6-methylphenyl)amino]-7,8-dimethoxyimidazo[1,5-a]quinoxalin-1-yl]carbonyl]alanine ethyl ester;

4-[(2-Chloro-6-methylphenyl)amino]-7,8-dimethoxy-N-pentylimidazo[1,5-a]quinoxaline-1-carboxamide;

N-[[4-[(2-Chloro-6-methylphenyl)amino]-7,8-dimethoxyimidazo[1,5-a]quinoxalin-1-yl]carbonyl]glycine ethyl ester;

(S)-4-[(2-Chloro-6-methylphenyl)amino]-7,8-dimethoxy-N-(1-phenylethyl)imidazo[1,5-a]quinoxaline-1-carboxamide;

4-[(2-Chloro-6-methylphenyl)amino]-N-cyclohexyl-7,8-dimethoxyimidazo[1,5-a]quinoxaline-1-carboxamide;

4-[(2-Chloro-6-methylphenyl)amino]-7,8-dimethoxy-N-(1-methylethyl)imidazo[1,5-a]quinoxaline-1-carboxamide;

N-[(2-Chloro-6-methylphenyl)amino]-7,8-dimethoxyimidazo[1,5-a]quinoxaline-1-propanol;

4-[(2-Chloro-6-methylphenyl)amino]imidazo[1,5-a]quinoxalin-9-ol;

N-(2-Chloro-6-methylphenyl)-7-(1,3-dioxolan-4-ylmethoxy)-8-methoxyimidazo[1,5-a]quinoxalin-4-amine;

N-(2-Chloro-6-methylphenyl)-8-methoxy-7-[(1-methyl-3-piperidinyl)methoxy]imidazo[1,5-a]quinoxalin-4-amine; and N-(2-Chloro-6-methylphenyl)-7,8-dimethoxy-1-methylimidazo[1,5-a]quinoxalin-4-amine.

9. A method for the treatment of a protein tyrosine kinase-associated disorder wherein protein tyrosine kinase is inhibited, comprising the step of administering to a subject in need thereof an amount effective therefor of at least one compound of the following formula I or salt thereof:

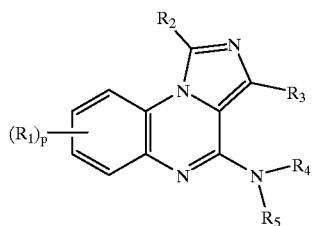

(I)

where
p is 0, 1, 2, 3 or 4;
each $R_1$, and $R_2$ and $R_3$, are independently selected from:
(1) hydrogen or $R_6$,
where $R_6$ is alkyl, alkenyl, alkynyl, cycloalkyl, cycloalkylalkyl, cycloalkenyl, cycloalkenylalkyl, aryl, aralkyl, heterocyclo, or heterocycloalkyl, each of which is unsubstituted or substituted with $Z_1$, $Z_2$ and one or more groups $Z_3$;
(2) —OH or —OR$_6$;
(3) —SH or —SR$_6$;
(4) —C(O)$_q$H, —C(O)$_q$R$_6$ or —O—C(O)$_q$R$_6$, where q is 1 or 2;
(5) —SO$_3$H or —S(O)$_q$R$_6$;
(6) halo;
(7) cyano;
(8) nitro;
(9) —Z$_4$—NR$_7$R$_8$;
(10) —Z$_4$—N(R$_9$)—Z$_5$—NR$_{10}$R$_{11}$;
(11) —Z$_4$—N(R$_{12}$)—Z$_5$—R$_6$;
(12) —SiR$_{13}$R$_{14}$R$_{15}$;
(13) —P(O)(OR$_6$)$_2$;
(14) —CH=N-OR$_6$;
(15) any two groups $R_1$ may together be alkylene or alkenylene completing a 3- to 8-membered saturated or unsaturated ring together with the carbon atoms to which they are attached, which ring is unsubstituted or substituted with $Z_1$, $Z_2$ and $Z_3$; or
(16) any two groups $R_1$ may, together with the carbons to which they are attached, form a heterocyclo group, which group is unsubstituted or substituted with $Z_1$, $Z_2$ and $Z_3$;

$R_4$ and $R_5$:
(1) are each independently hydrogen, $R_6$, or —C(O)R$_6$; or
(2) together with the nitrogen atom to which they are attached complete a 3- to 8-membered saturated or unsaturated heterocyclic ring which is unsubstituted or substituted with $Z_1$, $Z_2$ and $Z_3$, which heterocyclic ring may optionally have fused to it a benzene ring itself unsubstituted or substituted with $Z_1$, $Z_2$ and $Z_3$;

$R_7$, $R_8$, $R_9$, $R_{10}$, $R_{11}$ and $R_{12}$:
(1) are each independently hydrogen or $R_6$;
(2) $R_7$ and $R_8$ may together be alkylene or alkenylene, completing a 3- to 8-membered saturated or unsaturated ring with the nitrogen atom to which they are attached, which ring is unsubstituted or substituted with $Z_1$, $Z_2$ and $Z_3$; or
(3) any two of $R_9$, $R_{10}$ and $R_{11}$ may together be alkylene or alkenylene completing a 3- to 8-membered saturated or unsaturated ring together with the nitrogen atoms to which they are attached, which ring is unsubstituted or substituted with $Z_1$, $Z_2$ and $Z_3$;

$R_{13}$, $R_{14}$ and $R_{15}$ are each independently:
- (1) alkyl; or
- (2) phenyl;

$Z_1$, $Z_2$ and $Z_3$ are each independently:
- (1) hydrogen or $Z_6$, where $Z_6$ is (i) alkyl, alkenyl, alkynyl, cycloalkyl, cycloalkylalkyl, cycloalkenyl, cycloalkenylalkyl, aryl, aralkyl, alkylaryl, cycloalkylaryl, heterocyclo, or heterocycloalkyl; (ii) a group (i) which is itself substituted by one or more of the same or different groups (i); or (iii) a group (i) or (ii) which is substituted by one or more of the following groups (2) to (16) of the definition of $Z_1$, $Z_2$ and $Z_3$;
- (2) —OH or —$OZ_6$;
- (3) —SH or —$SZ_6$;
- (4) —C(O)$_q$H, —C(O)$_q Z_6$ or —O—C(O)$_q Z_6$;
- (5) —$SO_3$H or —S(O)$_q Z_6$;
- (6) halo;
- (7) cyano;
- (8) nitro;
- (9) —$Z_4$—$NZ_7 Z_8$;
- (10) —$Z_4$—N($Z_9$)—$Z_5$—$NZ_7 Z_8$;
- (11) —$Z_4$—N($Z_{10}$)—$Z_5$—$Z_6$;
- (12) —$Z_4$—N($Z_{10}$)—$Z_5$—H;
- (13) oxo;
- (14) —O—C(O)—$Z_6$;
- (15) any two of $Z_1$, $Z_2$, and $Z_3$ may together be alkylene or alkenylene completing a 3- to 8-membered saturated or unsaturated ring together with the atoms to which they are attached; or
- (16) any two of $Z_1$, $Z_2$, and $Z_3$ may together be —O—(CH$_2$)$_q$—O—;

$Z_4$ and $Z_5$ are each independently:
- (1) a single bond;
- (2) —$Z_{11}$—S(O)$_q$—$Z_{12}$—;
- (3) —$Z_{11}$—C(O)—$Z_{12}$—;
- (4) —$Z_{11}$—C(S)—$Z_{12}$—;
- (5) —$Z_{11}$—O—$Z_{12}$—;
- (6) —$Z_{11}$—S—$Z_{12}$—;
- (7) —$Z_{11}$—C(O)—$Z_{12}$—; or
- (8) —$Z_{11}$—C(O)—O—$Z_{12}$—;

$Z_7$, $Z_8$, $Z_9$ and $Z_{10}$:
- (1) are each independently hydrogen or $Z_6$;
- (2) $Z_7$ and $Z_8$, or $Z_6$ and $Z_{10}$, may together be alkylene or alkenylene, completing a 3- to 8-membered saturated or unsaturated ring together with the atoms to which they are attached, which ring is unsubstituted or substituted with $Z_1$, $Z_2$ and $Z_3$; or
- (3) $Z_7$ or $Z_8$, together with $Z_9$, may be alkylene or alkenylene completing a 3- to 8-membered saturated or unsaturated ring together with the nitrogen atoms to which they are attached, which ring is unsubstituted or substituted with $Z_1$, $Z_2$ and $Z_3$; and $Z_{11}$ and $Z_{12}$ are each independently:
- (1) a single bond;
- (2) alkylene;
- (3) alkenylene; or
- (4) alkynylene.

10. The method of claim 9, wherein said protein tyrosine kinase-associated disorder is transplant rejection.

11. The method of claim 9, wherein said protein tyrosine kinase-associated disorder is rheumatoid arthritis.

12. The method of claim 9, wherein said protein tyrosine kinase-associated disorder is multiple sclerosis.

13. The method of claim 9, wherein said protein tyrosine kinase-associated disorder is inflammatory bowel disease.

14. The method of claim 9, wherein said protein tyrosine kinase-associated disorder is lupus.

15. The method of claim 9, wherein said protein tyrosine kinase-associated disorder is graft vs. host disease.

16. The method of claim 9, wherein said protein tyrosine kinase-associated disorder is a T-cell mediated hypersensitivity disease.

17. The method of claim 9, wherein said protein tyrosine kinase-associated disorder is psoriasis.

18. The method of claim 9, wherein said protein tyrosine kinase-associated disorder is Hashimoto's thyroiditis.

19. The method of claim 9, wherein said protein tyrosine kinase-associated disorder is Guillain-Barre syndrome.

20. The method of claim 9, wherein said protein tyrosine kinase-associated disorder is a cancer where a Src-family kinase is activated or overexpressed or where Src-family kinase activity facilitates tumor growth or survival.

21. The method of claim 9, wherein said protein tyrosine kinase-associated disorder is contact dermatitis.

22. The method of claim 9, wherein said protein tyrosine kinase-associated disorder is an allergic disease.

23. The method of claim 9, wherein said protein tyrosine kinase-associated disorder is asthma.

24. The method of claim 9, wherein said protein tyrosine kinase-associated disorder is ischemic or reperfusion injury.

25. The method of claim 9, wherein said protein tyrosine kinase-associated disorder is atopic dermatitis.

26. The method of claim 9, wherein said protein tyrosine kinase-associated disorder is allergic rhinitis.

27. The method of claim 9, wherein said protein tyrosine kinase is Lck.

28. The method of claim 9, wherein said protein tyrosine kinase is Fyn.

29. The method of claim 9, wherein said protein tyrosine kinase is Lyn.

30. The method of claim 9, wherein said protein tyrosine kinase is Hck.

31. The method of claim 9, wherein said protein tyrosine kinase is Fgr.

32. The method of claim 9, wherein said protein tyrosine kinase is Src.

33. The method of claim 9, wherein said compound of the formula I or salt thereof is administered, simultaneously or sequentially, with an antiinflammatory, antiproliferative, chemotherapeutic agent, immunosuppressant or PTK inhibitor other than a compound of the formula I or salt thereof.

34. The method of claim 33, wherein said compound of the formula I or salt thereof is administered with one or more of another PTK inhibitor; cyclosporin A; CTLA4-Ig; antibodies selected from anti-ICAM-3, anti-IL-2 receptor (Anti-Tac), anti-CD45RB, anti-CD2, anti-CD3 (OKT-3), anti-CD4, anti-CD80, anti-CD86, and monoclonal antibody OKT3; agents blocking the interaction between CD40 and gp39; fusion proteins constructed from CD40 and gp39; inhibitors of NF-kappa B function; non-steroidal antiinflammatory drugs (NSAIDs); steroids; gold compounds; antiproliferative agents; FK506 (tacrolimus, Prograf); mycophenolate mofetil; cytotoxic drugs; TNF-α inhibitors; anti-TNF antibodies or soluble TNF receptor; and rapamycin (sirolimus or Rapamune) or derivatives thereof.

35. The method of claim 9, wherein said compound of the formula I or salt thereof is selected from the group consisting of:
- N-(2-Chloro-6-methylphenyl)-8-nitroimidazo[1,5-a]quinoxalin-4-amine;
- $N^4$-(2-Chloro-6-methylphenyl)imidazo[1,5-a]quinoxaline-4,8-diamine;
- N-[4-[(2-Chloro-6-methylphenyl)amino]imidazo[1,5-a]quinoxalin-8-yl]acetamide;

N-[4-[(2-Chloro-6-methylphenyl)amino]imidazo[1,5-a]
quinoxalin-8-yl]hexanamide;
N-[4-[(2-Chloro-6-methylphenyl)amino]imidazo[1,5-a]
quinoxalin-8-yl]-3-methoxypropanamide;
N-[4-[(2-Chloro-6-methylphenyl)amino]imidazo[1,5-a]
quinoxalin-8-yl]-N'-ethylurea;
N-(2-Bromophenyl)-8-methylimidazo[1,5-a]quinoxalin-
4-amine;
N-(2-Bromophenyl)-7-methylimidazo[1,5-a]quinoxalin-
4-amine;
N-(2-Bromophenyl)-1-methylimidazo[1,5-a]quinoxalin-
4-amine;
N-(2-Bromophenyl)-1-(phenylthio)imidazo[1,5-a]
quinoxalin-4-amine;
N-(2,6-Dimethylphenyl)-8-nitroimidazo[1,5-a]
quinoxalin-4-amine;
N$^4$-(2,6-Dimethylphenyl)imidazo[1,5-a]quinoxalin-4,8-
diamine;
N-[4-[(2,6-Dimethylphenyl)amino]imidazo[1,5-a]
quinoxalin-8-yl]acetamide;
N-[4-[(2,6-Dimethylphenyl)amino]imidazo[1,5-a]
quinoxalin-8-yl]hexanamide;
N-[4-[(2,6-Dimethylphenyl)amino]imidazo[1,5-a]
quinoxalin-8-yl]benzeneacetamide;
[2-[[4-[(2,6-Dimethylphenyl)amino]imidazo[1,5-a]
quinoxalin-8-yl]amino]-2-oxoethyl]carbamic acid, 1,1-
dimethylethyl ester;
N-(2-Chloro-6-methylphenyl)imidazo[1,5-a]quinoxalin-
4-amine;
N-(2-Methoxyphenyl)imidazo[1,5-a]quinoxalin-4-amine;
N-(2-Nitrophenyl)imidazo[1,5-a]quinoxalin-4-amine;
N-(2-Fluorophenyl)imidazo[1,5-a]quinoxalin-4-amine;
N-(2,6-Diethylphenyl)imidazo[1,5-a]quinoxalin-4-
amine;
4-[(Imidazo[1,5-a]quinoxalin-4-yl)amino]benzonitrile;
N-(2,3-Dihydro-1H-inden-5-yl)imidazo[1,5-a]
quinoxalin-4-amine;
N-[3-(Trifluoromethyl)phenyl]imidazo[1,5-a]quinoxalin-
4-amine;
N-(4-Decylphenyl)imidazo[1,5-a]quinoxalin-4-amine;
N-(2,6-Dimethylphenyl)imidazo[1,5-a]quinoxalin-4-
amine;
N-[2-Methyl-6-(1-methylethyl)phenyl]imidazo[1,5-a]
quinoxalin-4-amine;
N-([1,1'-Biphenyl]-3-yl)imidazo[1,5-a]quinoxalin-4-
amine;
N-[2,6-Bis(1-methylethyl)phenyl]imidazo[1,5-a]
quinoxalin-4-amine;
N-(2,5-Dimethylphenyl)imidazo[1,5-a]quinoxalin-4-
amine;
N-(2,3-Dimethylphenyl)imidazo[1,5-a]quinoxalin-4-
amine;
N-[3-Methyl-4-(1-methylethyl)phenyl]imidazo[1,5-a]
quinoxalin-4-amine;
N-(2,4-Dimethylphenyl)imidazo[1,5-a]quinoxalin-4-
amine;
N-([1,1'-Biphenyl]-4-yl)imidazo[1,5-a]quinoxalin-4-
amine;
N-[2-(Phenylmethyl)phenyl]imidazo[1,5-a]quinoxalin-4-
amine;
N-[4-(1,1-Dimethylethyl)phenyl]imidazo[1,5-a]
quinoxalin-4-amine;
N-(2-Propylphenyl)imidazo[1,5-a]quinoxalin-4-amine;
N-[3,5-Bis(1,1-dimethylethyl)phenyl]imidazo[1,5-a]
quinoxalin-4-amine;
N-(3-Ethylphenyl)imidazo[1,5-a]quinoxalin-4-amine;
N-[3-(1,1-Dimethylethyl)phenyl]imidazo[1,5-a]
quinoxalin-4-amine;
N-(4-Cyclohexylphenyl)imidazo[1,5-a]quinoxalin-4-
amine;
N-(2,6-Dimethoxyphenyl)imidazo[1,5-a]quinoxalin-4-
amine;
N-(3,4,5-Trimethoxyphenyl)imidazo[1,5-a]quinoxalin-4-
amine;
N-(2-Methoxy-6-methylphenyl)imidazo[1,5-a]
quinoxalin-4-amine;
N-(1,3-Benzodioxol-5-yl)-N-ethylimidazo[1,5-a]
quinoxalin-4-amine;
N-(3-Phenoxyphenyl)imidazo[1,5-a]quinoxalin-4-amine;
N-[3-(Trifluoromethoxy)phenyl]imidazo[1,5-a]
quinoxalin-4-amine;
N-[4-(4-Chlorophenoxy)phenyl]imidazo[1,5-a]
quinoxalin-4-amine;
N-(1,3-Benzodioxol-5-yl)imidazo[1,5-a]quinoxalin-4-
amine;
N-[3-(Phenylmethoxy)phenyl]imidazo[1,5-a]quinoxalin-
4-amine;
N-(2,3-Dimethoxyphenyl)imidazo[1,5-a]quinoxalin-4-
amine;
N-[2-(Trifluoromethoxy)phenyl]imidazo[1,5-a]
quinoxalin-4-amine;
N-(1,4-Benzodioxin-6-yl)imidazo[1,5-a]quinoxalin-4-
amine;
N-(4-Ethoxyphenyl)imidazo[1,5-a]quinoxalin-4-amine;
N-(4-Phenoxyphenyl)imidazo[1,5-a]quinoxalin-4-amine;
N-(4-Chlorophenyl)imidazo[1,5-a]quinoxalin-4-amine;
N-[3-Methoxy-5-(trifluoromethyl)phenyl]imidazo[1,5-a]
quinoxalin-4-amine;
N-(2-Bromo-5-methoxyphenyl)imidazo[1,5-a]
quinoxalin-4-amine;
N-(2-Chloro-6-methylphenyl)imidazo[1,5-a]quinoxalin-
4-amine;
N-(2-Bromo-4-chlorophenyl)imidazo[1,5-a]quinoxalin-
4-amine;
N-(2,6-Difluorophenyl)imidazo[1,5-a]quinoxalin-4-
amine;
N-(2-Iodophenyl)imidazo[1,5-a]quinoxalin-4-amine;
N-(2,5-Difluorophenyl)imidazo[1,5-a]quinoxalin-4-
amine;
N-(3,4-Difluorophenyl)imidazo[1,5-a]quinoxalin-4-
amine;
N-(4-Chloro-3-methylphenyl)imidazo[1,5-a]quinoxalin-
4-amine;
N-(3,4-Dichlorophenyl)-N-methylimidazo[1,5-a]
quinoxalin-4-amine;
N-(4-Bromophenyl)imidazo[1,5-a]quinoxalin-4-amine;
N-(2,4-Dibromophenyl)imidazo[1,5-a]quinoxalin-4-
amine;
N-(4-Fluoro-3-methylphenyl)imidazo[1,5-a]quinoxalin-
4-amine;
N-(2-Chloro-5-methylphenyl)imidazo[1,5-a]quinoxalin-
4-amine;
N-(2,5-Dibromophenyl)imidazo[1,5-a]quinoxalin-4-
amine;

N-(3,5-Dichlorophenyl)imidazo[1,5-a]quinoxalin-4-amine;
N-(4-Chlorophenyl)-N-methylimidazo[1,5-a]quinoxalin-4-amine;
N-(3,5-Dibromo-4-methylphenyl)imidazo[1,5-a]quinoxalin-4-amine;
N-(4-Chloro-1-naphthalenyl)imidazo[1,5-a]quinoxalin-4-amine;
N-(3,4,5-Trichlorophenyl)imidazo[1,5-a]quinoxalin-4-amine;
N-[4-(4-Morpholinyl)phenyl]imidazo[1,5-a]quinoxalin-4-amine;
N-[4-(Dimethylamino)phenyl]imidazo[1,5-a]quinoxalin-4-amine;
N-[2-(1H-Pyrrol-1-yl)phenyl]imidazo[1,5-a]quinoxalin-4-amine;
N-[4-(1-Piperidinyl)phenyl]imidazo[1,5-a]quinoxalin-4-amine;
N-[2-(1-Piperidinyl)phenyl]imidazo[1,5-a]quinoxalin-4-amine;
N-(6-Quinolinyl)imidazo[1,5-a]quinoxalin-4-amine;
N-(3-Pyridinyl)imidazo[1,5-a]quinoxalin-4-amine;
N-(2-Chlorophenyl)imidazo[1,5-a]quinoxalin-4-amine;
N-[2-Bromo-4-(trifluoromethoxy)phenyl]imidazo[1,5-a]quinoxalin-4-amine;
N-(2,4-Dichlorophenyl)imidazo[1,5-a]quinoxalin-4-amine;
N-(2-Bromo-4-methylphenyl)imidazo[1,5-a]quinoxalin-4-amine;
N-(3-Bromo-2-methylphenyl)imidazo[1,5-a]quinoxalin-4-amine;
N-(3-Fluorophenyl)imidazo[1,5-a]quinoxalin-4-amine;
N-(2-Chlorophenyl)-N-methylimidazo[1,5-a]quinoxalin-4-amine;
N-(3,5-Dibromophenyl)imidazo[1,5-a]quinoxalin-4-amine;
N-(4-Benzoylphenyl)imidazo[1,5-a]quinoxalin-4-amine;
N-(4-Pyridinyl)imidazo[1,5-a]quinoxalin-4-amine;
N-(Phenylmethyl)-N-(2-pyridinyl)imidazo[1,5-a]quinoxalin-4-amine;
N-(4-Bromo-2,6-dimethylphenyl)imidazo[1,5-a]quinoxalin-4-amine;
N-[2-Chloro-4-(1,1-dimethylethyl)phenyl]imidazo[1,5-a]quinoxalin-4-amine;
N-(2-Ethyl-6-methylphenyl)imidazo[1,5-a]quinoxalin-4-amine;
N-(5-Chloro-2-methylphenyl)imidazo[1,5-a]quinoxalin-4-amine;
N-(4-Chloro-2-methylphenyl)imidazo[1,5-a]quinoxalin-4-amine;
N-(4-Bromo-2-methylphenyl)imidazo[1,5-a]quinoxalin-4-amine;
N-(2-Chloro-4-methylphenyl)imidazo[1,5-a]quinoxalin-4-amine;
N-(1,3,5-Trimethyl-1H-pyrazol-4-yl)imidazo[1,5-a]quinoxalin-4-amine;
N-(4-Bromo-2-chloro-6-methylphenyl)imidazo[1,5-a]quinoxalin-4-amine;
N-(2-Chloro-4,6-dimethylphenyl)imidazo[1,5-a]quinoxalin-4-amine;
N-(2,6-Dichlorophenyl)imidazo[1,5-a]quinoxalin-4-amine;
N-(2,4,6-Trichlorophenyl)imidazo[1,5-a]quinoxalin-4-amine;
N-(2,6-Dibromophenyl)imidazo[1,5-a]quinoxalin-4-amine;
N-(2,4,6-Tribromophenyl)imidazo[1,5-a]quinoxalin-4-amine;
N-(3,5-Dichloro-2-pyridinyl)imidazo[1,5-a]quinoxalin-4-amine;
N-(2,6-Dibromo-4-methylphenyl)imidazo[1,5-a]quinoxalin-4-amine;
N-(2,6-Dibromo-4-propylphenyl)imidazo[1,5-a]quinoxalin-4-amine;
3-Chloro-4-[[imidazo[1,5-a]quinoxalin-4-yl]amino]benzonitrile;
N-(2,4,6-Trimethylphenyl)imidazo[1,5-a]quinoxalin-4-amine;
N-[2-(4-Morpholinyl)phenyl]imidazo[1,5-a]quinoxalin-4-amine;
1-(Imidazo[1,5-a]quinoxalin-4-yl)-1H-indole-5-carbonitrile;
N-[2-(1H-Imidazol-1-yl)phenyl]imidazo[1,5-a]quinoxalin-4-amine;
N-(2,4-Dimethoxyphenyl)imidazo[1,5-a]quinoxalin-4-amine;
N-Phenylimidazo[1,5-a]quinoxalin-4-amine;
N-(2-Phenoxyphenyl)imidazo[1,5-a]quinoxalin-4-amine;
N-[2-(1,1-Dimethylethyl)phenyl]imidazo[1,5-a]quinoxalin-4-amine;
N-Methyl-N-phenylimidazo[1,5-a]quinoxalin-4-amine;
N-(2,3-Dichlorophenyl)imidazo[1,5-a]quinoxalin-4-amine;
N-(2-Bromophenyl)-7-methoxyimidazo[1,5-a]quinoxalin-4-amine;
N-(2,6-Dimethylphenyl)-7-methoxyimidazo[1,5-a]quinoxalin-4-amine;
N-(2-Chloro-6-methylphenyl)-7-methoxyimidazo[1,5-a]quinoxalin-4-amine;
N-(2,4-Dimethylphenyl)-7-methoxyimidazo[1,5-a]quinoxalin-4-amine;
N-(2-Chlorophenyl)-7-methoxyimidazo[1,5-a]quinoxalin-4-amine;
N-(2,6-Dichlorophenyl)-7-methoxyimidazo[1,5-a]quinoxalin-4-amine;
N-(2-Chloro-4,6-dimethylphenyl)-7-methoxyimidazo[1,5-a]quinoxalin-4-amine;
7,8-Dimethoxy-N-(2,4,6-trimethylphenyl)imidazo[1,5-a]quinoxalin-4-amine;
N-(2,6-Dimethylphenyl)-7,8-dimethoxyimidazo[1,5-a]quinoxalin-4-amine;
N-[2-(3-Chlorophenyl)ethyl]imidazo[1,5-a]quinoxalin-4-amine;
N-[2-[(Phenylmethyl)thio]ethyl]imidazo[1,5-a]quinoxalin-4-amine;
N-[[2-[[2-(Hydroxymethyl)phenyl]thio]phenyl]methyl]imidazo[1,5-a]quinoxalin-4-amine;
N-[2-(1-Cyclohexen-1-yl)ethyl]imidazo[1,5-a]quinoxalin-4-amine;
N-[2-[Ethyl(3-methylphenyl)amino]ethyl]imidazo[1,5-a]quinoxalin-4-amine;
N-Hexylimidazo[1,5-a]quinoxalin-4-amine;
N-[2-(4-Methylphenyl)ethyl]imidazo[1,5-a]quinoxalin-4-amine;

N-[(2-Chlorophenyl)methyl]imidazo[1,5-a]quinoxalin-4-amine;
N-[3-(2-Methyl-1-piperidinyl)propyl]imidazo[1,5-a]quinoxalin-4-amine;
N-[2-(2-Pyridinyl)ethyl]imidazo[1,5-a]quinoxalin-4-amine;
N-[1-(1-Naphthalenyl)ethyl]imidazo[1,5-a]quinoxalin-4-amine;
N-[(Tetrahydro-2-furanyl)methyl]imidazo[1,5-a]quinoxalin-4-amine;
N-[2-(2,4-Dichlorophenyl)ethyl]imidazo[1,5-a]quinoxalin-4-amine;
N-[(2-Aminophenyl)methyl]imidazo[1,5-a]quinoxalin-4-amine;
4-[(Imidazo[1,5-a]quinoxalin-4-yl)amino]-1-piperidinecarboxylic acid, ethyl ester;
4-[4-(Phenylmethyl)-1-piperazinyl]imidazo[1,5-a]quinoxaline;
N-[[4-(Trifluoromethyl)phenyl]methyl]imidazo[1,5-a]quinoxalin-4-amine;
4-[4-(2-Pyridinyl)-1-piperazinyl]imidazo[1,5-a]quinoxaline;
(S)-N-[1-(Phenylmethyl)-3-pyrrolidinyl]imidazo[1,5-a]quinoxalin-4-amine;
N-[(2-Chloro-6-phenoxyphenyl)methyl]imidazo[1,5-a]quinoxalin-4-amine;
4-[4-[2-Nitro-4-(trifluoromethyl)phenyl]-1-piperazinyl]imidazo[1,5-a]quinoxaline;
N-Propylimidazo[1,5-a]quinoxalin-4-amine;
N-Cyclopropylimidazo[1,5-a]quinoxalin-4-amine;
N-[2-(4-Fluorophenyl)ethyl]imidazo[1,5-a]quinoxalin-4-amine;
N-Hexyl-N-methylimidazo[1,5-a]quinoxalin-4-amine;
N-Methyl-N-(phenylmethyl)imidazo[1,5-a]quinoxalin-4-amine;
N-(3-Methoxypropyl)imidazo[1,5-a]quinoxalin-4-amine;
[S-(R*,R*)]-2-[(Imidazo[1,5-a]quinoxalin-4-yl)amino]-1-phenyl-1,3-propanediol;
N-[(2-Methoxyphenyl)methyl]imidazo[1,5-a]quinoxalin-4-amine;
N-(4-Methyl-1-piperazinyl)imidazo[1,5-a]quinoxalin-4-amine;
N-(2-Furanylmethyl)imidazo[1,5-a]quinoxalin-4-amine;
N-(4-Morpholinyl)imidazo[1,5-a]quinoxalin-4-amine;
N-[(2,4-Difluorophenyl)methyl]imidazo[1,5-a]quinoxalin-4-amine;
N-(3-Pyridinylmethyl)imidazo[1,5-a]quinoxalin-4-amine;
N-(3,3-Dimethylbutyl)imidazo[1,5-a]quinoxalin-4-amine;
N-(Phenylmethyl)imidazo[1,5-a)quinoxalin-4-amine;
N-Cyclohexylimidazo[1,5-a]quinoxalin-4-amine;
4-(4-Morpholinyl)imidazo[1,5-a]quinoxaline;
N-(2-Bromophenyl)-3-phenylimidazo[1,5-a]quinoxalin-4-amine;
N-(2-Bromophenyl)-3-(4-morpholinylmethyl)imidazo[1,5-a]quinoxalin-4-amine;
N-(2-Bromophenyl)-7-chloroimidazo[1,5-a]quinoxalin-4-amine;
[4-[(2-Bromophenyl)amino]-7,8-dichloroimidazo[1,5-a]quinoxalin-3-yl]phosphonic acid, diethyl ester;
N-(2-Bromophenyl)-7-(1,1-dimethylethyl)imidazo[1,5-a]quinoxalin-4-amine;
[4-[(2-Bromophenyl)amino]-7-(1,1-dimethylethyl)imidazo[1,5-a]quinoxalin-3-yl]phosphonic acid, diethyl ester;
[4-[(2-Chlorophenyl)amino]imidazo[1,5-a]quinoxalin-3-yl]phosphonic acid, dimethyl ester;
7-Chloro-N-(2-chlorophenyl)imidazo[1,5-a]quinoxalin-4-amine;
7,8-Dichloro-N-(2-chlorophenyl)imidazo[1,5-a]quinoxalin-4-amine;
N-(2-Chlorophenyl)-7-(1,1-dimethylethyl)imidazo[1,5-a]quinoxalin-4-amine;
N-(2-Chlorophenyl)-7-(1,1-dimethylethyl)-3-(4-morpholinylmethyl)imidazo[1,5-a]quinoxalin-4-amine;
[4-[(2-Chloro-6-methylphenyl)amino]imidazo[1,5-a]quinoxalin-3-yl]phosphonic acid, dimethyl ester;
N-(2-Chloro-6-methylphenyl)-3-(4-morpholinylmethyl)imidazo[1,5-a]quinoxalin-4-amine;
7-Chloro-N-(2-chloro-6-methylphenyl)imidazo[1,5-a]quinoxalin-4-amine;
[7-Chloro-4-[(2-chloro-6-methylphenyl)amino]imidazo[1,5-a]quinoxalin-3-yl]phosphonic acid, diethyl ester;
7,8-Dichloro-N-(2-chloro-6-methylphenyl)imidazo[1,5-a]quinoxalin-4-amine;
N-(2-Chloro-6-methylphenyl)-7,8-dimethoxyimidazo[1,5-a]quinoxalin-4-amine;
7-Chloro-N-(2,4-dimethylphenyl)imidazo[1,5-a]quinoxalin-4-amine;
[7,8-Dichloro-4-[(2,4-dimethylphenyl)amino]imidazo[1,5-a]quinoxalin-3-yl]phosphonic acid, diethyl ester;
7,8-Dimethoxy-N-(2,4-dimethylphenyl)-3-(4-morpholinylmethyl)imidazo[1,5-a]quinoxalin-4-amine;
7-(1,1-Dimethylethyl)-N-(2,4-dimethylphenyl)imidazo[1,5-a]quinoxalin-4-amine;
[7-(1,1-Dimethylethyl)-4-[(2,4-dimethylphenyl)amino]imidazo[1,5-a]quinoxalin-3-yl]phosphonic acid, diethyl ester;
7-(1,1-Dimethylethyl)-N-(2,4-dimethylphenyl)-3-(4-morpholinylmethyl)imidazo[1,5-a]quinoxalin-4-amine;
[4-[(2,6-Dimethylphenyl)amino]imidazo[1,5-a]quinoxalin-3-yl]phosphonic acid, diethyl ester;
7-Chloro-N-(2,6-dimethylphenyl)imidazo[1,5-a]quinoxalin-4-amine;
[7-Chloro-4-[(2,6-dimethylphenyl)amino]imidazo[1,5-a]quinoxalin-3-yl]phosphonic acid, diethyl ester;
7-(1,1-Dimethylethyl)-N-(2,6-dimethylphenyl)imidazo[1,5-a]quinoxalin-4-amine;
[7-(1,1-Dimethylethyl)-4-[(2,6-dimethylphenyl)amino]imidazo[1,5-a]quinoxalin-3-yl]phosphonic acid, diethyl ester;
[4-[(2,4,6-Trimethylphenyl)amino]imidazo[1,5-a]quinoxalin-3-yl]phosphonic acid, diethyl ester;
7-Chloro-N-(2,4,6-trimethylphenyl)imidazo[1,5-a]quinoxalin-4-amine;
[7-Chloro-4-[(2,4,6-trimethylphenyl)aminolimidazo[1,5-a]quinoxalin-3-yl]phosphonic acid, diethyl ester;
7,8-Dichloro-N-(2,4,6-trimethylphenyl)imidazo[1,5-a]quinoxalin-4-amine;

[7,8-Dichloro-4-[(2,4,6-trimethylphenyl)amino]imidazo[1,5-a]quinoxalin-3-yl]phosphonic acid, diethyl ester;

[7-(1,1-Dimethylethyl)-4-[(2,4,6-trimethylphenyl)amino]imidazo[1,5-a]quinoxalin-3-yl]phosphonic acid, diethyl ester;

[4-[(2-Bromophenyl)amino]imidazo[1,5-a]quinoxalin-3-yl]phosphonic acid, dimethyl ester;

N-(2-Bromophenyl)-8-chloroimidazo[1,5-a]quinoxalin-4-amine;

[4-[(2-Bromophenyl)amino]-7,8-dichloroimidazo[1,5-a]quinoxalin-3-yl]phosphonic acid, dimethyl ester;

[4-[(2-Bromophenyl)amino]-8-(1,1-dimethylethyl)imidazo[1,5-a]quinoxalin-3-yl]phosphonic acid, diethyl ester;

[4-[(2-Bromophenyl)amino]-7-(1,1-dimethylethyl)imidazo[1,5-a]quinoxalin-3-yl]phosphonic acid, dimethyl ester;

8-Chloro-N-(2-chlorophenyl)imidazo[1,5-a]quinoxalin-4-amine;

[4-[(2-Chlorophenyl)amino]-7-(1,1-dimethylethyl)imidazo[1,5-a]quinoxalin-3-yl]phosphonic acid, dimethyl ester;

[7-Chloro-4-[(2-chloro-6-methylphenyl)amino]imidazo[1,5-a]quinoxalin-3-yl]phosphonic acid, dimethyl ester;

[7-Chloro-4-[(2,4-dimethylphenyl)amino]imidazo[1,5-a]quinoxalin-3-yl]phosphonic acid, dimethyl ester;

[8-Chloro-4-[(2,4-dimethylphenyl)amino]imidazo[1,5-a]quinoxalin-3-yl]phosphonic acid, dimethyl ester;

[7,8-Dichloro-4-[(2,4-dimethylphenyl)amino]imidazo[1,5-a]quinoxalin-3-yl]phosphonic acid, dimethyl ester;

[4-[(2,6-Dimethylphenyl)amino]imidazo[1,5-a]quinoxalin-3-yl]phosphonic acid, dimethyl ester;

[7-Chloro-4-[(2,6-dimethylphenyl)amino]imidazo[1,5-a]quinoxalin-3-yl]phosphonic acid, dimethyl ester;

[8-Chloro-4-[(2,4-dimethylphenyl)amino]imidazo[1,5-a]quinoxalin-3-yl]phosphonic acid, diethyl ester;

[4-[(2,4,6-Trimethylphenyl)amino]imidazo[1,5-a]quinoxalin-3-yl]phosphonic acid, dimethyl ester;

[7-Chloro-4-[(2,4,6-trimethylphenyl)amino]imidazo[1,5-a]quinoxalin-3-yl]phosphonic acid, dimethyl ester;

[8-Chloro-4-[(2,4,6-trimethylphenyl)amino]imidazo[1,5-a]quinoxalin-3-yl]phosphonic acid, diethyl ester;

[7,8-Dichloro-4-[(2,4,6-trimethylphenyl)amino]imidazo[1,5-a]quinoxalin-3-yl]phosphonic acid, dimethyl ester;

[7-(1,1-Dimethylethyl)-4-[(2,4,6-trimethylphenyl)amino]-imidazo[1,5-a]quinoxalin-3-yl]phosphonic acid, dimethyl ester;

N-(2-Chloro-4,6-dimethylphenyl)-7,8-dimethoxyimidazo[1,5-a]quinoxalin-4-amine;

N-(2,4-Dichloro-6-methylphenyl)-7,8-dimethoxyimidazo[1,5-a]quinoxalin-4-amine

N-(2,6-Dichloro-3-methylphenyl)-7,8-dimethoxyimidazo[1,5-a]quinoxalin-4-amine;

N-(2,6-Dichlorophenyl)-7,8-dimethoxyimidazo[1,5-a]quinoxalin-4-amine;

7,8-Dimethoxy-N-(2,4,6-trichlorophenyl)imidazo[1,5-a]quinoxalin-4-amine;

N-(4-Bromo-2,6-dichlorophenyl)-7,8-dimethoxyimidazo[1,5-a]quinoxalin-4-amine;

N-[2,6-Dichloro-4-(trifluoromethoxy)phenyl-7,8-dimethoxyimidazo[1,5-a]-quinoxalin-4-amine;

N-[2,6-Dichloro-4-(5-methyl-1,2,4-oxadiazol-3-yl)phenyl]-7,8-dimethoxyimidazo[1,5-a]-quinoxalin-4-amine;

N-(4-Bromo-2-chloro-6-methylphenyl)-7,8-dimethoxyimidazo[1,5-a]quinoxalin-4-amine;

N-(2,6-Dibromophenyl)-7,8-dimethoxyimidazo[1,5-a]-quinoxalin-4-amine;

N-(4-Bromo-2,6-dimethylphenyl)-7,8-dimethoxyimidazo[1,5-a]quinoxalin-4-amine;

7,8-Dimethoxy-N-(2,4,6-trimethyl-3-pyridinyl)imidazo[1,5-a]quinoxalin-4-amine;

9-Nitro-N-(2,4,6-trimethylphenyl)imidazo[1,5-a]quinoxalin-4-amine;

N-[2,6-Dimethyl-3-(1-methylethyl)phenyl]-9-nitroimidazo[1,5-a]quinoxalin-4-amine;

N-(3-Bromo-2,4,6-trimethylphenyl)-9-nitroimidazo[1,5-a]quinoxalin-4-amine;

N-(2-Chloro-4,6-dimethylphenyl)-9-nitroimidazo[1,5-a]quinoxalin-4-amine;

N-(2,4-Dichloro-6-methylphenyl)-9-nitroimidazo[1,5-a]quinoxalin-4-amine;

N-(2,6-Dichloro-3-methylphenyl)-9-nitroimidazo[1,5-a]quinoxalin-4-amine;

N-(2-Chlorophenyl)-9-nitroimidazo[1,5-a]quinoxalin-4-amine;

N-(2,6-Dichlorophenyl)-9-nitroimidazo[1,5-a]quinoxalin-4-amine;

9-Nitro-N-(2,4,6-trichlorophenyl)imidazo[1,5-a]quinoxalin-4-amine;

N-(4-Bromo-2,6-dichlorophenyl)-9-nitroimidazo[1,5-a]quinoxalin-4-amine;

N-(2,6-Dichloro-4-methoxyphenyl)-9-nitroimidazo[1,5-a]quinoxalin-4-amine;

N-[2,6-Dichloro-4-(trifluoromethoxy)-phenyl]-9-nitroimidazo[1,5-a]quinoxalin-4-amine;

N-[2,6-Dichloro-4-(5-methyl-1,2,4-oxadiazol-3-yl)phenyl]-9-nitroimidazo[1,5-a]quinoxalin-4-amine;

N-(4-Bromo-2-chloro-6-methylphenyl)-9-nitroimidazo[1,5-a]quinoxalin-4-amine;

N-(2-Bromophenyl)-9-nitroimidazo[1,5-a]quinoxalin-4-amine;

N-(2,6-Dibromophenyl)-9-nitroimidazo[1,5-a]quinoxalin-4-amine;

N-(2,4,6-Tribromophenyl)-9-nitroimidazo[1,5-a]quinoxalin-4-amine;

N-(2,6-Dibromo-4-propylphenyl)-9-nitroimidazo[1,5-a]quinoxalin-4-amine;

N-[2,6-Dibromo-4-(1-methylethyl)phenyl]-9-nitroimidazo[1,5-a]quinoxalin-4-amine;

N-[2-Bromo-4-(1-methylethyl)phenyl]-9-nitroimidazo[1,5-a]quinoxalin-4-amine;

N-(2,6-Dibromo-4-methylphenyl)-9-nitroimidazo[1,5-a]quinoxalin-4-amine;

N-(4-Bromo-2,6-dimethylphenyl)-9-nitroimidazo[1,5-a]quinoxalin-4-amine;

N-(3,5-Dichloro-4-pyridinyl)-9-nitroimidazo[1,5-a]quinoxalin-4-amine;

N-(2,6-Dimethylphenyl)-9-nitroimidazo-[1,5-a]quinoxalin-4-amine;

N-[4-[(2,6-Dimethylphenyl)amino]imidazo[1,5-a]quinoxalin-8-yl]-3-methoxypropanamide;

N-[4-[(2,6-Dimethylphenyl)amino]imidazo[1,5-a]quinoxalin-8-yl]-2-cyanoacetamide;

$N^4$-(2,6-Dimethylphenyl)-$N^8$,$N^8$-dimethylimidazo[1,5-a]quinoxaline-4,8-diamine;

$N^4$-(2,6-Dimethylphenyl)-$N^8$,$N^8$-diethylimidazo[1,5-a]quinoxaline-4,8-diamine;

4-[(2,6-Dimethylphenyl)amino]imidazo[1,5-a]quinoxaline-7,8-diol;

N-[4-[(2-Chloro-6-methylphenyl)amino]imidazo[1,5-a]quinoxalin-8-yl]-2-thiophenebutanamide;

$N^4$-(2,6-Dimethylphenyl)imidazo[1,5-a]quinoxaline-4,9-diamine;

$N^4$-(2,4,6-Trimethylphenyl)imidazo[1,5-a]quinoxaline-4,9-diamine;

$N^4$-[2,6-Dimethyl-3-(1-methylethyl)phenyl]imidazo[1,5-a]quinoxaline-4,9-diamine;

$N^4$-(3-Bromo-2,4,6-trimethylphenyl)imidazo[1,5-a]quinoxaline-4,9-diamine;

$N^4$-(2-Chloro-4,6-dimethylphenyl)imidazo[1,5-a]quinoxaline-4,9-diamine;

$N^4$-(2,4-Dichloro-6-methylphenyl)imidazo[1,5-a]quinoxaline-4,9-diamine;

N-(2-Chloro-6-methylphenyl)-8-iodoimidazo[1,5-a]quinoxalin-4-amine;

N-(2-Chloro-6-methylphenyl)-8-fluoroimidazo[1,5-a]quinoxalin-4-amine;

N-(2-Chloro-6-methylphenyl)-8-methoxyimidazo[1,5-a]quinoxalin-4-amine;

N-(2,6-Dimethylphenyl)-8-methoxyimidazo[1,5-a]quinoxalin-4-amine;

N-(2,6-Dichlorophenyl)-8-methoxyimidazo[1,5-a]quinoxalin-4-amine;

N-(2,4,6-Trimethylphenyl)-8-methoxyimidazo[1,5-a]quinoxalin-4-amine;

N-(2-Chlorophenyl)-8-methoxyimidazo[1,5-a]quinoxalin-4-amine;

N-(2-Chloro-6-methylphenyl)-3-methylimidazo[1,5-a]quinoxalin-4-amine;

N-(2,6-Dimethylphenyl)-3-methylimidazo[1,5-a]quinoxalin-4-amine;

N-(2-Chlorophenyl)-3-methylimidazo[1,5-a]quinoxalin-4-amine;

N-(2-Chloro-6-methylphenyl)-8-(4-methyl-1-piperazinyl)imidazo[1,5-a]quinoxalin-4-amine;

N-(2-Chloro-6-methylphenyl)-8-phenylimidazo[1,5-a]quinoxalin-4-amine;

N-(2-Chloro-6-methylphenyl)-8-(4-methoxyphenyl)imidazo[1,5-a]quinoxalin-4-amine;

$N^4$-(2-Chloro-6-methylphenyl)-$N^8$-ethylimidazo[1,5-a]quinoxaline-4,8-diamine;

$N^4$-(2-Chloro-6-methylphenyl)-$N^8$-methylimidazo[1,5-a]quinoxaline-4,8-diamine;

$N^4$-(2-Chloro-6-methylphenyl)-$N^8$-(1-methylethyl)imidazo[1,5-a]quinoxaline-4,8-diamine;

N-(2,6-Dichlorophenyl)-8-fluoroimidazo[1,5-a]quinoxalin-4-amine;

N-(2-Chloro-6-methylphenyl)-8-(1-piperazinyl)imidazo[1,5-a]quinoxalin-4-amine;

N-(2-Chloro-6-methylphenyl)-7-nitroimidazo[1,5-a]quinoxalin-4-amine;

$N^4$-(2-Chloro-6-methylphenyl)imidazo[1,5-a]quinoxaline-4,7-diamine;

N-[4-[(2-Chloro-6-methylphenyl)amino]imidazo[1,5-a]quinoxalin-7-yl]hexanamide;

$N^4$-(2-Chloro-6-methylphenyl)-$N^8$,$N^8$-diethylimidazo[1,5-a]quinoxaline-4,8-diamine;

$N^4$-(2-Chloro-6-methylphenyl)-$N^8$,$N^8$-dimethylimidazo[1,5-a]quinoxaline-4,8-diamine;

1-Acetyl-4-[4-[(2-chloro-6-methylphenyl)amino]imidazo[1,5-]quinoxalin-8-yl]piperazine;

$N^4$-(2-Chloro-6-methylphenyl)-$N^8$-(cyclopropylmethyl)imidazo[1,5-]quinoxaline-4,8-diamine;

$N^4$-(2-Chloro-6-methylphenyl)-$N^8$-(cyclohexylmethyl)imidazo[1,5-]quinoxaline-4,8-diamine;

$N^4$-(2-Chloro-6-methylphenyl)-$N^8$-(cyclopentyl)imidazo[1,5-a]quinoxaline-4,8-diamine;

N-[2-[[4-[(2-Chloro-6-methylphenyl)amino]imidazo[1,5-a]quinoxalin-8-yl]amino]ethyl]acetamide;

1-[3-[[4-[(2-Chloro-6-methylphenyl)amino]imidazo[1,5-a]quinoxalin-8-yl]amino]propyl]-2-pyrrolidinone;

$N^4$-(2-Chloro-6-methylphenyl)-$N^8$-[2-(dimethylamino)ethyl]imidazo 1,5-a]quinoxaline-4,8-diamine;

$N^4$-(2-Chloro-6-methylphenyl)-$N^8$-[2-(1-methyl-2-pyrrolidinyl)ethyl]imidazo[1,5-a]quinoxaline-4,8-diamine;

$N^4$-(2-Chloro-6-methylphenyl)-$N^8$-[2-(4-morpholinyl)ethyl]imidazo[1,5-a]quinoxaline-4,8-diamine;

$N^4$-(2-Chloro-6-methylphenyl)-$N^8$-[2-(2-pyridinyl)ethyl]imidazo[1,5-a]quinoxaline-4,8-diamine;

$N^4$-(2-Chloro-6-methylphenyl)-$N^8$-(3-1H-imidazol-1-ylpropyl)imidazo[1,5-a]quinoxaline-4,8-diamine;

$N^4$-(2-Chloro-6-methylphenyl)-$N^8$-[3-(4-morpholinyl)propyl]imidazol 1,5-a]quinoxaline-4,8-diamine;

N-(2-Chloro-6-methylphenyl)-8-[4-(2-pyridinyl)-1-piperazinyl]imidazo l1,5-a]quinoxalin-4-amine;

N-(2-Chloro-6-methylphenyl)-8-(4-ethyl-1-piperazinyl)imidazo[1,5-a]quinoxalin-4-amine;

4-[4-[(2-Chloro-6-methylphenyl)amino]imidazo[1,5-a]quinoxalin-8-yl]-1-piperazinecarboxylic acid ethyl ester;

N-(2-Chloro-6-methylphenyl)-8-(3,5-dimethyl-1-piperazinyl)imidazo[1,5-a]quinoxalin-4-amine;

4-[4-[(2-Chloro-6-methylphenyl)amino]imidazo[1,5-a]quinoxalin-8-yl]-1-piperazinecarboxaldehyde;

N-(2-Chloro-6-methylphenyl)-8-(1-piperidinyl)imidazo[1,5-]quinoxalin-4-amine;

N-(2-Chloro-6-methylphenyl)-8-(4-morpholinyl)imidazo[1,5-]quinoxalin-4-amine;

$N^4$-(2-Chloro-6-methylphenyl)-$N^8$-[(tetrahydro-2-uranyl)methyl]imidazo[1,5-a]quinoxaline-4,8-diamine;

4-[(2-Chloro-6-methylphenyl)amino]-7,8-dimethoxyimidazo[1,5-a]quinoxaline-1-methanol;

N-(3,5-Dimethyl[1,1'-biphenyl]-4-yl)-7,8-dimethoxyimidazo[1,5-a]quinoxalin-4-amine;

N-(2-Chloro-6-methylphenyl)-8-(phenylmethoxy)imidazo[1,5-a]quinoxalin-4-amine;

6-Bromo-N-(2-chloro-6-methylphenyl)-8-fluoroimidazo[1,5-a]quinoxalin-4-amine;

6-Bromo-N-(2-chloro-6-methylphenyl)-8-(4-methyl-1-piperazinyl)imidazo[1,5-a]quinoxalin-4-amine;

N-(2-Chloro-6-methylphenyl)-8-fluoro-6-(4-methyl-1-piperazinyl)imidazo[1,5-a]quinoxalin-4-amine;

N-(2-Chloro-6-methylphenyl)-6,8-bis(1-piperazinyl)imidazo[1,5-a]quinoxalin-4-amine;

6,8-Bis(4-acetyl-1-piperazinyl)-N-(2-chloro-6-methylphenyl)imidazo[1,5-a]quinoxalin-4-amine;

$N^4$-(2-Chloro-6-methylphenyl)-$N^7$,$N^7$-dimethylimidazo[1,5-a]quinoxaline-4,7-diamine;

[4-[[4-[(2-Chloro-6-methylphenyl)amino]imidazo[1,5-a]quinoxalin-7-yl]amino]-4-oxobutyl]carbamic acid 1,1-dimethylethyl ester;

$N^4$-(2-Chloro-6-methylphenyl)-$N^7$,$N^7$-diethylimidazo[1,5-a]quinoxaline-4,7-diamine;

N-[4-[(2-Chloro-6-methylphenyl)amino]imidazo[1,5-a]quinoxalin-7-yl]acetamide;

N-[4-[(2-Chloro-6-methylphenyl)amino]imidazo[1,5-a]quinoxalin-7-yl]benzeneacetamide;

$N^4$-(2-Chloro-6-methylphenyl)-$N^7$-methylimidazo[1,5-a]quinoxaline-4,7-diamine;

4-Amino-N-[4-[(2-chloro-6-methylphenyl)amino]imidazo[1,5-]quinoxalin-7-yl]butanamide dihydrochloride;

$N^4$-(2-Chloro-6-methylphenyl)-$N^7$-ethylimidazo[1,5-a]quinoxaline-7-diamine;

$N^4$-(2-Chloro-6-methylphenyl)-$N^7$-(phenylmethyl)imidazo[1,5-]quinoxaline-4,7-diamine;

N-[4-[(2-Chloro-6-methylphenyl)amino]imidazo[1,5-a]quinoxalin-8-yl]-3-hydroxy-3-methylbutanamide;

N-(2-Chloro-6-methylphenyl)-9-methoxyimidazo[1,5-a]quinoxalin-4-amine;

N-(2,6-Dichlorophenyl)-8-nitroimidazo[1,5-a]quinoxalin-4-amine;

$N^4$-(2,6-Dichlorophenyl)imidazo[1,5-a]quinoxaline-4,8-diamine;

N-(2-Chloro-6-methylphenyl)-7,8-dihydroxyimidazo[1,5-a]quinoxalin-4-amine;

N-(2-Chloro-6-methylphenyl)[1,3]dioxolo[4,5-g]imidazo[1,5-a]quinoxalin-4-amine;

N-(2-Chloro-6-methylphenyl)-2,3-dihydro-1,4-dioxino[2,3-g]imidazo[1,5-a]quinoxalin-7-amine;

N-[2,6-Dimethyl-4-[2-(dimethylamino)ethoxy]phenyl]-7,8-dimethoxyimidazo[1,5-a]quinoxalin-4-amine;

N-[2,6-Dimethyl-4-[2-(4-morpholinyl)ethoxy]phenyl]-7,8-dimethoxyimidazo[1,5-a]quinoxalin-4-amine;

4-[(2-Chloro-6-methylphenyl)amino]imidazo[1,5-a]quinoxaline-7-carboxylic acid methyl ester;

4-[(2-Chloro-6-methylphenyl)amino]imidazo[1,5-a]quinoxaline-7-carboxylic acid;

4-[(2-Chloro-6-methylphenyl)amino]imidazo(1,5-a]quinoxaline-7-carboxamide;

N-(2-Chloro-6-methylphenyl)-8-(2,6-dimethylphenyl)imidazo[1,5-a]quinoxalin-4-amine;

N-(2-Chloro-6-methylphenyl)-8-methoxy-7-[2-(4-morpholinyl)ethoxy]imidazo[1,5-a]quinoxalin-4-amine;

N-(2-Chloro-6-methylphenyl)-8-methoxy-7-[3-(4-morpholinyl)propoxy]imidazo[1,5-a]quinoxalin-4-amine;

N-(2-Chloro-6-methylphenyl)-7-[3-(dimethylamino)propoxy]-8-methoxyimidazo[1,5-a]quinoxalin-4-amine;

N-(2-Chloro-6-methylphenyl)-7-[2-(dimethylamino)ethoxy]-8-methoxyimidazo[1,5-a]quinoxalin-4-amine;

N-(2-Chloro-6-methylphenyl)-8-methoxy-7-(2-methoxyethoxy)imidazo[1,5-a]quinoxalin-4-amine;

7-[2-(Acetyloxy)ethoxy]-N-(2-chloro-6-methylphenyl)-8-methoxyimidazo[1,5-a]quinoxalin-4-amine;

N-(2-Chloro-6-methylphenyl)-7-(2-hydroxyethoxy)-8-methoxyimidazo[1,5-a]quinoxalin-4-amine;

N-(2-Chloro-6-methylphenyl)-8-methoxy-7-[(tetrahydro-2-furanyl)methoxy]imidazo[1,5-a]quinoxalin-4-amine;

N-(2-Chloro-6-methylphenyl)-8-methoxy-7-[(tetrahydro-3-furanyl)methoxy]imidazo[1,5-a]quinoxalin-4-amine;

N-(2-Chloro-6-methylphenyl)-8-methoxy-7-[(tetrahydro-3-furanyl)oxy]imidazo[1,5-a]quinoxalin-4-amine;

N-(2-Chloro-6-methylphenyl)-8-methoxy-7-[2-(1-methyl-2-pyrrolidinyl)ethoxy]imidazo[1,5-a]quinoxalin-4-amine;

N-(2-Chloro-6-methylphenyl)-8-methoxy-7-[(1-methyl-3-pyrrolidinyl)oxy]imidazo[1,5-a]quinoxalin-4-amine;

N-(2-Chloro-6-fluorophenyl)-7,8-dimethoxyimidazo[1,5-a]quinoxalin-4-amine;

N-(2-Chloro-6-fluorophenyl)-8-methoxy-7-[2-(4-morpholinyl)ethoxy]imidazo[1,5-a]quinoxalin-4-amine;

N-(2-Chloro-6-fluorophenyl)-8-methoxy-7-[3-(4-morpholinyl)propoxy]imidazo[1,5-a]quinoxalin-4-amine;

N-(2-Chloro-6-fluorophenyl)-7-[2-(dimethylamino)ethoxy]-8-methoxyimidazo[1,5-a]quinoxalin-4-amine;

N-(2-Chloro-6-fluorophenyl)-7-[3-(dimethylamino)propoxy]-8-methoxyimidazo[1,5-a]quinoxalin-4-amine;

N-(2-Chloro-6-fluorophenyl)-8-ethoxy-7-[2-(4-morpholinyl)ethoxy]imidazo[1,5-a]quinoxalin-4-amine;

N-(2-Chloro-6-fluorophenyl)-8-ethoxy-7-[3-(4-morpholinyl)propoxy]imidazo[1,5-a]quinoxalin-4-amine;

N-(2-Chloro-6-fluorophenyl)-7-[2-(dimethylamino)ethoxy]-8-ethoxyimidazo[1,5-a]quinoxalin-4-amine;

N-(2-Chloro-6-fluorophenyl)-7-[3-(dimethylamino)propoxy]-8-ethoxyimidazo[1,5-a]quinoxalin-4-amine;

N-(2-Chloro-6-fluorophenyl)-8-ethoxy-7-[(tetrahydro-3-furanyl)oxy]imidazo[1,5-a]quinoxalin-4-amine;

N-(2-Chloro-6-methylphenyl)-7-methoxy-8-[2-(4-morpholinyl)ethoxy]imidazo[1,5-a]quinoxalin-4-amine;

N-(2-Chloro-6-methylphenyl)-7-ethoxy-8-[2-(4-morpholinyl)ethoxy]imidazo[1,5-a]quinoxalin-4-amine;

N-(2-Chloro-6-methylphenyl)-8-[2-(4-morpholinyl)ethoxy]-7-[(tetrahydro-3-furanyl)oxy]imidazo[1,5-a]quinoxalin-4-amine;

3,5-Dichloro-N-cyclopropyl-4-[(7,8-dimethoxyimidazo[1,5-a]quinoxalin-4-yl)amino]benzamide;

N-(2-Bromo-4,6-difluorophenyl)-7,8-dimethoxyimidazo[1,5-a]quinoxalin-4-amine;

3,5-Dichloro-4-[(7,8-dimethoxyimidazo[1,5-a]quinoxalin-4-yl)amino]benzoic acid;

N-(2,4-Dibromo-6-fluorophenyl)-7,8-dimethoxyimidazo[1,5-a]quinoxalin-4-amine;

3,5-Dichloro-4-[(7,8-dimethoxyimidazo[1,5-a]quinoxalin-4-yl)amino]benzenesulfonamide;

3-Chloro-4-[(7,8-dimethoxyimidazo[1,5-a]quinoxalin-4-yl)amino]-5-methylbenzenesulfonic acid;

N-[2,6-Dichloro-4-(trifluoromethyl)phenyl]-7,8-dimethoxyimidazo[1,5-a]quinoxalin-4-amine;

N-(2,6-Dibromo-4-methylphenyl)-7,8-dimethoxyimidazo[1,5-a]quinoxalin-4-amine;

N-[2,4-Dichloro-6-(trifluoromethyl)phenyl]-7,8-dimethoxyimidazo[1,5-a]quinoxalin-4-amine;

N-(2,6-Dichloro-4-methoxyphenyl)-7,8-dimethoxyimidazo[1,5-a]quinoxalin-4-amine;
N-[2-Fluoro-6-(trifluoromethyl)phenyl]-7,8-dimethoxyimidazo[1,5-a]quinoxalin-4-amine;
N-(2-Bromo-6-chloro-4-fluorophenyl)-7,8-dimethoxyimidazo[1,5-a]quinoxalin-4-amine;
N-(2,6-Dibromo-4-fluorophenyl)-7,8-dimethoxyimidazo[1,5-a]quinoxalin-4-amine;
N-(2-Bromo-4,6-dimethylphenyl)-7,8-dimethoxyimidazo[1,5-a]quinoxalin-4-amine;
N-(2-Bromo-4-chloro-6-fluorophenyl)-7,8-dimethoxyimidazo[1,5-a]quinoxalin-4-amine;
N-(2,6-Difluorophenyl)-7,8-dimethoxyimidazo[1,5-a]quinoxalin-4-amine;
N-(2,4,6-Trifluorophenyl)-7,8-dimethoxyimidazo[1,5-a]quinoxalin-4-amine;
3-Chloro-4-[(7,8-dimethoxyimidazo[1,5-a]quinoxalin-4-yl)amino]-5-methylbenzonitrile;
3-Chloro-4-[(7,8-dimethoxyimidazo[1,5-a]quinoxalin-4-yl)amino]-5-methylbenzamide;
N-(2-Chloro-3,6-dimethylphenyl)-7,8-dimethoxyimidazo[1,5-a]quinoxalin-4-amine;
N-(2-Chloro-5,6-dimethylphenyl)-7,8-dimethoxyimidazo[1,5-a]quinoxalin-4-amine;
N-(2-Chloro-6-methylphenyl)-6-methoxyimidazo[1,5-a]quinoxalin-4-amine;
N-(2-Chloro-6-methylphenyl)-9-(phenylmethoxy)imidazo[1,5-a]quinoxalin-4-amine;
N-(2-Chloro-6-methylphenyl)-9-(2-hydroxyethoxy)imidazo[1,5-a]quinoxalin-4-amine;
N-(2-Chloro-6-methylphenyl)-9-[2-(dimethylamino)ethoxy]imidazo[1,5-a]quinoxalin-4-amine;
N-(2-Chloro-6-methylphenyl)-9-(3-hydroxypropoxy)imidazo[1,5-a]quinoxalin-4-amine;
N-(2-Chloro-6-methylphenyl)-9-(2-methoxyethoxy)imidazo[1,5-a]quinoxalin-4-amine;
N-(2-Chloro-6-methylphenyl)-9-[(tetrahydro-2H-pyran-4-yl)oxy]imidazo[1,5-a]quinoxalin-4-amine;
N-(2-Chloro-6-methylphenyl)-9-[2-(4-morpholinyl)ethoxy]imidazo[1,5-a]quinoxalin-4-amine;
8-Bromo-N-(2-chloro-6-fluorophenyl)imidazo[1,5-a]quinoxalin-4-amine;
N-(2-Chloro-6-fluorophenyl)-8-(3,5-dimethyl-1-piperazinyl)imidazo[1,5-a]quinoxalin-4-amine;
N-(2-Chloro-6-fluorophenyl)-8-(4-methyl-1-piperazinyl)imidazo[1,5-a]quinoxalin-4-amine;
N-(2-Chloro-6-fluorophenyl)-8-[[2-(2-pyridinyl)ethyl]amino]imidazo[1,5-a]quinoxalin-4-amine;
$N^4$-(2-Chloro-6-fluorophenyl)-$N^8$-[(tetrahydro-2-furanyl)methyl]imidazo[1,5-a]quinoxaline-4,8-diamine;
$N^8$-(2-Aminoethyl)-$N^4$-(2-chloro-6-fluorophenyl)imidazo[1,5-a]quinoxaline-4,8-diamine;
$N^4$-(2-Chloro-6-fluorophenyl)-$N^8$-[3-(4-methyl-1-piperazinyl)propyl]imidazo[1,5-a]quinoxaline-4,8-diamine;
$N^4$-(2-Chloro-6-fluorophenyl)-$N^8$-[2-(1-methyl-2-pyrrolidinyl)ethyl]imidazo[1,5-a]quinoxaline-4,8-diamine;
$N^4$-(2-Chloro-6-fluorophenyl)-$N^8$-[2-(4-morpholinyl)ethyl]imidazo[1,5-a]quinoxaline-4,8-diamine;
$N^4$-(2-Chloro-6-fluorophenyl)-$N^8$-[6-(dimethylamino)hexyl]imidazo[1,5-a]quinoxaline-4,8-diamine;
$N^4$-(2-Chloro-6-fluorophenyl)-$N^8$-[4-(dimethylamino)butyl]imidazo[1,5-a]quinoxaline-4,8-diamine;
$N^4$-(2-Chloro-6-fluorophenyl)-$N^8$-[3-(dimethylamino)propyl]imidazo[1,5-a]quinoxaline-4,8-diamine;
$N^4$-(2-Chloro-6-fluorophenyl)-$N^8$-[2-(dimethylamino)ethyl]imidazo[1,5-a]quinoxaline-4,8-diamine;
1-[3-[[4-(2-Chloro-6-fluorophenyl)imidazo[1,5-a]quinoxalin-8-yl]amino]propyl]-2-pyrrolidinone;
$N^4$-(2-Chloro-6-fluorophenyl)-$N^8$-[2-(4-pyridinyl)ethyl]imidazo[1,5-a]quinoxaline-4,8-diamine;
$N^4$-(2-Chloro-6-fluorophenyl)-$N^8$-[3-(4-morpholinyl)propyl]imidazo[1,5-a]quinoxaline-4,8-diamine;
$N^4$-(2-Chloro-6-fluorophenyl)-$N^8$-(cyclopropylmethyl)imidazo[1,5-a]quinoxaline-4,8-diamine;
7-Bromo-N-(2-chloro-6-methylphenyl)imidazo[1,5-a]quinoxalin-4-amine;
$N^4$-(2-Chloro-6-methylphenyl)-$N^7$-[4-(dimethylamino)butyl]imidazo[1,5-a]quinoxaline-4,7-diamine;
$N^4$-(2-Chloro-6-methylphenyl)-$N^7$-[6-(dimethylamino)hexyl]imidazo[1,5-a]quinoxaline-4,7-diamine;
$N^4$-(2-Chloro-6-methylphenyl)-$N^7$-[3-(4-methyl-1-piperazinyl)propyl]imidazo[1,5-a]quinoxaline-4,7-diamine;
$N^4$-(2-Chloro-6-methylphenyl)-$N^7$-cyclopropylimidazo[1,5-a]quinoxaline-4,7-diamine;
$N^4$-(2-Chloro-6-methylphenyl)-$N^7$-[1-(phenylmethyl)-4-piperidinyl]imidazo[1,5-a]quinoxaline-4,7-diamine;
$N^4$-(2-Chloro-6-methylphenyl)-$N^7$-[3-(methylphenylamino)propyl]imidazo[1,5-a]quinoxaline-4,7-diamine;
$N^7$-[(2-Aminophenyl)methyl]-$N^4$-(2-chloro-6-methylphenyl)imidazo[1,5-a]quinoxaline-4,7-diamine;
N-(2-Chloro-6-methylphenyl)-7-(4-morpholinyl)imidazo[1,5-a]quinoxalin-4-amine;
N-(2-Chloro-6-methylphenyl)-7-(4-methyl-1-piperazinyl)imidazo[1,5-a]quinoxalin-4-amine;
N-(2-Chloro-6-methylphenyl)-7-(1-piperazinyl)imidazo[1,5-a]quinoxalin-4-amine;
N-(2-Chloro-6-methylphenyl)-7-(3,5-dimethyl-1-piperazinyl)imidazo[1,5-a]quinoxalin-4-amine;
N-(2-Chloro-6-methylphenyl)-7-[4-[2-(dimethylamino)ethyl]-1-piperazinyl]imidazo[1,5-a]quinoxalin-4-amine;
N-(2-Chloro-6-methylphenyl)-7-[4-[3-(dimethylamino)propy]-1-piperazinyl]imidazo[1,5-a]quinoxalin-4-amine;
(S)-N-(2-Chloro-6-methylphenyl)-7-(3-methyl-1-piperazinyl)imidazo[1,5-a]quinoxalin-4-amine;
$N^4$-(2-Chloro-6-methylphenyl)-$N^7$-[2-(dimethylamino)ethyl]imidazo[1,5-a]quinoxaline-4,7-diamine;
$N^4$-(2-Chloro-6-methylphenyl)-$N^7$-[3-(dimethylamino)propyl]imidazo[1,5-a]quinoxaline-4,7-diamine;
$N^4$-(2-Chloro-6-methylphenyl)-$N^7$-(2-thienylmethyl)imidazo[1,5-a]quinoxaline-4,7-diamine;
$N^4$-(2-Chloro-6-methylphenyl)-$N^7$-[(2,3-dihydro-1,4-benzodioxin-2-yl)methyl]imidazo[1,5-a]quinoxaline-4,7-diamine;
$N^4$-(2-Chloro-6-methylphenyl)-$N^7$-[2-(2-thienyl)ethyl]imidazo[1,5-a]quinoxaline-4,7-diamine;
(R)-N-(2-Chloro-6-methylphenyl)-7-(3-methyl-1-piperazinyl)imidazo[1,5-a]quinoxalin-4-amine;
7-[4-(1,3-Benzodioxol-5-ylmethyl)-1-piperazinyl]-N-(2-chloro-6-methylphenyl)imidazo[1,5-a]quinoxalin-4-amine;

4-[4-[(2-Chloro-6-methylphenyl)amino]imidazo[1,5-a]quinoxalin-7-yl]-N-(1-methylethyl)-1-piperazineacetamide;

N-(2-Chloro-6-methylphenyl)-7-(4-phenyl-1-piperazinyl)imidazo[1,5-a]quinoxalin-4-amine;

1-[4-[(2-Chloro-6-methylphenyl)amino]imidazo[1,5-a]quinoxalin-7-yl]-4-(2-furanylcarbonyl)piperazine;

N-(2-Chloro-6-methylphenyl)-7-[4-(2-methoxyethyl)-1-piperazinyl]imidazo[1,5-a]quinoxalin-4-amine;

4-[(2-Chloro-6-methylphenyl)amino]-7,8-dimethoxyimidazo[1,5-a]quinoxaline-1-carboxaldehyde;

4-[(2-Chloro-6-methylphenyl)amino]-7,8-dimethoxyimidazo[1,5-a]quinoxaline-1-carboxaldehyde oxime;

4-[(2-Chloro-6-methylphenyl)amino]-8-methoxyimidazo[1,5-a]quinoxalin-7-ol;

2-[[4-[(2-Chloro-6-methylphenyl)amino]-7-hydroxyimidazo[1,5-a]quinoxalin-8-yl]oxy]-2-propenenitrile;

7-[(2-Chloro-6-methylphenyl)amino]-2,3-dihydro-1,4-dioxino[2,3-g]imidazo[1,5-a]quinoxaline-2-carbonitrile;

N-(2-Chloro-6-methylphenyl)-7,8-bis[3-(dimethylamino)propoxy]imidazo[1,5-a]quinoxalin-4-amine;

N-(2-Chloro-6-methylphenyl)-7,8-bis[2-(4-morpholinyl)ethoxy]imidazo[1,5-a]quinoxalin-4-amine;

N-Cyclohexyl-7,8-dimethoxyimidazo[1,5-a]quinoxaline-4-amine;

1-Chloro-N-(2-chloro-6-methylphenyl)-7,8-dimethoxyimidazo[1,5-a]quinoxalin-4-amine;

N-(2-Chloro-6-methylphenyl)-1,7,8-trimethoxyimidazo[1,5-a]quinoxalin-4-amine;

$N^4$-(2-Chloro-6-methylphenyl)-7,8-dimethoxy-$N^1$-[(4-methoxyphenyl)methyl]imidazo[1,5-a]quinoxaline-1,4-diamine;

N-[4-[(2-Chloro-6-methylphenyl)amino]-7,8-dimethoxyimidazo[1,5-a]quinoxalin-1-yl]-N-[(4-methoxyphenyl)methyl]acetamide;

N-[4-[(2-Chloro-6-methylphenyl)amino]-7,8-dimethoxyimidazo[1,5-a]quinoxalin-1-yl]acetamide;

$N^4$-(2-Chloro-6-methylphenyl)-7,8-dimethoxyimidazo[1,5-a]quinoxaline-1,4-diamine, dihydrochloride;

3-Chloro-N-(2-chloro-6-methylphenyl)imidazo[1,5-a]quinoxalin-4-amine;

4-[(2-Chloro-6-methylphenyl)amino]imidazo[1,5-a]quinoxaline-8-carbonitrile;

4-[(2-Chloro-6-methylphenyl)amino]imidazo[1,5-a]quinoxaline-8-carboxamide;

4-[(2-Chloro-6-methylphenyl)amino]imidazo[1,5-a]quinoxaline-8-carboxylic acid;

4-[(2-Chloro-6-methylphenyl)amino]imidazo[1,5-a]quinoxaline-8-carboxylic acid methyl ester;

4-[(2-Chloro-6-methylphenyl)amino]imidazo[1,5-a]quinoxalin-8-ol;

N-[2-Chloro-6-methyl-4-(4-morpholinyl)phenyl]-7,8-dimethoxyimidazo[1,5-a]quinoxalin-4-amine;

N-(2-Chloro-6-methylphenyl)-8-(hexahydro-4-methyl-1H-1,4-diazepin-1-yl)imidazo[1,5-a]quinoxalin-4-amine;

N-(2-Chloro-6-fluorophenyl)-8-(1H-imidazol-1-yl)imidazo[1,5-a]quinoxalin-4-amine;

N-(2-Chloro-6-methylphenyl)-7,9-dimethoxyimidazo[1,5-a]quinoxalin-4-amine;

N-(2-Chloro-6-fluorophenyl)-7,9-dimethoxyimidazo[1,5-a]quinoxalin-4-amine;

N-(2-Chloro-6-fluorophenyl)-6,8-dimethoxyimidazo[1,5-a]quinoxalin-4-amine;

N-(2-Chloro-6-methylphenyl)-8-[4-[[[3-(dimethylamino)propyl]amino]methyl]phenyl]imidazo[1,5-a]quinoxalin-4-amine;

N-(2-Chloro-6-methylphenyl)-7-methoxy-8-(1-piperazinyl)imidazo[1,5-a]quinoxalin-4-amine;

cis-N-(2-Chloro-6-methylphenyl)-8-(3,5-dimethyl-1-piperazinyl)-7-methoxyimidazo[1,5-a]quinoxalin-4-amine;

$N^4$-(2-Chloro-6-methylphenyl)-7-methoxy-$N^8$-[3-(4-morpholinyl)propyl]imidazo[1,5-a]quinoxaline-4,8-diamine;

N-(2-Chloro-6-methylphenyl)-8-(hexahydro-1H-1,4-diazepin-1-yl)-7-methoxyimidazo[1,5-a]quinoxalin-4-amine;

N-(2-Chloro-6-methylphenyl)-8-(hexahydro-4-methyl-1H-1,4-diazepin-1-yl)-7-methoxyimidazo[1,5-a]quinoxalin-4-amine;

N-(2-Chloro-6-methylphenyl)-7-[2-(4-morpholinyl)ethoxy]-8-(1-piperazinyl)imidazo[1,5-a]quinoxalin-4-amine;

cis-N-(2-Chloro-6-methylphenyl)-8-(3,5-dimethyl-1-piperazinyl)-7-[2-(4-morpholinyl)ethoxy]imidazo[1,5-a]quinoxalin-4-amine;

$N^4$-(2-Chloro-6-methylphenyl)-7-[2-(4-morpholinyl)ethoxy]-$N^8$-[3-(4-morpholinyl)propyl]imidazo[1,5-a]quinoxaline-4,8-diamine;

$N^4$-(2-Chloro-6-methylphenyl)-$N^8$-[2-(dimethylamino)ethyl]-7-[2-(4-morpholinyl)ethoxy]imidazo[1,5-a]quinoxaline-4,8-diamine;

$N^4$-(2-Chloro-6-methylphenyl)-$N^8$-[3-(dimethylamino)propyl]-7-[2-(4-morpholinyl)ethoxy]imidazo[1,5-a]quinoxaline-4,8-diamine;

$N^4$-(2-Chloro-6-methylphenyl)-$N^8$-[4-(dimethylamino)butyl]-7-[2-(4-morpholinyl)ethoxy]imidazo[1,5-a]quinoxaline-4,8-diamine;

N-[1-[4-[(2-Chloro-6-methylphenyl)amino]-7-[2-(4-morpholinyl)ethoxy]imidazo[1,5-a]quinoxalin-8-yl]-3-pyrrolidinyl]acetamide;

1-Acetyl-4-[4-[(2-Chloro-6-methylphenyl)amino]-7-[2-(4-morpholinyl)ethoxy]imidazo[1,5-a]quinoxalin-8-yl]piperazine;

N-(2-Chloro-6-methylphenyl)-8-(hexahydro-4-methyl-1H-1,4-diazepin-1-yl)-7-[2-(4-morpholinyl)ethoxy]imidazo[1,5-a]quinoxalin-4-amine;

N-(2-Chloro-6-methylphenyl)-7-[2-(4-morpholinyl)ethoxy]-8-phenylimidazo[1,5-a]quinoxalin-4-amine;

$N^4$-(2-Chloro-6-methylphenyl)-$N^1$,$N^1$-dimethyl-7,8-dimethoxyimidazo[1,5-a]quinoxaline-1,4-diamine;

N-(2-Chloro-6-methylphenyl)-8-[4-[[[3-(dimethylamino)propyl]amino]methyl]phenyl]-7-[2-(4-morpholinyl)ethoxy]imidazo[1,5-a]quinoxalin-4-amine;

$N^4$-(2-Chloro-6-methylphenyl)-8-methoxy-$N^7$-[2-(4-morpholinyl)ethyl]imidazo[1,5-a]quinoxaline-4,7-diamine;

$N^4$-(2-Chloro-6-methylphenyl)-$N^7$-[2-(dimethylamino)ethyl]-8-methoxyimidazo[1,5-a]quinoxaline-4,7-diamine;

cis-N-(2-Chloro-6-methylphenyl)-7-(3,5-dimethyl-1-piperazinyl)-8-methoxyimidazo[1,5-a]quinoxalin-4-amine;

N-(2-Chloro-6-methylphenyl)-7-[4-[2-(dimethylamino)ethyl]-1-piperazinyl]-8-methoxyimidazo[1,5-a]quinoxalin-4-amine;

$N^4$-(2-Chloro-6-fluorophenyl)-8-methoxy-$N^7$-[2-(4-morpholinyl)ethyl]imidazo[1,5-a]quinoxaline-4,7-diamine;

$N^4$-(2-Chloro-6-fluorophenyl)-$N^7$-[2-(dimethylamino)ethyl]-8-methoxyimidazo[1,5-a]quinoxaline-4,7-diamine;

cis-N-(2-Chloro-6-fluorophenyl)-7-(3,5-dimethyl-1-piperazinyl)-8-methoxyimidazo[1,5-a]quinoxalin-4-amine;

4-Amino-N-(2-chloro-6-methylphenyl)imidazo[1,5-a]quinoxaline-7-carboxamide;

4-Amino-N-(2,4,6-trimethylphenyl)imidazo[1,5-a]quinoxaline-7-carboxamide;

4-[(2-Chloro-6-methylphenyl)amino]-7,8-dimethoxy-α-methylimidazo[1,5-a]quinoxaline-1-methanol;

4-[(2-Chloro-6-methylphenyl)amino]-α-ethyl-7,8-dimethoxyimidazo[1,5-a]quinoxaline-1-methanol;

4-[(2-Chloro-6-methylphenyl)amino]-7,8-dimethoxy-α-(1-methylethyl)imidazo[1,5-a]quinoxaline-1-methanol;

4-[(2-Chloro-6-methylphenyl)amino]-N-ethyl-7,8-dimethoxyimidazo[1,5-a]quinoxaline-1-carboxamide;

4-[(2-Chloro-6-methylphenyl)amino]-N-(1,1-dimethylethyl)-7,8-dimethoxyimidazo[1,5-a]quinoxaline-1-carboxamide;

4-[(2-Chloro-6-methylphenyl)amino]-7,8-dimethoxy-N-(phenylmethyl)imidazo[1,5-a]quinoxaline-1-carboxamide;

N-[[4-[(2-Chloro-6-methylphenyl)amino]-7,8-dimethoxyimidazo[1,5-a]quinoxalin-1-yl]carbonyl]alanine ethyl ester;

4-[(2-Chloro-6-methylphenyl)amino]-7,8-dimethoxy-N-pentylimidazo[1,5-a]quinoxaline-1-carboxamide;

N-[[4-[(2-Chloro-6-methylphenyl)amino]-7,8-dimethoxyimidazo[1,5-a]quinoxalin-1-yl]carbonyl]glycine ethyl ester;

(S)-4-[(2-Chloro-6-methylphenyl)amino]-7,8-dimethoxy-N-(1-phenylethyl)imidazo[1,5-a]quinoxaline-1-carboxamide;

4-[(2-Chloro-6-methylphenyl)amino]-N-cyclohexyl-7,8-dimethoxyimidazo[1,5-a]quinoxaline-1-carboxamide;

4-[(2-Chloro-6-methylphenyl)amino]-7,8-dimethoxy-N-(1-methylethyl)imidazo[1,5-a]quinoxaline-1-carboxamide;

N-[(2-Chloro-6-methylphenyl)amino]-7,8-dimethoxyimidazo[1,5-a]quinoxaline-1-propanol;

4-[(2-Chloro-6-methylphenyl)amino]imidazo[1,5-a]quinoxalin-9-ol;

N-(2-Chloro-6-methylphenyl)-7-(1,3-dioxolan-4-ylmethoxy)-8-methoxyimidazo[1,5-a]quinoxalin-4-amine;

N-(2-Chloro-6-methylphenyl)-8-methoxy-7-[(1-methyl-3-piperidinyl)methoxy]imidazo[1,5-a]quinoxalin-4-amine; and N-(2-Chloro-6-methylphenyl)-7,8-dimethoxy-1-methylimidazo[1,5-a]quinoxalin-4-amine.

36. A method for the treatment of a T cell mediated disorder wherein T cell activation is inhibited, comprising the step of administering to a subject in need thereof an amount effective therefor of at least one compound of the following formula I or salt thereof:

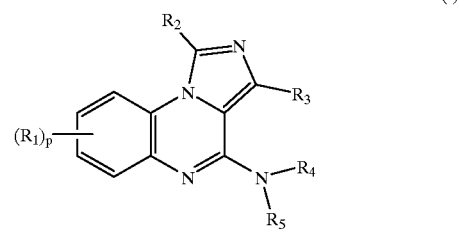

(I)

where p is 0, 1, 2, 3 or 4;

each $R_1$, and $R_2$ and $R_3$, are independently selected from:
(1) hydrogen or $R_6$,
where $R_6$ is alkyl, alkenyl, alkynyl, cycloalkyl, cycloalkylalkyl, cycloalkenyl, cycloalkenylalkyl, aryl, aralkyl, heterocyclo, or heterocycloalkyl, each of which is unsubstituted or substituted with $Z_1$, $Z_2$ and one or more groups $Z_3$;
(2) —OH or —$OR_6$;
(3) —SH or —$SR_6$;
(4) —$C(O)_qH$, $C(O)_qR_6$ or —O—$C(O)_qR_6$, where q is 1 or 2;
(5) —$SO_3H$ or —$S(O)_qR_6$;
(6) halo;
(7) cyano;
(8) nitro;
(9) —$Z_4$—$NR_7R_8$;
(10) —$Z_4$—$N(R_9)$—$Z_5$—$NR_{10}R_{11}$;
(11) —$Z_4$—$N(R_{12})$—$Z_5$—$R_6$;
(12) —$SiR_{13}R_{14}R_{15}$;
(13) —$P(O)(OR_6)_2$;
(14) —CH=N—$OR_6$;
(15) any two groups $R_1$ may together be alkylene or alkenylene completing a 3- to 8-membered saturated or unsaturated ring together with the carbon atoms to which they are attached, which ring is unsubstituted or substituted with $Z_1$, $Z_2$ and $Z_3$; or
(16) any two groups $R_1$ may, together with the carbons to which they are attached, form a heterocyclo group, which group is unsubstituted or substituted with $Z_1$, $Z_2$ and $Z_3$;

$R_4$ and $R_5$:
(1) are each independently hydrogen, $R_6$, or —$C(O)R_6$; or
(2) together with the nitrogen atom to which they are attached complete a 3- to 8-membered saturated or unsaturated heterocyclic ring which is unsubstituted or substituted with $Z_1$, $Z_2$ and $Z_3$, which heterocyclic ring may optionally have fused to it a benzene ring itself unsubstituted or substituted with $Z_1$, $Z_2$ and $Z_3$;

$R_7$, $R_8$, $R_9$, $R_{10}$, $R_{11}$ and $R_{12}$:
(1) are each independently hydrogen or $R_6$;
(2) $R_7$ and $R_8$ may together be alkylene or alkenylene, completing a 3- to 8-membered saturated or unsaturated ring with the nitrogen atom to which they are attached, which ring is unsubstituted or substituted with $Z_1$, $Z_2$ and $Z_3$; or
(3) any two of $R_9$, $R_{10}$ and $R_{11}$ may together be alkylene or alkenylene completing a 3- to 8-membered saturated or unsaturated ring together with the nitrogen atoms to which they are attached, which ring is unsubstituted or substituted with $Z_1$, $Z_2$ and $Z_3$;

$R_{13}$, $R_{14}$ and $R_{15}$ are each independently:
(1) alkyl; or
(2) phenyl;

$Z_1$, $Z_2$ and $Z_3$ are each independently:
(1) hydrogen or $Z_6$, where $Z_6$ is (i) alkyl, alkenyl, alkynyl, cycloalkyl, cycloalkylalkyl, cycloalkenyl, cycloalkenylalkyl, aryl, aralkyl, alkylaiyl, cycloalkylaryl, heterocyclo, or heterocycloalkyl; (ii) a group (i) which is itself substituted by one or more of the same or different groups (i); or (iii) a group (i) or (ii) which is substituted by one or more of the following groups (2) to (16) of the definition of $Z_1$, $Z_2$ and $Z_3$;
(2) —OH or —$OZ_6$;
(3) —SH or —$SZ_6$;
(4) —C(O)$_q$H, —C(O)$_q Z_6$ or —O—C(O)$_q Z_6$;
(5) —$SO_3$H or —S(O)$_q Z_6$;
(6) halo;
(7) cyano;
(8) nitro;
(9) —$Z_4$—$NZ_7 Z_8$;
(10) —$Z_4$—N($Z_9$)—$Z_5$—$NZ_7 Z_8$;
(11) —$Z_4$—N($Z_{10}$)—$Z_5$—$Z_6$;
(12) —$Z_4$—N($Z_{10}$)—$Z_5$—H;
(13) oxo;
(14) —O—C(O)—$Z_6$;
(15) any two of $Z_1$, $Z_2$, and $Z_3$ may together be alkylene or alkenylene completing a 3- to 8-membered saturated or unsaturated ring together with the atoms to which they are attached; or
(16) any two of $Z_1$, $Z_2$, and $Z_3$ may together be —O—(CH$_2$)$_q$—O—;

$Z_4$ and $Z_5$ are each independently:
(1) a single bond;
(2) —$Z_{11}$—S(O)$_q$—$Z_{12}$—;
(3) —$Z_{11}$—C(O)—$Z_{12}$—;
(4) —$Z_{11}$—C(S)—$Z_{12}$—;
(5) —$Z_{11}$—O—$Z_{12}$—;
(6) —$Z_{11}$—S—$Z_{12}$—;
(7) —$Z_{11}$—O—C(O)—$Z_{12}$—; or
(8) —$Z_{11}$—C(O)—O—$Z_{12}$—;

$Z_7$, $Z_8$, $Z_9$ and $Z_{10}$:
(1) are each independently hydrogen or $Z_6$;
(2) $Z_7$ and $Z_8$, or $Z_6$ and $Z_{10}$, may together be alkylene or alkenylene, completing a 3- to 8-membered saturated or unsaturated ring together with the atoms to which they are attached, which ring is unsubstituted or substituted with $Z_1$, $Z_2$ and $Z_3$; or
(3) $Z_7$ or $Z_8$, together with $Z_9$, may be alkylene or alkenylene completing a 3- to 8-membered saturated or unsaturated ring together with the nitrogen atoms to which they are attached, which ring is unsubstituted or substituted with $Z_1$, $Z_2$ and $Z_3$; and $Z_{11}$ and $Z_{12}$ are each independently:
(1) a single bond;
(2) alkylene;
(3) alkenylene; or
(4) alkynylene.

37. A pharmaceutical composition for the treatment of a protein tyrosin kinase-associated disorder, comprising a pharmaceutically acceptable vehicle or diluent and at least one compound of the following formula I or pharmaceutically acceptable salt thereof in an amount effective therefor:

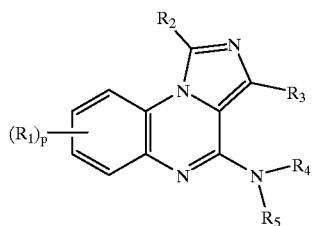

(I)

where
p is 0, 1, 2, 3 or 4;
each $R_1$, and $R_2$ and $R_3$, are independently selected from:
(1) hydrogen or $R_6$,
where $R_6$ is alkyl, alkenyl, alkynyl, cycloalkyl, cycloalkylalkyl, cycloalkenyl, cycloalkenylalkyl, aryl, aralkyl, heterocyclo, or heterocycloalkyl, each of which is unsubstituted or substituted with $Z_1$, $Z_2$ and one or more groups $Z_3$;
(2) —OH or —$OR_6$;
(3) —SH or —$SR_6$;
(4) —C(O)$_q$H —C(O)$_q R_6$or —O—C(O)$_q R_6$, where q is 1 or 2;
(5) —$SO_3$H or —S(O)$_q R_6$;
(6) halo;
(7) cyano;
(8) nitro;
(9) —$Z_4$—$NR_7 R_8$;
(10) —$Z_4$—N($R_9$)—$Z_5$—$NR_{10}R_{11}$;
(11) —$Z_4$—N($R_{12}$)—$Z_5$—$R_6$;
(12) —$SiR_{13}R_{14}R_{15}$;
(13) —P(O)(OR$_6$)$_2$;
(14) —CH=N—$OR_6$;
(15) any two groups $R_1$ may together be alkylene or alkenylene completing a 3- to 8-membered saturated or unsaturated ring together with the carbon atoms to which they are attached, which ring is unsubstituted or substituted with $Z_1$, $Z_2$ and $Z_3$; or
(16) any two groups $R_1$ may, together with the carbons to which they are attached, form a heterocyclo group, which group is unsubstituted or substituted with $Z_1$, $Z_2$ and $Z_3$;

$R_4$ and $R_5$:
(1) are each independently hydrogen, $R_6$, or —C(O)$R_6$; or
(2) together with the nitrogen atom to which they are attached complete a 3- to 8-membered saturated or unsaturated heterocyclic ring which is unsubstituted or substituted with $Z_1$, $Z_2$ and $Z_3$, which heterocyclic ring may optionally have fused to it a benzene ring itself unsubstituted or substituted with $Z_1$, $Z_2$ and $Z_3$;

$R_7$, $R_8$, $R_9$, $R_{10}$, $R_{11}$ and $R_{12}$:
(1) are each independently hydrogen or $R_6$;
(2) $R_7$ and $R_8$ may together be alkylene or alkenylene, completing a 3- to 8-membered saturated or unsaturated ring with the nitrogen atom to which they are attached, which ring is unsubstituted or substituted with $Z_1$, $Z_2$ and $Z_3$; or
(3) any two of $R_9$, $R_{10}$ and $R_{11}$ may together be alkylene or alkenylene completing a 3- to 8-membered saturated or unsaturated ring together with the nitrogen atoms to which they are attached, which ring is unsubstituted or substituted with $Z_1$, $Z_2$ and $Z_3$;

$R_{13}$, $R_{14}$ and $R_{15}$ are each independently:
(1) alkyl; or
(2) phenyl;

$Z_1$, $Z_2$ and $Z_3$ are each independently:
(1) hydrogen or $Z_6$, where $Z_6$ is (i) alkyl, alkenyl, alkynyl, cycloalkyl, cycloalkylalkyl, cycloalkenyl, cycloalkenylalkyl, aryl, aralkyl, alkylaryl, cycloalkylaryl, heterocyclo, or heterocycloalkyl; (ii) a group (i) which is itself substituted by one or more of the same or different groups (i); or (iii) a group (i) or (ii) which is substituted by one or more of the following groups (2) to (16) of the definition of $Z_1$, $Z_2$ and $Z_3$;
(2) —OH or —$OZ_6$;
(3) —SH or —$SZ_6$;
(4) —$C(O)_qH$, —$C(O)_qZ_6$ or —$OC(O)_qZ6$;
(5) —$SO_3H$ or —$S(O)_qZ_6$;
(6) halo;
(7) cyano;
(8) nitro;
(9) —$Z_4$—$NZ_7Z_8$;
(10) —$Z_4$—$N(Z_9)$—$Z_5$—$NZ_7Z_8$;
(11) —$Z_4$—$N(Z_{10})$—$Z_5$—$Z_6$;
(12) —$Z_4$—$N(Z_{10})$—$Z_5$—H;
(13) oxo;
(14) —O—$C(O)$—$Z_6$;
(15) any two of $Z_1$, $Z_2$, and $Z_3$ may together be alkylene or alkenylene completing a 3- to 8-membered saturated or unsaturated ring together with the atoms to which they are attached; or
(16) any two of $Z_1$, $Z_2$, and $Z_3$ may together be —O—$(CH_2)_q$—O—;

$Z_4$ and $Z_5$ are each independently:
(1) a single bond;
(2) —$Z_{11}$—$S(O)_q$—$Z_{12}$—;
(3) —$Z_{11}$—$C(O)$—$Z_{12}$—;
(4) —$Z_{11}$—$C(S)$—$Z_{12}$—;
(5) —$Z_{11}$—O—$Z_{12}$—;
(6) —$Z_{11}$—S—$Z_{12}$—;
(7) —$Z_{11}$—O—$C(O)$—$Z_{12}$—; or
(8) —$Z_{11}$—$C(O)$—O—$Z_{12}$—;

$Z_7$) $Z_8$, $Z_9$ and $Z_{10}$:
(1) are each independently hydrogen or $Z_6$;
(2) $Z_7$ and $Z_8$, or $Z_6$ and $Z_{10}$, may together be alkylene or alkenylene, completing a 3- to 8-membered saturated or unsaturated ring together with the atoms to which they are attached, which ring is unsubstituted or substituted with $Z_1$, $Z_2$ and $Z_3$; or
(3) $Z_7$ or $Z_8$, together with $Z_9$, may be alkylene or alkenylene completing a 3- to 8-membered saturated or unsaturated ring together with the nitrogen atoms to which they are attached, which ring is unsubstituted or substituted with $Z_1$, $Z_2$ and $Z_3$; and $Z_1$ and $Z_{12}$ are each independently:
(1) a single bond;
(2) alkylene;
(3) alkenylene; or
(4) alkynylene.

38. A pharmaceutical composition of claim 37, wherein said compound of the formula I or salt thereof is selected from the group consisting of:

N-(2-Chloro-6-methylphenyl)-8-nitroimidazo[1,5-a]quinoxalin-4-amine;

$N^4$-(2-Chloro-6-methylphenyl)imidazo[1,5-a]quinoxaline-4,8-diamine;

N-[4-[(2-Chloro-6-methylphenyl)amino]imidazo[1,5-a]quinoxalin-8-yl]acetamide;

N-[4-[(2-Chloro-6-methylphenyl)amino]imidazo[1,5-a]quinoxalin-8-yl]hexanamide;

N-[4-[(2-Chloro-6-methylphenyl)amino]imidazo[1,5-a]quinoxalin-8-yl]-3-methoxypropanamide;

N-[4-[(2-Chloro-6-methylphenyl)amino]imidazo[1,5-a]quinoxalin-8-yl]-N'-ethylurea;

N-(2-Bromophenyl)-8-methylimidazo[1,5-a]quinoxalin-4-amine;

N-(2-Bromophenyl)-7-methylimidazo[1,5-a]quinoxalin-4-amine;

N-(2-Bromophenyl)-1-methylimidazo[1,5-a]quinoxalin-4-amine;

N-(2-Bromophenyl)-1-(phenylthio)imidazo[1,5-a]quinoxalin-4-amine;

N-(2,6-Dimethylphenyl)-8-nitroimidazo[1,5-a]quinoxalin-4-amine;

$N^4$-(2,6-Dimethylphenyl)imidazo[1,5-a]quinoxalin-4,8-diamine;

N-[4-[(2,6-Dimethylphenyl)amino]imidazo[1,5-a]quinoxalin-8-yl]acetamide;

N-[4-[(2,6-Dimethylphenyl)amino]imidazo[1,5-a]quinoxalin-8-yl]hexanamide;

N-[4-[(2,6-Dimethylphenyl)amino]imidazo[1,5-a]quinoxalin-8-yl]benzeneacetamide;

[2-[[4-[(2,6-Dimethylphenyl)amino]imidazo[1,5-a]quinoxalin-8-yl]amino]-2-oxoethyl]carbamic acid, 1,1-dimethylethyl ester;

N-(2-Chloro-6-methylphenyl)imidazo[1,5-a]quinoxalin-4-amine;

N-(2-Methoxyphenyl)imidazo[1,5-a]quinoxalin-4-amine;

N-(2-Nitrophenyl)imidazo[1,5-a]quinoxalin-4-amine;

N-(2-Fluorophenyl)imidazo[1,5-a]quinoxalin-4-amine;

N-(2,6-Diethylphenyl)imidazo[1,5-a]quinoxalin-4-amine;

4-[(Imidazo[1,5-a]quinoxalin-4-yl)amino]benzonitrile;

N-(2,3-Dihydro-1H-inden-5-yl)imidazo[1,5-a]quinoxalin-4-amine;

N-[3-(Trifluoromethyl)phenyl]imidazo[1,5-a]quinoxalin-4-amine;

N-(4-Decylphenyl)imidazo[1,5-a]quinoxalin-4-amine;

N-(2,6-Dimethylphenyl)imidazo[1,5-a]quinoxalin-4-amine;

N-[2-Methyl-6-(1-methylethyl)phenyl]imidazo[1,5-a]quinoxalin-4-amine;

N-([1,1'-Biphenyl]-3-yl)imidazo[1,5-a]quinoxalin-4-amine;

N-[2,6-Bis(1-methylethyl)phenyl]imidazo[1,5-a]quinoxalin-4-amine;

N-(2,5-Dimethylphenyl)imidazo[1,5-a]quinoxalin-4-amine;

N-(2,3-Dimethylphenyl)imidazo[1,5-a]quinoxalin-4-amine;

N-[3-Methyl-4-(1-methylethyl)phenyl]imidazo[1,5-a]quinoxalin-4-amine;

N-(2,4-Dimethylphenyl)imidazo[1,5-a]quinoxalin-4-amine;

N-([1,1'-Biphenyl]-4-yl)imidazo[1,5-a]quinoxalin-4-amine;

N-[2-(Phenylmethyl)phenyl]imidazo[1,5-a]quinoxalin-4-amine;

N-[4-(1,1-Dimethylethyl)phenyl]imidazo[1,5-a]quinoxalin-4-amine;

N-(2-Propylphenyl)imidazo[1,5-a]quinoxalin-4-amine;
N-[3,5-Bis(1,1-dimethylethyl)phenyl]imidazo[1,5-a]quinoxalin-4-amine;
N-(3-Ethylphenyl)imidazo[1,5-a]quinoxalin-4-amine;
N-[3-(1,1-Dimethylethyl)phenyl]imidazo[1,5-a]quinoxalin-4-amine;
N-(4-Cyclohexylphenyl)imidazo[1,5-a]quinoxalin-4-amine;
N-(2,6-Dimethoxyphenyl)imidazo[1,5-a]quinoxalin-4-amine;
N-(3,4,5-Trimethoxyphenyl)imidazo[1,5-a]quinoxalin-4-amine;
N-(2-Methoxy-6-methylphenyl)imidazo[1,5-a]quinoxalin-4-amine;
N-(1,3-Benzodioxol-5-yl)-N-ethylimidazo[1,5-a]quinoxalin-4-amine;
N-(3-Phenoxyphenyl)imidazo[1,5-a]quinoxalin-4-amine;
N-[3-(Trifluoromethoxy)phenyl]imidazo[1,5-a]quinoxalin-4-amine;
N-[4-(4-Chlorophenoxy)phenyl]imidazo[1,5-a]quinoxalin-4-amine;
N-(1,3-Benzodioxol-5-yl)imidazo[1,5-a]quinoxalin-4-amine;
N-[3-(Phenylmethoxy)phenyl]imidazo[1,5-a]quinoxalin-4-amine;
N-(2,3-Dimethoxyphenyl)imidazo[1,5-a]quinoxalin-4-amine;
N-[2-(Trifluoromethoxy)phenyl]imidazo[1,5-a]quinoxalin-4-amine;
N-(1,4-Benzodioxin-6-yl)imidazo[1,5-a]quinoxalin-4-amine;
N-(4-Ethoxyphenyl)imidazo[1,5-a]quinoxalin-4-amine;
N-(4-Phenoxyphenyl)imidazo[1,5-a]quinoxalin-4-amine;
N-(4-Chlorophenyl)imidazo[1,5-a]quinoxalin-4-amine;
N-[3-Methoxy-5-(trifluoromethyl)phenyl]imidazo[1,5-a]quinoxalin-4-amine;
N-(2-Bromo-5-methoxyphenyl)imidazo[1,5-a]quinoxalin-4-amine;
N-(2-Chloro-6-methylphenyl)imidazo[1,5-a]quinoxalin-4-amine;
N-(2-Bromo-4-chlorophenyl)imidazo[1,5-a]quinoxalin-4-amine;
N-(2,6-Difluorophenyl)imidazo[1,5-a]quinoxalin-4-amine;
N-(2-Iodophenyl)imidazo[1,5-a]quinoxalin-4-amine;
N-(2,5-Difluorophenyl)imidazo[1,5-a]quinoxalin-4-amine;
N-(3,4-Difluorophenyl)imidazo[1,5-a]quinoxalin-4-amine;
N-(4-Chloro-3-methylphenyl)imidazo[1,5-a]quinoxalin-4-amine;
N-(3,4-Dichlorophenyl)-N-methylimidazo[1,5-a]quinoxalin-4-amine;
N-(4-Bromophenyl)imidazo[1,5-a]quinoxalin-4-amine;
N-(2,4-Dibromophenyl)imidazo[1,5-a]quinoxalin-4-amine;
N-(4-Fluoro-3-methylphenyl)imidazo[1,5-a]quinoxalin-4-amine;
N-(2-Chloro-5-methylphenyl)imidazo[1,5-a]quinoxalin-4-amine;
N-(2,5-Dibromophenyl)imidazo[1,5-a]quinoxalin-4-amine;
N-(3,5-Dichlorophenyl)imidazo[1,5-a]quinoxalin-4-amine;
N-(4-Chlorophenyl)-N-methylimidazo[1,5-a]quinoxalin-4-amine;
N-(3,5-Dibromo-4-methylphenyl)imidazo[1,5-a]quinoxalin-4-amine;
N-(4-Chloro-1-naphthalenyl)imidazo[1,5-a]quinoxalin-4-amine;
N-(3,4,5-Trichlorophenyl)imidazo[1,5-a]quinoxalin-4-amine;
N-[4-(4-Morpholinyl)phenyl]imidazo[1,5-a]quinoxalin-4-amine;
N-[4-(Dimethylamino)phenyl]imidazo[1,5-a]quinoxalin-4-amine;
N-[2-(1H-Pyrrol-1-yl)phenyl]imidazo[1,5-a]quinoxalin-4-amine;
N-[4-(1-Piperidinyl)phenyl]imidazo[1,5-a]quinoxalin-4-amine;
N-[2-(1-Piperidinyl)phenyl]imidazo[1,5-a]quinoxalin-4-amine;
N-(6-Quinolinyl)imidazo[1,5-a]quinoxalin-4-amine;
N-(3-Pyridinyl)imidazo[1,5-a]quinoxalin-4-amine;
N-(2-Chlorophenyl)imidazo[1,5-a]quinoxalin-4-amine;
N-[2-Bromo-4-(trifluoromethoxy)phenyl]imidazo[1,5-a]quinoxalin-4-amine;
N-(2,4-Dichlorophenyl)imidazo[1,5-a]quinoxalin-4-amine;
N-(2-Bromo-4-methylphenyl)imidazo[1,5-a]quinoxalin-4-amine;
N-(3-Bromo-2-methylphenyl)imidazo[1,5-a]quinoxalin-4-amine;
N-(3-Fluorophenyl)imidazo[1,5-a]quinoxalin-4-amine;
N-(2-Chlorophenyl)-N-methylimidazo[1,5-a]quinoxalin-4-amine;
N-(3,5-Dibromophenyl)imidazo[1,5-a]quinoxalin-4-amine;
N-(4-Benzoylphenyl)imidazo[1,5-a]quinoxalin-4-amine;
N-(4-Pyridinyl)imidazo[1,5-a]quinoxalin-4-amine;
N-(Phenylmethyl)-N-(2-pyridinyl)imidazo[1,5-a]quinoxalin-4-amine;
N-(4-Bromo-2,6-dimethylphenyl)imidazo[1,5-a]quinoxalin-4-amine;
N-[2-Chloro-4-(1,1-dimethylethyl)phenyl]imidazo[1,5-a]quinoxalin-4-amine;
N-(2-Ethyl-6-methylphenyl)imidazo[1,5-a]quinoxalin-4-amine;
N-(5-Chloro-2-methylphenyl)imidazo[1,5-a]quinoxalin-4-amine;
N-(4-Chloro-2-methylphenyl)imidazo[1,5-a]quinoxalin-4-amine;
N-(4-Bromo-2-methylphenyl)imidazo[1,5-a]quinoxalin-4-amine;
N-(2-Chloro-4-methylphenyl)imidazo[1,5-a]quinoxalin-4-amine;
N-(1,3,5-Trimethyl-1H-pyrazol-4-yl)imidazo[1,5-a]quinoxalin-4-amine;
N-(4-Bromo-2-chloro-6-methylphenyl)imidazo[1,5-a]quinoxalin-4-amine;
N-(2-Chloro-4,6-dimethylphenyl)imidazo[1,5-a]quinoxalin-4-amine;
N-(2,6-Dichlorophenyl)imidazo[1,5-a]quinoxalin-4-amine;

N-(2,4,6-Trichlorophenyl)imidazo[1,5-a]quinoxalin-4-amine;
N-(2,6-Dibromophenyl)imidazo[1,5-a]quinoxalin-4-amine;
N-(2,4,6-Tribromophenyl)imidazo[1,5-a]quinoxalin-4-amine;
N-(3,5-Dichloro-2-pyridinyl)imidazo[1,5-a]quinoxalin-4-amine;
N-(2,6-Dibromo-4-methylphenyl)imidazo[1,5-a]quinoxalin-4-amine;
N-(2,6-Dibromo-4-propylphenyl)imidazo[1,5-a]quinoxalin-4-amine;
3-Chloro-4-[[imidazo[1,5-a]quinoxalin-4-yl]amino]benzonitrile;
N-(2,4,6-Trimethylphenyl)imidazo[1,5-a]quinoxalin-4-amine;
N-[2-(4-Morpholinyl)phenyl]imidazo[1,5-a]quinoxalin-4-amine;
1-(Imidazo[1,5-a]quinoxalin-4-yl)-1H-indole-5-carbonitrile;
N-[2-(1H-Imidazol-1-yl)phenyl]imidazo[1,5-a]quinoxalin-4-amine;
N-(2,4-Dimethoxyphenyl)imidazo[1,5-a]quinoxalin-4-amine;
N-Phenylimidazo[1,5-a]quinoxalin-4-amine;
N-(2-Phenoxyphenyl)imidazo[1,5-a]quinoxalin-4-amine;
N-[2-(1,1-Dimethylethyl)phenyl]imidazo[1,5-a]quinoxalin-4-amine;
N-Methyl-N-phenylimidazo[1,5-a]quinoxalin-4-amine;
N-(2,3-Dichlorophenyl)imidazo[1,5-a]quinoxalin-4-amine;
N-(2-Bromophenyl)-7-methoxyimidazo[1,5-a]quinoxalin-4-amine;
N-(2,6-Dimethylphenyl)-7-methoxyimidazo[1,5-a]quinoxalin-4-amine;
N-(2-Chloro-6-methylphenyl)-7-methoxyimidazo[1,5-a]quinoxalin-4-amine;
N-(2,4-Dimethylphenyl)-7-methoxyimidazo[1,5-a]quinoxalin-4-amine;
N-(2-Chlorophenyl)-7-methoxyimidazo[1,5-a]quinoxalin-4-amine;
N-(2,6-Dichlorophenyl)-7-methoxyimidazo[1,5-a]quinoxalin-4-amine;
N-(2-Chloro-4,6-dimethylphenyl)-7-methoxyimidazo[1,5-a]quinoxalin-4-amine;
7,8-Dimethoxy-N-(2,4,6-trimethylphenyl)imidazo[1,5-a]quinoxalin-4-amine;
N-(2,6-Dimethylphenyl)-7,8-dimethoxyimidazo[1,5-a]quinoxalin-4-amine;
N-[2-(3-Chlorophenyl)ethyl]imidazo[1,5-a]quinoxalin-4-amine;
N-[2-[(Phenylmethyl)thio]ethyl]imidazo[1,5-a]quinoxalin-4-amine;
N-[[2-[[2-(Hydroxymethyl)phenyl]thio]phenyl]methyl]imidazo[1,5-a]quinoxalin-4-amine;
N-[2-(1-Cyclohexen-1-yl)ethyl]imidazo[1,5-a]quinoxalin-4-amine;
N-[2-[Ethyl(3-methylphenyl)amino]ethyl]imidazo[1,5-a]quinoxalin-4-amine;
N-Hexylimidazo[1,5-a]quinoxalin-4-amine;
N-[2-(4-Methylphenyl)ethyl]imidazo[1,5-a]quinoxalin-4-amine;
N-[(2-Chlorophenyl)methyl]imidazo[1,5-a]quinoxalin-4-amine;
N-[3-(2-Methyl-1-piperidinyl)propyl]imidazo[1,5-a]quinoxalin-4-amine;
N-[2-(2-Pyridinyl)ethyl]imidazo[1,5-a]quinoxalin-4-amine;
N-[1-(1-Naphthalenyl)ethyl]imidazo[1,5-a]quinoxalin-4-amine;
N-[(Tetrahydro-2-furanyl)methyl]imidazo[1,5-a]quinoxalin-4-amine;
N-[2-(2,4-Dichlorophenyl)ethyl]imidazo[1,5-a]quinoxalin-4-amine;
N-[(2-Aminophenyl)methyl]imidazo[1,5-a]quinoxalin-4-amine;
4-[(Imidazo[1,5-a]quinoxalin-4-yl)amino]-1-piperidinecarboxylic acid, ethyl ester;
4-[4-(Phenylmethyl)-1-piperazinyl]imidazo[1,5-a]quinoxaline;
N-[[4-(Trifluoromethyl)phenyl]methyl]imidazo[1,5-a]quinoxalin-4-amine;
4-[4-(2-Pyridinyl)-1-piperazinyl]imidazo[1,5-a]quinoxaline;
(S)-N-[1-(Phenylmethyl)-3-pyrrolidinyl]imidazo[1,5-a]quinoxalin-4-amine;
N-[(2-Chloro-6-phenoxyphenyl)methyl]imidazo[1,5-a]quinoxalin-4-amine;
4-[4-[2-Nitro-4-(trifluoromethyl)phenyl]-1-piperazinyl]imidazo[1,5-a]quinoxaline;
N-Propylimidazo[1,5-a]quinoxalin-4-amine;
N-Cyclopropylimidazo[1,5-a]quinoxalin-4-amine;
N-[2-(4-Fluorophenyl)ethyl]imidazo[1,5-a]quinoxalin-4-amine;
N-Hexyl-N-methylimidazo[1,5-a]quinoxalin-4-amine;
N-Methyl-N-(phenylmethyl)imidazo[1,5-a]quinoxalin-4-amine;
N-(3-Methoxypropyl)imidazo[1,5-a]quinoxalin-4-amine;
[S-(R*,R*)]-2-[(Imidazo[1,5-a]quinoxalin-4-yl)amino]-1-phenyl-1,3-propanediol;
N-[(2-Methoxyphenyl)methyl]imidazo[1,5-a]quinoxalin-4-amine;
N-(4-Methyl-1-piperazinyl)imidazo[1,5-a]quinoxalin-4-amine;
N-(2-Furanylmethyl)imidazo[1,5-a]quinoxalin-4-amine;
N-(4-Morpholinyl)imidazo[1,5-a]quinoxalin-4-amine;
N-[(2,4-Difluorophenyl)methyl]imidazo[1,5-a]quinoxalin-4-amine;
N-(3-Pyridinylmethyl)imidazo[1,5-a]quinoxalin-4-amine;
N-(3,3-Dimethylbutyl)imidazo[1,5-a]quinoxalin-4-amine;
N-(Phenylmethyl)imidazo[1,5-a]quinoxalin-4-amine;
N-Cyclohexylimidazo[1,5-a]quinoxalin-4-amine;
4-(4-Morpholinyl)imidazo[1,5-a]quinoxaline;
N-(2-Bromophenyl)-3-phenylimidazo[1,5-a]quinoxalin-4-amine;
N-(2-Bromophenyl)-3-(4-morpholinylmethyl)imidazo[1,5-a]quinoxalin-4-amine;
N-(2-Bromophenyl)-7-chloroimidazo[1,5-a]quinoxalin-4-amine;
[4-[(2-Bromophenyl)amino]-7,8-dichloroimidazo[1,5-a]quinoxalin-3-yl]phosphonic acid, diethyl ester;

N-(2-Bromophenyl)-7-(1,1-dimethylethyl)imidazo[1,5-a]
quinoxalin-4-amine;

[4-[(2-Bromophenyl)amino]-7-(1,1-dimethylethyl)
imidazo[1,5-a]quinoxalin-3-yl]phosphonic acid,
diethyl ester;

[4-[(2-Chlorophenyl)amino]imidazo[1,5-a]quinoxalin-3-
yl]phosphonic acid, dimethyl ester;

7-Chloro-N-(2-chlorophenyl)imidazo[1,5-a]quinoxalin-
4-amine;

7,8-Dichloro-N-(2-chlorophenyl)imidazo[1,5-a]
quinoxalin-4-amine;

N-(2-Chlorophenyl)-7-(1,1-dimethylethyl)imidazo[1,5-a]
quinoxalin-4-amine;

N-(2-Chlorophenyl)-7-(1,1-dimethylethyl)-3-(4-
morpholinylmethyl)imidazo[1,5-a]quinoxalin-4-
amine;

[4-[(2-Chloro-6-methylphenyl)amino]imidazo[1,5-a]
quinoxalin-3-yl]phosphonic acid, dimethyl ester;

N-(2-Chloro-6-methylphenyl)-3-(4-morpholinylmethyl)
imidazo[1,5-a]quinoxalin-4-amine;

7-Chloro-N-(2-chloro-6-methylphenyl)imidazo[1,5-a]
quinoxalin-4-amine;

[7-Chloro-4-[(2-chloro-6-methylphenyl)amino]imidazo
[1,5-a]quinoxalin-3-yl]phosphonic acid, diethyl ester;

7,8-Dichloro-N-(2-chloro-6-methylphenyl)imidazo[1,5-
a]quinoxalin-4-amine;

N-(2-Chloro-6-methylphenyl)-7,8-dimethoxyimidazo[1,
5-a]quinoxalin-4-amine;

7-Chloro-N-(2,4-dimethylphenyl)imidazo[1,5-a]
quinoxalin-4-amine;

[7,8-Dichloro-4-[(2,4-dimethylphenyl)amino]imidazo[1,
5-a]quinoxalin-3-yl]phosphonic acid, diethyl ester;

7,8-Dimethoxy-N-(2,4-dimethylphenyl)-3-(4-
morpholinylmethyl)imidazo[1,5-a]quinoxalin-4-
amine;

7-(1,1-Dimethylethyl)-N-(2,4-dimethylphenyl)imidazo
[1,5-a]quinoxalin-4-amine;

[7-(1,1-Dimethylethyl)-4-[(2,4-dimethylphenyl)amino]
imidazo[1,5-a]quinoxalin-3-yl]phosphonic acid,
diethyl ester;

7-(1,1-Dimethylethyl)-N-(2,4-dimethylphenyl)-3-(4-
morpholinylmethyl)imidazo[1,5-a]quinoxalin-4-
amine;

[4-[(2,6-Dimethylphenyl)amino]imidazo[1,5-a]
quinoxalin-3-yl]phosphonic acid, diethyl ester;

7-Chloro-N-(2,6-dimethylphenyl)imidazo[1,5-a]
quinoxalin-4-amine;

[7-Chloro-4-[(2,6-dimethylphenyl)amino]imidazo[1,5-a]
quinoxalin-3-yl]phosphonic acid, diethyl ester;

7-(1,1-Dimethylethyl)-N-(2,6-dimethylphenyl)imidazo
[1,5-a]quinoxalin-4-amine;

[7-(1,1-Dimethylethyl)-4-[(2,6-dimethylphenyl)amino]
imidazo[1,5-a]quinoxalin-3-yl]phosphonic acid,
diethyl ester;

[4-[(2,4,6-Trimethylphenyl)amino]imidazo[1,5-a]
quinoxalin-3-yl]phosphonic acid, diethyl ester;

7-Chloro-N-(2,4,6-trimethylphenyl)imidazo[1,5-a]
quinoxalin-4-amine;

[7-Chloro-4-[(2,4,6-trimethylphenyl)amino]imidazo[1,5-
a]quinoxalin-3-yl]phosphonic acid, diethyl ester;

7,8-Dichloro-N-(2,4,6-trimethylphenyl)imidazo[1,5-a]
quinoxalin-4-amine;

[7,8-Dichloro-4-[(2,4,6-trimethylphenyl)amino]imidazo
[1,5-a]quinoxalin-3-yl]phosphonic acid, diethyl ester;

[7-(1,1-Dimethylethyl)-4-[(2,4,6-trimethylphenyl)amino]
imidazo[1,5-a]quinoxalin-3-yl]phosphonic acid,
diethyl ester;

[4-[(2-Bromophenyl)amino]imidazo[1,5-a]quinoxalin-3-
yl]phosphonic acid, dimethyl ester;

N-(2-Bromophenyl)-8-chloroimidazo[1,5-a]quinoxalin-
4-amine;

[4-[(2-Bromophenyl)amino]-7,8-dichloroimidazo[1,5-a]
quinoxalin-3-yl]phosphonic acid, dimethyl ester;

[4-[(2-Bromophenyl)amino]-8-(1,1-dimethylethyl)
imidazo[1,5-a]quinoxalin-3-yl]phosphonic acid,
diethyl ester;

[4-[(2-Bromophenyl)amino]-7-(1,1-dimethylethyl)
imidazo[1,5-a]quinoxalin-3-yl]phosphonic acid, dimethyl ester;

8-Chloro-N-(2-chlorophenyl)imidazo[1,5-a]quinoxalin-
4-amine;

[4-[(2-Chlorophenyl)amino]-7-(1,1-dimethylethyl)
imidazo[1,5-a]quinoxalin-3-yl]phosphonic acid, dimethyl ester;

[7-Chloro-4-[(2-chloro-6-methylphenyl)amino]imidazo
[1,5-a]quinoxalin-3-yl]phosphonic acid, dimethyl
ester;

[7-Chloro-4-[(2,4-dimethylphenyl)amino]imidazo[1,5-a]
quinoxalin-3-yl]phosphonic acid, dimethyl ester;

[8-Chloro-4-[(2,4-dimethylphenyl)amino]imidazo[1,5-a]
quinoxalin-3-yl]phosphonic acid, dimethyl ester;

[7,8-Dichloro-4-[(2,4-dimethylphenyl)amino]imidazo[1,
5-a]quinoxalin-3-yl]phosphonic acid, dimethyl ester;

[4-[(2,6-Dimethylphenyl)amino]imidazo[1,5-a]
quinoxalin-3-yl]phosphonic acid, dimethyl ester;

[7-Chloro-4-[(2,6-dimethylphenyl)amino]imidazo[1,5-a]
quinoxalin-3-yl]phosphonic acid, dimethyl ester;

[8-Chloro-4-[(2,4-dimethylphenyl)amino]imidazo[1,5-a]
quinoxalin-3-yl]phosphonic acid, diethyl ester;

[4-[(2,4,6-Trimethylphenyl)amino]imidazo[1,5-a]
quinoxalin-3-yl]phosphonic acid, dimethyl ester;

[7-Chloro-4-[(2,4,6-trimethylphenyl)amino]imidazo[1,5-
a]quinoxalin-3-yl]phosphonic acid, dimethyl ester;

[8-Chloro-4-[(2,4,6-trimethylphenyl)amino]imidazo[1,5-
a]quinoxalin-3-yl]phosphonic acid, diethyl ester;

[7,8-Dichloro-4-[(2,4,6-trimethylphenyl)amino]imidazo
[1,5-a]quinoxalin-3-yl]phosphonic acid, dimethyl
ester;

[7-(1,1-Dimethylethyl)-4-[(2,4,6-trimethylphenyl)
amino]-imidazo[1,5-a]quinoxalin-3-yl]phosphonic
acid, dimethyl ester;

N-(2-Chloro-4,6-dimethylphenyl)-7,8-dimethoxyimidazo
[1,5-a]quinoxalin-4-amine;

N-(2,4-Dichloro-6-methylphenyl)-7,8-dimethoxyimidazo
[1,5-a]quinoxalin-4-amine;

N-(2,6-Dichloro-3-methylphenyl)-7,8-dimethoxyimidazo
[1,5-a]quinoxalin-4-amine;

N-(2,6-Dichlorophenyl)-7,8-dimethoxyimidazo[1,5a]
quinoxalin-4-amine;

7,8-Dimethoxy-N-(2,4,6-trichlorophenyl)imidazo[1,5-a]
quinoxalin-4-amine;

N-(4-Bromo-2,6-dichlorophenyl)-7,8-dimethoxyimidazo
[1,5-a]quinoxalin-4-amine;

N-[2,6-Dichloro-4-(trifluoromethoxy)phenyl]-7,8-
dimethoxyimidazo[1,5-a]-quinoxalin-4-amine;

N-[2,6-Dichloro-4-(5-methyl-1,2,4-oxadiazol-3-yl) phenyl]-7,8-dimethoxyimidazo[1,5-a]-quinoxalin-4-amine;
N-(4-Bromo-2-chloro-6-methylphenyl)-7,8-dimethoxyimidazo[1,5-a]quinoxalin-4-amine;
N-(2,6-Dibromophenyl)-7,8-dimethoxyimidazo[1,5-a]-quinoxalin-4-amine;
N-(4-Bromo-2,6-dimethylphenyl)-7,8-dimethoxyimidazo[1,5-a]quinoxalin-4-amine;
7,8-Dimethoxy-N-(2,4,6-trimethyl-3-pyridinyl)imidazo[1,5-a]quinoxalin-4-amine;
9-Nitro-N-(2,4,6-trimethylphenyl)imidazo[1,5-a]quinoxalin-4-amine;
N-[2,6-Dimethyl-3-(1-methylethyl)phenyl]-9-nitroimidazo[1,5-a]quinoxalin-4-amine;
N-(3-Bromo-2,4,6-trimethylphenyl)-9-nitroimidazo[1,5-a]quinoxalin-4-amine;
N-(2-Chloro-4,6-dimethylphenyl)-9-nitroimidazo[1,5-a]quinoxalin-4-amine;
N-(2,4-Dichloro-6-methylphenyl)-9-nitroimidazo[1,5-a]quinoxalin-4-amine;
N-(2,6-Dichloro-3-methylphenyl)-9-nitroimidazo[1,5-a]quinoxalin-4-amine;
N-(2-Chlorophenyl)-9-nitroimidazo[1,5-a]quinoxalin-4-amine;
N-(2,6-Dichlorophenyl)-9-nitroimidazo[1,5-a]quinoxalin-4-amine;
9-Nitro-N-(2,4,6-trichlorophenyl)imidazo[1,5-a]quinoxalin-4-amine;
N-(4-Bromo-2,6-dichlorophenyl)-9-nitroimidazo[1,5-a]quinoxalin-4-amine;
N-(2,6-Dichloro-4-methoxyphenyl)-9-nitroimidazo[1,5-a]quinoxalin-4-amine;
N-[2,6-Dichloro-4-(trifluoromethoxy)-phenyl]-9-nitroimidazo[1,5-a]quinoxalin-4-amine;
N-[2,6-Dichloro-4-(5-methyl-1,2,4-oxadiazol-3-yl) phenyl]-9-nitroimidazo[1,5-a]quinoxalin-4-amine;
N-(4-Bromo-2-chloro-6-methylphenyl)-9-nitroimidazo[1,5-a]quinoxalin-4-amine;
N-(2-Bromophenyl)-9-nitroimidazo[1,5-a]quinoxalin-4-amine;
N-(2,6-Dibromophenyl)-9-nitroimidazo[1,5-a]quinoxalin-4-amine;
N-(2,4,6-Tribromophenyl)-9-nitroimidazo[1,5-a]quinoxalin-4-amine;
N-(2,6-Dibromo-4-propylphenyl)-9-nitroimidazo[1,5-a]quinoxalin-4-amine;
N-[2,6-Dibromo-4-(1-methylethyl)phenyl]-9-nitroimidazo[1,5-a]quinoxalin-4-amine;
N-[2-Bromo-4-(1-methylethyl)phenyl]-9-nitroimidazo[1,5-a]quinoxalin-4-amine;
N-(2,6-Dibromo-4-methylphenyl)-9-nitroimidazo[1,5-a]quinoxalin-4-amine;
N-(4-Bromo-2,6-dimethylphenyl)-9-nitroimidazo[1,5-a]quinoxalin-4-amine;
N-(3,5-Dichloro-4-pyridinyl)-9-nitroimidazo[1,5-a]quinoxalin-4-amine;
N-(2,6-Dimethylphenyl)-9-nitroimidazo-[1,5-a]quinoxalin-4-amine;
N-[4-[(2,6-Dimethylphenyl)amino]imidazo[1,5-a]quinoxalin-8-yl]-3-methoxypropanamide;
N-[4-[(2,6-Dimethylphenyl)amino]imidazo[1,5-a]quinoxalin-8-yl]-2-cyanoacetamide;

$N^4$-(2,6-Dimethylphenyl)-$N^8$,$N^8$-dimethylimidazo[1,5-a]quinoxaline-4,8-diamine;
$N^4$-(2,6-Dimethylphenyl)-$N^8$,$N^8$-diethylimidazo[1,5-a]quinoxaline-4,8-diamine;
4-[(2,6-Dimethylphenyl)amino]imidazo[1,5-a]quinoxaline-7,8-diol;
N-[4-[(2-Chloro-6-methylphenyl)amino]imidazo[1,5-a]quinoxalin-8-yl]-2-thiophenebutanamide;
$N^4$-(2,6-Dimethylphenyl)imidazo[1,5-a]quinoxaline-4,9-diamine;
$N^4$-(2,4,6-Trimethylphenyl)imidazo[1,5-a]quinoxaline-4,9-diamine;
$N^4$-[2,6-Dimethyl-3-(1-methylethyl)phenyl]imidazo[1,5-a]quinoxaline-4,9-diamine;
$N^4$-(3-Bromo-2,4,6-trimethylphenyl)imidazo[1,5-a]quinoxaline-4,9-diamine;
$N^4$-(2-Chloro-4,6-dimethylphenyl)imidazo[1,5-a]quinoxaline-4,9-diamine;
$N^4$-(2,4-Dichloro-6-methylphenyl)imidazo[1,5-a]quinoxaline-4,9-diamine;
N-(2-Chloro-6-methylphenyl)-8-iodoimidazo[1,5-a]quinoxalin-4-amine;
N-(2-Chloro-6-methylphenyl)-8-fluoroimidazo[1,5-a]quinoxalin-4-amine;
N-(2-Chloro-6-methylphenyl)-8-methoxyimidazo[1,5-a]quinoxalin-4-amine;
N-(2,6-Dimethylphenyl)-8-methoxyimidazo[1,5-a]quinoxalin-4-amine;
N-(2,6-Dichlorophenyl)-8-methoxyimidazo[1,5-a]quinoxalin-4-amine;
N-(2,4,6-Trimethylphenyl)-8-methoxyimidazo[1,5-a]quinoxalin-4-amine;
N-(2-Chlorophenyl)-8-methoxyimidazo[1,5-a]quinoxalin-4-amine;
N-(2-Chloro-6-methylphenyl)-3-methylimidazo[1,5-a]quinoxalin-4-amine;
N-(2,6-Dimethylphenyl)-3-methylimidazo[1,5-a]quinoxalin-4-amine;
N-(2-Chlorophenyl)-3-methylimidazo[1,5-a]quinoxalin-4-amine;
N-(2-Chloro-6-methylphenyl)-8-(4-methyl-1-piperazinyl)imidazo[1,5-a]quinoxalin-4-amine;
N-(2-Chloro-6-methylphenyl)-8-phenylimidazo[1,5-a]quinoxalin-4-amine;
N-(2-Chloro-6-methylphenyl)-8-(4-methoxyphenyl) imidazo[1,5-a]quinoxalin-4-amine;
$N^4$-(2-Chloro-6-methylphenyl)-$N^8$-ethylimidazo[1,5-a]quinoxaline-4,8-diamine;
$N^4$-(2-Chloro-6-methylphenyl)-$N^8$-methylimidazo[1,5-a]quinoxaline-4,8-diamine;
$N^4$-(2-Chloro-6-methylphenyl)-$N^8$-(1-methylethyl) imidazo[1,5-a]quinoxaline-4,8-diamine;
N-(2,6-Dichlorophenyl)-8-fluoroimidazo[1,5-a]quinoxalin-4-amine;
N-(2-Chloro-6-methylphenyl)-8-(1-piperazinyl)imidazo[1,5-a]quinoxalin-4-amine;
N-(2-Chloro-6-methylphenyl)-7-nitroimidazo[1,5-a]quinoxalin-4-amine;
$N^4$-(2-Chloro-6-methylphenyl)imidazo[1,5-a]quinoxaline-4,7-diamine;
N-[4-[(2-Chloro-6-methylphenyl)amino]imidazo[1,5-a]quinoxalin-7-yl]hexanamide;

$N^4$-(2-Chloro-6-methylphenyl)-$N^8$,$N^8$-diethylimidazo[1,5-a]quinoxaline-4,8-diamine;

$N^4$-(2-Chloro-6-methylphenyl)-$N^8$,$N^8$-dimethylimidazo[1,5-a]quinoxaline-4,8-diamine;

1-Acetyl-4-[4-[(2-chloro-6-methylphenyl)amino]imidazo[1,5-a]quinoxalin-8-yl]piperazine;

$N^4$-(2-Chloro-6-methylphenyl)-$N^8$-(cyclopropylmethyl)imidazo[1,5-a]quinoxaline-4,8-diamine;

$N^4$-(2-Chloro-6-methylphenyl)-$N^8$-(cyclohexylmethyl)imidazo[1,5-a]quinoxaline-4,8-diamine;

$N^4$-(2-Chloro-6-methylphenyl)-$N^8$-(cyclopentyl)imidazo[1,5-a]quinoxaline-4,8-diamine;

N-[2-[[4-[(2-Chloro-6-methylphenyl)amino]imidazo[1,5-a]quinoxalin-8-yl]amino]ethyl]acetamide;

1-[3-[[4-[(2-Chloro-6-methylphenyl)amino]imidazo[1,5-a]quinoxalin-8-yl]amino]propyl]-2-pyrrolidinone;

$N^4$-(2-Chloro-6-methylphenyl)-$N^8$-[2-(dimethylamino)ethyl]imidazo[1,5-a]quinoxaline-4,8-diamine;

$N^4$-(2-Chloro-6-methylphenyl)-$N^8$-[2-(1-methyl-2-pyrrolidinyl)ethyl]imidazo[1,5-a]quinoxaline-4,8-diamine;

$N^4$-(2-Chloro-6-methylphenyl)-$N^8$-[2-(4-morpholinyl)ethyl]imidazo[1,5-a]quinoxaline-4,8-diamine;

$N^4$-(2-Chloro-6-methylphenyl)-$N^8$-[2-(2-pyridinyl)ethyl]imidazo[1,5-a]quinoxaline-4,8-diamine;

$N^4$-(2-Chloro-6-methylphenyl)-$N^8$-(3-1H-imidazol-1-ylpropyl)imidazo[1,5-a]quinoxaline-4,8-diamine;

$N^4$-(2-Chloro-6-methylphenyl)-$N^8$-[3-(4-morpholinyl)propyl]imidazo[1,5-a]quinoxaline-4,8-diamine;

N-(2-Chloro-6-methylphenyl)-8-[4-(2-pyridinyl)-1-piperazinyl]imidazo[1,5-a]quinoxalin-4-amine;

N-(2-Chloro-6-methylphenyl)-8-(4-ethyl-1-piperazinyl)imidazo[1,5-a]quinoxalin-4-amine;

4-[4-[(2-Chloro-6-methylphenyl)amino]imidazo[1,5-a]quinoxalin-8-yl]-1-piperazinecarboxylic acid ethyl ester;

N-(2-Chloro-6-methylphenyl)-8-(3,5-dimethyl-1-piperazinyl)imidazo[1,5-a]quinoxalin-4-amine;

4-[4-[(2-Chloro-6-methylphenyl)amino]imidazo[1,5-a]quinoxalin-8-yl]-1-piperazinecarboxaldehyde;

N-(2-Chloro-6-methylphenyl)-8-(1-piperidinyl)imidazo[1,5-a]quinoxalin-4-amine;

N-(2-Chloro-6-methylphenyl)-8-(4-morpholinyl)imidazo[1,5-a]quinoxalin-4-amine;

$N^4$-(2-Chloro-6-methylphenyl)-$N^8$-[(tetrahydro-2-furanyl)methyl]imidazo[1,5-a]quinoxaline-4,8-diamine;

4-[(2-Chloro-6-methylphenyl)amino]-7,8-dimethoxyimidazo[1,5-a]quinoxaline-1-methanol;

N-(3,5-Dimethyl[1,1'-biphenyl]-4-yl)-7,8-dimethoxyimidazo[1,5-a]quinoxalin-4-amine;

N-(2-Chloro-6-methylphenyl)-8-(phenylmethoxy)imidazo[1,5-a]quinoxalin-4-amine;

6-Bromo-N-(2-chloro-6-methylphenyl)-8-fluoroimidazo[1,5-a]quinoxalin-4-amine;

6-Bromo-N-(2-chloro-6-methylphenyl)-8-(4-methyl-1-piperazinyl)imidazo[1,5-a]quinoxalin-4-amine;

N-(2-Chloro-6-methylphenyl)-8-fluoro-6-(4-methyl-1-piperazinyl)imidazo[1,5-a]quinoxalin-4-amine;

N-(2-Chloro-6-methylphenyl)-6,8-bis(1-piperazinyl)imidazo[1,5-a]quinoxalin-4-amine;

6,8-Bis(4-acetyl-1-piperazinyl)-N-(2-chloro-6-methylphenyl)imidazo[1,5-a]quinoxalin-4-amine;

$N^4$-(2-Chloro-6-methylphenyl)-$N^7$,$N^7$-dimethylimidazo[1,5-a]quinoxaline-4,7-diamine;

[4-[[4-[(2-Chloro-6-methylphenyl)amino]imidazo[1,5-a]quinoxalin-7-yl]amino]-4-oxobutyl]carbamic acid 1,1-dimethylethyl ester;

$N^4$-(2-Chloro-6-methylphenyl)-$N^7$,$N^7$-diethylimidazo[1,5-a]quinoxaline-4,7-diamine;

N-[4-[(2-Chloro-6-methylphenyl)amino]imidazo[1,5-a]quinoxalin-7-yl]acetamide;

N-[4-[(2-Chloro-6-methylphenyl)amino]imidazo[1,5-a]quinoxalin-7-yl]benzeneacetamide;

$N^4$-(2-Chloro-6-methylphenyl)-$N^7$-methylimidazo[1,5-a]quinoxaline-4,7-diamine;

4-Amino-N-[4-[(2-chloro-6-methylphenyl)amino]imidazo[1,5-a]quinoxalin-7-yl]butanamide dihydrochloride;

$N^4$-(2-Chloro-6-methylphenyl)-$N^7$-ethylimidazo[1,5-a]quinoxaline-4,7-diamine;

$N^4$-(2-Chloro-6-methylphenyl)-$N^7$-(phenylmethyl)imidazo[1,5-a]quinoxaline-4,7-diamine;

N-[4-[(2-Chloro-6-methylphenyl)amino]imidazo[1,5-a]quinoxalin-8-yl]-3-hydroxy-3-methylbutanamide;

N-(2-Chloro-6-methylphenyl)-9-methoxyimidazo[1,5-a]quinoxalin-4-amine;

N-(2,6-Dichlorophenyl)-8-nitroimidazo[1,5-a]quinoxalin-4-amine;

$N^4$-(2,6-Dichlorophenyl)imidazo[1,5-a]quinoxaline-4,8-diamine;

N-(2-Chloro-6-methylphenyl)-7,8-dihydroxyimidazo[1,5-a]quinoxalin-4-amine;

N-(2-Chloro-6-methylphenyl)[1,3]dioxolo[4,5-g]imidazo[1,5-a]quinoxalin-4-amine;

N-(2-Chloro-6-methylphenyl)-2,3-dihydro-1,4-dioxino[2,3-g]imidazo[1,5-a]quinoxalin-7-amine;

N-[2,6-Dimethyl-4-[2-(dimethylamino)ethoxy]phenyl]-7,8-dimethoxyimidazo[1,5-a]quinoxalin-4-amine;

N-[2,6-Dimethyl-4-[2-(4-morpholinyl)ethoxy]phenyl]-7,8-dimethoxyimidazo[1,5-a]quinoxalin-4-amine;

4-[(2-Chloro-6-methylphenyl)amino]imidazo[1,5-a]quinoxaline-7-carboxylic acid methyl ester;

4-[(2-Chloro-6-methylphenyl)amino]imidazo[1,5-a]quinoxaline-7-carboxylic acid;

4-[(2-Chloro-6-methylphenyl)amino]imidazo[1,5-a]quinoxaline-7-carboxamide;

N-(2-Chloro-6-methylphenyl)-8-(2,6-dimethylphenyl)imidazo[1,5-a]quinoxalin-4-amine;

N-(2-Chloro-6-methylphenyl)-8-methoxy-7-[2-(4-morpholinyl)ethoxy]imidazo[1,5-a]quinoxalin-4-amine;

N-(2-Chloro-6-methylphenyl)-8-methoxy-7-[3-(4-morpholinyl)propoxy]imidazo[1,5-a]quinoxalin-4-amine;

N-(2-Chloro-6-methylphenyl)-7-[3-(dimethylamino)propoxy]-8-methoxyimidazo[1,5-a]quinoxalin-4-amine;

N-(2-Chloro-6-methylphenyl)-7-[2-(dimethylamino)ethoxy]-8-methoxyimidazo[1,5-a]quinoxalin-4-amine;

N-(2-Chloro-6-methylphenyl)-8-methoxy-7-(2-methoxyethoxy)imidazo[1,5-a]quinoxalin-4-amine;

7-[2-(Acetyloxy)ethoxy]-N-(2-chloro-6-methylphenyl)-8-methoxyimidazo[1,5-a]quinoxalin-4-amine;

N-(2-Chloro-6-methylphenyl)-7-(2-hydroxyethoxy)-8-methoxyimidazo[1,5-a]quinoxalin-4-amine;

N-(2-Chloro-6-methylphenyl)-8-methoxy-7-[(tetrahydro-2-furanyl)methoxy]imidazo[1,5-a]quinoxalin-4-amine;

N-(2-Chloro-6-methylphenyl)-8-methoxy-7-[(tetrahydro-3-furanyl)methoxy]imidazo[1,5-a]quinoxalin-4-amine;

N-(2-Chloro-6-methylphenyl)-8-methoxy-7-[(tetrahydro-3-furanyl)oxy]imidazo[1,5-a]quinoxalin-4-amine;

N-(2-Chloro-6-methylphenyl)-8-methoxy-7-[2-(1-methyl-2-pyrrolidinyl)ethoxy]imidazo[1,5-a]quinoxalin-4-amine;

N-(2-Chloro-6-methylphenyl)-8-methoxy-7-[(1-methyl-3-pyrrolidinyl)oxy]imidazo[1,5-a]quinoxalin-4-amine;

N-(2-Chloro-6-fluorophenyl)-7,8-dimethoxyimidazo[1,5-a]quinoxalin-4-amine;

N-(2-Chloro-6-fluorophenyl)-8-methoxy-7-[2-(4-morpholinyl)ethoxy]imidazo[1,5-a]quinoxalin-4-amine;

N-(2-Chloro-6-fluorophenyl)-8-methoxy-7-[3-(4-morpholinyl)propoxy]imidazo[1,5-a]quinoxalin-4-amine;

N-(2-Chloro-6-fluorophenyl)-7-[2-(dimethylamino)ethoxy]-8-methoxyimidazo[1,5-a]quinoxalin-4-amine;

N-(2-Chloro-6-fluorophenyl)-7-[3-(dimethylamino)propoxy]-8-methoxyimidazo[1,5-a]quinoxalin-4-amine;

N-(2-Chloro-6-fluorophenyl)-8-ethoxy-7-[2-(4-morpholinyl)ethoxy]imidazo[1,5-a]quinoxalin-4-amine;

N-(2-Chloro-6-fluorophenyl)-8-ethoxy-7-[3-(4-morpholinyl)propoxy]imidazo[1,5-a]quinoxalin-4-amine;

N-(2-Chloro-6-fluorophenyl)-7-[2-(dimethylamino)ethoxy]-8-ethoxyimidazo[1,5-a]quinoxalin-4-amine;

N-(2-Chloro-6-fluorophenyl)-7-[3-(dimethylamino)propoxy]-8-ethoxyimidazo[1,5-a]quinoxalin-4-amine;

N-(2-Chloro-6-fluorophenyl)-8-ethoxy-7-[(tetrahydro-3-furanyl)oxy]imidazo[1,5-a]quinoxalin-4-amine;

N-(2-Chloro-6-methylphenyl)-7-methoxy-8-[2-(4-morpholinyl)ethoxy]imidazo[1,5-a]quinoxalin-4-amine;

N-(2-Chloro-6-methylphenyl)-7-ethoxy-8-[2-(4-morpholinyl)ethoxy]imidazo[1,5-a]quinoxalin-4-amine;

N-(2-Chloro-6-methylphenyl)-8-[2-(4-morpholinyl)ethoxy]-7-[(tetrahydro-3-furanyl)oxy]imidazo[1,5-a]quinoxalin-4-amine;

3,5-Dichloro-N-cyclopropyl-4-[(7,8-dimethoxyimidazo[1,5-a]quinoxalin-4-yl)amino]benzamide;

N-(2-Bromo-4,6-difluorophenyl)-7,8-dimethoxyimidazo[1,5-a]quinoxalin-4-amine;

3,5-Dichloro-4-[(7,8-dimethoxyimidazo[1,5-a]quinoxalin-4-yl)amino]benzoic acid;

N-(2,4-Dibromo-6-fluorophenyl)-7,8-dimethoxyimidazo[1,5-a]quinoxalin-4-amine;

3,5-Dichloro-4-[(7,8-dimethoxyimidazo[1,5-a]quinoxalin-4-yl)amino]benzenesulfonamide;

3-Chloro-4-[(7,8-dimethoxyimidazo[1,5-a]quinoxalin-4-yl)amino]-5-methylbenzenesulfonic acid;

N-[2,6-Dichloro-4-(trifluoromethyl)phenyl]-7,8-dimethoxyimidazo[1,5-a]quinoxalin-4-amine;

N-(2,6-Dibromo-4-methylphenyl)-7,8-dimethoxyimidazo[1,5-a]quinoxalin-4-amine;

N-[2,4-Dichloro-6-(trifluoromethyl)phenyl]-7,8-dimethoxyimidazo[1,5-a]quinoxalin-4-amine;

N-(2,6-Dichloro-4-methoxyphenyl)-7,8-dimethoxyimidazo[1,5-a]quinoxalin-4-amine;

N-[2-Fluoro-6-(trifluoromethyl)phenyl]-7,8-dimethoxyimidazo[1,5-a]quinoxalin-4-amine;

N-(2-Bromo-6-chloro-4-fluorophenyl)-7,8-dimethoxyimidazo[1,5-a]quinoxalin-4-amine;

N-(2,6-Dibromo-4-fluorophenyl)-7,8-dimethoxyimidazo[1,5-a]quinoxalin-4-amine;

N-(2-Bromo-4,6-dimethylphenyl)-7,8-dimethoxyimidazo[1,5-a]quinoxalin-4-amine;

N-(2-Bromo-4-chloro-6-fluorophenyl)-7,8-dimethoxyimidazo[1,5-a]quinoxalin-4-amine;

N-(2,6-Difluorophenyl)-7,8-dimethoxyimidazo[1,5-a]quinoxalin-4-amine;

N-(2,4,6-Trifluorophenyl)-7,8-dimethoxyimidazo[1,5-a]quinoxalin-4-amine;

3-Chloro-4-[(7,8-dimethoxyimidazo[1,5-a]quinoxalin-4-yl)amino]-5-methylbenzonitrile;

3-Chloro-4-[(7,8-dimethoxyimidazo[1,5-a]quinoxalin-4-yl)amino]-5-methylbenzamide;

N-(2-Chloro-3,6-dimethylphenyl)-7,8-dimethoxyimidazo[1,5-a]quinoxalin-4-amine;

N-(2-Chloro-5,6-dimethylphenyl)-7,8-dimethoxyimidazo[1,5-a]quinoxalin-4-amine;

N-(2-Chloro-6-methylphenyl)-6-methoxyimidazo[1,5-a]quinoxalin-4-amine;

N-(2-Chloro-6-methylphenyl)-9-(phenylmethoxy)imidazo[1,5-a]quinoxalin-4-amine;

N-(2-Chloro-6-methylphenyl)-9-(2-hydroxyethoxy)imidazo[1,5-a]quinoxalin-4-amine;

N-(2-Chloro-6-methylphenyl)-9-[2-(dimethylamino)ethoxy]imidazo[1,5-a]quinoxalin-4-amine;

N-(2-Chloro-6-methylphenyl)-9-(3-hydroxypropoxy)imidazo[1,5-a]quinoxalin-4-amine;

N-(2-Chloro-6-methylphenyl)-9-(2-methoxyethoxy)imidazo[1,5-a]quinoxalin-4-amine;

N-(2-Chloro-6-methylphenyl)-9-[(tetrahydro-2H-pyran-4-yl)oxy]imidazo[1,5-a]quinoxalin-4-amine;

N-(2-Chloro-6-methylphenyl)-9-[2-(4-morpholinyl)ethoxy]imidazo[1,5-a]quinoxalin-4-amine;

8-Bromo-N-(2-chloro-6-fluorophenyl)imidazo[1,5-a]quinoxalin-4-amine;

N-(2-Chloro-6-fluorophenyl)-8-(3,5-dimethyl-1-piperazinyl)imidazo[1,5-a]quinoxalin-4-amine;

N-(2-Chloro-6-fluorophenyl)-8-(4-methyl-1-piperazinyl)imidazo[1,5-a]quinoxalin-4-amine;

N-(2-Chloro-6-fluorophenyl)-8-[[2-(2-pyridinyl)ethyl]amino]imidazo[1,5-a]quinoxalin-4-amine;

$N^4$-(2-Chloro-6-fluorophenyl)-$N^8$-[(tetrahydro-2-furanyl)methyl]imidazo[1,5-a]quinoxaline-4,8-diamine;

$N^8$-(2-Aminoethyl)-$N^4$-(2-chloro-6-fluorophenyl)imidazo[1,5-a]quinoxaline-4,8-diamine;

$N^4$-(2-Chloro-6-fluorophenyl)-$N^8$-[3-(4-methyl-1-piperazinyl)propyl]imidazo[1,5-a]quinoxaline-4,8-diamine;

$N^4$-(2-Chloro-6-fluorophenyl)-$N^8$-[2-(1-methyl-2-pyrrolidinyl)ethyl]imidazo[1,5-a]quinoxaline-4,8-diamine;

$N^4$-(2-Chloro-6-fluorophenyl)-$N^8$-[2-(4-morpholinyl)ethyl]imidazo[1,5-a]quinoxaline-4,8-diamine;

$N^4$-(2-Chloro-6-fluorophenyl)-$N^8$-[6-(dimethylamino)hexyl]imidazo[1,5-a]quinoxaline-4,8-diamine;

$N^4$-(2-Chloro-6-fluorophenyl)-$N^8$-[4-(dimethylamino) butyl]imidazo[1,5-a]quinoxaline-4,8-diamine;

$N^4$-(2-Chloro-6-fluorophenyl)-$N^8$-[3-(dimethylamino) propyl]imidazo[1,5-a]quinoxaline-4,8-diamine;

$N^4$-(2-Chloro-6-fluorophenyl)-$N^8$-[2-(dimethylamino) ethyl]imidazo[1,5-a]quinoxaline-4,8-diamine;

1-[3-[[4-(2-Chloro-6-fluorophenyl)imidazo[1,5-a] quinoxalin-8-yl]amino]propyl]-2-pyrrolidinone;

$N^4$-(2-Chloro-6-fluorophenyl)-$N^8$-[2-(4-pyridinyl)ethyl] imidazo[1,5-a]quinoxaline-4,8-diamine;

$N^4$-(2-Chloro-6-fluorophenyl)-$N^8$-[3-(4-morpholinyl) propyl]imidazo[1,5-a]quinoxaline-4,8-diamine;

$N^4$-(2-Chloro-6-fluorophenyl)-$N^8$-(cyclopropylmethyl) imidazo[1,5-a]quinoxaline-4,8-diamine;

7-Bromo-N-(2-chloro-6-methylphenyl)imidazo[1,5-a] quinoxalin-4-amine;

$N^4$-(2-Chloro-6-methylphenyl)-$N^7$-[4-(dimethylamino) butyl]imidazo[1,5-a]quinoxaline-4,7-diamine;

$N^4$-(2-Chloro-6-methylphenyl)-$N^7$-[6-(dimethylamino) hexyl]imidazo[1,5-a]quinoxaline-4,7-diamine;

$N^4$-(2-Chloro-6-methylphenyl)-$N^7$-[3-(4-methyl-1-piperazinyl)propyl]imidazo[1,5-a]quinoxaline-4,7-diamine;

$N^4$-(2-Chloro-6-methylphenyl)-$N^7$-cyclopropylimidazo [1,5-a]quinoxaline-4,7-diamine;

$N^4$-(2-Chloro-6-methylphenyl)-$N^7$-[1-(phenylmethyl)-4-piperidinyl]imidazo[1,5-a]quinoxaline-4,7-diamine;

$N^4$-(2-Chloro-6-methylphenyl)-$N^7$-[3-(methylphenylamino)propyl]imidazo[1,5-a] quinoxaline-4,7-diamine;

$N^7$-[(2-Aminophenyl)methyl]-$N^4$-(2-chloro-6-methylphenyl)imidazo[1,5-a]quinoxaline-4,7-diamine;

N-(2-Chloro-6-methylphenyl)-7-(4-morpholinyl)imidazo [1,5-a]quinoxalin-4-amine;

N-(2-Chloro-6-methylphenyl)-7-(4-methyl-1-piperazinyl)imidazo[1,5-a]quinoxalin-4-amine;

N-(2-Chloro-6-methylphenyl)-7-(1-piperazinyl)imidazo [1,5-a]quinoxalin-4-amine;

N-(2-Chloro-6-methylphenyl)-7-(3,5-dimethyl-1-piperazinyl)imidazo[1,5-a]quinoxalin-4-amine;

N-(2-Chloro-6-methylphenyl)-7-[4-[2-(dimethylamino) ethyl]-1-piperazinyl]imidazo[1,5-a]quinoxalin-4-amine;

N-(2-Chloro-6-methylphenyl)-7-[4-[3-(dimethylamino) propyl]-1-piperazinyl]imidazo[1,5-a]quinoxalin-4-amine;

(S)-N-(2-Chloro-6-methylphenyl)-7-(3-methyl-1-piperazinyl)imidazo[1,5-a]quinoxalin-4-amine;

$N^4$-(2-Chloro-6-methylphenyl)-$N^7$-[2-(dimethylamino) ethyl]imidazo[1,5-a]quinoxaline-4,7-diamine;

$N^4$-(2-Chloro-6-methylphenyl)-$N^7$-[3-(dimethylamino) propyl]imidazo[1,5-a]quinoxaline-4,7-diamine;

$N^4$-(2-Chloro-6-methylphenyl)-$N^7$-(2-thienylmethyl) imidazo[1,5-a]quinoxaline-4,7-diamine;

$N^4$-(2-Chloro-6-methylphenyl)-$N^7$-[(2,3-dihydro-1,4-benzodioxin-2-yl)methyl]imidazo[1,5-a]quinoxaline-4,7-diamine;

$N^4$-(2-Chloro-6-methylphenyl)-$N^7$-[2-(2-thienyl)ethyl] imidazo[1,5-a]quinoxaline-4,7-diamine;

(R)-N-(2-Chloro-6-methylphenyl)-7-(3-methyl-1-piperazinyl)imidazo[1,5-a]quinoxalin-4-amine;

7-[4-(1,3-Benzodioxol-5-ylmethyl)-1-piperazinyl]-N-(2-chloro-6-methylphenyl)imidazo[1,5-a]quinoxalin-4-amine;

4-[4-[(2-Chloro-6-methylphenyl)amino]imidazo[1,5-a] quinoxalin-7-yl]-N-(1-methylethyl)-1-piperazineacetamide;

N-(2-Chloro-6-methylphenyl)-7-(4-phenyl-1-piperazinyl)imidazo[1,5-a]quinoxalin-4-amine;

1-[4-[(2-Chloro-6-methylphenyl)amino]imidazo[1,5-a] quinoxalin-7-yl]-4-(2-furanylcarbonyl)piperazine;

N-(2-Chloro-6-methylphenyl)-7-[4-(2-methoxyethyl)-1-piperazinyl]imidazo[1,5-a]quinoxalin-4-amine;

4-[(2-Chloro-6-methylphenyl)amino]-7,8-dimethoxyimidazo[1,5-a]quinoxaline-1-carboxaldehyde;

4-[(2-Chloro-6-methylphenyl)amino]-7,8-dimethoxyimidazo[1,5-a]quinoxaline-1-carboxaldehyde oxime;

4-[(2-Chloro-6-methylphenyl)amino]-8-methoxyimidazo [1,5-a]quinoxalin-7-ol;

2-[[4-[(2-Chloro-6-methylphenyl)amino]-7-hydroxyimidazo[1,5-a]quinoxalin-8-yl]oxy]-2-propenenitrile;

7-[(2-Chloro-6-methylphenyl)amino]-2,3-dihydro-1,4-dioxino[2,3-g]imidazo[1,5-a]quinoxaline-2-carbonitrile;

N-(2-Chloro-6-methylphenyl)-7,8-bis[3-(dimethylamino) propoxy]imidazo[1,5-a]quinoxalin-4-amine;

N-(2-Chloro-6-methylphenyl)-7,8-bis[2-(4-morpholinyl) ethoxy]imidazo[1,5-a]quinoxalin-4-amine;

N-Cyclohexyl-7,8-dimethoxyimidazo[1,5-a]quinoxaline-4-amine;

1-Chloro-N-(2-chloro-6-methylphenyl)-7,8-dimethoxyimidazo[1,5-a]quinoxalin-4-amine;

N-(2-Chloro-6-methylphenyl)-1,7,8-trimethoxyimidazo [1,5-a]quinoxalin-4-amine;

$N^4$-(2-Chloro-6-methylphenyl)-7,8-dimethoxy-$N^1$-[(4-methoxyphenyl)methyl]imidazo[1,5-a]quinoxaline-1,4-diamine;

N-[4-[(2-Chloro-6-methylphenyl)amino]-7,8-dimethoxyimidazo[1,5-a]quinoxalin-1-yl]-N-[(4-methoxyphenyl)methyl]acetamide;

N-[4-[(2-Chloro-6-methylphenyl)amino]-7,8-dimethoxyimidazo[1,5-a]quinoxalin-1-yl]acetamide;

$N^4$-(2-Chloro-6-methylphenyl)-7,8-dimethoxyimidazo[1, 5-a]quinoxaline-1,4-diamine, dihydrochloride;

3-Chloro-N-(2-chloro-6-methylphenyl)imidazo[1,5-a] quinoxalin-4-amine;

4-[(2-Chloro-6-methylphenyl)amino]imidazo[1,5-a] quinoxaline-8-carbonitrile;

4-[(2-Chloro-6-methylphenyl)amino]imidazo[1,5-a] quinoxaline-8-carboxamide;

4-[(2-Chloro-6-methylphenyl)amino]imidazo[1,5-a] quinoxaline-8-carboxylic acid;

4-[(2-Chloro-6-methylphenyl)amino]imidazo[1,5-a] quinoxaline-8-carboxylic acid methyl ester;

4-[(2-Chloro-6-methylphenyl)amino]imidazo[1,5-a] quinoxalin-8-ol;

N-[2-Chloro-6-methyl-4-(4-morpholinyl)phenyl]-7,8-dimethoxyimidazo[1,5-a]quinoxalin-4-amine;

N-(2-Chloro-6-methylphenyl)-8-(hexahydro-4-methyl-1H-1,4-diazepin-1-yl)imidazo[1,5-a]quinoxalin-4-amine;

N-(2-Chloro-6-fluorophenyl)-8-(1H-imidazol-1-yl) imidazo[1,5-a]quinoxalin-4-amine;

N-(2-Chloro-6-methylphenyl)-7,9-dimethoxyimidazo[1,5-a]quinoxalin-4-amine;

N-(2-Chloro-6-fluorophenyl)-7,9-dimethoxyimidazo[1,5-a]quinoxalin-4-amine;

N-(2-Chloro-6-fluorophenyl)-6,8-dimethoxyimidazo[1,5-a]quinoxalin-4-amine;

N-(2-Chloro-6-methylphenyl)-8-[4-[[[3-(dimethylamino)propyl]amino]methyl]phenyl]imidazo[1,5-a]quinoxalin-4-amine;

N-(2-Chloro-6-methylphenyl)-7-methoxy-8-(1-piperazinyl)imidazo[1,5-a]quinoxalin-4-amine;

cis-N-(2-Chloro-6-methylphenyl)-8-(3,5-dimethyl-1-piperazinyl)-7-methoxyimidazo[1,5-a]quinoxalin-4-amine;

$N^4$-(2-Chloro-6-methylphenyl)-7-methoxy-$N^8$-[3-(4-morpholinyl)propyl]imidazo[1,5-a]quinoxaline-4,8-diamine;

N-(2-Chloro-6-methylphenyl)-8-(hexahydro-1H-1,4-diazepin-1-yl)-7-methoxyimidazo[1,5-a]quinoxalin-4-amine;

N-(2-Chloro-6-methylphenyl)-8-(hexahydro-4-methyl-1H-1,4-diazepin-1-yl)-7-methoxyimidazo[1,5-a]quinoxalin-4-amine;

N-(2-Chloro-6-methylphenyl)-7-[2-(4-morpholinyl)ethoxy]-8-(1-piperazinyl)imidazo[1,5-a]quinoxalin-4-amine;

cis-N-(2-Chloro-6-methylphenyl)-8-(3,5-dimethyl-1-piperazinyl)-7-[2-(4-morpholinyl)ethoxy]imidazo[1,5-a]quinoxalin-4-amine;

$N^4$-(2-Chloro-6-methylphenyl)-7-[2-(4-morpholinyl)ethoxy]-$N^8$-[3-(4-morpholinyl)propyl]imidazo[1,5-a]quinoxaline-4,8-diamine;

$N^4$-(2-Chloro-6-methylphenyl)-$N^8$-[2-(dimethylamino)ethyl]-7-[2-(4-morpholinyl)ethoxy]imidazo[1,5-a]quinoxaline-4,8-diamine;

$N^4$-(2-Chloro-6-methylphenyl)-$N^8$-[3-(dimethylamino)propyl]-7-[2-(4-morpholinyl)ethoxy]imidazo[1,5-a]quinoxaline-4,8-diamine;

$N^4$-(2-Chloro-6-methylphenyl)-$N^8$-[4-(dimethylamino)butyl]-7-[2-(4-morpholinyl)ethoxy]imidazo[1,5-a]quinoxaline-4,8-diamine;

N-[1-[4-[(2-Chloro-6-methylphenyl)amino]-7-[2-(4-morpholinyl)ethoxy]imidazo[1,5-a]quinoxalin-8-yl]-3-pyrrolidinyl]acetamide;

1-Acetyl-4-[4-[(2-Chloro-6-methylphenyl)amino]-7-[2-(4-morpholinyl)ethoxy]imidazo[1,5-a]quinoxalin-8-yl]piperazine;

N-(2-Chloro-6-methylphenyl)-8-(hexahydro-4-methyl-1H-1,4-diazepin-1-yl)-7-[2-(4-morpholinyl)ethoxy]imidazo[1,5-a]quinoxalin-4-amine;

N-(2-Chloro-6-methylphenyl)-7-[2-(4-morpholinyl)ethoxy]-8-phenylimidazo[1,5-a]quinoxalin-4-amine;

$N^4$-(2-Chloro-6-methylphenyl)-$N^1$,$N^1$-dimethyl-7,8-dimethoxyimidazo[1,5-a]quinoxaline-1,4-diamine;

N-(2-Chloro-6-methylphenyl)-8-[4-[[[3-(dimethylamino)propyl]amino]methyl]phenyl]-7-[2-(4-morpholinyl)ethoxy]imidazo[1,5-a]quinoxalin-4-amine;

$N^4$-(2-Chloro-6-methylphenyl)-8-methoxy-$N^7$-[2-(4-morpholinyl)ethyl]imidazo[1,5-a]quinoxaline-4,7-diamine;

$N^4$-(2-Chloro-6-methylphenyl)-$N^7$-[2-(dimethylamino)ethyl]-8-methoxyimidazo[1,5-a]quinoxaline-4,7-diamine;

cis-N-(2-Chloro-6-methylphenyl)-7-(3,5-dimethyl-1-piperazinyl)-8-methoxyimidazo[1,5-a]quinoxalin-4-amine;

N-(2-Chloro-6-methylphenyl)-7-[4-[2-(dimethylamino)ethyl]-1-piperazinyl]-8-methoxyimidazo[1,5-a]quinoxalin-4-amine;

$N^4$-(2-Chloro-6-fluorophenyl)-8-methoxy-$N^7$-[2-(4-morpholinyl)ethyl]imidazo[1,5-a]quinoxaline-4,7-diamine;

$N^4$-(2-Chloro-6-fluorophenyl)-$N^7$-[2-(dimethylamino)ethyl]-8-methoxyimidazo[1,5-a]quinoxaline-4,7-diamine;

cis-N-(2-Chloro-6-fluorophenyl)-7-(3,5-dimethyl-1-piperazinyl)-8-methoxyimidazo[1,5-a]quinoxalin-4-amine;

4-Amino-N-(2-chloro-6-methylphenyl)imidazo[1,5-a]quinoxaline-7-carboxamide;

4-Amino-N-(2,4,6-trimethylphenyl)imidazo[1,5-a]quinoxaline-7-carboxamide;

4-[(2-Chloro-6-methylphenyl)amino]-7,8-dimethoxy-α-methylimidazo[1,5-a]quinoxaline-1-methanol;

4-[(2-Chloro-6-methylphenyl)amino]-α-ethyl-7,8-dimethoxyimidazo[1,5-a]quinoxaline-1-methanol;

4-[(2-Chloro-6-methylphenyl)amino]-7,8-dimethoxy-α-(1-methylethyl)imidazo[1,5-a]quinoxaline-1-methanol;

4-[(2-Chloro-6-methylphenyl)amino]-N-ethyl-7,8-dimethoxyimidazo[1,5-a]quinoxaline-1-carboxamide;

4-[(2-Chloro-6-methylphenyl)amino]-N-(1,1-dimethylethyl)-7,8-dimethoxyimidazo[1,5-a]quinoxaline-1-carboxamide;

4-[(2-Chloro-6-methylphenyl)amino]-7,8-dimethoxy-N-(phenylmethyl)imidazo[1,5-a]quinoxaline-1-carboxamide;

N-[[4-[(2-Chloro-6-methylphenyl)amino]-7,8-dimethoxyimidazo[1,5-a]quinoxalin-1-yl]carbonyl]alanine ethyl ester;

4-[(2-Chloro-6-methylphenyl)amino]-7,8-dimethoxy-N-pentylimidazo[1,5-a]quinoxaline-1-carboxamide;

N-[[4-[(2-Chloro-6-methylphenyl)amino]-7,8-dimethoxyimidazo[1,5-a]quinoxalin-1-yl]carbonyl]glycine ethyl ester;

(S)-4-[(2-Chloro-6-methylphenyl)amino]-7,8-dimethoxy-N-(1-phenylethyl)imidazo[1,5-a]quinoxaline-1-carboxamide;

4-[(2-Chloro-6-methylphenyl)amino]-N-cyclohexyl-7,8-dimethoxyimidazo[1,5-a]quinoxaline-1-carboxamide;

4-[(2-Chloro-6-methylphenyl)amino]-7,8-dimethoxy-N-(1-methylethyl)imidazo[1,5-a]quinoxaline-1-carboxamide;

N-[(2-Chloro-6-methylphenyl)amino]-7,8-dimethoxyimidazo[1,5-a]quinoxaline-1-propanol;

4-[(2-Chloro-6-methylphenyl)amino]imidazo[1,5-a]quinoxalin-9-ol;

N-(2-Chloro-6-methylphenyl)-7-(1,3-dioxolan-4-ylmethoxy)-8-methoxyimidazo[1,5-a]quinoxalin-4-amine;

N-(2-Chloro-6-methylphenyl)-8-methoxy-7-[(1-methyl-3-piperidinyl)methoxy]imidazo[1,5-a]quinoxalin-4-amine; and N-(2-Chloro-6-methylphenyl)-7,8-dimethoxy-1-methylimidazo[1,5-a]quinoxalin-4-amine.

39. An imidazoquinoxaline compound of the following formula I or a salt thereof:

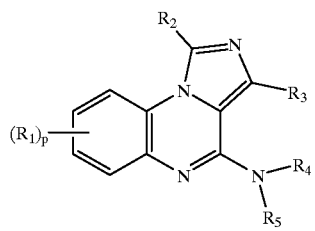

(I)

where p is 0, 1, 2, 3 or 4;

each $R_1$, and $R_2$ and $R_3$, are independently selected from:
(1) hydrogen or $R_6$,
   where $R_6$ is alkyl, alkenyl, alkynyl, cycloalkyl, cycloalkylalkyl, cycloalkenyl, cycloalkenylalkyl, aryl, aralkyl, heterocyclo, or heterocycloalkyl, each of which is unsubstituted or substituted with $Z_1$, $Z_2$ and one or more groups $Z_3$;
(2) —OH or —$OR_6$;
(3) —SH or —$SR_6$;
(4) —$C(O)_qH$, —$C(O)_qR_6$ or —O—$C(O)_qR_6$, where q is 1 or 2;
(5) —$SO_3H$ or —$S(O)_qR_6$;
(6) halo;
(7) cyano;
(8) nitro;
(9) —$Z_4$—$NR_7R_8$;
(10) —$Z_4$—$N(R_9)$—$Z_5$—$NR_{10}R_{11}$;
(11) —$Z_4$—$N(R_{12})$—$Z_5$—$R_6$;
(12) —$SiR_{13}R_{14}R_{15}$;
(13) —$P(O)(OR_6)_2$;
(14) any two groups $R_1$ may together be alkylene or alkenylene completing a 3- to 8-membered saturated or unsaturated ring together with the carbon atoms to which they are attached, which ring is unsubstituted or substituted with $Z_1$, $Z_2$ and $Z_3$; or
(15) any two groups $R_1$ may, together with the carbons to which they are attached, form a heterocyclo group, which group is unsubstituted or substituted with $Z_1$, $Z_2$ and $Z_3$;

$R_4$ and $R_5$:
(1) are each independently hydrogen, $R_6$, or —$C(O)R_6$; or
(2) together with the nitrogen atom to which they are attached complete a 3- to 8-membered saturated or unsaturated heterocyclic ring which is unsubstituted or substituted with $Z_1$, $Z_2$ and $Z_3$, which heterocyclic ring may optionally have fused to it a benzene ring itself unsubstituted or substituted with $Z_1$, $Z_2$ and $Z_3$;

$R_7$, $R_8$, $R_9$, $R_{10}$, $R_{11}$ and $R_{12}$:
(1) are each independently hydrogen or $R_6$;
(2) $R_7$ and $R_8$ may together be alkylene or alkenylene, completing a 3- to 8-membered saturated or unsaturated ring with the nitrogen atom to which they are attached, which ring is unsubstituted or substituted with $Z_1$, $Z_2$ and $Z_3$; or
(3) any two of $R_9$, $R_{10}$ and $R_{11}$ may together be alkylene or alkenylene completing a 3- to 8-membered saturated or unsaturated ring together with the nitrogen atoms to which they are attached, which ring is unsubstituted or substituted with $Z_1$, $Z_2$ and $Z_3$;

$R_{13}$, $R_{14}$ and $R_{15}$ are each independently:
(1) alkyl; or
(2) phenyl;

$Z_1$, $Z_2$ and $Z_3$ are each independently:
(1) hydrogen or $Z_6$, where $Z_6$ is (i) alkyl, alkenyl, alkynyl, cycloalkyl, cycloalkylalkyl, cycloalkenyl, cycloalkenylalkyl, aryl, aralkyl, alkylaryl, cycloalkylaryl, heterocyclo, or heterocycloalkyl; (ii) a group (i) which is itself substituted by one or more of the same or different groups (i); or (iii) a group (i) or (ii) which is substituted by one or more of the following groups (2) to (16) of the definition of $Z_1$, $Z_2$ and $Z_3$;
(2) —OH or —$OZ_6$;
(3) —SH or —$SZ_6$;
(4) —$C(O)_qH$, —$C(O)_qZ_6$ or —O—$C(O)_qZ_6$;
(5) —$SO_3H$ or —$S(O)_qZ_6$;
(6) halo;
(7) cyano;
(8) nitro;
(9) —$Z_4$—$NZ_7Z_8$;
(10) —$Z_4$—$N(Z_9)$—$Z_5$—$NZ_7Z_8$;
(11) —$Z_4$—$N(Z_{10})$—$Z_5$—$Z_6$;
(12) —$Z_4$—$N(Z_{10})$—$Z_5$—H;
(13) oxo;
(14) —O—$C(O)$—$Z_6$;
(15) any two of $Z_1$, $Z_2$, and $Z_3$ may together be alkylene or alkenylene completing a 3- to 8-membered saturated or unsaturated ring together with the atoms to which they are attached; or
(16) any two of $Z_1$, $Z_2$, and $Z_3$ may together be —O—$(CH_2)_q$—O—;

$Z_4$ and $Z_5$ are each independently:
(1) a single bond;
(2) —$Z_{11}$—$S(O)_q$—$Z_{12}$—;
(3) —$Z_{11}$—$C(O)$—$Z_{12}$—;
(4) —$Z_{11}$—$C(S)$—$Z_{12}$—;
(5) —$Z_{11}$—O—$Z_{12}$—;
(6) —$Z_{11}$—S—$Z_{12}$—;
(7) —$Z_{11}$—O—$C(O)$—$Z_{12}$—; or
(8) —$Z_{11}$—$C(O)$—O—$Z_{12}$—;

$Z_7$, $Z_8$, $Z_9$ and $Z_{10}$:
(1) are each independently hydrogen or $Z_6$;
(2) $Z_7$ and $Z_8$, or $Z_6$ and $Z_{10}$, may together be alkylene or alkenylene, completing a 3- to 8-membered saturated or unsaturated ring together with the atoms to which they are attached, which ring is unsubstituted or substituted with $Z_1$, $Z_2$ and $Z_3$; or
(3) $Z_7$ or $Z_8$, together with $Z_9$, may be alkylene or alkenylene completing a 3- to 8-membered saturated or unsaturated ring together with the nitrogen atoms to which they are attached, which ring is unsubstituted or substituted with $Z_1$, $Z_2$ and $Z_3$; and $Z_{11}$ and $Z_{12}$ are each independently:
(1) a single bond;
(2) alkylene;
(3) alkenylene; or
(4) alkynylene;

with the proviso that said compound is not selected from the group of compounds consisting of
4-amino-7-trifluoromethylimidazo[1,5-a]quinoxaline-3-carboxylic acid ethyl ester;
1-ethyl-3-methylimidazo[1,5-a]quinoxalin-4-amine;
3-(5-Cyclopropyl-1,2,4-oxadiazol-3-yl)imidazo[1,5-a]quinoxalin-4-amine;
3-(5-Cyclopropyl-1,2,4-oxadiazol-3-yl)-N,N-dimethylimidazo[1,5-a]quinoxalin-4-amine hydrochloride;

3-(3-Cyclopropyl-1,2,4-oxadiazol-5-yl)-N,N-dimethylimidazo[1,5-a]quinoxalin-4-amine;
3-(3-Cyclopropyl-1,2,4-oxadiazol-5-yl)-N-ethyl-N-methylimidazo[1,5-a]quinoxalin-4-amine;
3-(3-Cyclopropyl-1,2,4-oxadiazol-5-yl)-N-methylimidazo[1,5-a]quinoxalin-4-amnine;
3-(5-Cyclopropyl-1,2,4-oxadiazol-3-yl)-4-(4-morpholinyl)imidazo[1,5-a]quinoxaline;
3-(5-Cyclopropyl-1,2,4-oxadiazol-3-yl)-N-ethyl-N-methylimidazo[1,5-a]quinoxalin-4-amine hydrochloride;
4-(N-Ethyl-N-methylamino)imidazo[1,5-a]quinoxaline-3-carboxylic acid ethyl ester;
1-Phenylimidazo[1,5-a]quinoxalin-4-amine; and
N-Cyclopentyl-1-phenylimidazo[1,5-a]quinoxalin-4-amine.

40. A pharmaceutically acceptable compound of claim 1 or tautomer thereof.

41. A compound of claim 1 wherein
$R^3$ is other than oxadiazolyl or oxadiazoly substituted with alkyl or cycloalkyl, when
1) p is 0;
2) $R_2$ is hydrogen; and
3) $R^4$ and $R^5$ are independently hydrogen, alkyl, alkoxy or cycloalkyl, or $R^4$ and $R^5$ together with the nitrogen atom to which they are attached complete to a 3- to 8-membered heterocyclic ring.

* * * * *